United States Patent
Wu et al.

(10) Patent No.: US 10,278,973 B2
(45) Date of Patent: May 7, 2019

(54) HYDROXYL PURINE COMPOUNDS AND USE THEREOF

(71) Applicant: GUANGDONG RAYNOVENT BIOTECH CO., LTD., Dongguan (CN)

(72) Inventors: Lingyun Wu, Shanghai (CN); Xiaoxin Chen, Dongguan (CN); Peng Zhang, Shanghai (CN); Xing Liu, Dongguan (CN); Li Zhang, Shanghai (CN); Zhuowei Liu, Dongguan (CN); Shuhui Chen, Shanghai, CA (US); Chaofeng Long, Dongguan (CN)

(73) Assignee: GUANGDONG RAYNOVENT BIOTECH CO., LTD., Dongguan (CN)

( * ) Notice: Subject to any disclaimer, the term of this patent is extended or adjusted under 35 U.S.C. 154(b) by 0 days.

(21) Appl. No.: 15/575,037

(22) PCT Filed: May 5, 2016

(86) PCT No.: PCT/CN2016/081102
§ 371 (c)(1),
(2) Date: Nov. 17, 2017

(87) PCT Pub. No.: WO2016/184312
PCT Pub. Date: Nov. 24, 2016

(65) Prior Publication Data
US 2018/0140607 A1 May 24, 2018

(30) Foreign Application Priority Data

May 20, 2015 (CN) .......................... 2015 1 0259502

(51) Int. Cl.
| | |
|---|---|
| C07D 473/06 | (2006.01) |
| C07D 473/10 | (2006.01) |
| C07D 487/04 | (2006.01) |
| C07D 475/02 | (2006.01) |
| C07D 239/96 | (2006.01) |
| A61K 31/522 | (2006.01) |
| A61K 31/519 | (2006.01) |
| A61P 29/00 | (2006.01) |
| C07D 471/04 | (2006.01) |
| C07K 14/525 | (2006.01) |

(52) U.S. Cl.
CPC .......... *A61K 31/522* (2013.01); *A61K 31/519* (2013.01); *A61P 29/00* (2018.01); *C07D 239/96* (2013.01); *C07D 471/04* (2013.01); *C07D 473/06* (2013.01); *C07D 473/10* (2013.01); *C07D 475/02* (2013.01); *C07D 487/04* (2013.01); *C07K 14/525* (2013.01)

(58) Field of Classification Search
CPC .. C07D 473/06; C07D 473/10; C07D 487/04; C07D 475/02; C07D 239/96
See application file for complete search history.

(56) References Cited

FOREIGN PATENT DOCUMENTS

| | | |
|---|---|---|
| EP | 3205652 A1 | 8/2017 |
| WO | 9852948 A1 | 11/1998 |
| WO | 02064080 A2 | 8/2002 |
| WO | 2002068420 A1 | 9/2002 |
| WO | 2004006912 A2 | 1/2004 |
| WO | 2004013068 A1 | 2/2004 |
| WO | 2006136822 A1 | 12/2006 |
| WO | 2015169999 A1 | 11/2015 |
| WO | 2016044792 A1 | 3/2016 |
| WO | 2016054971 A1 | 4/2016 |

OTHER PUBLICATIONS

Weil et al. (Bull. pharm. inst. Poland (1928), No. 2, 175-6). Abstract.*
Yago (Japan. Circulation J. (1962), 26, 407-18). Abstarct.*
Avico et al. (Farmaco, Edizione Scientifica (1962), 17, 73-80). Abstract.*
Yoshida et al. (JP 37004545). (1962). Abstract.*
Berge et al.—"Pharmaceutical salts",—Journal of pharmaceutical Science, 1977 66:1-19.
H Maehr, —"A proposed new convention for graphic presentation of molecular geometry and topography."—J. Chem. Ed., 1985, 62:114-120.
Remington: The Science and Practice of Pharmacy, 21st Ed., Lippincott, Williams & Wilkins (2005), (Part 1 of 3; pp. 702-798).
Remington: The Science and Practice of Pharmacy, 21st Ed., Lippincott, Williams & Wilkins (2005), (Part 2 of 3; pp. 799-948).
Remington: The Science and Practice of Pharmacy, 21st Ed., Lippincott, Williams & Wilkins (2005), (Part 3 of 3; pp. 949-1057).
STN Retrieval System CA Registry Database Retrieval Result (Mar. 16, 2011) Compound CA registration No. 1268606-01-4.
Extended European Search Report of counterpart European Application No. 16795799.2 dated May 17, 2018, 10 pages.
Sinha et al., Eur. J. Immunol, 1995, 147-153.

(Continued)

*Primary Examiner* — Bruck Kifle
(74) *Attorney, Agent, or Firm* — Dilworth IP, LLC

(57) ABSTRACT

Disclosed are a series of hydroxyl purine compounds and the use thereof as PDE2 or TNFα inhibitors, in particular, the compounds as shown in formula (I), or tautomers thereof or pharmaceutically acceptable salts thereof.

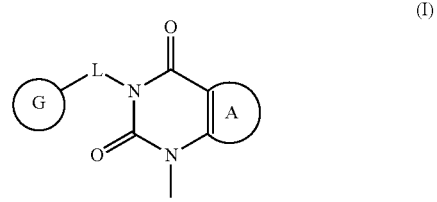

(I)

10 Claims, No Drawings

(56) References Cited

OTHER PUBLICATIONS

PCT International Search Report and Written Opinion dated Aug. 19, 2016 from corresponding Application No. PCT/CN2016/081102, 16 pages.

* cited by examiner

HYDROXYL PURINE COMPOUNDS AND USE THEREOF

FIELD OF INVENTION

The present invention relates to a series of hydroxyl purine compounds and use thereof as PDE2 or TNFα inhibitors, specifically relates to a compound represented by formula (I), a tautomer thereof or a pharmaceutically acceptable salt thereof.

BACKGROUND OF THE INVENTION

Phosphodiesterase (PDE) catalyzes the hydrolization of cyclic nucleotides cGMP and cAMP, and regulates various physiological responses by controlling the intramolecular concentrations of these two important second messengers. The abnormal intramolecular regulation of the cyclic nucleotides cGMP and cAMP is the cause of many diseases, there are already a number of drugs that can improve and treat diseases by inhibiting the PDE activity, such as PDE5 inhibitors for pulmonary hypertension and PDE4 inhibitors for arthritis caused by psoriasis. There are eleven categories of the currently known phosphodiesterase genes, each category can be expressed in several subtypes, with a total of more than 100 PDE subtypes. Different subtypes have different structure and different tissue distribution, the activity of cyclic nucleotides cGMP and cAMP and the physiological function of regulation are also very different.

PDE2 phosphodiesterase can catalyze the hydrolization of cyclic nucleotides cGMP and cAMP, meanwhile cAMP activity is regulated by cGMP, which plays a key role in intracellular balance of cGMP and cAMP function. PDE2 is widely expressed in human tissues, mainly distributed in the heart, central nervous system, liver, adrenal gland, endothelial cells, and platelets and so on. PDE2 is involved in regulating various physiological activities, such as learning, memory and cognitive processes of the maincenter, the maintenance of the basic rhythm of the heart, smooth muscle and endothelial cells, the maintenance of the permeability of endothelial cells, the regulation of inflammatory response. The knockout of the PDE2 gene will lead to the death of mouse embryos. Inhibition of PDE2 activity may be used for a variety of maincenter diseases, cardiovascular diseases, and controlling inflammation.

The non-selective PDE inhibitory activity of a variety of natural and synthetic purine compounds has been found very early, such as caffeine, theophylline, pentoxifylline and so on. Pentoxifylline (PDE2 activity) has been approved for clinical use in lower limbs claudication caused by peripheral vascular occlusion, the main functions of which are reducing blood viscosity, improving erythrocyte deformation, inhibiting platelet aggregation, etc. Novel high-selectivitive PDE2 inhibitors have also been reported to control the division of endothelial cells and the regeneration of blood vessels, and to improve maincenter disgnosia. However, overall, the development and application of novel selectivitive PDE2 inhibitors are still very limited, and the discovery and application of novel PDE2 inhibitors has broad prospects.

Tumor necrosis factor alpha (TNFα) is a cytokine with multiple biological activities, which has a significant impact on the occurrence, development and prognosis of multiple diseases. TNFα is mainly produced by monocytes and macrophage cells, which is involved in the immunomodulation and the cytokine network coordination. Under normal circumstances, TNFα plays an important role in immune defense and immune surveillance, but in some cases it has adverse effects. Research shows that the overexpression of TNFα can induce the expression of proinflammatory cytokines such as interleukin 1 (IL-1) and IL-6, increase the permeability of endothelial cells and up-regulate the expression of adhesion molecules and activate neutrophils and eosinophils, and induce bone synovial cells and cartilage cells to secrete acute phase substances and tissue-degrading enzymes and the like to promote the occurrence of inflammation. These pathologic reactions play a very important role in occurrence and development of many immune-mediated inflammatory diseases (IMID), such as rheumatoid arthritis (RA), psoriatic arthritis (PsA), ankylosing spondylitis (AS), inflammatory bowel disease (IBD), juvenile chronic arthritis (JCA) and vasculitis, etc. Studies have shown that TNFα is an ideal target for above multiple IMIDs, and the use of TNFα antagonists (TNFα inhibitors) to neutralize excess TNFα is an ideal way to effectively prevent chronic inflammatory diseases due to TNFα overexpression. PDE2 regulates the expression of TNFα according to the mechanism, therefor the level of TNFα can be controlled by regulating the PDE2 activity, so as to control the inflammation.

SUMMARY OF THE INVENTION

The present invention provides a compound of formula (I), a tautomer thereof or a pharmaceutically acceptable salt thereof,

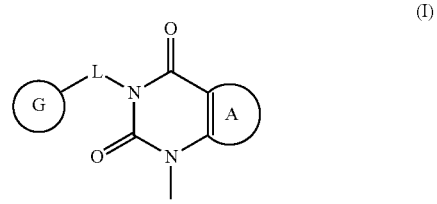

(I)

wherein,
the moiety

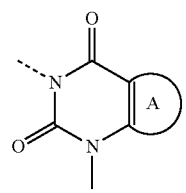

may be replaced by

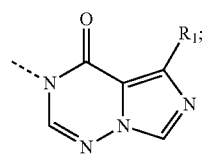

the ring A is selected from a 5- to 6-membered aryl or heteroaryl, each of which is optionally substituted by 1 or 2 $R_1$;

G is selected from a 5- to 9-membered aromatic ring or heteroaromatic ring,

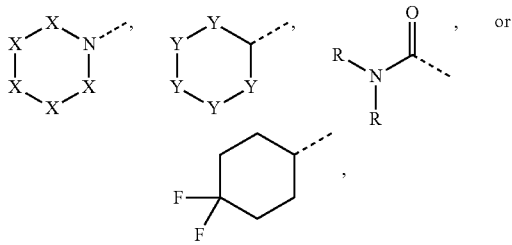

the 5- to 9-membered aromatic ring or heteroaromatic ring is optionally substituted by 1 to 3 and

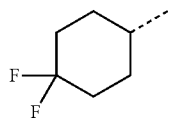

is optionally substituted by 1 to 3 R;

wherein one of X is selected from $C(R)_2$ or a single bond, the remaining X are selected from $C(R)_2$, $N(R)$, O, S, $C(=O)$, $S(=O)$, $S(=O)_2$, or —$C(=O)N(R)$—;

wherein one of Y is selected from $C(R)_2$ or a single bond, at least two of the other four Y are independently selected from a heteroatom or a heteroatomic group, the remaining Y is/are $C(R)_2$;

the "hetero-" refers to a heteroatom or a heteroatomic group, each of which is independently selected from $N(R)$, O, S, $C(=O)$, $S(=O)$, $S(=O)_2$, or —$C(=O)N(R)$—, the number of the heteroatom on each of the defined groups is independently selected from 1, 2 or 3;

L is

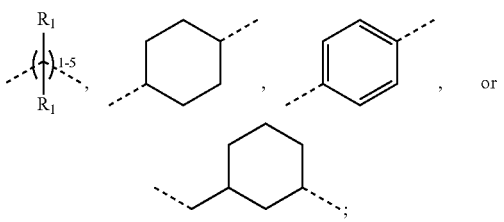

each of $R_1$ is independently selected from H, a halogen, OH, $NH_2$, and the group, optionally substituted by 1 to 3 $R_2$, consisting of: a $C_{1-6}$ alkyl or heteroalkyl, a 3- to 6-membered cycloalkyl or heterocycloalkyl, a $C_{1-6}$ alkyl or heteroalkyl substituted by a 3- to 6-membered cycloalkyl or heterocycloalkyl, and a $C_{1-6}$ alkyl or heteroalkyl substituted by a 5- to 6-membered aryl or heteroaryl;

$R_2$ is selected from a halogen, OH, $NH_2$, Me, $CF_3$, OMe, or $OCF_3$;

when L is

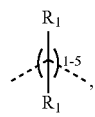

$R_1$ is optionally connected to G to form a spiro ring together;

R is selected from H, a halogen, $N(R')(R')$, or a $C_{1-3}$ alkyl or heteroalkyl optionally substituted by 1 to 3 R';

R' is selected from H, a halogen, $NH_2$, Me, $CF_3$, OMe, or $OCF_3$.

In an embodiment of the present invention, each of the aforesaid $R_1$ is independently selected from H, a halogen, OH, $NH_2$, and the group, optionally substituted by 1 to 3 $R_2$, consisting of: a $C_{1-4}$ alkyl or heteroalkyl, a 3- to 5-membered cycloalkyl or heterocycloalkyl, a $C_{1-3}$ alkyl or heteroalkyl substituted by a 3- to 6-membered cycloalkyl or heterocycloalkyl, and a $C_{1-3}$ alkyl or heteroalkyl substituted by a 5- to 6-membered aryl or heteroaryl.

In an embodiment of the present invention, each of the aforesaid $R_1$ is independently selected from H, a halogen, OH, $NH_2$, and the group, optionally substituted by 1 to 3 $R_2$, consisting of: Me,

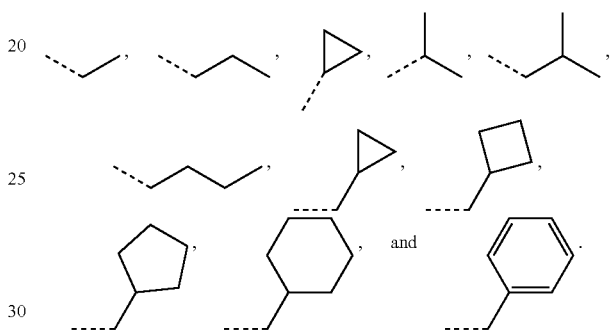

In an embodiment of the present invention, each of the aforesaid $R_1$ is selected from H, a halogen, OH, $NH_2$, Me,

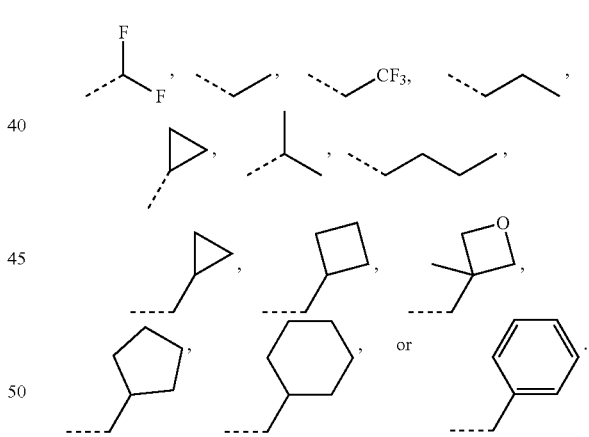

In an embodiment of the present invention, the aforesaid L is selected from

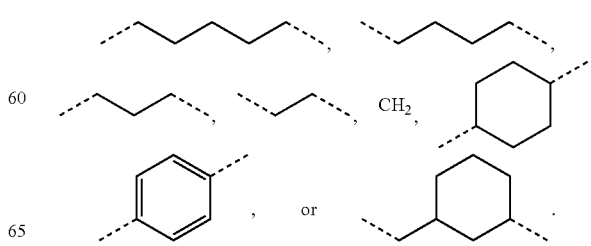

In an embodiment of the present invention, the aforesaid ring A is selected from the group, optionally substituted by 1 or 2 $R_1$, consisting of: pyrrolyl, pyrazolyl, imidazolyl, pyridyl, pyrazinyl, pyridazinyl, pyrimidinyl, and phenyl.

In an embodiment of the present invention, the aforesaid ring A is selected from the group, optionally substituted by 1 or 2 $R_1$, consisting of:

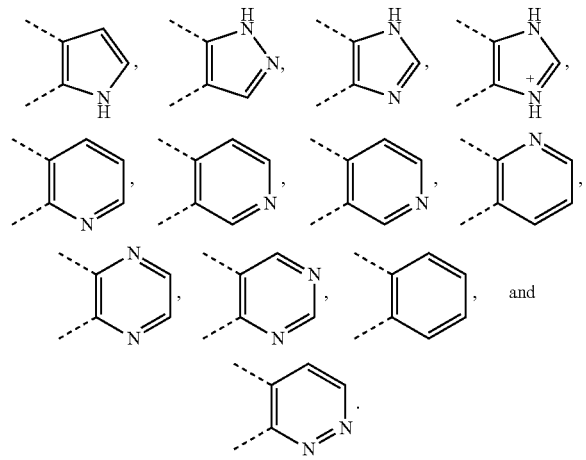

and

In an embodiment of the present invention, the aforesaid ring A is selected from

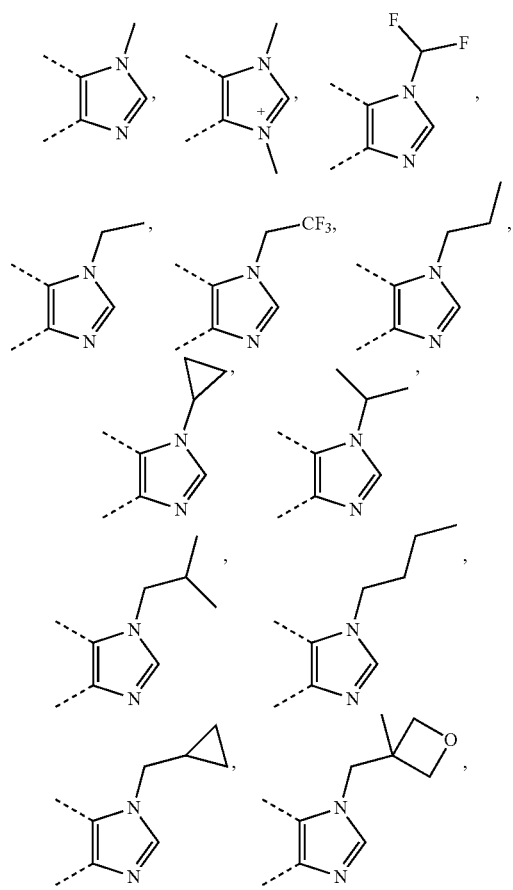

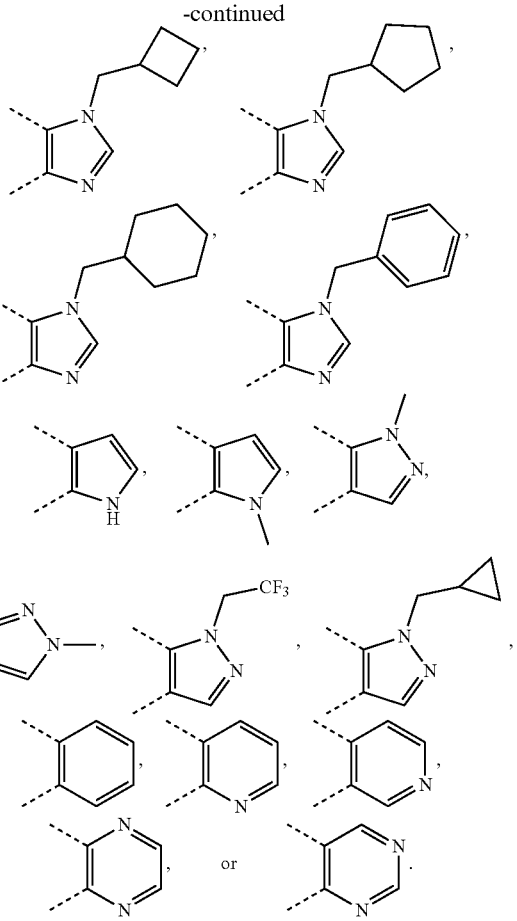

In an embodiment of the present invention, the aforesaid moiety

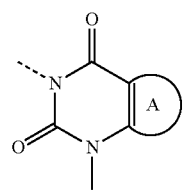

is selected from

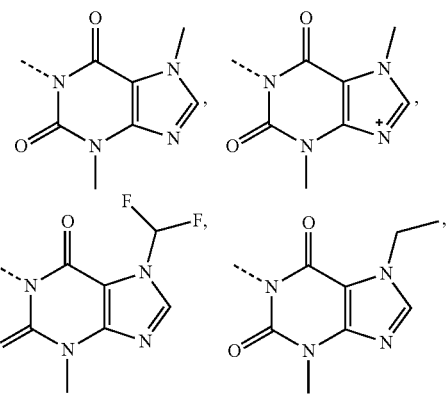

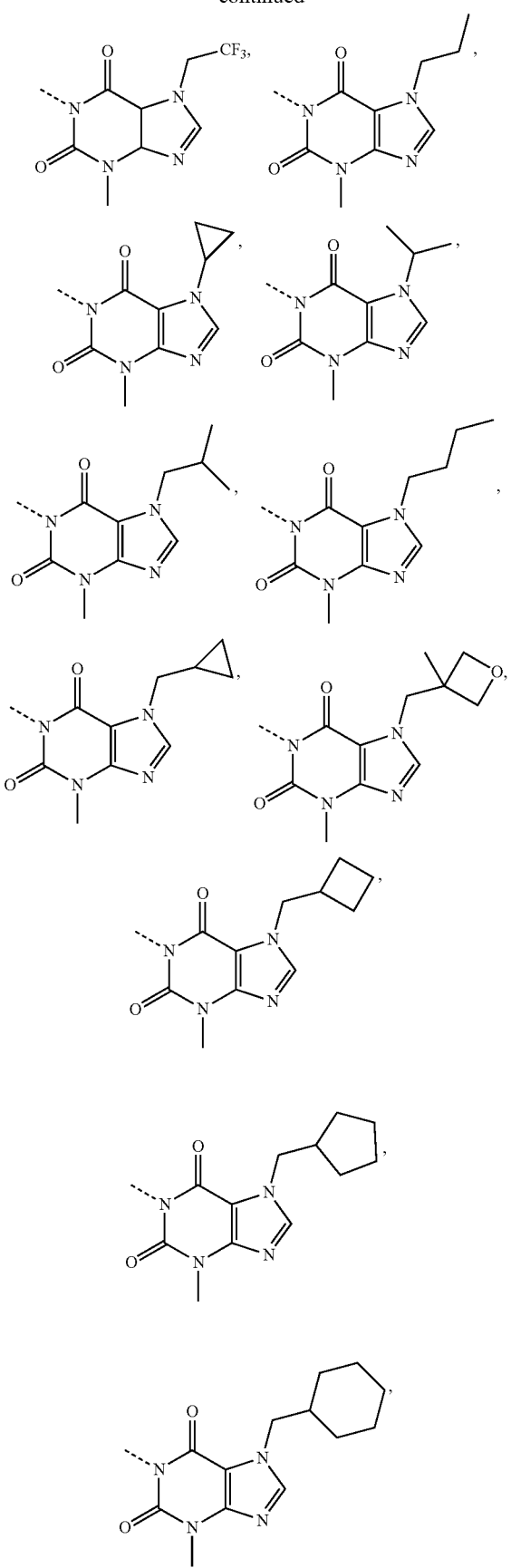
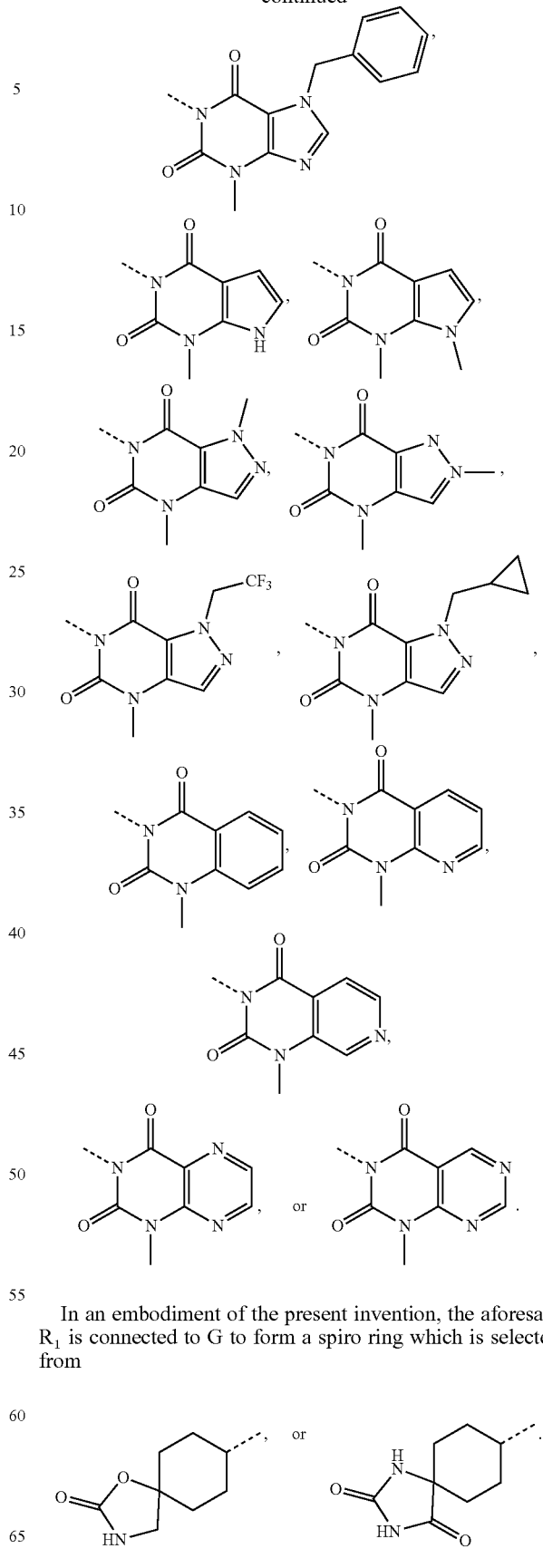
In an embodiment of the present invention, the aforesaid $R_1$ is connected to G to form a spiro ring which is selected from In an embodiment of the present invention, the aforesaid R is selected from H, Me,

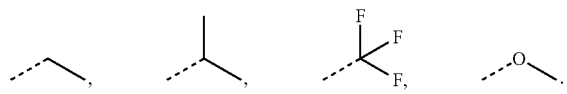

In an embodiment of the present invention, the aforesaid G is selected from

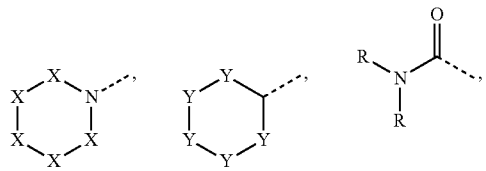

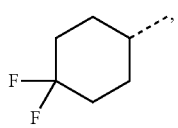

and the group, optionally substituted by 1 to 3 R, consisting of: imidazolyl, pyrazolyl, thiazolyl, isoxazolyl, oxazolyl, 1,3,4-oxadiazolyl, 2H-1,2,3-triazolyl, 1H-1,2,3-triazolyl, 2H-tetrazolyl, 1H-tetrazolyl, pyridyl, benzofuranyl, indolyl, benzothiazolyl, and 4,5,6,7-tetrahydro-2H-indazolyl.

In an embodiment of the present invention, the aforesaid G is selected from

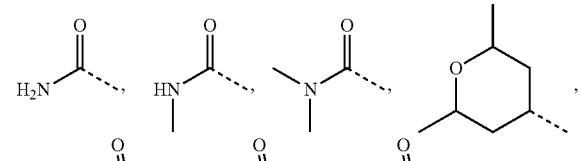

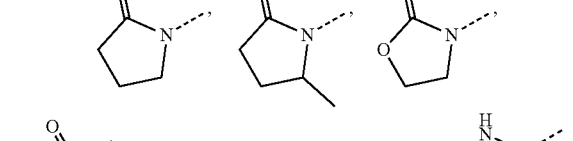

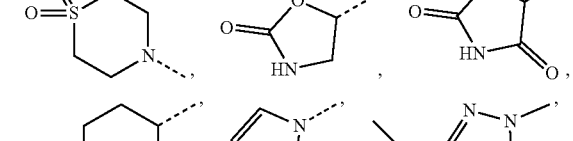

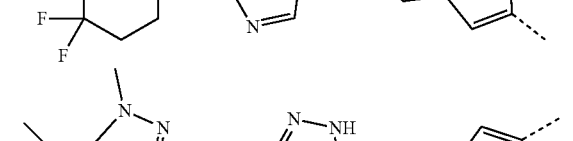

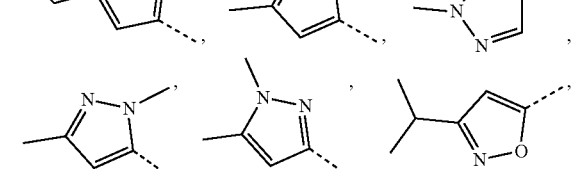

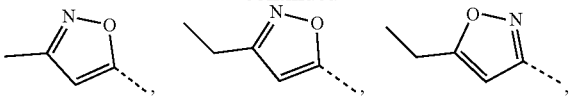

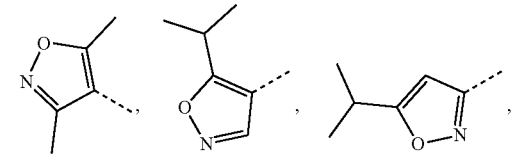

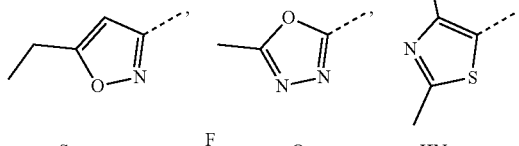

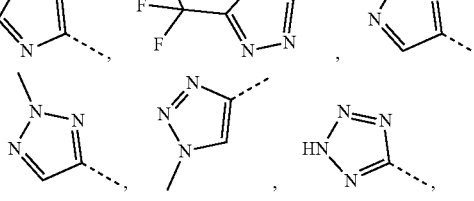

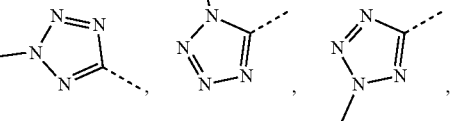

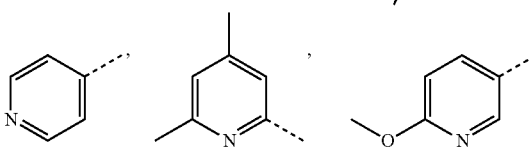

The compound of the present invention is selected from:

| Compound | Structure |
|---|---|
| 1 | 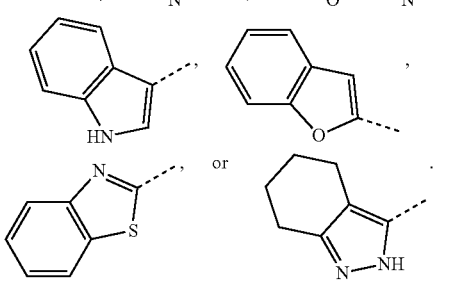 |

-continued
| Compound | Structure |
|---|---|
| 2 | 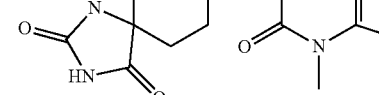 |
| 3 | 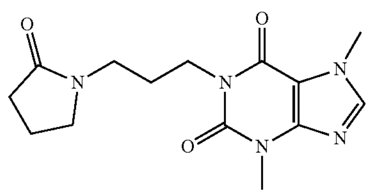 [SMILES: Cn1cnc2c1c(=O)n(CCCN1CCCC1=O)c(=O)n2C] |
| 4 | 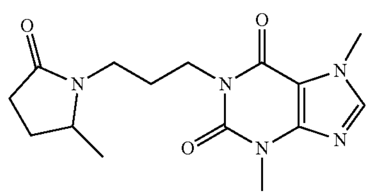 [SMILES: CC1CCC(=O)N1CCCn1c(=O)c2c(ncn2C)n(C)c1=O] |
| 5 | 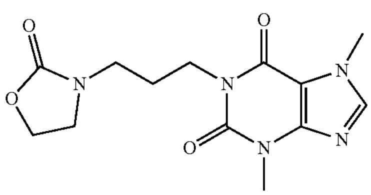 [SMILES: Cn1cnc2c1c(=O)n(CCCN1CCOC1=O)c(=O)n2C] |
| 6 | 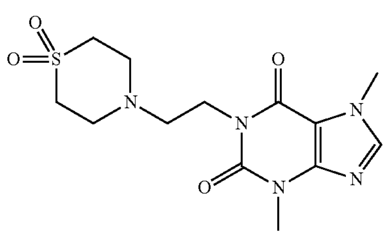 [SMILES: Cn1cnc2c1c(=O)n(CCN1CCS(=O)(=O)CC1)c(=O)n2C] |
| 7 | 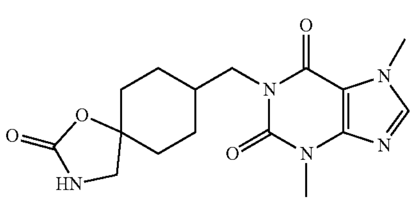 [SMILES: Cn1cnc2c1c(=O)n(CC1CCC3(CC1)CNC(=O)O3)c(=O)n2C] |
-continued
| Compound | Structure |
|---|---|
| 8 | 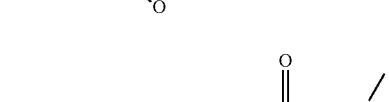 |
| 9 | 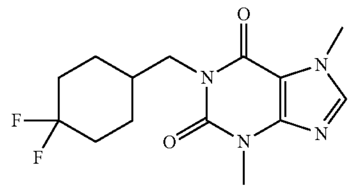 [SMILES: Cn1cnc2c1c(=O)n(CC1CCC(F)(F)CC1)c(=O)n2C] |
| 10 | 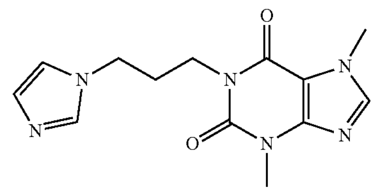 [SMILES: Cn1cnc2c1c(=O)n(CCCn1ccnc1)c(=O)n2C] |
| 11 | 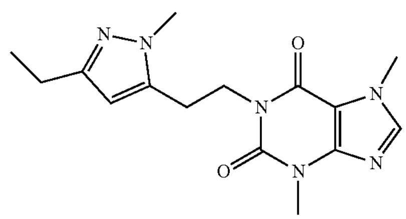 [SMILES: CCc1cc(CCn2c(=O)c3c(ncn3C)n(C)c2=O)n(C)n1] |
| 12 | 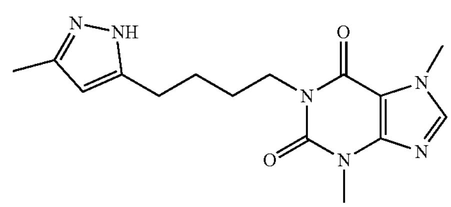 [SMILES: Cc1cc(CCCCn2c(=O)c3c(ncn3C)n(C)c2=O)[nH]n1] |
| 13 | 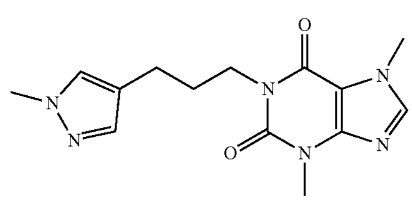 [SMILES: Cn1cc(CCCn2c(=O)c3c(ncn3C)n(C)c2=O)cn1] |

| Compound | Structure |
|---|---|
| 14 | 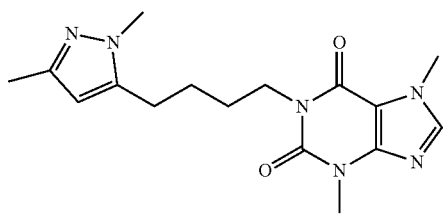 [SMILES: Cc1cc(CCCCn2c(=O)c3c(ncn3C)n(C)c2=O)n(C)n1] |
|  | 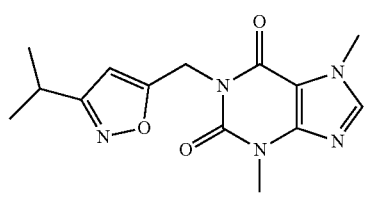 [SMILES: CC(C)c1cc(Cn2c(=O)c3c(ncn3C)n(C)c2=O)on1] |
| 15 | 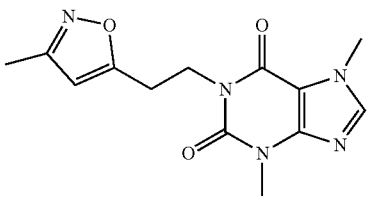 [SMILES: Cc1cc(CCn2c(=O)c3c(ncn3C)n(C)c2=O)on1] |
| 16 | 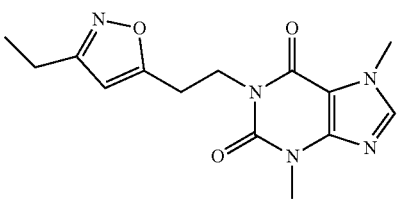 [SMILES: CCc1cc(CCn2c(=O)c3c(ncn3C)n(C)c2=O)on1] |
| 17 | |
|  | |
| 18 | 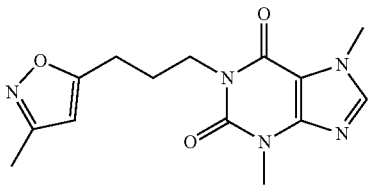 [SMILES: Cc1cc(CCCn2c(=O)c3c(ncn3C)n(C)c2=O)on1] |
| Compound | Structure |
|---|---|
| 19 | 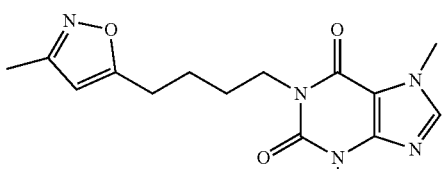 |
| 20 | 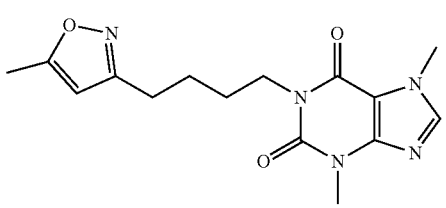 [SMILES: Cc1cc(CCCCn2c(=O)c3c(ncn3C)n(C)c2=O)no1] |
| 21 | 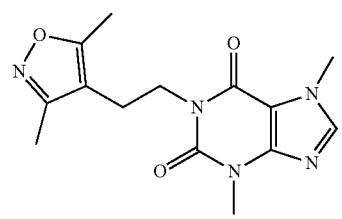 [SMILES: Cc1noc(C)c1CCn1c(=O)c2c(ncn2C)n(C)c1=O] |
| 22 | 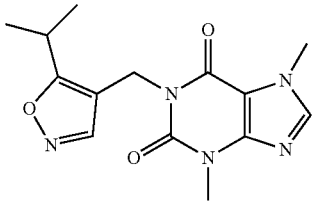 [SMILES: CC(C)c1oncc1Cn1c(=O)c2c(ncn2C)n(C)c1=O] |
| 23 | 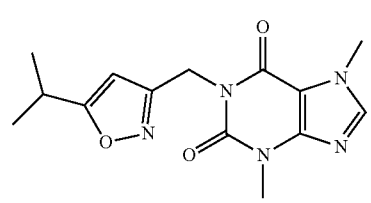 [SMILES: CC(C)c1cc(Cn2c(=O)c3c(ncn3C)n(C)c2=O)no1] |
| 24 | 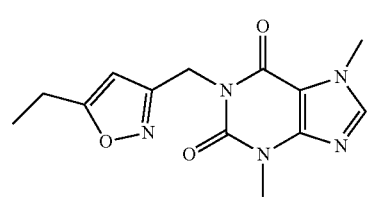 [SMILES: CCc1cc(Cn2c(=O)c3c(ncn3C)n(C)c2=O)no1] |
| 25 | 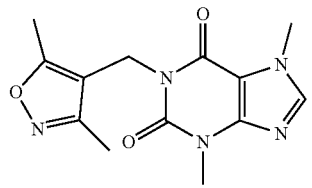 [SMILES: Cc1noc(C)c1Cn1c(=O)c2c(ncn2C)n(C)c1=O] |

-continued

| Compound | Structure |
|---|---|
| 26 | (structure) |
| 27 | (structure) |
| 28 | (structure) |
| 29 | (structure) |
| 30 | (structure) |
| 31 | (structure) |
| 32 | (structure) |

-continued

| Compound | Structure |
|---|---|
| 33 | (structure) |
| 34 | (structure) |
| 35 | (structure) |
| 36 | (structure) |
| 37 | (structure) |

| Compound | Structure |
|---|---|
| 38 | |
| 39 | |
| 40 | |
| 41 | |
| 42 | |
| 43 | 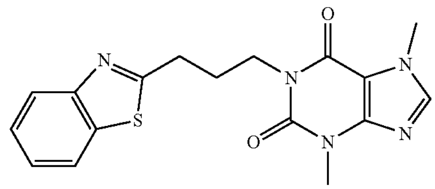 [SMILES: Cn1cnc2c1c(=O)n(CCCc1nc3ccccc3s1)c(=O)n2C] |
| 44 | 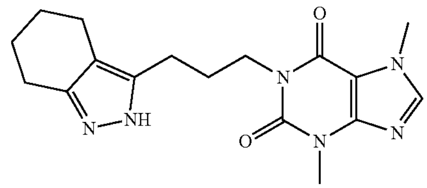 [SMILES: Cn1cnc2c1c(=O)n(CCCc1[nH]nc3c1CCCC3)c(=O)n2C] |
| 45 | 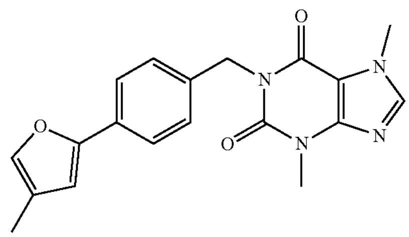 [SMILES: Cc1coc(-c2ccc(Cn3c(=O)c4c(ncn4C)n(C)c3=O)cc2)c1] |
| 46 | 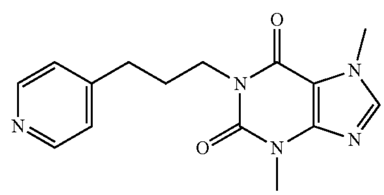 [SMILES: Cn1cnc2c1c(=O)n(CCCc1ccncc1)c(=O)n2C] |
| 47 | 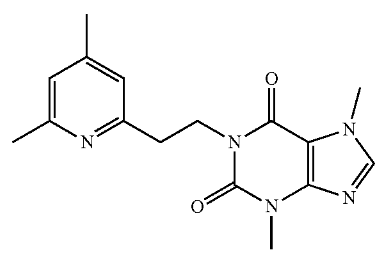 [SMILES: Cc1cc(C)nc(CCn2c(=O)c3c(ncn3C)n(C)c2=O)c1] |
| 48 | 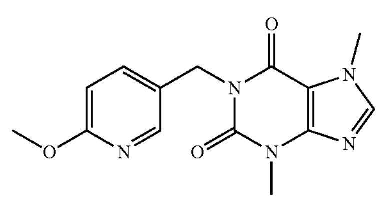 [SMILES: COc1ccc(Cn2c(=O)c3c(ncn3C)n(C)c2=O)cn1] |
| 49 | 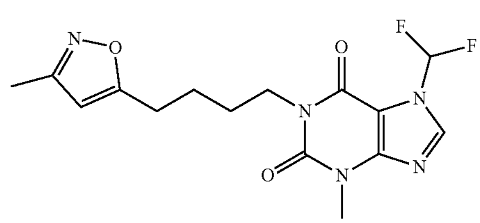 [SMILES: Cc1cc(CCCCn2c(=O)c3c(ncn3C(F)F)n(C)c2=O)on1] |

| Compound | Structure |
|---|---|
| 49 | 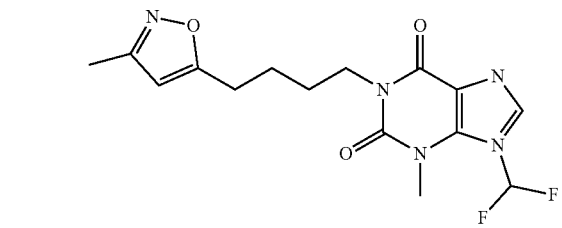 |
| 50 | 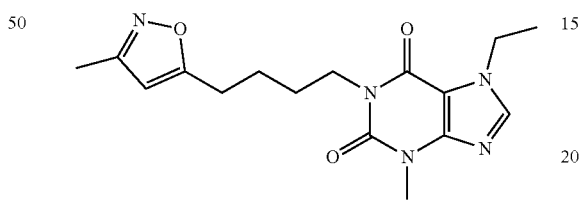 |
| 51 | 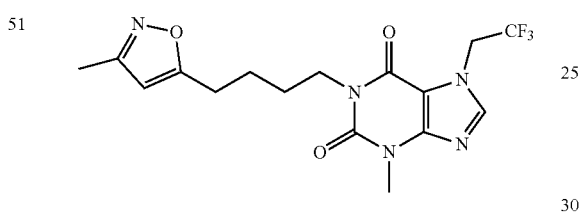 |
| 52 | 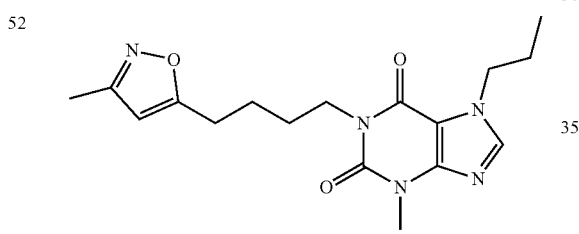 |
| 53 | 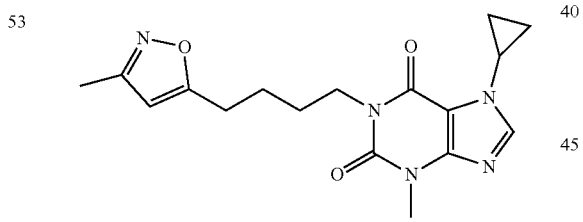 |
| 54 |  |
| 55 | 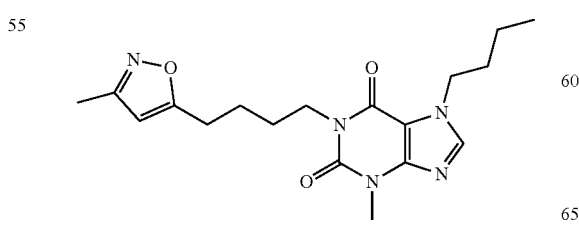 |
| Compound | Structure |
|---|---|
| 56 | 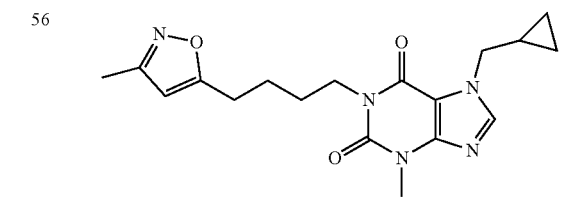 |
| 57 | 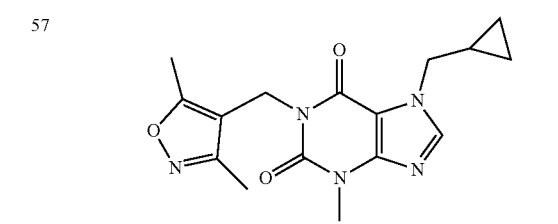 |
| 58 |  |
| 59 | 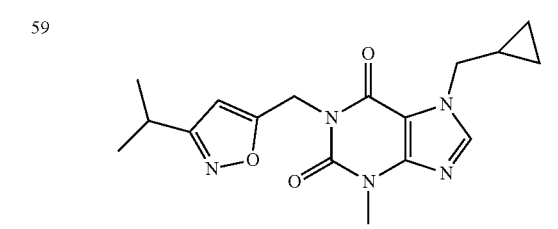 |
| 60 | 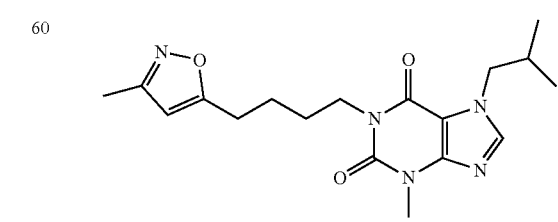 |
| 61 | 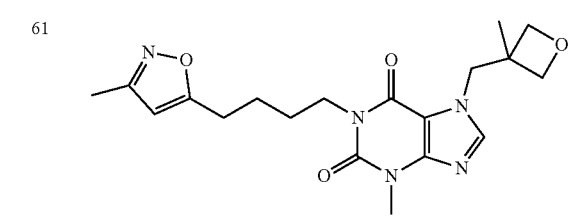 |
| 62 | 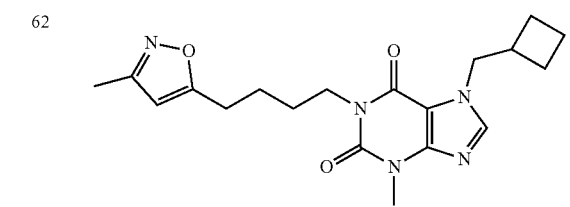 |

-continued

| Compound | Structure |
|---|---|
| 63 | (3-methylisoxazol-5-yl)propyl / 7-(cyclopentylmethyl) xanthine derivative |
| 64 | (3-methylisoxazol-5-yl)propyl / 7-(cyclohexylmethyl) xanthine derivative |
| 65 | (3-methylisoxazol-5-yl)propyl / 7-benzyl xanthine derivative |
| 66 | (3-methylisoxazol-5-yl)propyl pyrrolo[2,3-d]pyrimidine-2,4-dione, N-methyl, NH |
| 67 | (3-methylisoxazol-5-yl)propyl pyrrolo[2,3-d]pyrimidine-2,4-dione, N,N-dimethyl |
| 68 | (3-methylisoxazol-5-yl)propyl pyrazolo[3,4-d]pyrimidine-dione, 1,4-dimethyl |
| 69 | (3-methylisoxazol-5-yl)butyl pyrazolo[3,4-d]pyrimidine-dione, 2,4-dimethyl |

-continued

| Compound | Structure |
|---|---|
| 70 | (3-isopropylisoxazol-5-yl)methyl / 2,2,2-trifluoroethyl pyrazolo[3,4-d]pyrimidine-dione |
| 71 | (2,4-dimethylthiazol-5-yl)ethyl / 2,2,2-trifluoroethyl pyrazolo[3,4-d]pyrimidine-dione |
| 72 | benzofuran-2-yl butyl / 2,2,2-trifluoroethyl pyrazolo[3,4-d]pyrimidine-dione |
| 73 | indol-3-yl propyl / 2,2,2-trifluoroethyl pyrazolo[3,4-d]pyrimidine-dione |
| 74 | (3-methylisoxazol-5-yl)propyl / 2,2,2-trifluoroethyl pyrazolo[3,4-d]pyrimidine-dione |
| 75 | (3-methylisoxazol-5-yl)butyl / 2,2,2-trifluoroethyl pyrazolo[3,4-d]pyrimidine-dione |
| 76 | (3-isopropylisoxazol-5-yl)methyl / cyclopropylmethyl pyrazolo[3,4-d]pyrimidine-dione |

| Compound | Structure |
|---|---|
| 77 | 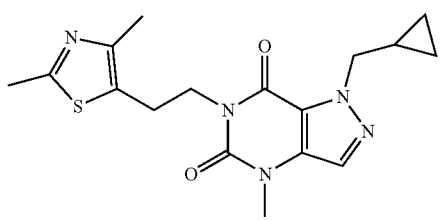 [SMILES: Cc1nc(C)c(CCn2c(=O)c3c(cnn3CC3CC3)n(C)c2=O)s1] |
| 78 | 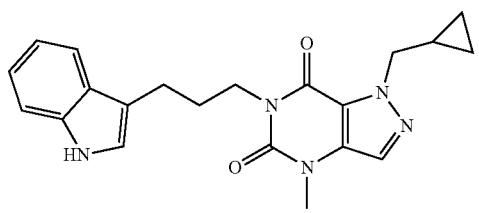 [SMILES: Cn1c(=O)n(CCCc2c[nH]c3ccccc23)c(=O)c2c1cnn2CC1CC1] |
| 79 | 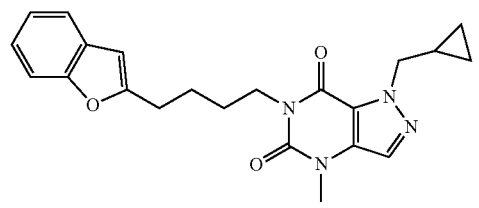 [SMILES: Cn1c(=O)n(CCCCc2cc3ccccc3o2)c(=O)c2c1cnn2CC1CC1] |
| 80 | 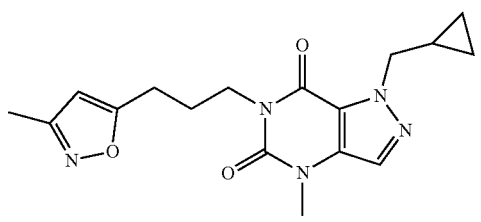 [SMILES: Cc1cc(CCCn2c(=O)c3c(cnn3CC3CC3)n(C)c2=O)on1] |
| 81 | 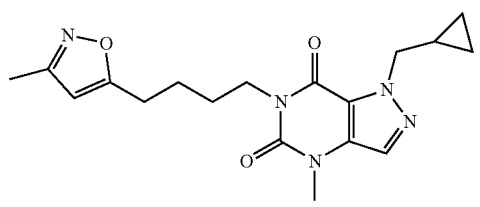 [SMILES: Cc1cc(CCCCn2c(=O)c3c(cnn3CC3CC3)n(C)c2=O)on1] |
| 82 |  |
| 83 | 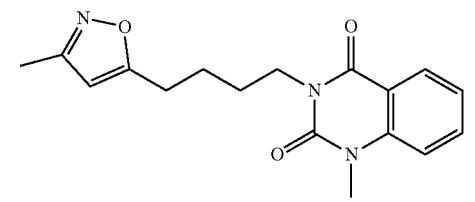 [SMILES: Cc1cc(CCCCn2c(=O)c3ccccc3n(C)c2=O)on1] |
| Compound | Structure |
|---|---|
| 84 | 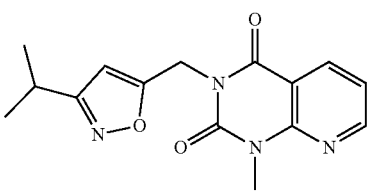 [SMILES: CC(C)c1cc(Cn2c(=O)c3cccnc3n(C)c2=O)on1] |
| 85 | 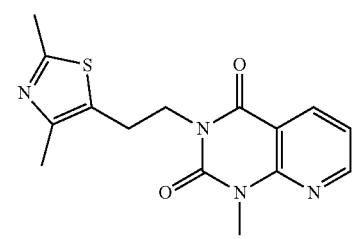 [SMILES: Cc1nc(C)c(CCn2c(=O)c3cccnc3n(C)c2=O)s1] |
| 86 | 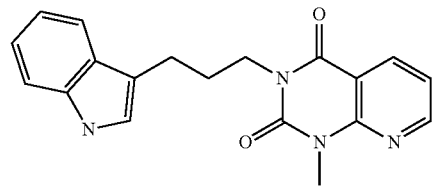 [SMILES: Cn1c(=O)n(CCCc2c[nH]c3ccccc23)c(=O)c2cccnc21] |
| 87 | 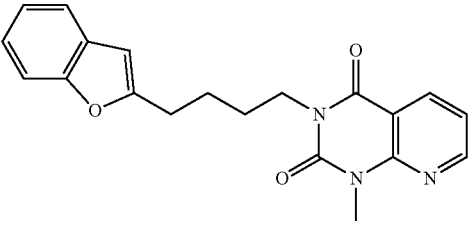 [SMILES: Cn1c(=O)n(CCCCc2cc3ccccc3o2)c(=O)c2cccnc21] |
| 88 | 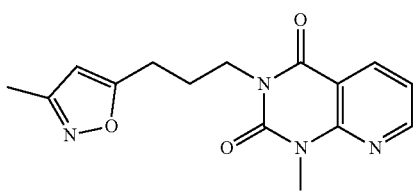 [SMILES: Cc1cc(CCCn2c(=O)c3cccnc3n(C)c2=O)on1] |
| 89 | 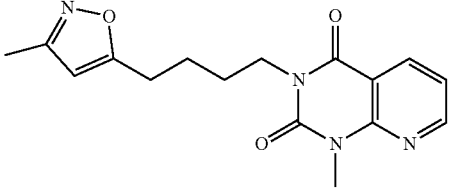 [SMILES: Cc1cc(CCCCn2c(=O)c3cccnc3n(C)c2=O)on1] |
| 90 | 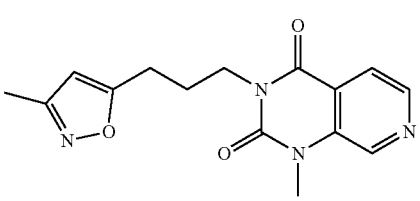 [SMILES: Cc1cc(CCCn2c(=O)c3ccncc3n(C)c2=O)on1] |

| Compound | Structure |
|---|---|
| 91 | 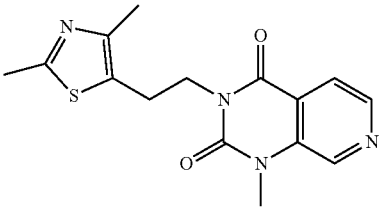 [SMILES: Cc1nc(C)c(CCn2c(=O)c3ccncc3n(C)c2=O)s1] |
| 92 | 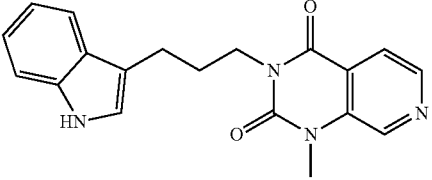 [SMILES: Cn1c(=O)n(CCCc2c[nH]c3ccccc23)c(=O)c2ccncc21] |
| 93 | 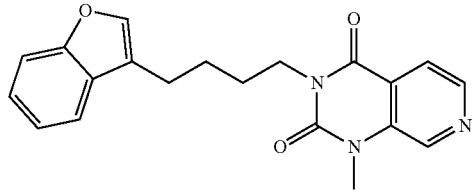 [SMILES: Cn1c(=O)n(CCCCc2coc3ccccc23)c(=O)c2ccncc21] |
| 94 | 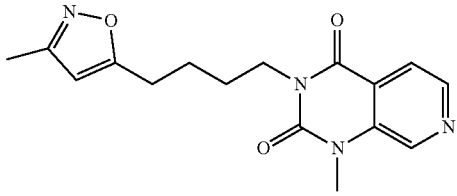 [SMILES: Cc1cc(CCCCn2c(=O)c3ccncc3n(C)c2=O)on1] |
| 95 | 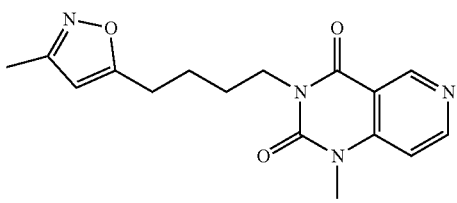 |
| 96 | 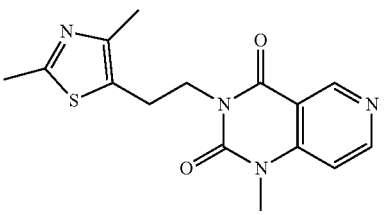 [SMILES: Cc1nc(C)c(CCn2c(=O)c3cnccc3n(C)c2=O)s1] |
| 97 | 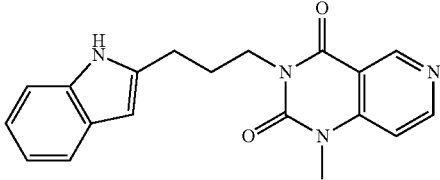 [SMILES: Cn1c(=O)n(CCCc2cc3ccccc3[nH]2)c(=O)c2cnccc21] |
| 98 | 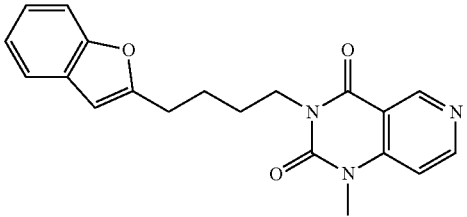 [SMILES: Cn1c(=O)n(CCCCc2cc3ccccc3o2)c(=O)c2cnccc21] |
| 99 | 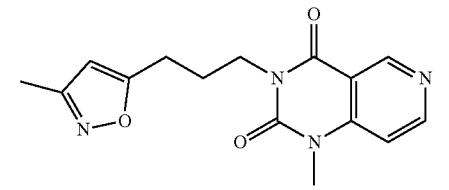 [SMILES: Cc1cc(CCCn2c(=O)c3cnccc3n(C)c2=O)on1] |
| 100 | 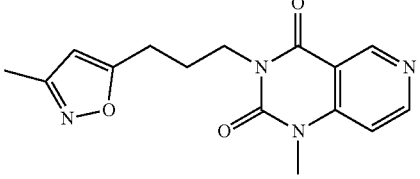 |
| 101 | 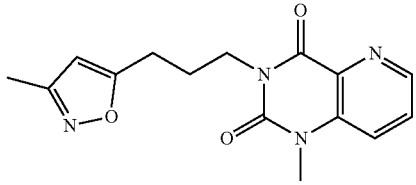 [SMILES: Cc1cc(CCCn2c(=O)c3ncccc3n(C)c2=O)on1] |
| 102 | 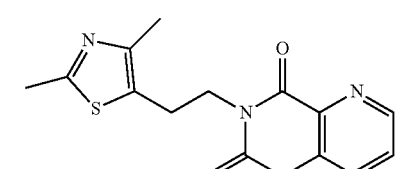 |
| 103 | 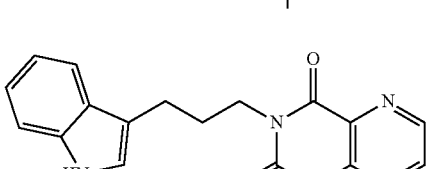 |
| 104 | 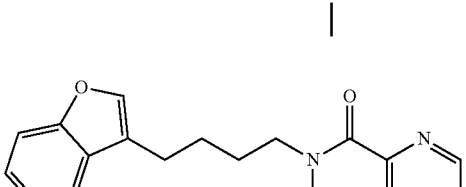 |

| Compound | Structure |
|---|---|
| 105 | 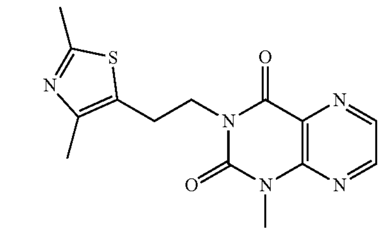 [SMILES: Cc1nc(C)c(CCn2c(=O)c3nccnc3n(C)c2=O)s1] |
| 106 | 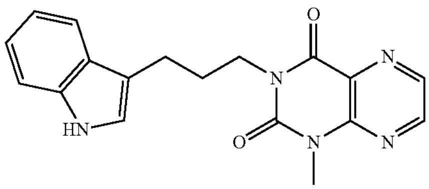 [SMILES: Cn1c(=O)n(CCCc2c[nH]c3ccccc23)c(=O)c2nccnc21] |
| 107 | 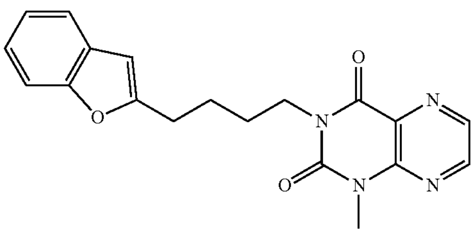 [SMILES: Cn1c(=O)n(CCCCc2cc3ccccc3o2)c(=O)c2nccnc21] |
| 108 | 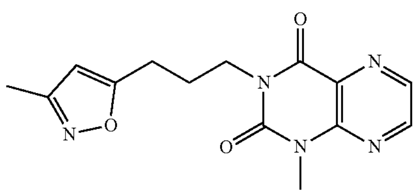 [SMILES: Cc1cc(CCCn2c(=O)c3nccnc3n(C)c2=O)on1] |
| 109 | 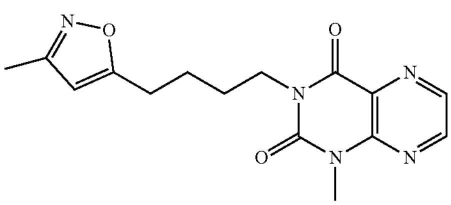 [SMILES: Cc1cc(CCCCn2c(=O)c3nccnc3n(C)c2=O)on1] |
| 110 | 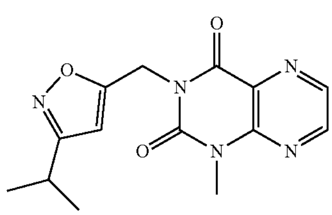 [SMILES: CC(C)c1cc(Cn2c(=O)c3nccnc3n(C)c2=O)on1] |
| 111 | 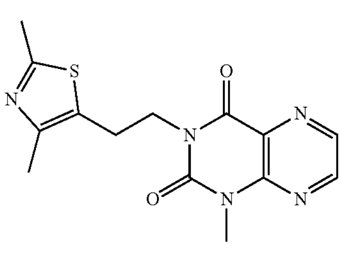 [SMILES: Cc1nc(C)c(CCn2c(=O)c3nccnc3n(C)c2=O)s1] |
| 112 | |
| 113 | |
| 114 | |
| 115 | |

The present invention also provides a use of the above compound, the tautomer thereof or the pharmaceutically acceptable salt thereof in the preparation of PDE2 inhibitors and TNFα inhibitors.

Related Definitions

Unless otherwise indicated, the following terms and phrases used herein are intended to have the following meanings. A specific term or phrase should not be considered uncertain or unclear in the absence of a specific definition while should be understood according to the ordinary meaning. When a trade name appears herein, it refers to the corresponding commodity or its active ingredient.

$C_{1-12}$ is selected from the group consisting of $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from the group consisting of $C_3$, $C_4$, $C_5$, $C_6$, $C_7$, $C_8$, $C_9$, $C_{10}$, $C_{11}$ and $C_{12}$.

Herein, the term "pharmaceutically acceptable" is aimed at those compounds, materials, compositions and/or dosage forms, which are within the scope of reliable medical judgment and applicable for use in contact with human and animal tissue but without too much toxicity, irritation, allergic reactions or other problems or complications, also meet the reasonable benefit/risk ratio.

The term "pharmaceutically acceptable salt" refers to the salt of the compound of the present invention, which is prepared by the compound with specific substituent discovered by the present invention and relatively non-toxic acid or base. When the compound of the present invention contains a relatively acidic functional group, a base-addition salt can be obtained by contacting the compound in a neutral form with sufficient amount of the base in a pure solution or suitable inert solvent. The pharmaceutically acceptable base-addition salt includes the salt of sodium, potassium, calcium, ammonium, organic ammonia or magnesium or the like. When the compound of the present invention contains a relatively basic functional group, an acid-addition salt can be obtained by contacting the compound in a neutral form with sufficient amount of the acid in a pure solution or suitable inert solvent. Examples of the pharmaceutically acceptable acid-addition salt include a salt of inorganic acid, the inorganic acid includes such as hydrochloric acid, hydrobromic acid, nitric acid, carbonic acid, bicarbonate, phosphoric acid, hydrogen phosphate, dihydrogen phosphate, sulfuric acid, hydrogen sulfate, hydriodic acid, phosphorous acid etc; and salt of organic acid, the organic acid includes such as acetic acid, propionic acid, isobutyric acid, maleic acid, malonic acid, benzoic acid, succinic acid, suberic acid, fumaric acid, lactic acid, mandelic acid, phthalic acid, phenylsulfonic acid, p-toluene sulfonic acid, citric acid, tartaric acid, methylsulfonic acid and the like; and also includes salt of amino acid (e.g. arginine etc.), and salt of organic acid such as glucuronic acid and the like (see Berge et al., "Pharmaceutical Salts", Journal of Pharmaceutical Science 66: 1-19 (1977)). Some specific compound of the present invention contains both alkaline and acidic functional groups so as to be transformed to be any basic-addition or acid-addition salt.

Preferably, the neutral form of a compound is regenerated by contacting a salt with a base or an acid in a conventional manner and then separating the parent compound. The difference between a parent form of a compound and the various salt forms lies in some physical properties, such as that the solubility in a polar solvent is different.

The "pharmaceutically acceptable salt" in the present invention belongs to the derivatives of the compound of the present invention, wherein, the parent compound is modified by salifying with an acid or an alkali. Examples of the pharmaceutically acceptable salt include but not limited to: an inorganic acid or organic acid salt of an alkali such as amine, an alkali metal or organic salt of acid radical such as carboxylic acid and so on. The pharmaceutically acceptable salt includes conventionally non-toxic salts or quaternary ammonium salts of the parent compound, such as a salt formed by a non-toxic inorganic acid or organic acid. The conventionally non-toxic salt includes but not limited to those salts derived from inorganic acids and organic acids, the inorganic acids or organic acids are selected from 2-acetoxybenzoic acid, 2-isethionic acid, acetic acid, ascorbic acid, phenylsulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydriodate, hydroxyl, hydroxynaphthoic, isethionic acid, lactic acid, lactose, dodecanesulfonic acid, maleic acid, malic acid, mandelic acid, methanesulfonic acid, nitric acid, oxalic acid, pamoic acid, pantothenic acid, phenylacetic acid, phosphoric acid, polygalacturonan, propionic acid, salicylic acid, stearic acid, folinate acid, succinic acid, aminosulfonic acid, sulfanilic acid, sulphuric acid, tannic acid, tartaric acid and p-toluene sulfonic acid.

The pharmaceutically acceptable salts of the present invention can be synthesized by conventional chemical methods from acid radical or basic group-containing parent compounds. In general, such salts are prepared by reacting the compounds in the form of a free acid or base with a stoichiometric amount of a suitable base or acid in water or an organic solvent or a mixture of both. In general, non-aqueous media such as ether, ethyl acetate, ethanol, isopropanol or acetonitrile are preferred.

In addition to the salt form, the compounds provided by the present invention are also in the form of prodrugs. The prodrugs of the compounds described herein are readily chemically altered under physiological conditions to be converted into the compounds of the present invention. In addition, the prodrugs may be converted to the compounds of the present invention by chemical or biochemical methods in vivo environment.

Some compounds of the present invention can exist in the form of non-solvate or solvate forms, including hydrate forms. In general, the solvate form is similar to the non-solvate form, both of which are included within the scope of the present invention.

Some compounds of the present invention can contain asymmetric carbon atoms (optical center) or double bonds. The racemic isomers, diastereomers, geometric isomers and single isomers are included within the scope of the present invention.

The diagrammatic representation of the racemic isomer, the ambiscalemic and scalemic or the enantiopure compound of the present invention is from Maehr, J. Chem. Ed. 1985, 62: 114-120. Unless otherwise indicated, the absolute configuration of a stereocenter is represented by the wedge and dashed lines. When the compound of the present invention contains a vinyl double bond or other geometric asymmetric center, unless otherwise specified, E, Z geometric isomers are included. Similarly, all tautomeric forms are included within the scope of the present invention.

The compound of the present invention may exist as a specific geometric or stereoisomeric isomer. The present invention envisages all of this class of compounds, including cis- and trans-isomers, (−)- and (+)-enantiomers, (R)- and -enantiomers, diastereomers, (D)-isomer, (L)-isomer, as well as racemic mixtures and other mixtures, such as enantiomers- or diastereoisomers-enriched mixtures, all of these mixtures are within the scope of the present invention. Other asymmetric carbon atoms may exist in substituents such as in an alkyl. All of these isomers and their mixtures are included within the scope of the present invention.

Optically active (R)- and -isomers, (D)- and (L)-isomers can be prepared by chiral synthesis or chiral reagents or other conventional techniques. If an enantiomer of a compound of the present invention is wanted, asymmetric synthesis or derivatization action of the chiral auxiliaries can be employed in preparation, in which the resulting diastereomer mixtures are isolated, and the auxiliary groups are cleaved to provide the pure desired enantiomer. Alternatively, when a molecule contains an alkaline functional group (such as amino) or an acidic functional groups (such as carboxyl), a salt of diastereomer is formed with an appropriate optical active acid or alkali, and then the pure enantiomer can be recycled after resolution on the salt of diastereomer by common methods which is known in the art. In addition, the separation of an enantiomer and a diastereomer is usually realized by the chromatographic method, the chromatography method employs a chiral stationary phase, and optionally combined with the chemical derivatization method (e.g. an amine generates a carbamate).

One or more atoms constituting the compounds of the present invention may comprise an unnatural proportion of atomic isotopes. For example, the compound can be labeled by a radioactive isotope, such as tritium ($^3$H), iodine-125 ($^{125}$I) or C-14 ($^{14}$C). All the variations in the isotopic composition of the compound disclosed in the present invention, whether radioactive or not, are included within the scope of the present invention.

The term "a pharmaceutically acceptable carrier" refers to any formulation or carrier medium which is capable of delivering effective amount of the active substance disclosed in the present invention, does not interfere with the biological activity of the active substance, and is with no toxic side-effects on host or patient, representative carrier includes water, oil, vegetables and minerals, cream base, lotion matrix, ointment matrix etc. The matrix comprises a suspension, a viscosity increaser, transdermal enhancers etc. Their formulation are well known to the person in cosmetic or topical drug art. For additional information about the carrier, reference can be made to Remington: The Science and Practice of Pharmacy, 21st Ed., Lippincott, Williams & Wilkins (2005), the content of which is incorporated into this article as reference.

The term "excipient" usually refers to a carrier, diluent and/or medium required for the preparation of an effective pharmaceutical composition.

In terms of drug or pharmacological active agent, the term "effective amount" or "therapeutically effective amount" refers to enough quantity of the drug or formulation that can achieve desired effects but is with no toxicity. For the oral formulation of the present invention, "an effective amount" of one active substance in the composition is the amount required to achieve desired effects in combination with another active substance in the composition. The determination of the effective amount varies from person to person, which depends on the age and the general situation of the recipient, also on the specific active substance. In one case, an appropriate effective amount can be determined by the person skilled in the art according to conventional tests.

The term "active ingredient", "therapeutic agent", "active substance" or "active agent" refers to a chemical entity, which can effectively treat disorder, illness or disease of a target subject.

The term "substituted" refers to one or more hydrogen atoms in a specific atom optionally substituted by a substituent, including a deuterium and a variant of hydrogen, as long as the valence state of the specific atom is normal and the compound obtained after substitution is stable. When the substituent is a ketone group (i.e. =O), it means that two hydrogen atoms are substituted. A substitution of ketone group does not occur in an aryl. The term "optionally substituted" means that it may be substituted or not be substituted, unless otherwise specified, the type and number of substituents can be arbitrary under the premise of stability available in chemistry.

When any parameter (e.g. R) shows an occurrence for more than one time in the composition or structure of the compound, the definition of each occurrence is independent. Therefore, for example, if a group is substituted by 0-2 of R, the group may optionally be substituted by at most two R, and R has an independent option in each case. In addition, the combination of substituents and/or their variants is allowed only if such a combination will lead to a stable compound.

When one of the parameters is selected from a single bond, it indicates that the two groups to which it is attached are directly connected, for example, when the L in A-L-Z represents a single bond, it indicates that the structure actually is A-Z.

When bonds of a substituent can be crossly connected to two atoms of a ring, the substituent can be bonded to arbitrary atoms in the ring. When the listed substituent does not specify through which atom it is connected to the compound included in the general structure formula but not specifically mentioned, the substituent can be bonded through any of its atoms. The combination of substituents and/or their variants is allowed only if such a combination will lead to a stable compound. For example, the moiety

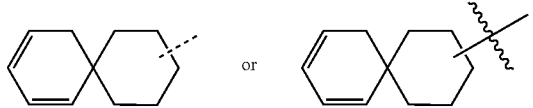

represents that the substituent can be connected on any atom in the cyclohexyl or cyclohexadiene.

Substituents of alkyl and heteroalkyl radicals are generally referred to as "alkyl substituents", and may be selected from, but not limited to, the group consisting of the following groups: —R', —OR', =O, =NR', =N—OR', —NR'R", —SR', halogen, —SiR'R"R'", OC(O)R', —C(O)R', —CO$_2$R', —CONR'R", —OC(O)NR'R", —NR"C(O)R', NR'C(O)NR"R'", —NR"C(O)$_2$R', —NR''''—C(NR'R"R''') =NR'''', NR''''C(NR'R")=NR''', —S(O)R', —S(O)$_2$R', —S(O)$_2$NR'R", NR"SO$_2$R', —CN, —NO$_2$, —N$_3$, —CH(Ph)$_2$ and fluoro (C$_1$-C$_4$)alkyl. The number of substituents is 0-(2m'+1), wherein m' is the total number of carbon atoms in such groups. R', R", R'", R'''' and R''''' are preferably independently selected from hydrogen, substituted or unsubstituted heteroalkyl, substituted or unsubstituted aryl (for example, aryl substituted by 1-3 halogen atoms), substituted or unsubstituted alkyl, alkoxy, thioalkoxy or aralkyl. When the compound of the present invention comprises more than one R groups, for example, each R group is independently selected, and the same applies to each of R', R", R'", R'''' and R'''''. When R' and R" are attached to the same nitrogen atom, they may bind to the nitrogen atom to form a 5-, 6- or 7-membered ring. For example, —NR'R" is intended to include but not limited to 1-pyrrolidinyl and 4-morpholinyl. According to the above discussion of substituents, it will be understood by those skilled in the art that the term "alkyl" is intended to include groups in which carbon atoms are bonded to non-hydrogen groups, such as haloalkyl (e.g., —CF$_3$, —CH$_2$CF$_3$) and acyl groups (e.g., —C(O)CH$_3$, —C(O)CF$_3$, —C(O)CH$_2$OCH$_3$, etc.).

Similar to the substituents of alkyl radicals, aryl and heteroaryl substituents are collectively referred to as "aryl substituents", which are selected from the group consisting of: —R', —OR', —NR'R", —SR', halogen, —SiR'R"R'", OC(O)R', —C(O)R', —CO$_2$R', —CONR'R", —OC(O)NR'R", —NR"C(O)R', —NR'C(O)NR"R'", —NR"C(O)2R', —NR''''—C(NR'R"R''')=NR'''', NR''''C(NR'R")=NR''', —S(O)R', —S(O)$_2$R', —S(O)$_2$NR'R", NR"SO$_2$R', —CN, —NO$_2$, —N$_3$, —CH(Ph)$_2$, fluoro (C$_1$-C$_4$)alkoxyl, and fluoro (C$_1$-C$_4$)alkyl. The number of substituents is from 0 to the total number of the open valence on aromatic ring; wherein, R', R", R", R'" and R'" are preferably independently selected from hydrogen, substituted or unsubstituted alkyl, substituted or unsubstituted heteroalkyl, substituted or unsubstituted aryl and substituted or unsubstituted heteroalyl. When the compound of the present invention comprises more than one R groups, for example, each R group is independently selected, and the same applies to each of R', R", R'", R'''' and R'''''.

The two substituents on adjacent atoms of an aryl or heteroalyl ring may be optionally substituted by substituents of the general formula -T-C(O)—(CRR')q-U—, wherein T and U are independently selected from —NR—, —O—, CRR'— or a single bond, and q is an integer from 0 to 3. Alternatively, the two substituents on adjacent atoms of an aryl or heteroaryl ring may be optionally substituted by substituents of the general formula -A(CH2)rB—, wherein A and B are independently selected from —CRR'—, —O—, —NR—, —S—, S(O)—, —S(O)$_2$—, —S(O)$_2$NR'— or a single bond, r is an integer from 1 to 4. Optionally, a single bond on the resulting new ring may be replaced by a double bond. As an alternative, the two substituents on adjacent atoms of an aryl or heteroaryl ring may be optionally substituted by substituents of the general formula -A(CH2)rB—, wherein s and d are independently selected from integers from 0 to 3, X is —O—, —NR', —S—, —S(O)—, —S(O)$_2$— or —S(O)$_2$NR'—. Substituents R, R', R" and R'" are preferably independently selected from hydrogen and substituted or unsubstituted ($C_1$-$C_6$) alkyl.

Unless otherwise specified, the term "halogenated" or "halogen" itself or as a part of another substituent refers to fluorine, chlorine, bromine or iodine atom. In addition, the term "halogenated alkyl" is intended to include monohalogenated alkyl and polyhalogenated alkyl. For example, the term "halogenated ($C_1$-$C_4$) alkyl" is intended to include but not limited to trifluoromethyl, 2,2,2-trifluoroethyl, 4-chlorobutyl and 3-bromopropyl, etc.

Examples of halogenated alkyl include but not limited to: trifluoromethyl, trichloromethyl, pentafluoroethyl, and pentachloroethyl. The "alkoxy" represents that the alkyl group with a specific number of carbon atoms is connected by an oxygen bridge. The $C_{1-6}$ alkoxy includes $C_1$, $C_2$, $C_3$, $C_4$, $C_5$ and $C_6$ alkoxy. Examples of alkoxy include but not limited to: methoxy, ethoxy, n-propoxy, iso-propoxy, n-butoxy, sec-butoxy, tert-butoxy, n-pentyloxy and S-pentyloxy. The "cycloalkyl" includes saturated cyclic group, such as cyclopropyl, cyclobutyl or cyclopentyl. The 3- to 7-membered cycloalkyl includes $C_3$, $C_4$, $C_5$, $C_6$ and $C_7$ cycloalkyl. The "alkenyl" includes linear or branched hydrocarbon chain, wherein any stable sites on the chain exist one or more C—C double bonds, such as vinyl and propenyl.

The term "halo" or "halogen" refers to fluorine, chlorine, bromine and iodine.

Unless otherwise specified, the term "hetero-" refers to a heteroatom or a heteroatomic group (i.e. a group containing a heteroatom), including atoms except carbon (C) and hydrogen (H) and groups containing these heteroatoms, such as including oxygen (O), nitrogen (N), sulfur, silicon (Si), germanium (Ge), aluminum (Al), boron (B), —O—, —S—, =O, =S, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)— or —S(=O) N(H)—.

Unless otherwise specified, the "ring" refers to substituted or unsubstituted cycloalkyl, heterocycloalkyl, cycloalkenyl, heterocycloalkenyl, cycloalkynyl, heterocycloalkynyl, aryl or heteroaryl. The ring includes a single ring, a joint ring, a spiro ring, a fused ring or a bridged ring. A number of the atoms in the ring is usually defined as the member of the ring, for example, "5- to 7-membered ring" is a ring looped with 5 to 7 atoms. Unless otherwise specified, the ring optionally contains 1-3 of heteroatoms. Therefore, "5- to 7-membered ring" includes, for example, phenyl pyridine and piperidinyl; on the other hand, the term "5- to 7-membered heterocycloalkyl ring" includes pyridyl and piperidinyl, but does not include phenyl. The term "ring" also includes a ring system containing at least one ring, wherein each ring is of the above definition independently.

Unless otherwise specified, the term "heterocycle" or "heterocyclyl" refers to a stable monocyclic, bicyclic or tricyclic ring containing a heteroatom and a heteroatomic group, they can be saturated, partially unsaturated or unsaturated (aromatic), they contain carbon atoms and 1, 2, 3 or 4 of heteroatom in the ring which is independently selected from the group consisting of N, O and S, wherein any of the heterocycle can be fused to a benzene ring to form a bicyclic ring. Nitrogen and sulfur atoms can be optionally oxidized (i.e., NO and S(O)$_p$). The nitrogen atom can be substituted or unsubstituted (i.e. N or NR, wherein R is H or other substituent that has been defined herein). The heterocycle can be attached to the side group of any heteroatom or carbon atom to form a stable structure. If the formed compound is stable, the heterocycle described herein can be substituted on its carbon or nitrogen atom. The nitrogen atom in the heterocycle is optionally quaternized. As a preferred embodiment of the present invention, when the total number of S and O atoms contained in the heterocycle exceeds 1, these heteroatoms are not adjacent to each other. As another preferred embodiment of the present invention, the total number of S and O atoms in the heterocycle is no more than 1. As used herein, the term "aromatic heterocyclic group" or "heteroaryl" refers to a stable 5-, 6-, 7-membered monocycle or bicycle or 7-, 8-, 9- or 10-membered bicyclic heteroaromatic ring, which contains carbon atoms and 1, 2, 3 or 4 of heteroatom in the ring which independently selected from the group consisting of N, O and S. The nitrogen atom can be substituted or unsubstituted (i.e. N or NR, wherein R is H or other substituent that has been defined herein). Nitrogen and sulfur atoms can be optionally oxidized (i.e., NO and S(O)$_p$). It is worth noting that, the total number of S and O atoms in the heteroaromatic ring is no more than 1. Bridged rings are also included in the definition of the heterocycle. When one or more atoms (i.e. C, O, N, or S) are connected to two nonadjacent carbon atoms or nitrogen atoms, a bridged ring is formed. The preferred bridged ring includes but not limited to: one carbon atom, two carbon atoms, one nitrogen atom, two nitrogen atoms and one carbon-nitrogen group. It is worth noting that, a bridge always converts a monocyclic ring into a tricyclic ring. In the bridged ring, the substituent in the ring can also locate on the bridge.

Examples of heterocyclic compound include but not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indoalkenyl, indolinyl, indolizinyl, indolyl, 3H-indolyl, isatino group, isobenzofuranyl, pyranyl, isoindolyl, isoindolinyl, isoindolyl, indolyl, isoquinolyl, isothiazolyl, isoxazolyl, methylenedioxyphenyl, morpholinyl, naphthyridinyl, octahydroisoquinolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, isoxazolyl, hydroxyl indolyl, pyrimidyl, phenanthridinyl, phenanthrolinyl, phenazine, phenothiazine, benzopurinyl, phenoxazinyl, phthalazinyl, piperazinyl, piperidyl, oxopiperidinyl, 4-oxopiperidinyl, piperonyl, pteridyl, purinyl, pyranyl, pyrazinyl, pyrazolidinyl, pyrazolinyl, pyrazolyl, pyridazinyl, oxazolopyridine, pyridinoimidazole, pyridinothiazole, pyridyl, pyrimidinyl, pyrrolidinyl, pyrrolinyl, 2H-pyrrolyl, pyrrolyl, pyrazolyl, quinazolinyl, quinolyl, 4H-quinolizinyl, quinoxalinyl, quinuclidinyl, tetrahydrofuryl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazyl, isothiazolylthienyl, thienyl, thiophenoxazolyl, thiophenothiazolyl, thiophenoimidazolyl, thienyl, triazinyl, 1,2,3-triazolyl, 1,2,4-triazolyl, 1,2,5-triazolyl, 1,3,4-triazolyl and xanthenyl. Fused ring and spiro ring compound are also included.

Unless otherwise specified, the term "hydrocarbonyl" or its specific concept (such as alkyl, alkenyl, alkynyl, phenyl, etc.) itself or as a part of another substituent represents a linear, branched or cyclic hydrocarbonyl or a combination thereof, which can be fully saturated, monocyclic or polycyclic unsaturated, can be monosubstituted, disubstituted or polysubstituted, can be univalent (such as methyl), bivalent (such as methylene) or multivalent (such as methenyl), can include bivalent or multivalent atomic groups, with a specified number of carbon atoms (such as that $C_1$-$C_{10}$ refers to having 1~10 carbon atoms). The term "hydrocarbonyl" includes but not limited to an aliphatic hydrocarbonyl and aromatic hydrocarbonyl, the aliphatic hydrocarbonyl includes linear and cyclic structures, specifically includes but not limited to alkyl, alkenyl and alkynyl, the aromatic hydrocarbonyl includes but not limited to 6- to 12-membered aromatic hydrocarbonyl such as benzene, naphthalene and the like. In some embodiments, the term "hydrocarbonyl" refers to linear or branched groups or their combination, which can be completely saturated, monocyclic or polycyclic unsaturated, can include divalent and polyvalent groups. Examples of saturated hydrocarbonyl include but not limited to homologues or isomers of methyl, ethyl, n-propyl, iso-propyl, n-butyl, tert-butyl, iso-butyl, sec-butyl, iso-butyl, cyclohexyl, (cyclohexyl) methyl, cyclopropyl methyl, and n-amyl, n-hexyl, n-heptyl, n-octyl and the like. Unsaturated alkyl has one or more double or triple bond, examples of which includes but not limited to vinyl, 2-propenyl, butenyl, crotyl, 2-isopentenyl, 2-butadienyl, 2,4-(pentadienyl), 3-(1, 4-pentadienyl), acetenyl, 1- and 3-propinyl, 3-butynyl, and more advanced homologues and isomers.

Unless otherwise specified, the term "heterohydrocarbonyl" or its specific concept (such as heteroalkyl, heteroalkenyl, heteroalkynyl, heteroaryl, etc.) itself or the term combining with another term refers to a stable linear, branched or cyclic hydrocarbonyl or their combinations, which consists of a certain number of carbon atoms and at least one heteroatom. In some embodiments, the term "heteroalkyl" itself or the term combining with another term refers to a stable linear, branched hydrocarbonyl or their combinations, which consists of a certain number of carbon atoms and at least one heteroatom. In a typical embodiment, the heteroatom is selected from the group consisting of B, O, N and S, in which the nitrogen and sulfur atoms are optionally oxidized, and the nitrogen atom is optionally quaternized. The heteroatoms or heteroatom radical can be located in any internal position of the heterohydrocarbonyl (including the position where hydrocarbonyl is attached to the rest part of the molecule). Examples include but not limited to —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. At most two heteroatoms are adjacent, such as —$CH_2$—NH—$OCH_3$.

The terms "alkoxy", "alkylamino" and "alkylthio" (or thioalkoxy) are the idiomatic expressions, which refers to the alkyl group is attached to the rest of molecule through an oxygen, an amino, or a sulfur atom, respectively.

Unless otherwise specified, the term "cyclohydrocarbonyl", "heterocyclohydrocarbonyl" or its hyponyms (such as aryl, heteroaryl, cycloalkyl, heterocycloalkyl, cycloalkenyl, heterocyclovinyl, cycloalkynyl, heterocycloalkynyl, etc.) itself or the term combining with other terms respectively refers to a cyclic "hydrocarbonyl", "heterohydrocarbonyl". In addition, in terms of heterohydrocarbonyl or heterocyclohydrocarbonyl (such as heteroalkyl, heterocycloalkyl), heteroatoms can occupy the position where the heterocyclic ring is attached to the rest part of the molecule. Examples of the cycloalkyl include but not limited to cyclopentyl, cyclohexyl, 1-cyclohexenyl, 3-cyclohexenyl, cycloheptyl etc. Unrestricted examples of the heterocyclyl include 1-(1,2,5, 6-tetrahydropyridinyl), 1-piperidyl, 2-piperidyl, 3-piperidyl, 4-morpholinyl, 3-morpholinyl, tetrahydrofuran-2-yl, tetrahydrofuranylindol-3-yl, tetrahydrothiophene-2-yl, tetrahydrothiophene-3-yl, 1-piperazinyl and 2-piperazinyl.

Unless otherwise specified, the term "aryl" refers to a polyunsaturated aromatic hydrocarbon substituent, which can be monosubstituted, disubstituted or multisubstituted, can be univalent, bivalent or multivalent. It can be monocyclic or polycyclic (preferably 1-3 rings; wherein at least one ring is aromatic). They fuse together or connect by a covalent linkage. The term "heteroaryl" refers to an aryl (or ring) containing 1-4 heteroatoms. In an exemplary embodiment, the heteroatom is selected from the group consisting of B, N, O, and S, in which the nitrogen and sulfur atoms are optionally oxidized, and the nitrogen atom is optionally quaternized. The heteroaryl group can be connected to the rest part of the molecule via a heteroatom. Unrestricted examples of an aryl or a heteroaryl include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzoimidazolyl, 5-indolyl, 1-isoquinolyl, 5-isoquinolyl, 2-quinoxalyl, 5-quinoxalyl, 3-quinolyl and 6-quinolyl. Any one of the substituents in the aryl and heteroaryl ring system is selected from the acceptable substituents described below.

For the sake of briefness, when used in combination with other terms (e.g. aryloxy, arylthio, aralkyl), the aryl includes the definition of aryl and heteroaryl ring defined above. Therefore, the term "aralkyl" is intended to include the groups that aryl attached to alkyl (e.g. benzyl, phenyl ethyl, pyridyl methyl), including those alkyls wherein carbon atoms (such as methylene) has been replaced by such as oxygen atoms, such as phenoxy methyl, 2-pyridyloxymethyl-3-(1-naphthoxy) propyl, etc.

The term "leaving group" refers to a functional group or atom which can be replaced by another functional group or atom through a substitution reaction (e.g., nucleophilic substitution reaction). For example, representative leaving groups include triflate; chlorine, bromine, iodine; sulfonate, such as mesylate, tosylate, p-bromobenzene sulfonate, p-tosylate etc.; acyloxy, such as acetoxy, trifluoroacetoxy and so on.

The term "protecting group" includes but not limited to "the protecting group of an amino", "the protecting group of a hydroxyl", or "the protecting group of a mercapto". The term "the protecting group of an amino" refers to a protecting group that is suitable for preventing side reactions occur at the nitrogen atom of an amino group. A representative protecting group of an amino includes but not limited to: formyl; acyl, such as alkanoyl (such as acetyl, trichloroacetyl or trifluoroacetyl); alkoxycarbonyl, such as tert-butoxycarbonyl (Boc); aryl methoxycarbonyl, such as benzyloxycarbonyl (Cbz) and 9-fluorenylmethoxycarbonyl (Fmoc); aryl methyl, such as benzyl (Bn), triphenyl methyl (Tr), 1,1-bis-(4'-methoxyphenyl) methyl; silyl, such as trimethylsilyl (TMS) and tert-butyldimethylsilyl (TBS) and etc. The term "the protecting group of a hydroxyl" refers to a protecting group that is suitable for preventing side reactions of a hydroxyl group. A representative protecting group of a hydroxyl includes but not limited to: alkyl, such as methyl, ethyl, and tert-butyl; acyl, such as alkanoyl (such as acetyl); aryl methyl, such as benzyl (Bn), p-methoxybenzyl (PMB), 9-fluorenylmethyl (Fm) and diphenylmethyl (diphenylmethyl, DPM); silyl, such as trimethylsilyl (TMS) and tert-butyldimethylsilyl (TBS) and etc.

The compound of the present invention can be prepared through many synthetic methods which are well-known to the person skilled in the art, including the specific embodiments listed below and their combination with other chemical synthetic methods and the equivalent alternative methods which are known to the person skilled in the art, the preferred embodiments include but not limited to the embodiments of the present invention.

The solvents used in the present invention are commercially available, which can be used without further purification. The present invention adopts the following abbreviations: aq represents water; HATU represents O-(7-azabenzotriazol-1-yl)-N,N,N',N'-tetramethyluronium hexafluorophosphate; EDC represents N-(3-dimethylaminopropyl)-N'-ethyl carbodiimide hydrochloride; m-CPBA represents m-chloroperbenzoic acid; eq represents equivalent, equal-quantitative; CDI represents carbonyl diimidazole; DCM represents dichloromethane; PE represents petroleum ether; DIAD represents diisopropyl azodicarboxylate; DMF represents N,N-dimethylformamide; DMSO represents dimethylsulfoxide; EtOAc represents ethyl acetate; EtOH represents ethanol; MeOH represents methanol; Cbz represents benzyloxycarbonyl, a protecting group of an amino; Boc represents tert-butoxycarbonyl, a protecting group of an amine; HOAc represents acetic acid; NaCNBH$_3$ represents sodium cyanoborohydride; r.t. represents room temperature; O/N represents overnight; THF represents tetrahydrofuran; Boc$_2$O represents di-tert-butyl dicarbonate; TFA represents trifluoroacetic acid; DIPEA represents diisopropylethylamine; SOCl$_2$ represents thionyl chloride; CS$_2$ represents carbon disulfide; TsOH represents p-toluene sulfonic acid; NFSI represents N-fluorobenzenesulfonimide; NCS represents N-chlorosuccinimide; n-Bu$_4$NF represents tetrabutylammonium fluoride; iPrOH represents 2-propanol; mp represents melting point; LDA represents lithium diisopropylamide; TMSCF$_3$ represents trifluoromethyltrimethylsilane; Ti(Oi-Pr)$_4$ represents tetraisopropyl titanate; MsCl represents methanesulfonyl chloride; DMAP represents N,N-dimethyl-4-aminopyridine; TEA represents triethylamine; BnBr represents benzyl bromide; DIEA represents diisopropylethylamine; BH$_3$DMS represents borane dimethyl sulfide; DMP represents Dess-Martin periodinane; TBAF represents tetrabutylammonium fluoride; HOBT represents 1-hydroxybenzotriazole; AIBN represents 2,2'-azo bisisobutyronitrile; NBS represents N-bromosuccinimide.

Compounds are named by manual work or software ChemDraw®, commercially available compounds are named in accordance with suppliers' catalogue.

DETAILED DESCRIPTION OF THE PREFERRED EMBODIMENT

Example 1

5-(3,7-Dimethyl-2,6-dioxo-2,3,6,7-tetrahydro-H-purin-1-yl)pentanamide

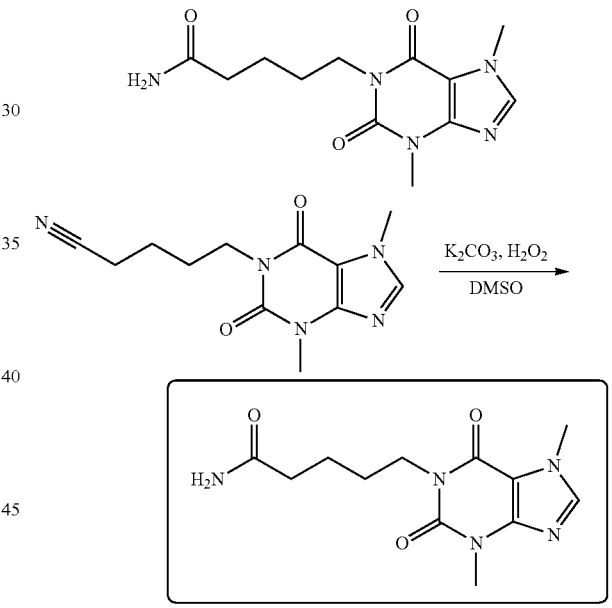

5-(3,7-Dimethyl-2,6-dioxo-2,3,6,7-tetrahydro-1H-purin-1-yl)pentanenitrile (300 mg, 1.03 mmol) was dissolved in dimethyl sulfoxide (5 mL), potassium carbonate (272 mg, 1.97 mmol) and hydrogen peroxide (0.5 mL) were added at 0° C., and the reaction was stirred at 20° C. for 12 hours. The reaction was quenched by addition of saturated aqueous sodium thiosulfate solution (20 mL), and extracted with ethyl acetate (20 mL×3). The organic phases were combined, dried over anhydrous sodium sulfate and filtered, and the filtrate was concentrated under reduced pressure. 5-(3,7-Dimethyl-2,6-dioxo-2,3,6,7-tetrahydro-1H-purin-1-yl) pentanamide (150 mg) was obtained after purification by preparative HPLC with a yield of 52%.

$^1$H NMR: (400 MHz, Methanol-d$_4$) δ 8.76 (s, 1H), 4.13 (s, 3H), 4.05-4.04 (m, 2H), 3.58 (s, 3H), 2.54-2.52 (m, 2H), 1.75-1.73 (m, 4H). MS-ESI calcd. [M+H]$^+$ 280, found 280.

Example 2

5-(3,7-Dimethyl-2,6-dioxo-2,3,6,7-tetrahydro-1H-purin-1-yl)-N,N-dimethylpentanamide 5-(3,7-Dimethyl-2,6-dioxo-2,3,6,7-tetrahydro-1H-purin-1-yl)-N-methylpentanamide

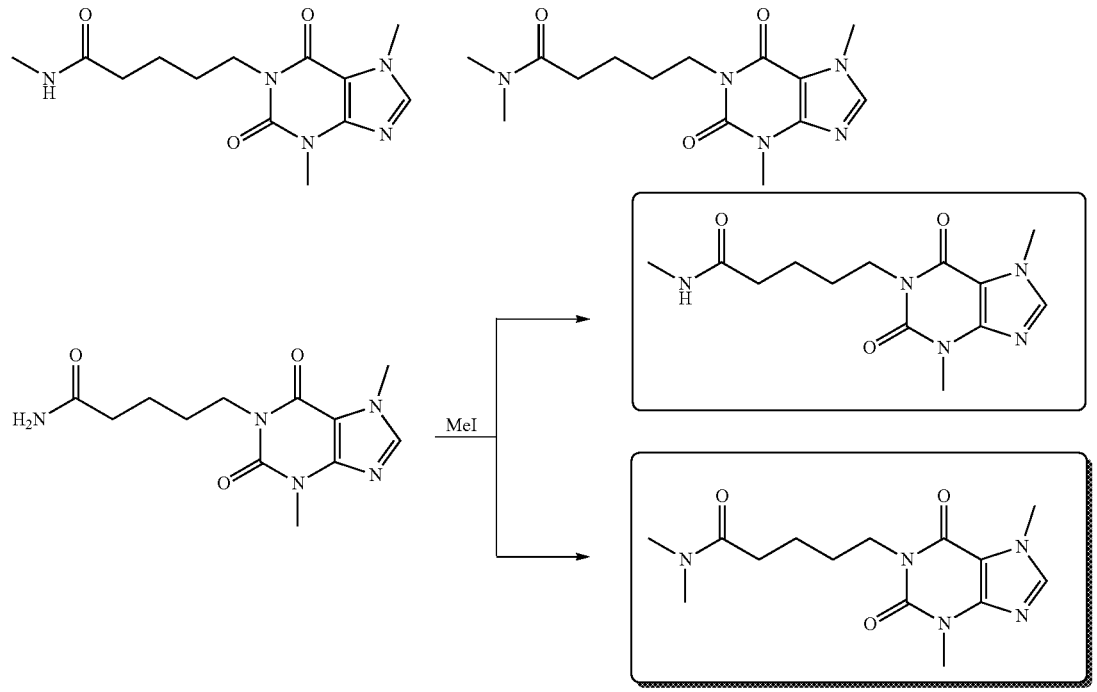

5-(3,7-dimethyl-2,6-dioxo-2,3,6,7-tetrahydro-1H-purin-1-yl)pentanenitrile (200 mg, 0.717 mmol) was dissolved in N,N-dimethylformamide (5 mL), sodium hydride (86.0 mg, 2.15 mmol) were added at 0° C., and the reaction was stirred at 0° C. for 0.5 hours. Methyl iodide (305 mg, 2.15 mmol) was added and the reaction was stirred at 25° C. for 12 hours. The reaction was quenched by addition of water (30 mL), and extracted with ethyl acetate (30 mL×3). The organic phase was dried over anhydrous sodium sulfate and filtered, and the filtrate was concentrated under reduced pressure. 5-(3,7-Dimethyl-2,6-dioxo-2,3,6,7-tetrahydro-1H-purin-1-yl)-N,N-dimethylpentanamide (product 1) (50.0 mg) was obtained after purification by preparative HPLC with a yield of 23%.

$^1$H NMR: (400 MHz, Methanol-$d_4$) δ 8.54 (s, 1H), 4.09 (s, 3H), 4.05-4.03 (m, 2H), 3.57 (s, 3H), 2.82 (s, 3H), 2.39-2.37 (m, 2H), 1.71-1.68 (m, 4H). MS-ESI calcd. [M+H]$^+$ 294, found 294.

Example 3

3,7-Dimethyl-1-(3-(2-oxopyrrolidin-1-yl)propyl)-1H-purine-2,6(3H,7H)-dione

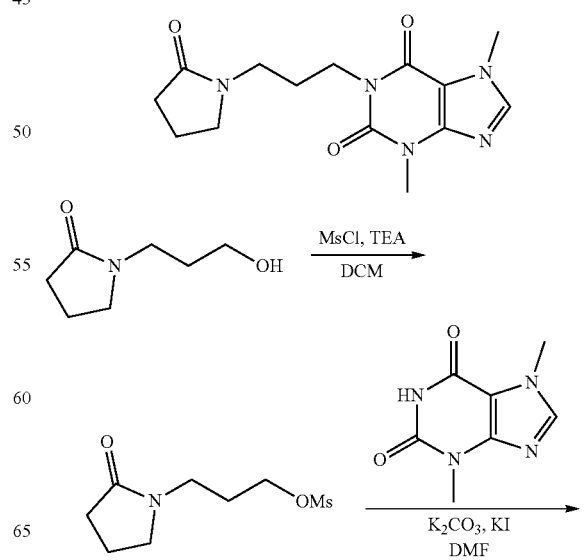

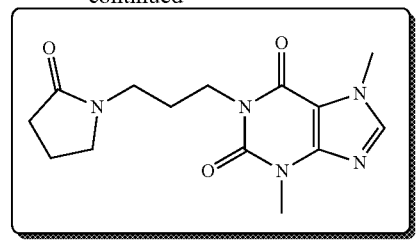

Step 1

3-(2-Oxopyrrolidinyl-1-yl)propyl methanesulfonic Acid 1-(3-Hydroxypropyl)-2-pyrrolidone (200 mg, 1.40 mmol) was dissolved in anhydrous dichloromethane (5 mL). Triethylamine (282 mg, 2.80 mmol) and methanesulfonyl chloride (192 mg, 1.68 mmol) were added at 0° C. under nitrogen atmosphere. The reaction solution was slowly warmed to room temperature, and stirred for 2 hours. Water (40 mL) was added to quench the reaction. The reaction solution was extracted with ethyl acetate (30 mL×2) and the organic phases were combined and washed with saturated sodium chloride solution (30 mL×2), dried over anhydrous sodium sulfate and filtered, and the filtrate was concentrated under reduced pressure to give 3-(2-oxypyrrolidinyl-1-yl)propyl methanesulfonic acid (164 mg, as a yellow oil), with a yield of 53%. MS-ESI calcd. [M+H]$^+$ 222, found 222.

Step 2

3,7-Dimethyl-1-(3-(2-oxopyrrolidin-1-yl)propyl)-1H-purine-2,6(3H, 7H)-dione 3-(2-oxopyrrolidin-1-yl) propyl methanesulfonic acid (164 mg, 0.740 mmol) was dissolved in anhydrous N,N-methylformamide (5 mL). Potassium carbonate (135 mg, 1.48 mmol), potassium iodide (13.0 mg, 0.0740 mmol) and 2,6-hydroxy-3,7-dimethylpurine (160 mg, 0.888 mmol) were added at room temperature under nitrogen atmosphere. The reaction was heated to 130° C. and stirred for 3 hours. Water (40 mL) was added to quench the reaction. The reaction solution was extracted with ethyl acetate (30 mL×2), and the organic phases were combined, washed with saturated sodium chloride solution (30 mL×2), dried over anhydrous sodium sulfate, filtered and the filtrate was concentrated under reduced pressure. 3,7-Dimethyl-1-(3-(2-oxopyrrolidinyl-1-yl)propyl)-1H-purine-2,6(3H,7H)-dione (20.0 mg) was obtained after purification by preparative HPLC, with a yield of 10%. MS-ESI calcd. [M+H]$^+$ 306, found 306.

Example 4

3,7-Dimethyl-1-(3-(2-oxooxazolidin-3-yl)propyl)-1H-purine-2,6(3H,7H)-dione

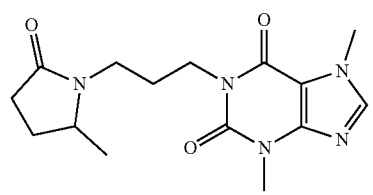
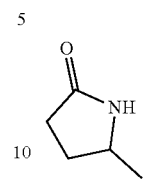
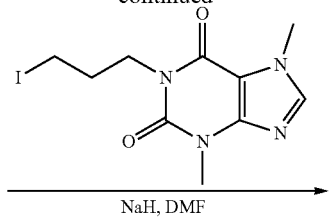
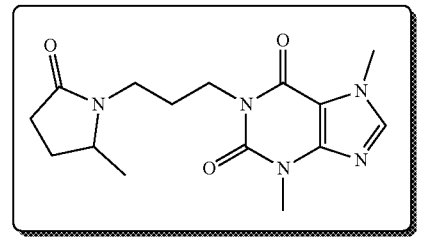

Sodium hydride (27.6 mg, 0.690 mmol) was added to a solution of oxazolidin-2-one (68.3 mg, 0.690 mmol) in N,N-dimethylformamide (1 mL) at 0° C. The reaction solution was stirred at 20° C. for 1 hour. A solution of 1-(3-iodopropyl)-3,7-dimethyl-1H-purine-2,6(3H,7H)-dione in N,N-dimethylformamide (1 mL) was added dropwise to the reaction solution at 0° C. The reaction solution was stirred at 20° C. for 12 hours and then cooled to 0° C. The reaction was quenched by addition of saturated ammonium chloride solution (10 mL) and extracted with ethyl acetate (10 mL×3). The organic phases were combined and washed with brine (10 mL×3), dried over anhydrous sodium sulfate and concentrated under reduced pressure. 3,7-Dimethyl-1-(3-(2-oxooxazolidin-3-yl)propyl)-1H-purine-2,6(3H,7H)-dione (50.0 mg) was obtained after purification by preparative HPLC with a yield of 27%.

$^1$H NMR: (400 MHz, Methanol-d$_4$) δ 7.85 (s, 1H), 3.95 (s, 3H), 3.92 (s, 3H), 3.61-3.57 (m, 2H), 3.09-3.08 (m, 2H), 2.40-2.34 (m, 2H), 2.28-2.25 (m, 2H), 1.87-1.78 (m, 2H), 1.63-1.60 (m, 1H), 1.24-1.23 (m, 3H). MS-ESI calcd. [M+H]$^+$ 320, found 320.

Example 5

3,7-Dimethyl-1-(3-(2-oxooxazolidin-3-yl)propyl)-1H-purine-2,6(3H,7H)-dione

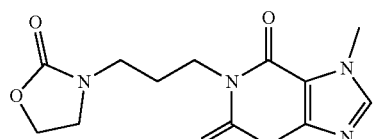
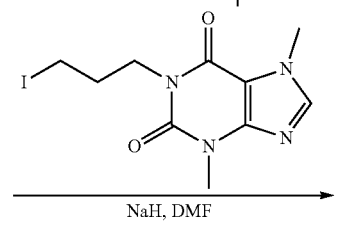

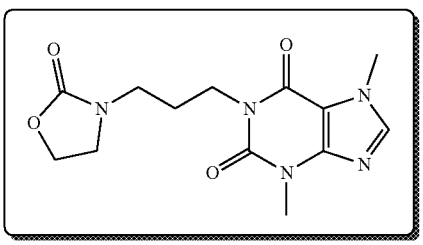

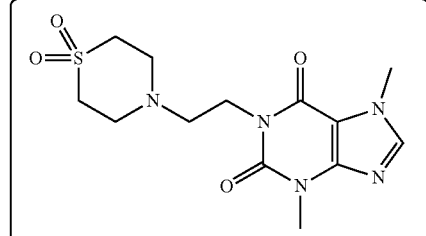

Sodium hydride (27.6 mg, 0.690 mmol) was added to a solution of oxazolidin-2-one (60.0 mg, 0.690 mmol) in N,N-dimethylformamide (1 mL) at 0° C. The reaction solution was stirred at 20° C. for 1 hour. A solution of 1-(3-iodopropyl)-3,7-dimethyl-1H-purine-2,6(3H,7H)-dione in N,N-dimethylformamide (1 mL) was added dropwise to the reaction solution at 0° C. The reaction solution was stirred at 20° C. for 12 hours and then cooled to 0° C. The reaction was quenched by addition of saturated ammonium chloride solution (100 mL) and extracted with ethyl acetate (30 mL×3). The organic phases were combined and washed with brine (30 mL×3), dried over anhydrous sodium sulfate and concentrated under reduced pressure. 3,7-Dimethyl-1-(3-(2-oxooxazolidin-3-yl)propyl)-1H-purine-2,6(3H,7H)-dione (50.0 mg) was obtained after purification by preparative HPLC with a yield of 28%.

$^1$H NMR: (400 MHz, Methanol-$d_4$) δ 7.85 (s, 1H), 4.38-4.34 (m, 2H), 3.99-3.97 (m, 2H), 3.95 (s, 3H), 3.69-3.65 (m, 2H), 3.49 (s, 3H), 3.32-3.29 (m, 2H), 2.21-1.88 (m, 2H). MS-ESI calcd. [M+H]$^+$ 308, found 308.

Example 6

1-(2-(1,1-Dioxide morpholinyl)ethyl)-3,7-dimethyl-1H-purine-2,6(3H,7H)-dione

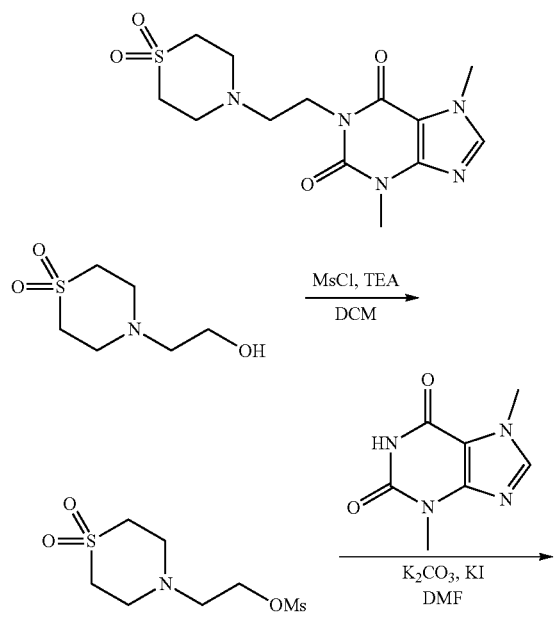

Step 1

2-(1,1-Dioxide morpholinyl)ethyl methanesulfonate 4-(2-Hydroxyethyl) thiomorpholine 1,1-dioxide (300 mg, 1.67 mmol) was dissolved in anhydrous dichloromethane (5 mL). Triethylamine (423 mg, 4.17 mmol) and methanesulfonyl chloride (228 mg, 2.01 mmol) were added at 0° C. under nitrogen atmosphere. The reaction solution was slowly allowed to warm to room temperature and stirred for 2 hours. Water (40 mL) was added to quench the reaction. The reaction solution was extracted with ethyl acetate and the organic phases were combined, and washed successively with water and saturated sodium chloride solution, dried over anhydrous sodium sulfate, filtered and the filtrate was concentrated under reduced pressure to give 2-(1,1-dioxide morpholinyl) ethyl methanesulfonate (230 mg, as a yellow oil), with a yield of 53%. MS-ESI calcd. [M+H]$^+$ 258, found 258.

Step 2

1-(2-(1,1-Dioxide morpholinyl)ethyl)-3,7-dimethyl-1H-purine-2,6(3H,7H)-dione 2-(1,1-dioxide morpholinyl)ethyl methanesulfonate (200 mg, 0.780 mmol) was dissolved in anhydrous N,N-dimethylformamide (5 mL). Potassium carbonate (215 mg, 1.56 mmol), potassium iodide (13.0 mg, 0.0780 mmol) and 3,7-dimethyl-1H-purine-2,6(3H,7H)-dione (168 mg, 0.936 mmol) were added at room temperature under nitrogen atmosphere. The reaction was heated to 130° C. and stirred for 3 hours. Water (40 mL) was added to quench the reaction. The reaction solution was extracted with ethyl acetate (30 mL×2), and the organic phases were combined, washed with saturated sodium chloride solution (30 mL×2), dried over anhydrous magnesium sulfate, filtered and the filtrate was concentrated under reduced pressure. 1-(2-(1,1-Dioxide morpholinyl)ethyl)-3,7-dimethyl-1H-purine-2,6(3H,7H)-dione (23.0 mg) was obtained after purification by preparative HPLC, with a yield of 10%.

$^1$H NMR: (400 MHz, Methanol-$d_4$) δ 7.86 (s, 1H), 3.97 (s, 3H), 3.53-3.35 (m, 4H), 3.34 (s, 3H), 2.40-2.36 (m, 2H), 2.11-2.04 (m, 4H), 1.92-1.88 (m, 2H). MS-ESI calcd. [M+H]$^+$ 342, found 342.

Example 7

3,7-Dimethyl-1-((2-oxo-1-oxa-3-azaspiro[4.5]decane-8-yl)methyl)-1H-purine-2,6(3H,7H)-dione

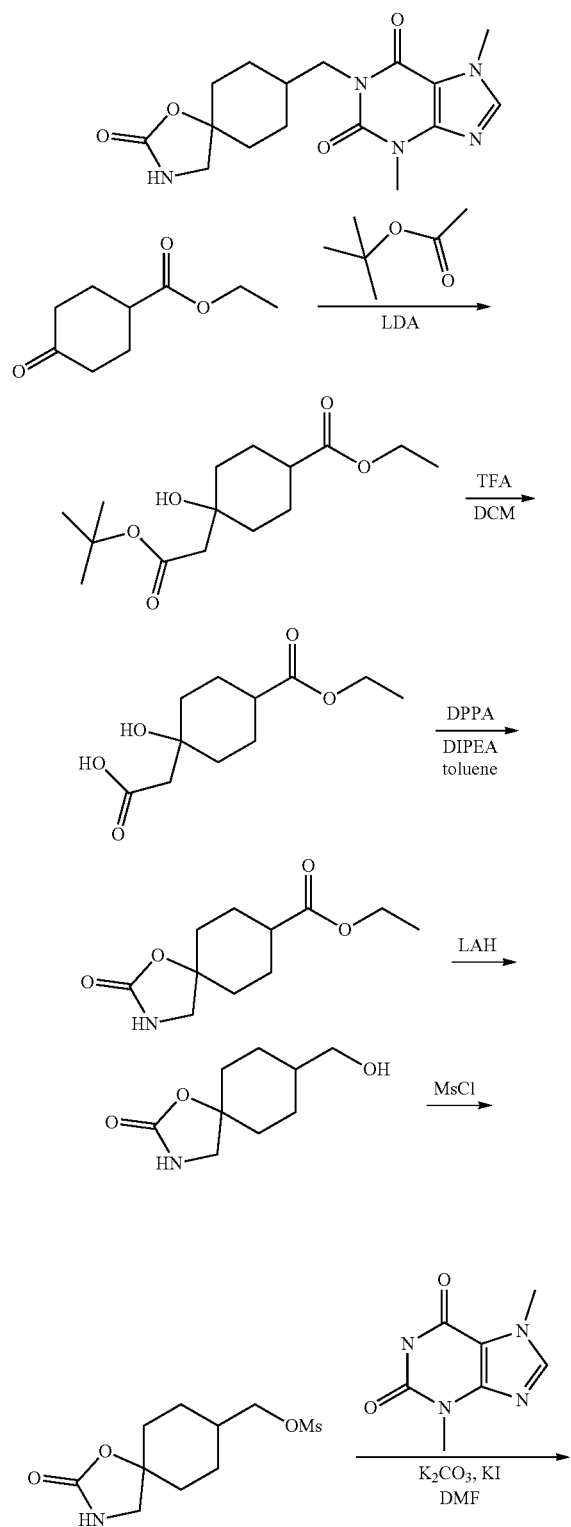

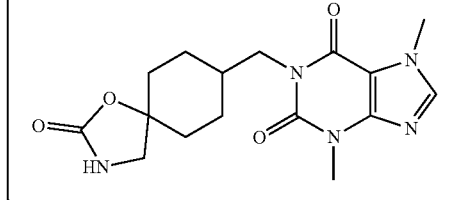

Step 1

Ethyl 4-(2-(tert-butoxy)-2-oxoethyl)-4-hydroxycyclohexyl carboxylate

Lithium diisopropylamide (1.6 mL, 2M n-hexane solution, 3.2 mmol) was added to anhydrous tetrahydrofuran (5 mL) at −65° C. under nitrogen atmosphere and stirred, followed by the dropwise addition of t-butyl acetate (0.360 g, 3.08 mmol). After completion of the dropwise addition, the reaction solution was added dropwise to a solution of cyclohexanone ethyl formate (0.500 g, 2.93 mmol) in tetrahydrofuran (5 mL) and the reaction was stirred at −65° C. for 1 hour. The reaction solution was diluted with 20 mL of ethyl acetate and washed with saturated aqueous ammonium chloride solution (20 mL) and brine (30 mL×2). The organic phases were combined, dried over anhydrous sodium sulfate, concentrated, and purified by silica gel column chromatography on silica gel (5:1 petroleum ether/ethyl acetate, $R_f$=0.5) to give ethyl 4-(2-(tert-butoxy)-2-oxoethyl)-4-hydroxycyclohexyl carboxylate (0.650 g, as a yellow oil) with a yield of 78%.

$^1$H NMR: (400 MHz, CDCl$_3$) δ 4.15-4.09 (m, 2H), 2.46-2.03 (m, 3H), 2.00-1.54 (m, 8H), 1.50 (s, 9H), 1.26-1.23 (m, 3H).

Step 2

Ethyl 2-(4-(ethoxycarbonyl)-1-hydroxycyclohexyl) carboxylate

Ethyl 4-(2-(tert-butoxy)-2-oxoethyl)-4-hydroxycyclohexyl carboxylate (25.2 g, 0.0880 mol) was dissolved in anhydrous dichloromethane (200 mL). Trifluoroacetic acid (100 g, 0.880 mol) was added dropwise to the solution at 0° C., and the reaction was continued at room temperature for 4 hours after stirring at 0° C. for 1 hour. Sodium carbonate solid was added to the reaction solution until the excess trifluoroacetic acid was completely consumed. The reaction solution was then washed with anhydrous dichloromethane (50 mL×3). The organic phases were combined, dried over anhydrous sodium sulfate, concentrated and purified by silica gel column chromatography (1:1 petroleum ether/ethyl acetate, $R_f$=0.2) to give ethyl 2-(4-(ethoxycarbonyl)-1-hydroxycyclohexyl) carboxylate (11.5 g, as a brown oil) with a yield of 56%.

$^1$H NMR: (400 MHz, DMSO-d$_6$) 4.06-3.97 (m, 2H), 2.39-2.25 (m, 3H), 1.78-1.35 (m, 8H), 1.13 (t, J=7.0 Hz, 3H).

Step 3

Ethyl-2-oxo-1-oxa-3-azaspiro[4.5]decane-8-carboxylate

Ethyl 2-(4-(ethoxycarbonyl)-1-hydroxycyclohexyl) carboxylate (500 mg, 2.17 mmol) was dissolved in toluene (30 mL), and N,N-diisopropylethylamine (560 mg, 4.34 mmol) and diphenylphosphoryl azide (718 mg, 2.60 mmol) were added at room temperature. The reaction was stirred under nitrogen atmosphere and heated to reflux overnight. The reaction was concentrated and purified by silica gel column chromatography (3:1 petroleum ether/ethyl acetate, $R_f$=0.6) to give ethyl-2-oxo-1-oxa-3-azaspiro[4.5]decane-8-carboxylate (380 mg, as a white solid) with a yield of 77%.

Step 4

8-(Hydroxymethyl)-1-oxa-3-azaspiro[4.5]decane-2-one

Lithium aluminum tetrahydrate (1.6 g, 4.62 mmol) was added to anhydrous tetrahydrofuran (20 mL) at 0° C., and ethyl-2-oxo-1-oxa-3-azaspiro[4,5]decane-8-carboxylate (1.00 g, 4.40 mmol in 5 mL of tetrahydrofuran) was slowly added dropwise. The reaction was stirred at 0° C. for 1 hour and then water (1 mL), 15% aqueous sodium hydroxide solution (3 mL) and water (1 mL) were added successively to quench the reaction. The mixture was stirred at 0° C. for 0.5 hour, and then filtered. The filtrate was concentrated under reduced pressure and purified by silica gel column chromatography (3:1 petroleum ether/ethyl acetate, $R_f$=0.3) to give 8-(hydroxymethyl)-3-oxaspiro[4.5]decane-2-one (550 mg, white solid) with a yield of 67%.

$^1$H NMR: (400 MHz, DMSO-$d_6$) 7.41 (br, 1H), 4.46-4.42 (m, 1H), 3.25-3.14 (m, 4H), 1.91-0.96 (m, 9H).

Step 5

(2-Oxo-1-oxa-3-azaspiro[4.5]decane-8-yl) methyl methanesulfonate 8-(Hydroxymethyl)-1-oxa-3-azaspiro[4.5]decane-2-one (200 mg, 1.08 mmol) was dissolved in anhydrous dichloromethane (20 mL), and N,N-diisopropylethylamine (0.81 mL, 1.62 mmol) was added, methanesulfonyl chloride (148 mg, 1.30 mmol) was added dropwise at 0° C. and the reaction was stirred at 0° C. for 0.5 h. The reaction solution was quenched by adding water (10 mL), and extracted with ethyl acetate (20 mL). The organic phase was dried over anhydrous sodium sulfate, concentrated and purified by silica gel column chromatography (3:1 petroleum ether/ethyl acetate, $R_f$=0.5) to give (2-oxo-1-oxa-3-azaspiro[4.5]decane-8-yl) methyl methanesulfonate (285 mg, as a white solid) with a yield of 100%. MS-ESI calcd. [M+H]$^+$ 264, found 264.

Step 6

3,7-Dimethyl-1-((2-oxo-1-oxa-3-azaspiro[4.5]decane-8-yl)methyl)-1H-purine-2,6(3H,7H)-dione 3,7-Dimethyl-1-(2-oxo-1-oxa-3-azaspiro[4.5]decane-8-yl)methyl methanesulfonate (285 mg, 1.08 mmol) was dissolved in N,N-dimethylformamide (5 mL), and then potassium carbonate (300 mg, 2.16 mmol), potassium iodide (18.0 mg, 0.100 mmol) and 3,7-dimethyl-1H-purine-2,6(3H,7H)-dione (205 mg, 1.13 mmol) were added. The reaction was heated to 120° C. to react for 2 hours. The reaction solution was diluted with ethyl acetate (20 mL), washed with brine (20 mL×2), dried over anhydrous sodium sulfate, concentrated and purified by preparative high performance liquid chromatography (HPLC) to give 3,7-dimethyl-(5-oxo-1-oxa-3-azaspiro[4.5]decane-8-yl)methyl)-1H-purine-2,6(3H,7H)-dione (50.0 mg) with a yield of 13%.

$^1$H NMR: (400 MHz, Methanol-$d_4$) 7.85 (s, 1H), 4.10-3.87 (m, 5H), 3.52-3.04 (m, 5H), 2.00-1.19 (m, 9H). MS-ESI calcd. [M+H]$^+$ 348, found 348.

Example 8

1-((2,4-Dioxo-1,3-diazaspiro[4.5]decane-8-yl)methyl)-3,7-dimethyl-1H-purine-2,6(3H,7H)-dione

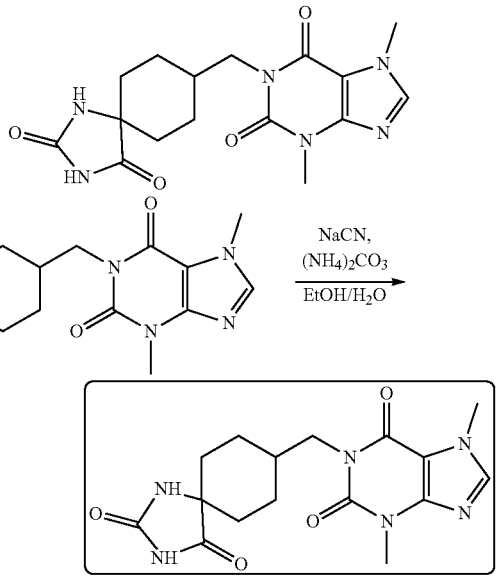

3,7-Dimethyl-1-((4-oxocyclohexyl)methyl)-1H-purine-2,6(3H,7H)-dione (100 mg, 0.340 mmol) and ammonium carbonate (80.0 mg, 0.750 mmol) were dissolved in ethanol/water (1 mL/1 mL), and sodium cyanide (35.0 mg, 0.720 mmol) in water (0.4 mL) was slowly added at room temperature. The reaction solution was heated to 50° C. for 16 hours, cooled to room temperature and quenched by the addition of saturated sodium carbonate solution (20 mL). The reaction solution was extracted with ethyl acetate (30 mL×2), and the organic phase was dried over anhydrous sodium sulfate, filtered, and the filtrate was concentrated under reduced pressure and purified by preparative HPLC to give the product 1-((2,4-dioxo-1,3-diazaspiro[4.5]decane-8-yl)methyl)-3,7-dimethyl-1H-purine-2,6(3H,7H)-dione (12.0 mg) with a yield of 10%.

$^1$H NMR: (400 MHz, Methanol-$d_4$) δ7.87 (s, 1H), 3.98 (s, 3H), 3.92 (d, J=7.0 Hz, 2H), 3.54 (s, 3H), 2.01-1.95 (m, 1H), 1.90-1.86 (m, 2H), 1.79-1.64 (m, 6H). MS-ESI calcd. [M+H]$^+$361, found 361.

Example 9

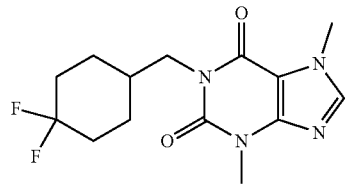

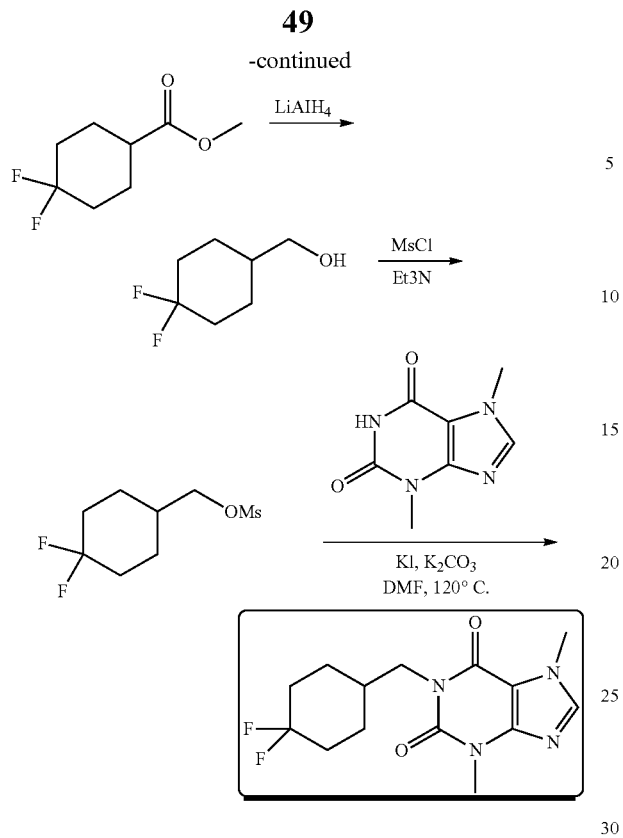

Step 1

(4,4-Difluoro-cyclohexyl)methanol 4,4-Difluoro-cyclohexanecarboxylate (500 mg, 2.60 mmol) was dissolved in tetrahydrofuran (15 mL), and lithium aluminum hydride (1.48 g, 3.90 mmol) was added in batches at 0° C., and stirred to react for 18 hours under nitrogen atmosphere. The reaction solution was cooled to 0° C. and water (1.50 mL), 15% sodium hydroxide (1.50 mL) and water (4.50 mL) were added successively slowly. The solution was filtered, and the filtrate was concentrated under reduced pressure to give the product (4,4-difluoro-cyclohexyl)methanol (300 mg, as a colorless liquid) with a yield of 77%.

$^1$H NMR: (400 MHz, CDCl$_3$) δ 3.58-3.44 (m, 2H), 2.20-2.05 (m, 2H), 1.93-1.42 (m, 6H), 1.40-1.20 (m, 2H). MS-ESI calcd. [M+H]$^+$ 151, found 151.

Step 2

4,4-Difluorocyclohexylmethyl methanesulfonate (4,4-Difluoro-cyclohexyl)methanol (300 mg, 2.00 mmol) and triethylamine (303 mg, 3.00 mmol) were dissolved in dichloromethane (10 mL), and methanesulfonyl chloride (458 mg, 4.00 mmol) was slowly added at 0° C. The reaction solution was stirred at 0° C. for 4 hours. The reaction was quenched with water (10 mL) and extracted with dichloromethane (30 mL×2). The organic phases were combined, washed with saturated aqueous sodium bicarbonate solution (50 mL), dried over anhydrous sodium sulfate, filtered and the filtrate was concentrated under reduced pressure to give 4,4-difluorocyclohexylmethyl methanesulfonate (350 mg, as a white solid) with a yield of 77%.

MS-ESI calcd. [M+H]$^+$ 229, found 229.

Step 3

1-(4,4-Difluoro-cyclohexylmethyl)-3,7-dimethyl-3,7-dihydro-purine-2,6-dione 3,7-Dimethyl-1H-purine-2,6(3H,7H)-dione (78.9 mg, 0.438 mmol) was dissolved in N,N-dimethylformamide (100 mL). 4,4-Difluorocyclohexylmethyl methanesulfonate (78.9 mg, 0.438 mmol), potassium carbonate (121 mg, 0.876 mmol) and potassium iodide (87.3 mg, 0.526 mmol) were added. The reaction solution was heated to 120° C. and stirred for 3 hours, and then concentrated under reduced pressure, the residue was purified by silica gel column chromatography (1:1 petroleum ether/ethyl acetate, R$_f$=0.3) to give 1-(4,4-difluoro-cyclohexylmethyl)-3,7-dimethyl-3,7-dihydro-purine-2,6-dione (30.0 mg) with a yield of 22%.

$^1$H NMR: (400 MHz, CDCl$_3$) δ 7.53 (s, 1H), 4.00 (s, 3H), 3.95 (d, J=6.8 Hz, 2H), 3.59 (s, 3H), 2.18-2.05 (m, 2H), 2.02-1.87 (m, 1H), 1.82-1.62 (m, 4H), 1.60-1.40 (m, 2H). MS-ESI calcd. [M+H]$^+$ 313, found 313.

Example 10

1-(3-(1H-imidazol-1-yl)propyl)-3,7-dimethyl-1H-purine-2,6(3H,7H)-dione

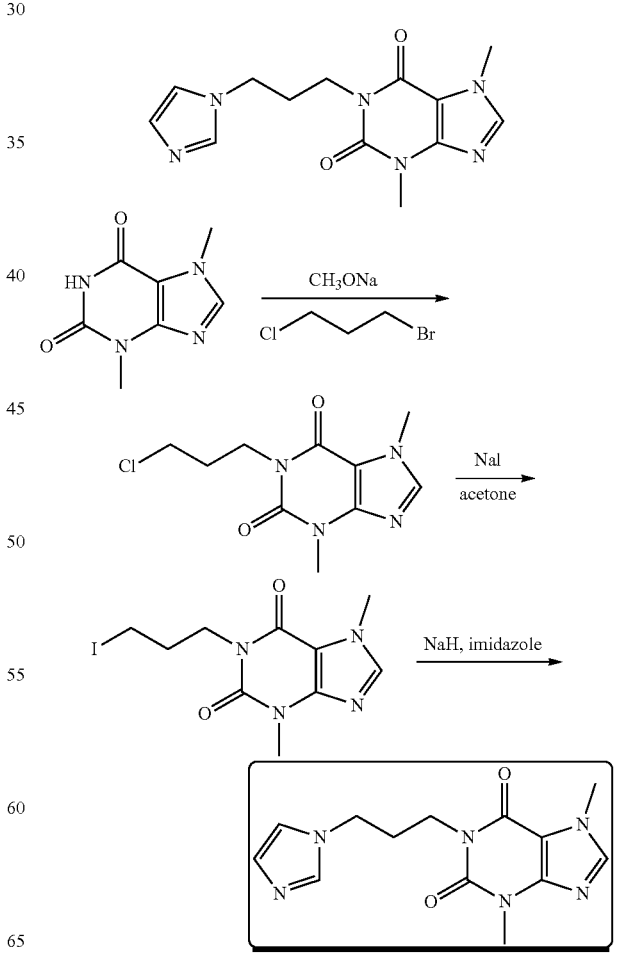

51

Step 1

1-(3-Chloropropyl)-3,7-dimethyl-1H-purine-2,6(3H,7H)-dione 3,7-Dimethyl-1H-purine-2,6(3H,7H)-dione (9.00 g, 49.9 mmol) was dissolved in methanol (12 mL) and freshly prepared sodium methoxide (9.64 g, 49.9 mmol) and 1-bromo-3-chloropropane (47.2 g, 299 mmol) were added. The reaction was stirred at 80° C. under nitrogen atmosphere for 12 hours. The reaction solution was concentrated under reduced pressure and then dissolved in dichloromethane (50 mL), filtered, and the filtrate was concentrated and dried in vacuo to give 1-(3-chloropropyl)-3,7-dimethyl-1H-purine-3H,7H)-dione (10.0 g, as a white solid) with a yield of 78%.

$^1$H NMR: (400 MHz, CDCl$_3$) δ 7.49 (s, 1H), 4.16-4.13 (m, 2H), 3.96 (s, 3H), 3.69-3.66 (m, 2H), 3.58 (s, 3H), 2.25-2.24 (m, 1H), 2.14-2.12 (m, 1H). MS-ESI calcd. [M+H]$^+$ 257, found 257.

Step 2

1-(3-Iodopropyl)-3,7-dimethyl-1H-purine-2,6(3H,7H)-dione 1-(3-Chloropropyl)-3,7-dimethyl-1H-purine-2,6(3H,7H)-dione (12.8 g, 49.9 mmol) was dissolved in acetone (250 mL) and sodium iodide (9.36 g, 62.4 mmol) was added. The reaction solution was stirred at 70° C. for 48 hours and then concentrated under reduced pressure. And the residue was purified by silica gel column chromatography (5:1 petroleum ether/ethyl acetate, R$_f$=0.4) to give 1-(3-iodopropyl)-3,7-dimethyl-1H-purine-2,6(3H,7H)-dione (10.0 g, as a pale yellow solid) with a yield of 58%.

$^1$H NMR: (400 MHz, CDCl$_3$) δ 7.50 (s, 1H), 4.09-4.05 (m, 2H), 3.97 (s, 3H), 3.56 (s, 3H), 3.20-3.17 (m, 2H), 2.23-2.20 (m, 2H). MS-ESI calcd. [M+H]$^+$ 349, found 349.

Step 3

1-(3-(1H-imidazol-1-yl) propyl)-3,7-dimethyl-1H-purine-2,6(3H,7H)-dione

Sodium hydride (28.0 mg, 0.690 mmol) was added to a solution of imidazole (46.9 mg, 0.690 mmol) in N,N-dimethylformamide (1 mL) at 0° C. The reaction solution was stirred at 20° C. for 1 hour. A solution of 1-(3-iodopropyl)-3,7-dimethyl-1H-purine-2,6(3H,7H)-dione (200 mg, 0.570 mmol) in N,N-dimethylformamide (1 mL) was added dropwise to the reaction solution at 0° C. The reaction solution was slowly warmed to 20° C., stirred for 12 hours and then cooled to 0° C. The reaction solution was quenched by addition of saturated ammonium chloride solution (10 mL) and extracted with ethyl acetate (10 mL×3). The organic phases were combined and washed with brine (10 mL×3), dried over anhydrous sodium sulfate and concentrated under reduced pressure. And the residue was purified by preparative HPLC to give 1-(3-(1H-imidazol-1-yl) propyl)-3,7-dimethyl-1H-purine-2,6(3H,7H)-dione (50.0 mg) with a yield of 30%.

$^1$H NMR: (400 MHz, Methanol-d$_4$) δ7.86 (s, 1H), 7.79 (s, 1H), 7.21 (s, 1H), 6.96 (s, 1H), 4.13-4.09 (m, 2H), 4.06-4.03 (m, 2H), 3.96 (s, 3H), 3.51 (s, 3H), 2.21-2.16 (m, 2H). MS-ESI calcd. [M+H]$^+$ 289, found 289.

52

Example 11

1-(2-(3-Ethyl-1-methyl-1H-pyrazol-5-yl)ethyl)-3,7-dimethyl-1H-purine-2,6(3H,7H)-dione 1-(2-(5-Ethyl-1-methyl-1H-pyrazol-3-yl)ethyl)-3,7-dimethyl-1H-purine-2,6(3H,7H)-dione

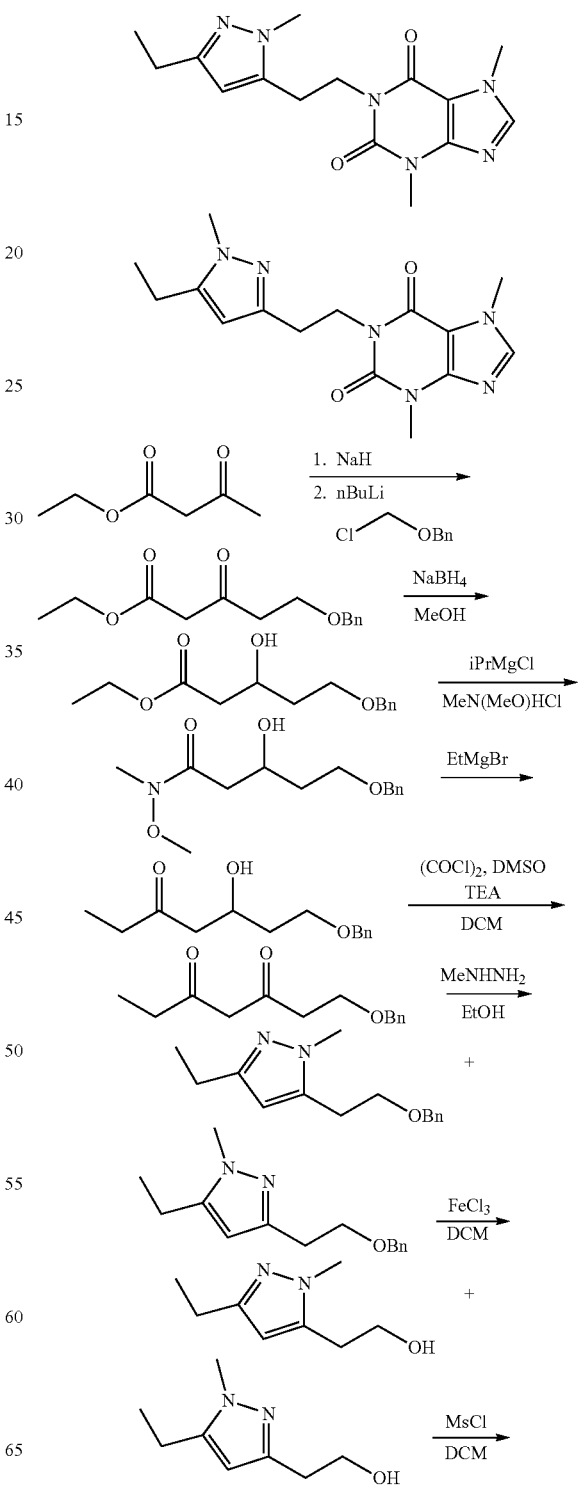

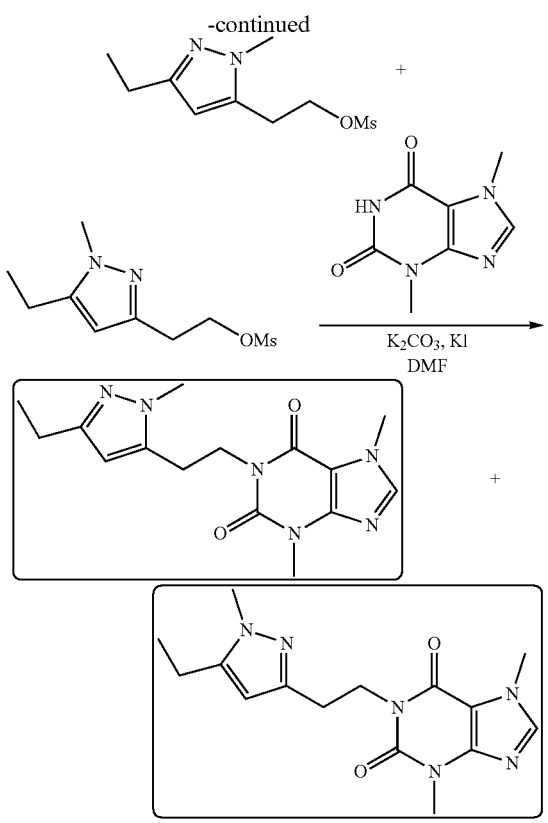

Step 1

Ethyl 5-benzyloxy-3-oxopentanoate

Sodium hydride (3.38 g, 84.6 mmol, 60%) was added to tetrahydrofuran (300 mL) at 0° C. under nitrogen atmosphere. Ethylacetoacetate (10.0 g, 76.9 mmol) was then slowly added into and the reaction was slowly cooled to −10° C. and stirred for 10 minutes. Then n-butyllithium (0.3 mL, 2.5 M n-hexane solution, 0.75 mmol) was added slowly at this temperature and the stirring was continued for 10 minutes. ((2-Chloroethoxy)methyl)benzene (12.6 g, 80.7 mmol) was slowly added dropwise to this reaction solution to react for 30 minutes. The reaction was quenched by addition of ammonium chloride solution (100 mL) and extracted with ethyl acetate (50 mL×5). The organic phases were combined, washed with brine (50 mL), dried over anhydrous sodium sulfate, filtered, concentrated under reduced pressure and purified by silica gel column chromatography (1:40 petroleum ether: ethyl acetate, $R_f$=0.3) to give ethyl 5-(benzyloxy)-3-oxopentanoate (9.02 g, as a yellow oil) with a yield of 47%.

$^1$H NMR: (400 MHz, Methanol-$d_4$) δ7.35-7.27 (m, 5H), 4.50 (s, 2H), 4.20-4.15 (m, 2H), 3.76-3.73 (m, 2H), 3.47 (s, 2H), 2.82 (t, J=6.0 Hz, 2H), 1.26 (t, J=6.0 Hz, 3H).

Step 2

Ethyl 5-(benzyloxy)-3-hydroxypentanoate

Sodium borohydride (864 mg, 24.0 mmol) was added to a solution of ethyl 5-(benzyloxy)-3-oxopentanoate (6.00 g, 24.0 mmol) in methanol (50.0 mL) at 0° C. The reaction solution was stirred at this temperature for 2.5 hours. After completion of the reaction, the reaction was quenched with dilute hydrochloric acid and extracted with ethyl acetate (50 mL×3). The organic phases were combined, washed with brine (20 mL), dried over anhydrous sodium sulfate, filtered, concentrated under reduced pressure and purified by silica gel column chromatography (10:1 petroleum ether: ethyl acetate, $R_f$=0.2) to give ethyl 5-(benzyloxy)-3-hydroxypentanoate (3.40 g, as a yellow oil) with a yield of 56%.

$^1$H NMR: (400 MHz, CDCl$_3$) δ 7.37-7.29 (m, 5H), 4.53 (s, 2H), 4.28-4.20 (m, 1H), 4.18-4.14 (m, 2H), 3.72-3.66 (m, 2H), 2.51-2.49 (m, 2H), 1.85-1.78 (m, 2H), 1.29-1.26 (m, 3H).

Step 3

5-(Benzyloxy)-3-hydroxy-N-methoxy-N-methylpentanamide

A solution of ethyl 5-(benzyloxy)-3-hydroxypentanoate (3.20 g, 12.7 mmol) and N,O-dimethylhydroxylamine hydrochloride (3.02 g, 31.8 mmol) in tetrahydrofuran (50 mL) was slowly added dropwise to the isopropylmagnesium chloride (2 M tetrahydrofuran solution, 44.0 mL, 57.2 mmol) at −10° C. under nitrogen atmosphere. The reaction solution was slowly warmed to 0° C. and stirred for 3 hours. The reaction was then quenched with ammonium chloride solution (50 mL) and extracted with ethyl acetate (30 mL×3). The organic phases were combined, washed with brine (10 mL), dried over anhydrous sodium sulfate, filtered, concentrated under reduced pressure and purified by silica gel column chromatography (5:1 petroleum ether: ethyl acetate, $R_f$=0.2) to give 5-(benzyloxy)-3-hydroxy-N-methoxy-N-methylpentanamide (2.50 g, as a yellow oil) with a yield of 74%.

MS-ESI calcd. [M+H]$^+$ 268, found 268.

Step 4

7-(Benzyloxy)-5-hydroxyheptan-3-one

Ethylmagnesium bromide (1.2 mL, 3 M ether solution, 3.5 mmol) was slowly added to a solution of 5-(benzyloxy)-3-hydroxy-N-methoxy-N-methylpentanamide (380 mg, 1.42 mmol) in tetrahydrofuran (10.0 mL) under nitrogen atmosphere. The reaction solution was slowly warmed to 0° C. and stirred for 3 hours. The reaction was quenched with ammonium chloride solution (50 mL) and extracted with ethyl acetate (6 mL×3). The organic phases were combined, washed with brine (5.0 mL), dried over anhydrous sodium sulfate, filtered and concentrated under reduced pressure to give 7-(benzyloxy)-5-hydroxyheptan-3-one (180 mg, as a colorless oil) with a yield of 74%.

MS-ESI calcd. [M+H]$^+$ 237, found 237.

Step 5

1-(Benzyloxy)heptane-3,5-dione

Oxalyl chloride (1.21 g, 9.54 mmol) was slowly added dropwise to a solution of dimethyl sulfoxide (1.50 g, 19.1 mmol) in dichloromethane (50 mL) at −65° C. under nitrogen atmosphere. The reaction solution was stirred at the temperature for 20 minutes, and 7-(benzyloxy)-5-hydroxyheptan-3-one (750 mg, 3.18 mmol) was added and the stirring was continued for 2 hours. Triethylamine (3.30 g, 32.5 mmol) was added and the stirring was continued at −65° C. for 1 hour and the temperature was slowly warmed to 25° C. The reaction solution was extracted with dichloromethane (10 mL×2) after adding brine (5 mL). The organic phases were combined, dried over anhydrous sodium sulfate, filtered, concentrated under reduced pressure, and purified by preparative TLC plate (5:1 petroleum ether: ethyl acetate, $R_f$=0.5) to give 1-(benzyloxy)heptane-3,5-dione (220 mg, as a yellow oil) with a yield of 30%.

$^1$H NMR: (400 MHz, CDCl$_3$) δ 7.37-7.29 (m, 5H), 5.56 (s, 2H), 4.54-4.50 (m, 2H), 3.77-3.74 (m, 2H), 2.60 (t, J=8.0 Hz, 2H), 2.36-2.30 (m, 2H), 1.14 (t, J=8.0 Hz, 3H).

Step 6

5-(2-(Benzyloxy)ethyl)-3-ethyl-1-methyl-1H-pyrazole 3-(2-(Benzyloxy)ethyl)-5-ethyl-1-methyl-1H-pyrazole 1-(Benzyloxy)heptane-3,5-dione (120 mg, 0.513 mmol) and methylhydrazine hydrochloride (423 mg, 5.13 mmol) was dissolved in ethanol (10 mL). The reaction solution was refluxed for 1.5 hours and concentrated under reduced pressure to give a mixture of 5-(2-(benzyloxy)ethyl)-3-ethyl-1-methyl-1H-pyrazole and 3-(2-(benzyloxy)ethyl)-5-ethyl-1-methyl-1H-pyrazole (100 mg, as a yellow oil) with a yield of 80%.

MS-ESI calcd. [M+H]$^+$ 245, found 245.

Step 7

2-(3-Ethyl-1-methyl-1H-pyrazol-5-yl)ethanol 2-(5-Ethyl-1-methyl-1H-pyrazol-3-yl)ethanol A mixture of 5-(2-(benzyloxy)ethyl)-3-ethyl-1-methyl-1H-pyrazole and 3-(2-(benzyloxy)ethyl)-5-ethyl-1-methyl-1H-pyrazole (100 mg, 0.409 mmol) was added to a solution of ferric chloride (665 mg, 4.09 mmol) in dichloromethane (3 mL) at 25° C., and stirred for 20 minutes at 25° C. Water (5 mL) was added to quench the reaction, and the pH was adjusted to 6, and the reaction solution was extracted with ethyl acetate (10.0 mL×5). The organic phases were combined, washed with brine (10 mL), dried over anhydrous sodium sulfate, filtered, concentrated under reduced pressure, and purified by preparative TLC (3:1 petroleum ether/ethyl acetate, $R_f$=0.5) to give a mixture of 2-(3-ethyl-1-methyl-1H-pyrazol-5-yl) ethanol and 2-(5-ethyl-1-methyl-1H-pyrazol-3-yl) ethanol (52.0 mg, as a yellow oil) with a yield of 88%.

MS-ESI calcd. [M+H]$^+$ 155, found 155.

Step 8

2-(3-Ethyl-1-methyl-1H-pyrazol-5-yl)ethyl methanesulfonate 2-(5-Ethyl-1-methyl-1H-pyrazol-3-yl)ethyl methanesulfonate A mixture of 2-(3-ethyl-1-methyl-1H-pyrazol-5-yl)ethanol and 2-(5-ethyl-1-methyl-1H-pyrazol-3-yl)ethanol (56.0 mg, 0.364 mmol) was dissolved in dichloromethane (5 mL) and N,N-diisopropylethylamine (186 mg, 1.44 mmol) was added. The reaction solution was cooled to 0° C. and methanesulfonyl chloride (46.1 mg, 0.404 mmol) was added dropwise, and the reaction was slowly warmed to 25° C. and stirred for 3.5 hours. The reaction was quenched with water and extracted with ethyl acetate (10 mL×3). The organic phases were combined, washed with brine (10 mL), dried over anhydrous sodium sulfate, filtered and concentrated under reduced pressure to give a mixture of 2-(3-ethyl-1-methyl-1H-pyrazol-5-yl)ethyl methanesulfonate and 2-(5-ethyl-1-methyl-1H-pyrazol-3-yl)ethyl methanesulfonate (102 mg, as a yellow oil).

MS-ESI calcd. [M+H]$^+$ 233, found 233.

Step 9

1-(2-(3-Ethyl-1-methyl-1H-pyrazol-5-yl)ethyl)-3,7-dimethyl-1H-purine-2,6(3H,7H)-dione 1-(2-(5-ethyl-1-methyl-1H-pyrazol-3-yl)ethyl)-3,7-dimethyl-1H-purine-2,6(3H,7H)-dione A mixture of 2-(3-ethyl-1-methyl-1H-pyrazol-5-yl) ethyl methanesulfonate and 2-(5-ethyl-1-methyl-1H-pyrazol-3-yl) ethyl methanesulfonate (100 mg, 0.431 mmol), 3-methyl-1H-purine-2,6(3H,7H)-dione (116 mg, 0.646 mmol), potassium carbonate (178 mg, 1.29 mmol) and potassium iodide (10.7 mg, 0.0650 mmol) were dissolved in N,N-dimethylformamide (8 mL) and the reaction was heated to 130° C. and stirred for 2.5 hours, and then concentrated under reduced pressure, and purified by preparative HPLC to give 1-(2-(3-ethyl-1-methyl-1H-pyrazol-5-yl)ethyl)-3,7-dimethyl-1H-purine-2,6(3H,7H)-dione (product 1) (15.0 mg) and 1-(2-(5-ethyl-1-methyl-1H-pyrazol-3-yl)ethyl)-3,7-dimethyl-1H-purine-2,6(3H,7H)-dione (product 2) (16.0 mg) with a yield of 29%.

1-(2-(3-Ethyl-1-methyl-1H-pyrazol-5-yl)ethyl)-3,7-dimethyl-1H-purine-2,6(3H,7H)-dione $^1$H NMR: (400 MHz, Methanol-d$_4$) δ 7.87 (s, 1H), 5.88 (s, 1H), 4.19 (t, J=8.0 Hz, 2H), 3.96 (s, 3H), 3.81 (s, 3H), 3.52 (s, 3H), 2.96 (t, J=8.0 Hz, 2H). 2.54-2.48 (q, J=7.6 Hz, 2H), 1.14 (t, J=7.6 Hz, 3H). MS-ESI calcd. [M+H]$^+$ 317, found 317.

1-(2-(5-Ethyl-1-methyl-1H-pyrazol-3-yl)ethyl)-3,7-dimethyl-1H-purine-2,6(3H,7H)-dione $^1$H NMR: (400 MHz, Methanol-d$_4$) δ 7.86 (s, 1H), 5.96 (s, 1H), 4.20 (t, J=8.0 Hz, 2H), 3.96 (s, 3H), 3.68 (s, 3H), 3.52 (s, 3H), 2.86 (t, J=8.0 Hz, 2H), 2.64-2.58 (q, J=7.6 Hz, 2H), 1.23 (t, J=7.6 Hz, 3H). MS-ESI calcd. [M+H]$^+$ 317, found 317.

Example 12

3,7-Dimethyl-1-(4-(3-methyl-1H-pyrazol-5-yl)butyl)-1H-purine-2,6(3H,7H)-dione

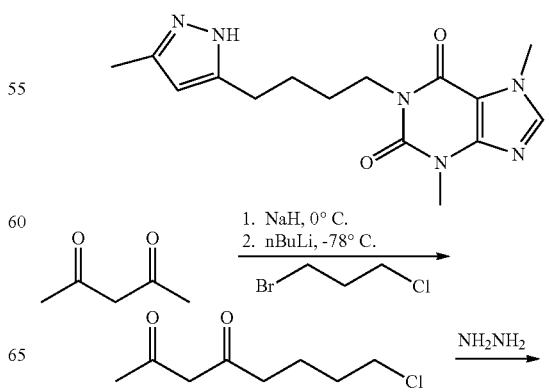

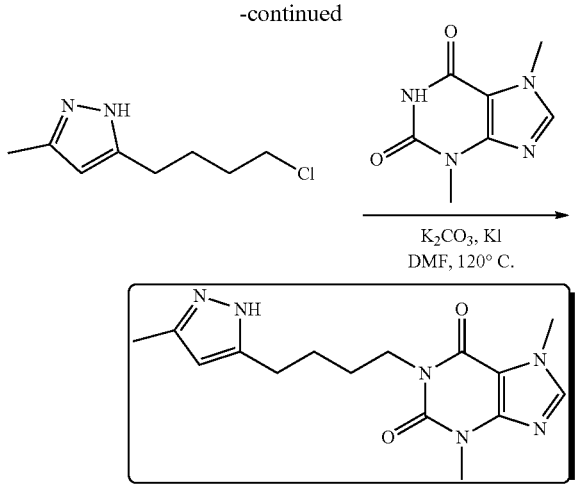

Step 1

8-Chlorooctane-2,4-dione

Pentane-2,4-dione (1.00 g, 10.0 mmol) was dissolved in tetrahydrofuran (20 mL). Sodium hydride (440 mg, 11.0 mmol, 60%) was added at 0° C. under nitrogen atmosphere. The reaction solution was stirred at 0° C. for 40 minutes, cooled to −78° C., and then n-butyllithium (4.2 mL, 2.5 M n-hexane solution, 10.5 mmol) was added dropwise and stirred at −78° C. for 40 minutes. 1-Bromo-3-chloropropane (1.65 g, 10.5 mmol) was added and stirred for 3 hours. The reaction was allowed to warm to 0° C. and quenched by the addition of saturated ammonium chloride solution (30 mL). The reaction mixture was extracted with ethyl acetate (30 mL×2). The organic phases were combined, dried over anhydrous sodium sulfate, filtered and the filtrate was concentrated under reduced pressure, and purified by silica gel column chromatography (10:1 petroleum ether/ethyl acetate, $R_f$=0.7) to give 8-chlorooctane-2,4-dione (1.30 g, as a yellow oil) with a yield of 74%.

$^1$H NMR: (400 MHz, CDCl$_3$) δ 5.50 (s, 2H), 3.55 (t, J=6.0 Hz, 2H), 2.31 (t, J=7.2 Hz, 2H), 2.05 (s, 3H), 1.86-1.63 (m, 4H). MS-ESI calcd. [M+H]$^+$ 177, found 177.

Step 2

5-(4-Chlorobutyl)-3-methyl-1H-pyrazole

8-Chlorooctane-2,4-dione (500 mg, 2.83 mmol) was dissolved in ethanol (10 mL), 85% hydrazine hydrate (160 mg, 4.25 mmol) was added and the reaction was heated under reflux for 16 hours. The reaction mixture was concentrated under reduced pressure and the residue was purified by silica gel column chromatography (1:1 petroleum ether/ethyl acetate, $R_f$=0.5) to give 5-(4-chlorobutyl)-3-methyl-1H-pyrazole (100 mg, as a colorless oil) with a yield of 20%.

$^1$H NMR: (400 MHz, CDCl$_3$) δ 8.07 (brs, 1H), 5.83 (s, 1H), 3.54 (t, J=6.0 Hz, 2H), 2.65 (t, J=7.2 Hz, 2H), 2.28 (s, 3H), 1.88-1.73 (m, 4H). MS-ESI calcd. [M+H]$^+$ 173, found 173.

Step 3

3,7-Dimethyl-1-(4-(3-methyl-1H-pyrazol-5-yl)butyl)-1H-purine-2,6(3H,7H)-dione 5-(4-Chlorobutyl)-3-methyl-1H-pyrazole (100 mg, 0.580 mmol) was dissolved in N,N-dimethylformamide (3 mL). 3,7-Dimethyl-1H-purine-2,6(3H,7H)-dione (104 mg, 0.580 mmol), potassium carbonate (120 mg, 0.870 mmol) and potassium iodide (115 mg, 0.700 mmol) were added. The reaction solution was heated to 120° C. and stirred for 16 hours, and then concentrated under reduced pressure, and purified by preparative HPLC to give 3,7-dimethyl-1-(4-(3-methyl-1H-pyrazol-5-yl)butyl)-1H-purine-2,6(3H,7H)-dione (25.0 mg) with a yield of 14%.

$^1$H NMR: (400 MHz, Methanol-d$_4$) δ 7.99 (s, 1H), 6.46 (s, 1H), 4.06-3.90 (m, 5H), 3.52 (s, 3H), 2.88-2.77 (m, 2H), 2.44 (s, 3H), 1.84-1.62 (m, 4H). MS-ESI calcd. [M+H]$^+$ 317, found 317.

Example 13

3,7-Dimethyl-1-[3-(1-methyl-4-pyrazolyl)-propyl]-3,7-dihydro-purine-2,6-dione

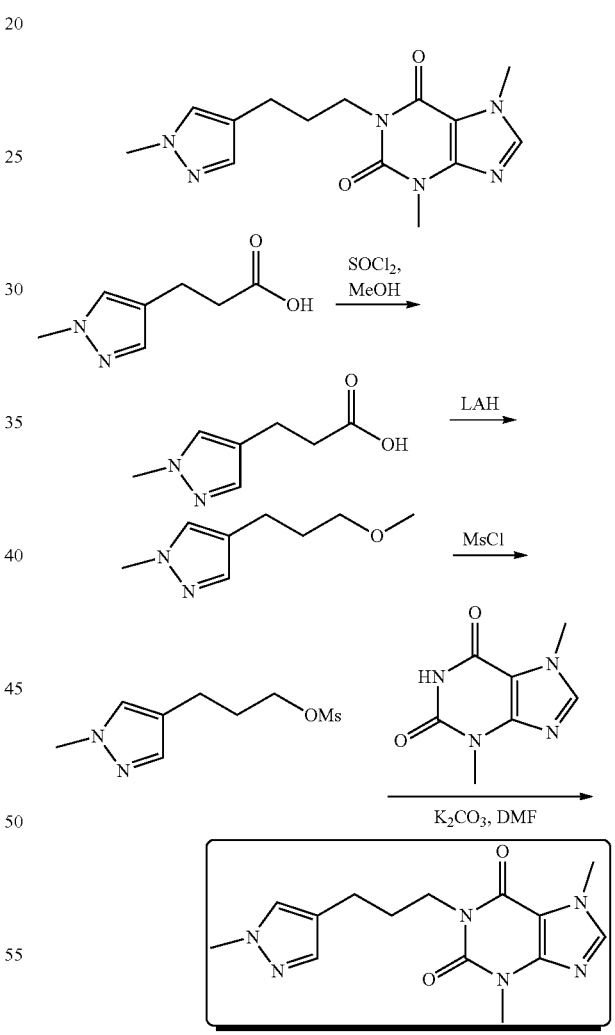

Step 1

Methyl 3-(1-methyl-4-pyrazolyl)-propionate 3-(1-Methyl-4-pyrazolyl)-propionic acid (150 mg, 0.974 mmol) was dissolved in methanol (3 mL), and thionyl chloride (229 mg, 1.95 mmol) was added at 0° C. to react for 0.5 h. The reaction was quenched with water (10 mL), extracted with ethyl acetate (10 mL×3), dried over anhydrous sodium sulfate, filtered and the filtrate was concentrated under reduced pressure and purified by preparative TLC plate (3:1 petroleum ether/ethyl acetate, $R_f$ value=0.5) to give methyl 3-(1-methyl-4-pyrazolyl)-propionate (140 mg, as a yellow oil) with a yield of 83%. MS-ESI calcd. [M+H]$^+$ 169, found 169.

Step 2

3-(1-Methyl-4-pyrazolyl)-1-propanol

Methyl 3-(1-methyl-4-pyrazolyl)-propionate (140 mg, 0.833 mmol) was dissolved in tetrahydrofuran (10 mL), and lithium aluminum hydride (67.0 mg, 1.70 mmol) was added at 0° C. to react for 1 hour. The reaction was quenched with water (10 mL), extracted with ethyl acetate (10 mL×3), dried over anhydrous sodium sulfate, filtered and the filtrate was concentrated under reduced pressure and purified by preparative TLC plate (1:1 petroleum ether/ethyl acetate, $R_f$ value=0.5) to give 3-(1-methyl-4-pyrazolyl)-1-propanol (90.0 mg, as a yellow oil) with a yield of 77%. MS-ESI calcd. [M+H]$^+$ 141, found 141.

Step 3

3-(1-Methyl-4-pyrazolyl)-propyl methanesulfonate 3-(1-Methyl-4-pyrazolyl)-1-propanol (90.0 mg, 0.642 mmol) and triethylamine (173 mg, 1.71 mmol) were dissolved in dichloromethane (5 mL). Methanesulfonyl chloride (128 mg, 1.14 mmol) was added at 0° C. The reaction solution was slowly allowed to warm to room temperature and stirred for 2 hours. The reaction was quenched by adding aqueous sodium bicarbonate solution (10 mL) and extracted with dichloromethane (30 mL×3). The organic phases were combined, washed with saturated sodium chloride solution (30 mL×2), dried over anhydrous sodium sulfate, filtered and the filtrate was concentrated under reduced pressure to give 3-(1-methyl-4-pyrazolyl)-propyl methanesulfonate (90.0 mg, as a yellow oil) with a yield of 69%. MS-ESI calcd. [M+H]$^+$ 219, found 219.

Step 4

3,7-Dimethyl-1-[3-(1-methyl-4-pyrazolyl)-propyl]-3,7-dihydro-purine-2,6-dione 3-(1-Methyl-4-pyrazolyl)-propyl methanesulfonate (90.0 mg, 0.413 mmol), 3,7-dimethyl-1H-purine-2,6(3H, 7H)-dione (74.3 mg, 0.413 mmol) and potassium carbonate (114 mg, 0.826 mmol) were dissolved in N,N-dimethylformamide (3 mL). The reaction solution was heated to 120° C. and stirred for 3 hours, then cooled to room temperature and filtered, and the filtrate was concentrated under reduced pressure and purified by preparative HPLC to give 3,7-dimethyl-1-[3-(1-methyl-4-pyrazolyl)-propyl]-3,7-dihydro-purine-2,6-dione (25.0 mg) with a yield of 30%.

$^1$H NMR: (400 MHz, Methanol-d$_4$) δ 7.87 (s, 1H), 7.42 (s, 1H), 7.32 (s, 1H), 4.06-4.02 (m, 2H), 3.98 (s, 3H), 3.80 (s, 3H), 3.52 (s, 3H), 2.57-2.53 (m, 2H), 1.97-1.89 (m, 2H). MS-ESI calcd. [M+H]$^+$ 303, found 303.

Example 14

1-(4-(1,3-Dimethyl-1H-pyrazol-5-yl)butyl)-3,7-dimethyl-1H-purine-2,6(3H,7H)-dione 1-(4-(1,3-Dimethyl-1H-pyrazol-5-yl)butyl)-3,7-dimethyl-1H-purine-2,6(3H,7H)-dione

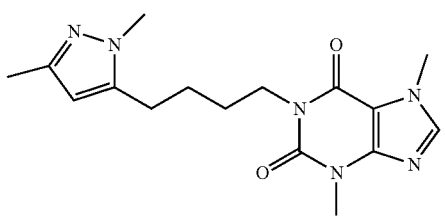

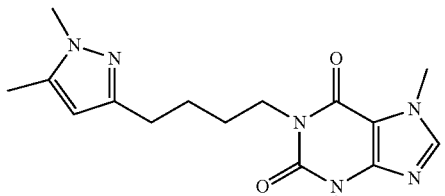

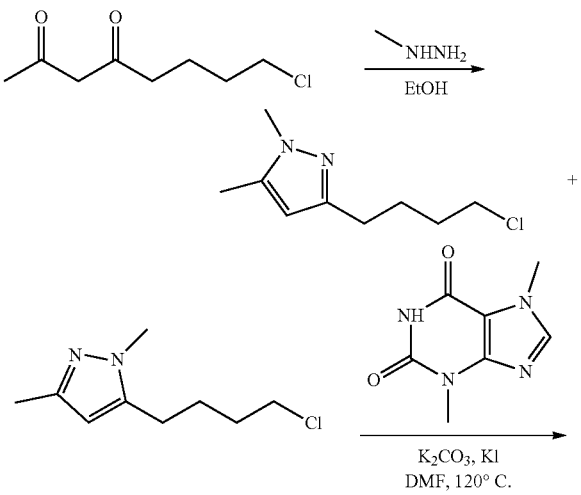

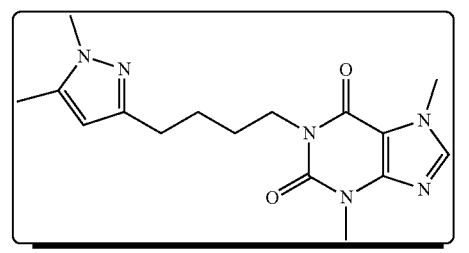

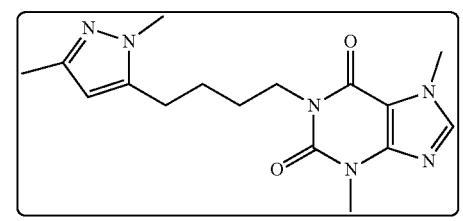

Step 1

3-(4-Chlorobutyl)-1,5-dimethyl-1H-pyrazole 5-(4-Chlorobutyl)-1,3-dimethyl-1H-pyrazole 8-Chloro-octane-2,4-dione (500 mg, 2.83 mmol) was dissolved in ethanol (10 mL). Methylhydrazine (195 mg, 4.25 mmol) was added and the reaction was heated under reflux for 16 hours. The reaction was concentrated under reduced pressure and the residue was purified by silica gel column chromatography (2:1 petroleum ether/ethyl acetate, $R_f$=0.5) to give a mixture of 3-(4-chlorobutyl)-1,5-dimethyl-1H-pyrazole and 5-(4-chlorobutyl)-1,3-dimethyl-1H-pyrazole (100 mg, as a colorless oil) with a yield of 20%.

$^1$H NMR: (400 MHz, CDCl$_3$) δ 5.80 (s, 1H), 3.73-3.65 (m, 3H), 3.60-3.49 (m, 2H), 2.61-2.51 (m, 2H), 2.25-2.15 (m, 3H), 1.90-1.68 (m, 4H). MS-ESI calcd. [M+H]$^+$ 187, found 187.

Step 2

1-(4-(1,3-Dimethyl-1H-pyrazol-5-yl)butyl)-3,7-dimethyl-1H-purine-2,6(3H,7H)-dione 1-(4-(1,5-Dimethyl-1H-pyrazol-3-yl)butyl)-3,7-dimethyl-1H-purine-2,6(3H,7H)-dione A mixture of 3-(4-chlorobutyl)-1,5-dimethyl-1H-pyrazole and 5-(4-chlorobutyl)-1,3-dimethyl-1H-pyrazole (330 mg, 1.76 mmol) was dissolved in N,N-dimethylformamide (10 mL), potassium carbonate (364 mg, 2.64 mmol), 3,7-dimethyl-1H-purine-2,6(3H,7H)-dione (315 mg, 1.76 mmol) and potassium iodide (350 mg, 2.11 mmol) were added. The reaction solution was heated to 120° C. and stirred for 16 hours. The reaction solution was cooled to room temperature and quenched by the addition of water (30 mL). The reaction mixture was extracted with ethyl acetate (30 mL×2). The organic phases were combined, washed with brine (20 mL), dried over anhydrous sodium sulfate and filtered. The filtrate was concentrated under reduced pressure and purified by silica gel column chromatography (1:1 petroleum ether/ethyl acetate, $R_f$=0.5) to give the substituted isomeric mixture (350 mg, as a yellow oil) with a yield of 60%. The isomeric mixture was purified by preparative SFC to obtain substituted isomer products respectively. Separation method: Separation column: Chiralpak AD 250×30 mm, I.D. 10 um; Mobile phase: supercritical carbon dioxide/methanol (0.1%) ammonia=60/40, at 80 mL/min; Wavelength: 220 nm.

1-(4-(1,3-dimethyl-1H-pyrazol-5-yl)butyl)-3,7-dimethyl-1H-purine-2,6(3H,7H)-dione (40.0 mg) (Isomer 1, first peak).

$^1$H NMR: (400 MHz, CDCl$_3$) δ 7.50 (s, 1H), 5.79 (s, 1H), 4.04 (t, J=7.2 Hz, 2H), 3.98 (s, 3H), 3.70 (s, 3H), 3.57 (s, 3H), 2.58 (t, J=7.2 Hz, 2H), 2.19 (s, 3H), 1.80-1.60 (m, 4H). MS-ESI calcd. [M+H]$^+$ 331, found 331.

1-(4-(1,5-dimethyl-1H-pyrazol-3-yl)butyl)-3,7-dimethyl-1H-purine-2,6(3H,7H)-dione (200 mg) (Isomer 2, second peak).

$^1$H NMR: (400 MHz, CDCl$_3$) δ 7.49 (s, 1H), 5.81 (s, 1H), 4.04 (t, J=7.2 Hz, 2H), 3.98 (s, 3H), 3.69 (s, 3H), 3.57 (s, 3H), 2.59 (t, J=7.2 Hz, 2H), 2.21 (s, 3H), 1.78-1.60 (m, 4H). MS-ESI calcd. [M+H]$^+$ 331, found 331.

Example 15

1-((3-Isopropylisoxazol-5-yl)methyl)-3,7-dimethyl-1H-purine-2,6(3H,7H)-dione

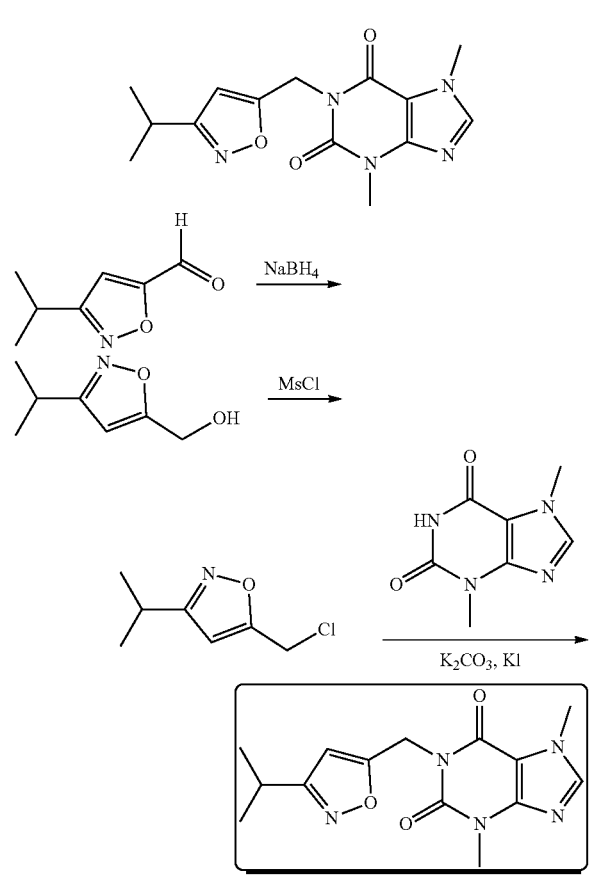

Step 1

(3-Isopropylisoxazol-5-yl)methanol (3-isopropylisoxazol-5-yl) formaldehyde (200 mg, 1.44 mmol) was dissolved in anhydrous methanol (5 mL). Sodium borohydride (109 mg, 2.88 mmol) was added at 0° C. to react for 1 hour. The reaction was quenched by the addition of water (10 mL) and extracted with ethyl acetate (10 mL×3). The organic phases were combined, dried over anhydrous sodium sulfate, concentrated under reduced pressure, and purified by preparative TLC plate (1:1 petroleum ether/ethyl acetate, $R_f$=0.3) to give (3-isopropylisoxazol-5-yl)methanol (150 mg, as a yellow oil) with a yield of 74%.

$^1$H NMR: (400 MHz, Methanol-d$_4$) δ 6.27 (s, 1H), 4.63 (s, 2H), 3.06-2.99 (m, 1H), 1.22 (d, J=3.4 Hz, 6H).

Step 2

5-(Chloromethyl)-3-isopropylisoxazole (3-isopropylisoxazol-5-yl) methanol (150 mg, 1.06 mmol) and triethylamine (322 mg, 3.16 mmol) were dissolved in anhydrous dichloromethane (5 mL). Methanesulfonyl chloride (237 mg, 2.12 mmol) was added at 0° C. The reaction solution was slowly warmed to 25° C. and stirred for 2 hours. The reaction was quenched by the addition of saturated sodium bicarbonate aqueous solution (10 mL) and extracted with dichloromethane (10 mL×3). The organic phases were combined, washed with saturated sodium chloride aqueous solution (30 mL), dried over anhydrous sodium sulfate, and concentrated under reduced pressure to give 5-(chloromethyl)-3-isopropylisoxazole (72.5 mg, as a yellow oil) with a yield of 43%.

$^1$H NMR: (400 MHz, Methanol-$d_4$) δ 6.44 (s, 1H), 4.74 (s, 2H), 3.27-3.25 (m, 1H), 1.35 (d, J=3.4 Hz, 6H).

Step 3

1-((3-Isopropylisoxazol-5-yl)methyl)-3,7-dimethyl-1H-purine-2,6(3H,7H)-dione 5-(Chloromethyl)-3-isopropylisoxazole (72.5 mg, 0.457 mmol), 3,7-dimethyl-1H-purine-2,6(3H,7H)-dione (85.5 mg, 0.457 mmol), potassium iodide (7.2 mg, 0.0457 mmol) and potassium carbonate (126 mg, 0.913 mmol) were dissolved in anhydrous N,N-dimethylformamide (3 mL). The reaction solution was heated to 120° C. to react for 3 hours. The reaction solution was cooled to 20° C., filtered, and purified by preparative HPLC to give 1-((3-isopropylisoxazol-5-yl)methyl)-3,7-dimethyl-1H-purine-2,6(3H,7H)-dione (20.0 mg) with a yield of 14%.

$^1$H NMR: (400 MHz, Methanol-$d_4$) δ 7.88 (s, 1H), 6.24 (s, 1H), 5.23 (s, 2H), 3.96 (s, 3H), 3.52 (s, 3H), 3.01-2.93 (m, 1H), 1.22 (d, J=3.4 Hz, 6H). MS-ESI calcd. [M+H]$^+$ 304, found 304.

Example 16

3,7-Dimethyl-1-(2-(3-methylisoxazol-5-yl)ethyl)-1H-purine-2,6(3H,7H)-dione

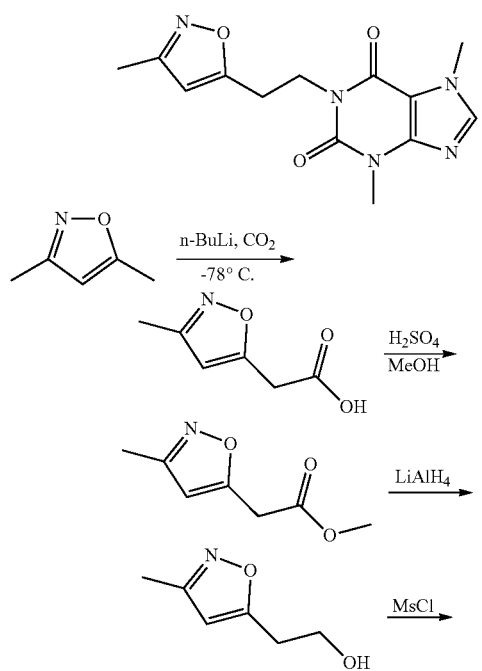

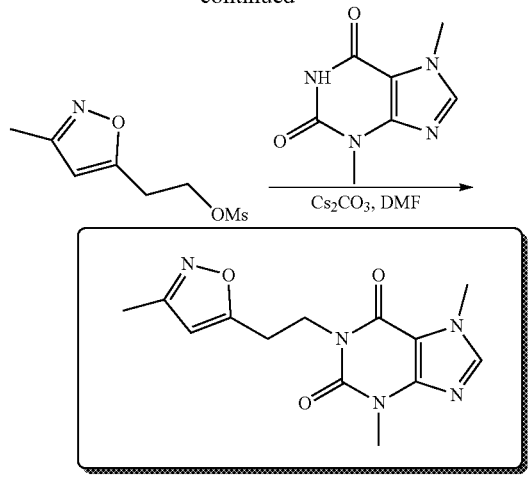

Step 1

2-(3-Methylisoxazol-5-yl) acetic acid 3,5-Dimethylisoxazole (5.00 g, 51.5 mmol) was dissolved in tetrahydrofuran (50 mL). n-butyllithium (23 mL, 2.5 M n-hexane solution, 57 mmol) was added at −78° C. under nitrogen atmosphere, and stirred for 1 hour. The carbon dioxide gas was passed through the reaction solution and the solution was stirred at room temperature and 1 atm for another 1 hour. Then the reaction solution was quenched by adding saturated ammonium chloride (30 mL), and concentrated under reduced pressure. The aqueous phase was adjusted to pH 3, and extracted with ethyl acetate (30 mL×3). The organic phases were combined, washed with saturated sodium chloride aqueous solution (30 mL×2), dried over anhydrous sodium sulfate, filtered and the filtrate was concentrated under reduced pressure to give 2-(3-methylisoxazol-5-yl) acetic acid (2.40 g, as a white solid) with a yield of 89%.

$^1$H NMR: (400 MHz, CDCl$_3$) δ 6.14 (s, 1H), 3.85 (s, 2H), 2.30 (s, 3H). MS-ESI calcd. [M+H]$^+$ 142, found 142.

Step 2

Methyl 2-(3-methylisoxazol-5-yl) acetate 2-(3-Methylisoxazol-5-yl) acetic acid (2.40 g, 17.0 mmol) was dissolved in methanol (30 mL), and conc. sulfuric acid (8.34 g, 85.0 mmol) was added. The reaction solution was heated under reflux for 2 hours, and then concentrated under reduced pressure. The residue was diluted with water (30 mL), adjusted to pH 8 with saturated sodium bicarbonate aqueous solution (20 mL) and extracted with ethyl acetate (30 mL×2). The organic phases were combined, washed with saturated sodium chloride aqueous solution (20 mL), dried over anhydrous sodium sulfate, filtered and the filtrate was concentrated under reduced pressure, then purified by silica gel column chromatography (5:1 petroleum ether/ethyl acetate, $R_f$=0.5) to give methyl 2-(3-methylisoxazol-5-yl) acetate (2.00 g, as a yellow oil) with a yield of 76%.

$^1$H NMR: (400 MHz, CDCl$_3$) δ 6.10 (s, 1H), 3.79 (s, 2H), 3.75 (s, 3H), 2.29 (s, 3H). MS-ESI calcd. [M+H]$^+$ 156, found 156.

Step 3

2-(3-Methylisoxazol-5-yl) ethanol

Methyl 2-(3-methylisoxazol-5-yl) acetate (2.00 g, 12.9 mmol) was dissolved in tetrahydrofuran (30 mL). Lithium aluminum hydride (725 mg, 19.4 mmol) was added in batches at 0° C. under nitrogen atmosphere and the reaction solution was stirred at 0° C. for 1 hour. Water (0.7 mL) and 15% sodium hydroxide solution (0.7 mL) were added to the reaction solution, followed by quenching with water (2.1 mL). The filtrate was dried over anhydrous sodium sulfate and concentrated under reduced pressure to give 2-(3-methylisoxazol-5-yl) ethanol (1.20 g, as a yellow oil) with a yield of 72%.

$^1$H NMR: (400 MHz, CDCl$_3$) δ 5.94 (s, 1H), 3.93 (t, J=6.0 Hz, 2H), 2.98 (t, J=6.0 Hz, 2H), 2.69 (br, 1H), 2.26 (s, 3H). MS-ESI calcd. [M+H]$^+$ 128, found 128.

Step 4

2-(3-Methylisoxazol-5-yl)ethyl methanesulfonate 2-(3-Methylisoxazol-5-yl) ethanol (1.00 g, 7.87 mmol) was dissolved in dichloromethane (15 mL) and cooled to 0° C., and then triethylamine (1.19 g, 11.8 mmol) and methanesulfonyl chloride (1.35 g, 11.8 mmol) were added. The reaction solution was slowly allowed to warm to room temperature and stirred for 1 hour. The reaction solution was diluted with dichloromethane (30 mL), followed by adding 1 N hydrochloric acid (20 mL), and allowed to stand still for partition after fully stirring. The organic layer was separated, washed with saturated sodium bicarbonate aqueous solution (30 mL) and brine (20 mL) successively, dried over anhydrous sodium sulfate and filtered. The filtrate was concentrated under reduced pressure and purified by silica gel column chromatography (5:1 petroleum ether/ethyl acetate, R$_f$=0.5) to give 2-(3-methylisoxazol-5-yl)ethyl methanesulfonate (350 mg, as a yellow oil) with a yield of 22%.

$^1$H NMR: (400 MHz, CDCl$_3$) δ 6.01 (s, 1H), 4.50 (t, J=6.0 Hz, 2H), 3.19 (t, J=6.0 Hz, 2H), 2.99 (s, 3H), 2.28 (s, 3H). MS-ESI calcd. [M+H]$^+$ 206, found 206.

Step 5

3,7-Dimethyl-1-(2-(3-methylisoxazol-5-yl)ethyl)-1H-purine-2,6(3H,7H)-dione 2-(3-Methylisoxazol-5-yl)ethyl methanesulfonate (150 mg, 0.730 mmol), 3,7-dimethyl-1H-purine-2,6(3H,7H)-dione (132 mg, 0.730 mmol) and cesium carbonate (357 mg, 1.10 mmol) were dissolved in N,N-dimethylformamide (3 mL). The reaction was heated to 100° C. and stirred overnight. The reaction solution was cooled to room temperature, quenched by addition of water (15 mL) and extracted with ethyl acetate (10 mL×3). The organic phases were combined, washed with brine (10 mL), dried over anhydrous sodium sulfate and filtered. The filtrate was concentrated under reduced pressure and purified by silica gel column chromatography to give 3,7-dimethyl-1-(2-(3-methylisoxazol-5-yl)ethyl)-1H-purine-2,6(3H,7H)-dione (20.0 mg) with a yield of 10%.

$^1$H NMR: (400 MHz, Methanol-d$_4$) δ 8.38 (s, 1H), 6.13 (s, 1H), 4.30 (t, J=7.2 Hz, 2H), 4.04 (s, 3H), 3.54 (s, 3H), 3.10 (t, J=7.2 Hz, 2H), 2.24 (s, 3H). MS-ESI calcd. [M+H]$^+$ 290, found 290.

Example 17

1-(2-(3-Ethylisoxazol-5-yl)ethyl)-3,7-dimethyl-1H-purine-2,6(3H,7H)-dione

1-(2-(5-Ethylisoxazol-3-yl)ethyl)-3,7-dimethyl-1H-purine-2,6(3H, 7H)-dione

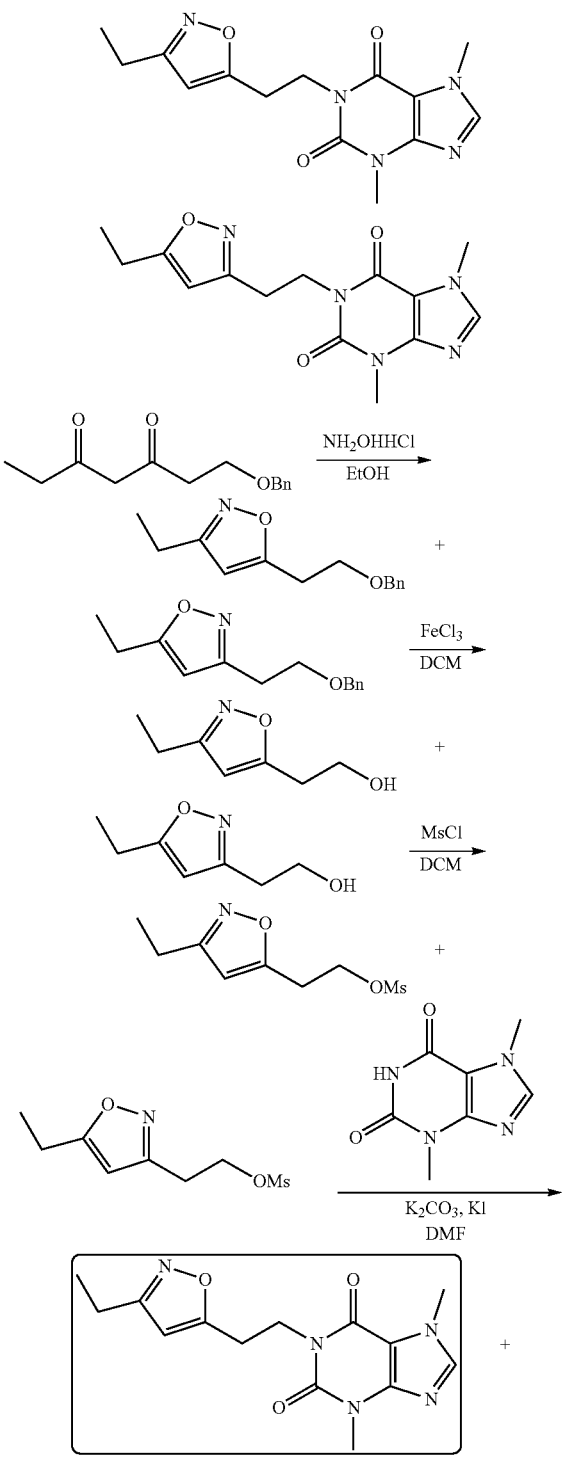

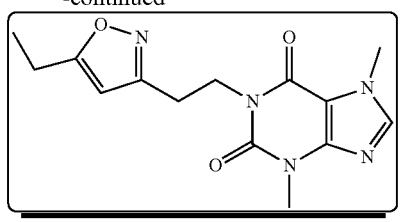

Step 1

5-(2-(Benzyloxy)ethyl)-3-ethylisoxazole

3-(2-(Benzyloxy) ethyl)-5-ethylisoxazole 1-(Benzyloxy)heptane-3,5-dione (100 mg, 0.427 mmol) and hydroxylamine hydrochloride (299 mg, 4.27 mmol) were dissolved in ethanol (2 mL). The reaction solution was refluxed for 1.5 hours, and then concentrated under reduced pressure to give a mixture of 5-(2-(benzyloxy)ethyl)-3-ethylisoxazole and 3-(2-(benzyloxy)ethyl)-5-ethylisoxazole (81.0 mg, as a yellow oil) with a yield of 82%. MS-ESI calcd. [M+H]$^+$ 232, found 232.

Step 2

2-(3-Ethylisoxazol-5-yl)ethanol

2-(5-Ethylisoxazol-3-yl)ethanol

A solution of the mixture of 5-(2-(benzyloxy)ethyl)-3-ethylisoxazole and 3-(2-(benzyloxy)ethyl)-5-ethylisoxazole (80.0 mg, 0.346 mmol) in dichloromethane (20 mL) was added to a solution of ferric chloride (562 mg, 3.46 mmol) in dichloromethane (3 mL) at 25° C., and stirred for 20 minutes. Water (5 mL) was added to quench the reaction, and pH was adjusted to 6. The reaction solution was extracted with ethyl acetate (20 mL×5). The organic phases were combined, washed with brine (10 mL), dried over anhydrous sodium sulfate, filtered and concentrated under reduced pressure to give a mixture of 2-(3-ethylisoxazol-5-yl) ethanol and 2-(5-ethylisoxazol-3-yl) ethanol (52.0 mg, as a yellow oil). MS-ESI calcd. [M+H]$^+$ 142, found 142.

Step 3

2-(3-Ethylisoxazol-5-yl)ethyl methanesulfonate

2-(5-Ethylisoxazol-3-yl)ethyl methanesulfonate

A mixture of 2-(3-ethylisoxazol-5-yl)ethanol and 2-(5-ethylisoxazol-3-yl)ethanol (36.0 mg, 0.255 mmol) was dissolved in dichloromethane (5 mL), and N,N-diisopropylethylamine (98.7 mg, 0.765 mmol) was added. The reaction solution was cooled to 0° C., followed by adding methanesulfonyl chloride (630 mg, 5.53 mmol) dropwise, and then slowly warmed to 25° C. and stirred for 3.5 hours. The reaction was quenched with water and extracted with ethyl acetate (20 mL×3). The organic phases were combined, washed with brine (10 mL), dried over anhydrous sodium sulfate, filtered and concentrated under reduced pressure to give a mixture of 2-(3-ethylisoxazol-5-yl)ethyl methanesulfonate and 2-(5-ethylisoxazol-3-yl)ethyl methanesulfonate (60.0 mg, as a yellow oil). MS-ESI calcd. [M+H]$^+$ 220, found 220.

Step 4

1-(2-(3-Ethylisoxazol-5-yl)ethyl)-3,7-dimethyl-1H-purine-2,6(3H,7H)-dione

1-(2-(5-Ethylisoxazol-3-yl)ethyl)-3,7-dimethyl-1H-purine-2,6(3H,7H)-dione

A mixture of 2-(3-ethylisoxazol-5-yl)ethyl methanesulfonate and 2-(5-ethylisoxazol-3-yl)ethyl methanesulfonate (60.0 mg, 0.274 mmol), 3-methyl-1H-purine-2,6(3H,7H)-dione (74.0 mg, 0.411 mmol), potassium carbonate (113 mg, 0.822 mmol) and potassium iodide (5.0 mg, 0.027 mmol) were dissolved in N,N-dimethylformamide (8.0 mL), and the reaction solution was heated to 130° C. and stirred for 2.5 hours. The reaction solution was concentrated under reduced pressure, and purified by preparative HPLC to give 1-(2-(3-ethylisoxazol-5-yl)ethyl)-3,7-dimethyl-1H-purine-2,6(3H,7H)-dione (isomer 1) (13.0 mg). $^1$H NMR: (400 MHz, Methanol-d$_4$) δ 7.88 (s, 1H), 6.15 (s, 1H), 4.30 (t, J=7.6 Hz, 2H), 3.96 (s, 3H), 3.52 (s, 3H), 3.10 (t, J=7.2 Hz, 2H), 2.66-2.63 (m, 2H), 1.23 (t, J=7.6 Hz, 3H). MS-ESI calcd. [M+H]$^+$ 304, found 304. 1-(2-(5-ethylisoxazol-3-yl)ethyl)-3,7-dimethyl-1H-purine-2,6(3H,7H)-dione (isomer 2) (13.0 mg). Yield: 30%. $^1$H NMR: (400 MHz, Methanol-d$_4$) δ 7.87 (s, 1H), 6.13 (s, 1H), 4.28 (t, J=7.2 Hz, 2H), 3.96 (s, 3H), 3.52 (s, 3H), 2.97 (t, J=7.6 Hz, 2H), 2.78-2.72 (m, 2H), 1.27 (t, J=7.6 Hz, 3H). MS-ESI calcd. [M+H]$^+$ 304, found 304.

Example 18

3,7-Dimethyl-1-(3-(3-methylisoxazol-5-yl)propyl)-1H-purine-2,6(3H,7H)-dione

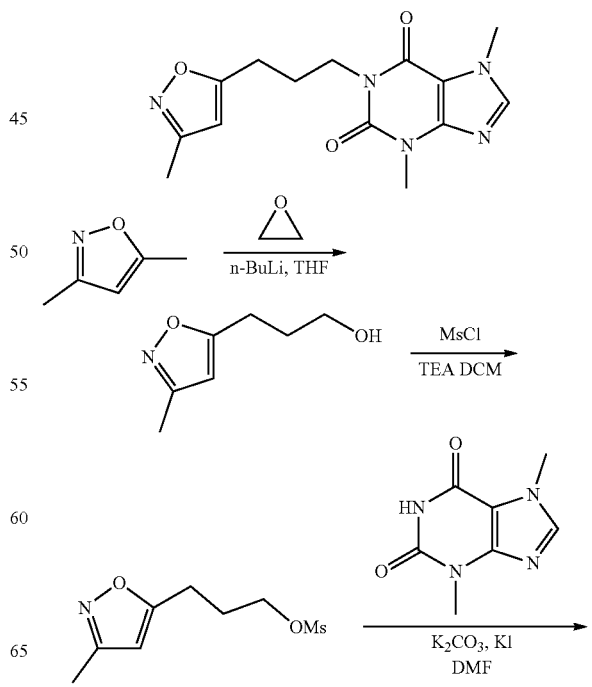

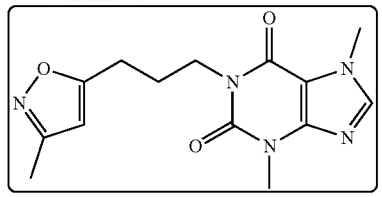

Step 1

3-(3-Methylisoxazol-5-yl)-1-propanol 3,5-Dimethyl-isoxazole (1.90 g, 19.6 mmol) was dissolved in anhydrous tetrahydrofuran (20 mL) and a solution of n-butyllithium (2.5 M n-hexane solution, 8 mL, 19.6 mmol) was slowly added dropwise at −68° C. under nitrogen atmosphere, and the reaction was stirred at −68° C. for 2 hours. Ethylene oxide (862 mg, 19.6 mmol) was slowly added and the stirring was continued for 1 hour. Water (100 mL) was added to quench the reaction. The reaction solution was extracted with ethyl acetate (30 mL×3), and the organic phases were combined, washed with saturated sodium chloride solution (30 mL×3), dried over anhydrous magnesium sulfate, filtered and the filtrate was concentrated under reduced pressure, and purified by silica gel column chromatography (3:1 petroleum ether/ethyl acetate, $R_f$ value=0.6) to give 3-(3-methylisoxazol-5-yl)-1-propanol (1.10 g, as a yellow oil) with a yield of 40%. MS-ESI calcd. $[M+H]^+$ 142, found 142.

Step 2

3-(3-Methylisoxazol-5-yl)propyl methanesulfonate 3-(3-Methylisoxazol-5-yl)-1-propanol (260 mg, 1.84 mmol) was dissolved in anhydrous dichloromethane (5 mL). Triethylamine (465 mg, 4.60 mmol) and methanesulfonyl chloride (252 mg, 2.20 mmol) were added at 0° C. under nitrogen atmosphere. The reaction solution was slowly allowed to warm to room temperature and stirred for 2 hours. Water (60 mL) was added to quench the reaction. The reaction solution was extracted with ethyl acetate (30 mL×3) and the organic phases were combined, washed with saturated sodium chloride solution (30 mL×2), dried over anhydrous magnesium sulfate, filtered and the filtrate was concentrated under reduced pressure and purified by silica gel column chromatography (2:1 petroleum ether/ethyl acetate, $R_f$ value=0.3) to give 3-(3-methylisoxazol-5-yl)propyl methanesulfonate (215 mg, as a yellow oil) with a yield of 53%. MS-ESI calcd. $[M+H]^+$ 220, found 220.

Step 3

3,7-Dimethyl-1-(3-(3-methylisoxazol-5-yl)propyl)-1H-purine-2,6(3H,7H)-dione 3-(3-Methylisoxazol-5-yl)propyl methanesulfonate (100 mg, 0.450 mmol) was dissolved in anhydrous N,N-methylformamide (5 mL). Potassium carbonate (126 mg, 0.900 mmol), potassium iodide (8.0 mg, 0.045 mmol) and 2,6-hydroxy-3,7-dimethylpurine (98.0 mg, 0.550 mmol) were added at room temperature under nitrogen atmosphere. The reaction solution was heated to 130° C. and stirred for 3 hours. Water (40 mL) was added to quench the reaction, and the reaction solution was extracted with ethyl acetate (30 mL×3). The organic phases were combined, washed with saturated sodium chloride solution (30 mL×2), dried over anhydrous magnesium sulfate, filtered and the filtrate was concentrated under reduced pressure. The resulting product was purified by preparative HPLC to give 3,7-dimethyl-1-(3-(3-methylisoxazol-5-yl)propyl)-1H-purine-2,6(3H,7H)-dione (23.0 mg) with a yield of 16%.

$^1$H NMR: (400 MHz, CDCl$_3$) δ 7.52 (s, 1H), 5.93 (s, 1H), 4.11 (t, J=7.2 Hz, 2H), 3.99 (s, 3H), 3.58 (s, 3H), 2.80 (t, J=8.0 Hz, 2H), 2.24 (s, 3H), 2.11-2.03 (m, 2H). MS-ESI calcd. $[M+H]^+$ 304, found 304.

Example 19

5-(4-Bromobutyl)-3-methylisoxazole

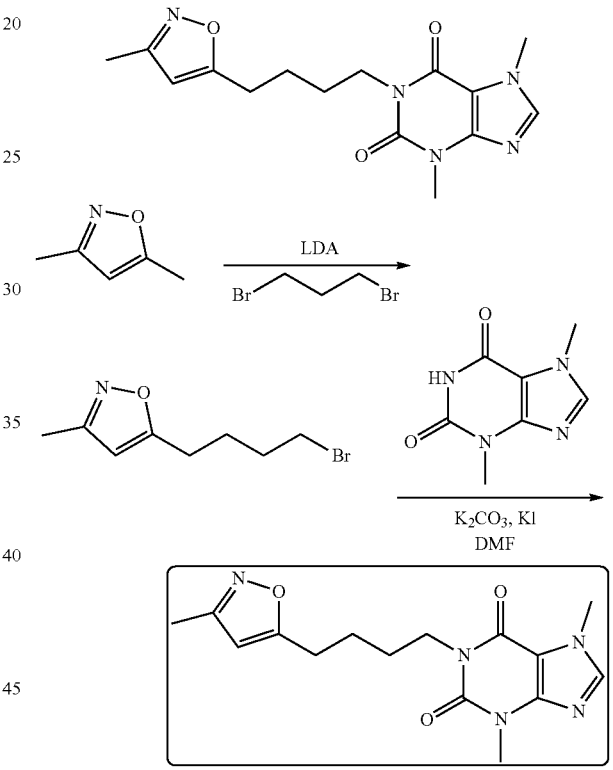

Step 1

5-(4-Bromobutyl)-3-methylisoxazole 3,5-Dimethylisoxazole (2.00 g, 20.6 mmol) and 1,3-dibromopropane (25.0 g, 124 mmol) were dissolved in tetrahydrofuran (100 mL) and a solution of lithium diisopropylamide (20.6 mmol) in tetrahydrofuran (10.3 mL, 2 M) was added at −60° C. under nitrogen atmosphere. The reaction was stirred at −60° C. for 1 hour and then slowly warmed to 20° C. and stirred for 2 hours. The reaction solution was quenched by the addition of saturated ammonium chloride solution (100 mL). The mixture was extracted with ethyl acetate (100 mL×3). The organic phase was washed with brine (100 mL×3), dried over anhydrous sodium sulfate and concentrated under reduced pressure. The reaction mixture was purified by silica gel column chromatography (5:1 petroleum ether/ethyl acetate, R$_f$=0.6) to give 5-(4-bromobutyl)-3-methylisoxazole (2.00 g, as a white solid) with a yield of 50%.

$^1$H NMR: (400 MHz, CDCl$_3$) δ 5.81 (s, 1H), 3.41-3.34 (m, 2H), 2.79-2.70 (m, 2H), 2.24 (s, 3H), 1.89-1.82 (m, 4H). MS-ESI calcd. [M+H]$^+$ 218 and 220, found 218 and 220.

Step 2

3,7-Dimethyl-1-(4-(3-methylisoxazol-5-yl)butyl)-1H-purine-2,6(3H,7H)-dione 3,7-Dimethyl-1H-purine-2,6(3H,7H)-dione (150 mg, 0.833 mmol) was dissolved in N,N-dimethylformamide (5 mL), and 5-(4-bromobutyl)-3-methylisoxazole (272 mg, 1.25 mmol) and potassium carbonate (345 mg, 2.50 mmol) were added. The reaction solution was stirred at 80° C. for 12 hours. Water (30 mL) was added and the reaction solution was extracted with ethyl acetate (100 mL×3). The organic phase was washed with brine (100 mL×3), dried over anhydrous sodium sulfate and concentrated under reduced pressure. The residue was purified by silica gel column chromatography (5:1 petroleum ether/ethyl acetate, Rf=0.6) to give 3,7-dimethyl-1-(4-(3-methylisoxazol-5-yl)butyl)-1H-purine-2,6(3H,7H)-dione (50.0 mg) with a yield of 19%.

$^1$H NMR: (400 MHz, Methanol-d$_4$) δ 7.85 (s, 1H), 6.03 (s, 1H), 4.02-3.99 (m, 2H), 3.96 (s,), 3.51 (s, 3H), 2.79-2.76 (m, 2H), 2.22 (s, 3H), 1.72-1.70 (m, 4H). MS-ESI calcd. [M+H]$^+$ 318, found 318.

Example 20

3,7-Dimethyl-1-(4-(5-methylisoxazol-3-yl)butyl)-1H-purine-2,6(3H,7H)-dione

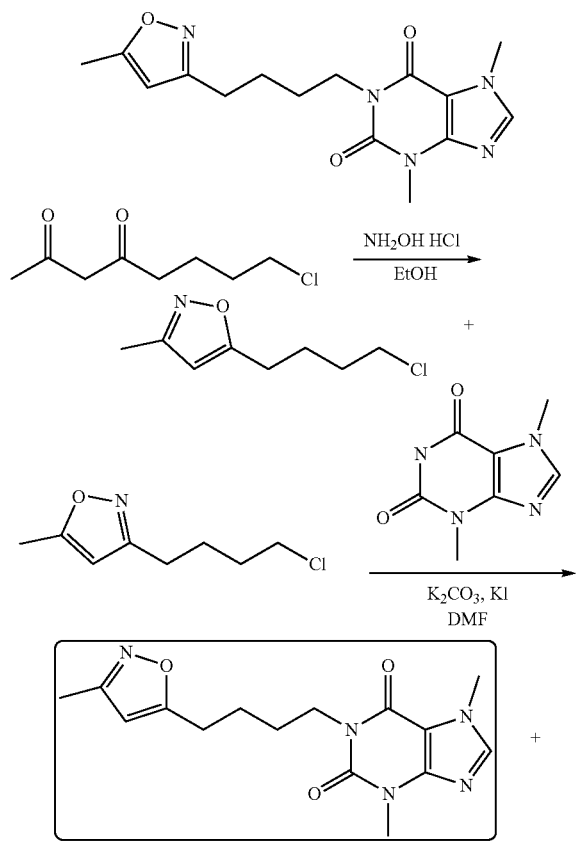

Step 1

5-(4-Chlorobutyl)-3-methylisoxazole 3-(4-Chlorobutyl)-5-methylisoxazole

8-Chlorooctane-2,4-dione (1.00 g, 5.70 mmol) was dissolved in anhydrous ethanol (5 mL) and hydroxylamine hydrochloride (3.90 g, 57.0 mmol) was added at room temperature under nitrogen atmosphere. The reaction solution was heated to 100° C. and stirred for 3 hours. Water (60 mL) was added to quench the reaction. The reaction solution was extracted with ethyl acetate (30 mL×3). The organic phases were combined, washed with saturated sodium chloride solution (30 mL×2), dried over anhydrous magnesium sulfate, filtered, the filtrate was concentrated under reduced pressure and purified by silica gel column chromatography (10:1 petroleum ether/ethyl acetate, R$_f$=0.3) to give a mixture of 5-(4-chlorobutyl)-3-methylisoxazole and 3-(4-chlorobutyl)-5-methylisoxazole (900 mg, as a yellow oil) with a yield of 92%. MS-ESI calcd. [M+H]$^+$ 174, found 174.

Step 2

3,7-Dimethyl-1,4-(5-methylisoxazol-3-yl)butyl)-1H-purine-2,6(3H,7H)-dione

A mixture of 5-(4-chlorobutyl)-3-methylisoxazole and 3-(4-chlorobutyl)-5-methylisoxazole (400 mg, 2.32 mmol) was dissolved in N,N-dimethylformamide (10 mL). Potassium carbonate (638 mg, 4.64 mmol), potassium iodide (38.0 mg, 0.230 mmol) and 2,6-hydroxy-3,7-dimethylpurine (502 mg, 2.80 mmol) were added at room temperature under nitrogen atmosphere. The reaction solution was heated to 130° C. and stirred for 3 hours. Water (60 mL) was added to quench the reaction. The reaction solution was extracted with ethyl acetate (30 mL×3) and the organic phases were combined, washed with saturated sodium chloride solution (30 mL×3), dried over anhydrous magnesium sulfate, filtered, the filtrate was concentrated under reduced pressure and purified with a highly performance preparative plate to obtain a mixture of two substituted isomers (400 mg, as a yellow solid) with a yield of 68%. The mixture was separated by chiral resolution to give 3,7-dimethyl-1,4-(3-methylisoxazol-3-yl)butyl)-1H-purine-2,6(3H,7H)-dione (Example 19, first peak) (40.0 mg) and 3,7-dimethyl-1-4-(5-methylisoxazol-3-yl)butyl)-1H-purine-2,6(3H,7H)-dione (Example 20, second peak) (50.0 mg).

3,7-Dimethyl-1-4-(5-methylisoxazol-3-yl)butyl)-1H-purine-2,6(3H,7H)-dione $^1$H NMR: (400 MHz, CDCl$_3$) δ 7.50 (s, 1H), 5.81 (s, 1H), 4.03-3.99 (m, 2H), 3.96 (s, 3H), 3.54 (s, 3H), 2.66-2.62 (m, 2H), 2.34 (s, 3H), 1.70-1.69 (m, 4H). MS-ESI calcd. [M+H]$^+$ 318, found 318.

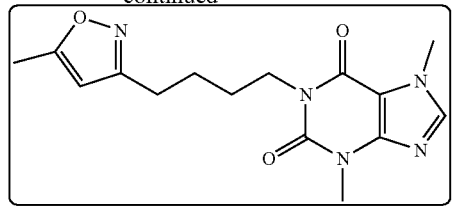

Example 21

1-(2-(3,5-Dimethylisoxazol-4-yl)ethyl)-3,7-dimethyl-1H-purine-2,6(3H,7H)-dione

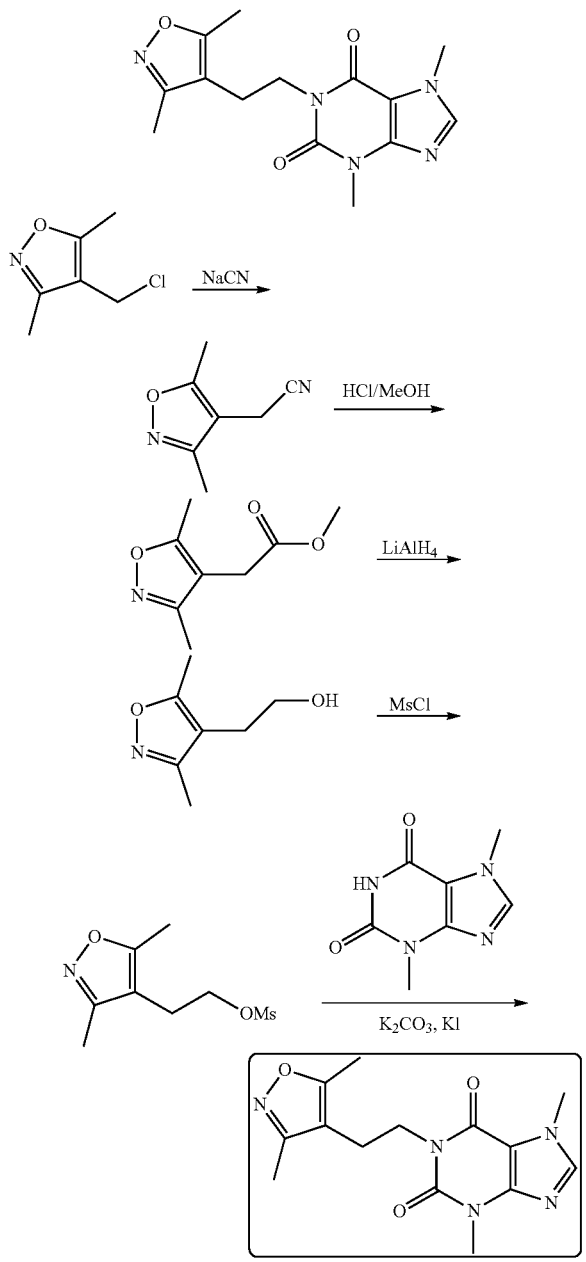

Step 1

2-(3,5-Dimethylisoxazol-4-yl)acetonitrile

4-Chloromethyl-3,5-dimethylisoxazole (300 mg, 2.07 mmol) was dissolved in dimethyl sulfoxide (3 mL) and sodium cyanide (121 mg, 2.48 mmol) was added at 25° C. The reaction was warmed to 60° C. and reacted for 3 hours. The reaction was cooled to 25° C., followed by adding water (10 mL). The reaction was extracted with ethyl acetate (10 mL×3). The organic phases were combined, dried over anhydrous sodium sulfate and concentrated under reduced pressure to give 2-(3,5-dimethylisoxazol-4-yl)acetonitrile (200 mg, as a yellow oil) with a yield of 71%.

$^1$H NMR: (400 MHz, Methanol-$d_4$) δ 3.67 (s, 2H), 2.30 (s, 3H), 2.28 (s, 3H).

Step 2

2-(3,5-dimethylisoxazol-4-yl)acetate 2-(3,5-Dimethylisoxazol-4-yl)acetonitrile (200 mg, 1.08 mmol) was dissolved in hydrochloride/methanol (5 mL). The reaction was warmed to 60° C. and reacted for 3 hours. The reaction was cooled to 25° C., water (10 mL) was added and the pH was adjusted to about 7 with saturated sodium bicarbonate solution (10 mL). The reaction was extracted with ethyl acetate (10 mL×3). The organic phases were combined, dried over anhydrous sodium sulfate and concentrated under reduced pressure to give methyl 2-(3,5-dimethylisoxazol-4-yl)acetate (200 mg, as a yellow oil) with a yield of 80%.

$^1$H NMR: (400 MHz, Methanol-$d_4$) δ 3.72 (s, 3H), 3.46 (s, 2H), 2.35 (s, 3H), 2.20 (s, 3H).

Step 3

2-(3,5-Dimethylisoxazol-4-yl)ethanol

Methyl 2-(3,5-dimethylisoxazol-4-yl)acetate (180 mg, 1.06 mmol) was dissolved in anhydrous tetrahydrofuran (2 mL), and lithium aluminum tetrahydrate (80.5 mg, 2.12 mmol) was added at 0° C. The reaction solution was heated to 25° C. and stirred for 1 hour. The reaction was quenched by adding water (2 mL), extracted with ethyl acetate (10 mL×3), dried over anhydrous sodium sulfate and filtered. The filtrate was concentrated under reduced pressure and purified by preparative TLC plate (1:1 petroleum ether/ethyl acetate, $R_f$=0.2) to give 2-(3,5-dimethylisoxazol-4-yl)ethanol (100.0 mg, as a yellow oil) with a yield of 67%.

$^1$H NMR: (400 MHz, Methanol-$d_4$) δ 3.65-3.62 (m, 2H), 2.59-2.55 (m, 2H), 2.38 (s, 3H), 2.25 (s, 3H).

Step 4

2-(3,5-Dimethylisoxazol-4-yl)ethyl methanesulfonate 2-(3,5-Dimethylisoxazol-4-yl)ethanol (100 mg, 0.708 mmol) was dissolved in dichloromethane (3 mL), and triethylamine (143 mg, 1.42 mmol) and methanesulfonyl chloride (79.3 mg, 0.708 mmol) were added at 0° C. The reaction solution was reacted at 25° C. for 2 hours, and then quenched by adding sodium bicarbonate saturated aqueous solution (10 mL) and extracted with dichloromethane (10 mL×3). The organic phases were combined, washed with saturated sodium chloride solution (10 mL×3), dried over anhydrous sodium sulfate, filtered, and the filtrate was concentrated under reduced pressure to give 2-(3,5-dimethylisoxazol-4-yl)ethyl methanesulfonate (100 mg, as a yellow oil) with a yield of 64%.

Step 5

1-(2-(3,5-Dimethylisoxazol-4-yl)ethyl)-3,7-dimethyl-1H-purine-2,6(3H,7H)-dione 2-(3,5-Dimethylisoxazol-4-yl)ethyl methanesulfonate (100 mg, 0.457 mmol), 3,7-dimethyl-1H-purine-2,6(3H, 7H)-dione (82.2 mg, 0.457 mmol), potassium iodide (7.2 mg, 0.046 mmol) and potassium carbonate (126 mg, 0.914 mmol) were dissolved in anhydrous N,N-dimethylformamide (3 mL). The reaction solution was heated to 120° C. and reacted for 3 hours. The reaction solution was cooled to 20° C., filtered and purified by preparative HPLC to give 1-(2-(3,5-dimethylisoxazol-4-yl)ethyl)-3,7-dimethyl-1H-purine-2,6(3H,7H)-dione (50.0 mg) with a yield of 36%.

$^1$H NMR: (400 MHz, Methanol-$d_4$) δ 7.88 (s, 1H), 4.11-4.07 (m, 2H), 3.97 (s, 3H), 3.54 (s, 3H), 2.74-2.71 (m, 2H), 2.30 (s, 3H), 2.29 (s, 3H). MS-ESI calcd. [M+H]$^+$ 304, found 304.

Example 22

1-((5-Isopropylisoxazol-4-yl)-3,7-dimethyl-1H-purine-2,6(3H,7H)-dione

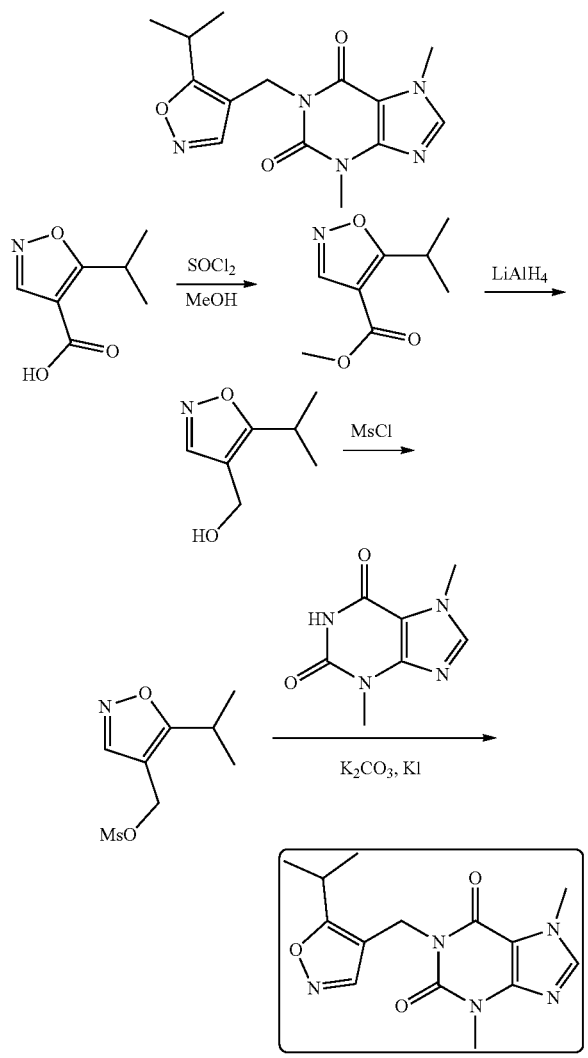

Step 1

Methyl 5-isopropylisoxazol-4-carboxylate

5-Isopropylisoxazol-4-carboxylic acid (1.00 g, 6.45 mmol) was dissolved in methanol (2 mL), and thionyl chloride (1.51 g, 12.9 mmol) was slowly added at 0° C. The reaction solution was slowly warmed to 25° C. and stirred for 12 hours. The reaction was quenched by addition of water (30 mL), extracted with ethyl acetate (100 mL×3). The organic phase was dried over anhydrous sodium sulfate, filtered and the filtrate was concentrated under reduced pressure to give the product methyl 5-isopropylisoxazol-4-carboxylate (800 mg, as a yellow oil) with a yield of 73%.

$^1$H NMR: (400 MHz, Methanol-$d_4$) δ 6.55 (s, 1H), 3.95 (s, 3H), 3.20-3.17 (m, 1H), 1.35 (d, J=3.4 Hz, 6H).

Step 2

(5-Isopropylisoxazol-4-yl)methanol

Lithium aluminum hydride (231 mg, 5.92 mmol) was slowly dissolved in tetrahydrofuran (60 mL) at 0° C. under nitrogen atmosphere and a solution of methyl 5-isopropylisoxazol-4-carboxylate (500 mg, 2.96 mmol) in tetrahydrofuran (10 mL) was added slowly. The reaction solution was slowly warmed to 25° C. and stirred for 1.5 hours. The reaction solution was cooled to 0° C., followed by slowly adding water (2.3 mL), 15% sodium hydroxide solution (2.3 mL) and water (9.9 mL) successively. The reaction was warmed to 25° C., stirred for half an hour, filtered and the filter cake was washed with tetrahydrofuran (10 mL×3). The filtrate was concentrated under reduced pressure to give the product (5-isopropylisoxazol-4-yl) methanol (250 mg, as a yellow oil) with a yield of 60%.

$^1$H NMR: (400 MHz, Methanol-$d_4$) δ 6.18 (s, 1H), 4.62 (s, 2H), 3.12-3.08 (m, 1H), 1.32 (d, J=3.4 Hz, 6H).

Step 3

(5-Isopropylisoxazol-4-yl)methyl methanesulfonate (5-Isopropylisoxazol-4-yl)methanol (250 mg, 1.77 mmol) and triethylamine (358 mg, 3.55 mmol) were dissolved in dichloromethane (5 mL) at 0° C., and methanesulfonyl chloride (238 mg, 2.12 mmol) was added. The reaction solution was slowly warmed to 25° C. and stirred overnight. The reaction was quenched with water (30 mL) and extracted with dichloromethane (10 mL×3). The organic phases were combined, dried over anhydrous sodium sulfate, filtered and the filtrate was concentrated under reduced pressure to give the product (5-isopropylisoxazole-4-yl) methyl methanesulfonate (200 mg, as a yellow oil) with a yield of 52%.

$^1$H NMR: (400 MHz, Methanol-$d_4$) δ 6.38 (s, 1H), 5.29 (s, 2H), 3.28 (s, 3H), 3.11-3.06 (m, 1H), 1.24 (d, J=3.4 Hz, 6H).

Step 4

1-((5-Isopropylisoxazol-4-yl)methyl)-3,7-dimethyl-1H-purine-2,6(3H,7H)-dione (5-Isopropylisoxazol-4-yl)methanesulfonate (219 mg, 1.00 mmol), 3,7-dimethyl-1H-purine-2,6(3H,7H)-dione (180 mg, 1.00 mmol) and potassium carbonate (414 mg, 3.00 mmol) were dissolved in N,N-dimethylformamide (4 mL), and potassium iodide (17.0 mg, 0.100 mmol) was added and the reaction was heated to 120° C. and stirred for 3 hours. The reaction solution was cooled to 25° C. followed by adding brine (30 mL), and then extracted with ethyl acetate (100 mL×3). The organic phases were combined, dried over anhydrous sodium sulfate, filtered and the filtrate was concentrated under reduced pressure. The residue was purified by preparative HPLC to give 1-((5-isopropylisoxazol-4-yl)3,7-dimethyl-1H-purine-2,6(3H,7H)-dione (50.0 mg) with a yield of 17%.

$^1$H NMR: (400 MHz, Methanol-d$_4$) δ 7.92 (s, 1H), 6.27 (s, 1H), 5.27 (s, 2H), 4.00 (s, 3H), 3.56 (s, 3H), 3.03-2.97 (m, 1H), 1.26 (d, J=3.4 Hz, 6H). MS-ESI calcd. [M+H]$^+$ 304, found 304.

Example 23

1-((5-Isopropylisoxazol-3-yl)methyl)-3,7-dimethyl-1H-purine-2,6(3H,7H)-dione

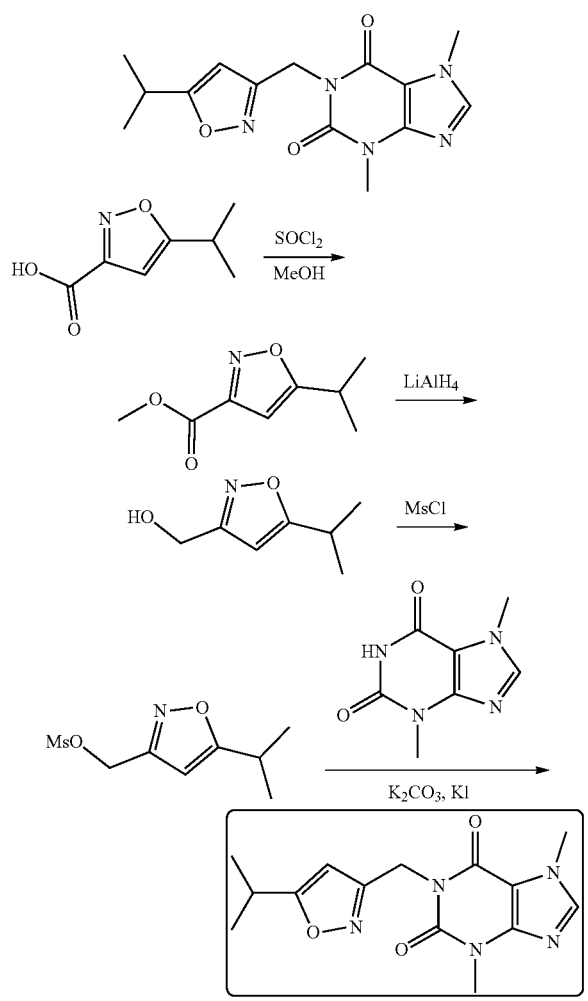

Step 1

Methyl 5-isopropylisoxazole3-carboxylate

5-Isopropylisoxazol-3-carboxylic acid (1.00 g, 6.45 mmol) was dissolved in methanol (20 mL), and thionyl chloride (1.51 g, 12.9 mmol) was slowly added at 0° C. The reaction solution was slowly warmed to 25° C. and stirred for 12 hours. The reaction was quenched by addition of water (20 mL), extracted with ethyl acetate (100 mL×3). The organic phase was dried over anhydrous sodium sulfate, filtered and the filtrate was concentrated under reduced pressure to give the product methyl 5-isopropylisoxazol-3-carboxylate (800 mg, as a yellow oil) with a yield of 73%.

$^1$H NMR: (400 MHz, Methanol-d$_4$) δ 7.05 (s, 1H), 3.93 (s, 3H), 3.12-3.08 (m, 1H), 1.30 (d, J=3.6 Hz, 6H).

Step 2

(5-Isopropylisoxazol-3-yl)methanol

Lithium aluminum hydride (231 mg, 5.92 mmol) was slowly dissolved in tetrahydrofuran (60 mL) at 0° C. under nitrogen atmosphere and a solution of methyl 5-isopropylisoxazol-3-carboxylate (500 mg, 2.96 mmol) in tetrahydrofuran (10 mL) was slowly added. The reaction solution was slowly warmed to 25° C. and stirred for 1.5 hours. The reaction solution was cooled to 0° C., followed by slowly adding water (0.2 mL), 15% sodium hydroxide (0.2 mL) and water (0.7 mL) successively. The reaction was warmed to 25° C., stirred for half an hour, filtered and the filter cake was washed with tetrahydrofuran (10 mL×3). The filtrate was concentrated under reduced pressure to give the product (5-isopropylisoxazol-3-yl)methanol (250 mg, as a yellow oil) with a yield of 60%.

$^1$H NMR: (400 MHz, Methanol-d$_4$) δ 6.29 (s, 1H), 4.64 (s, 2H), 3.08-3.01 (m, 1H), 1.29 (d, J=3.4 Hz, 6H).

Step 3

(5-isopropylisoxazol-3-yl)methyl methanesulfonate (5-Isopropylisoxazol-3-yl)methanol (250 mg, 1.77 mmol) and triethylamine (358 mg, 3.55 mmol) were dissolved in dichloromethane (5 mL), and methanesulfonyl chloride (238 mg, 2.12 mmol) was added at 0° C. The reaction solution was slowly warmed to 25° C. and stirred overnight. The reaction was quenched with water (20 mL) and extracted with dichloromethane (10 mL×3). The organic phases were combined, dried over anhydrous sodium sulfate and filtered. The filtrate was concentrated under reduced pressure to give the product (5-isopropylisoxazol-3-yl)methyl methanesulfonate (200 mg, as a yellow oil) with a yield of 52%.

$^1$H NMR: (400 MHz, Methanol-d$_4$) δ 6.67 (s, 1H), 5.37 (s, 2H), 3.27 (s, 3H), 3.02-2.99 (m, 1H), 1.20 (d, J=3.4 Hz, 6H).

Step 4

1-((5-Isopropylisoxazol-3-yl)methyl)-3,7-dimethyl-1H-purine-2,6(3H,7H)-dione (5-Isopropylisoxazol-3-yl)methanesulfonate (219 mg, 1.00 mmol), 3,7-dimethyl-1H-purine-2,6(3H,7H)-dione (180 mg, 1.00 mmol) and potassium carbonate (414 mg, 3.00 mmol) were dissolved in N,N-dimethylformamide (4 mL), potassium iodide (17.0 mg, 0.100 mmol) was added and the reaction was heated to 120° C., and stirred for 3 hours. The reaction solution was cooled to 25° C. followed by adding brine (20 mL), and then extracted with ethyl acetate (20 mL×3). The organic phases were combined, dried over anhydrous sodium sulfate, filtered and the filtrate was concentrated under reduced pressure. The residue was purified by preparative HPLC to give 1-((5-isopropylisoxazol-3-yl)-3,7-dimethyl-1H-purine-2,6(3H,7H)-dione (50.0 mg) with a yield of 17%.

$^1$H NMR: (400 MHz, Methanol-d$_4$) δ 7.91 (s, 1H), 6.13 (s, 1H), 5.22 (s, 2H), 4.00 (s, 3H), 3.56 (s, 3H), 3.09-3.03 (m, 1H), 1.29 (d, J=3.4 Hz, 6H). MS-ESI calcd. [M+H]$^+$ 304, found 304.

Example 24

1-(5-Ethyl-isoxazol-3-ylmethyl)-3,7-dimethyl-3,7-dihydro-purine-2,6-dione

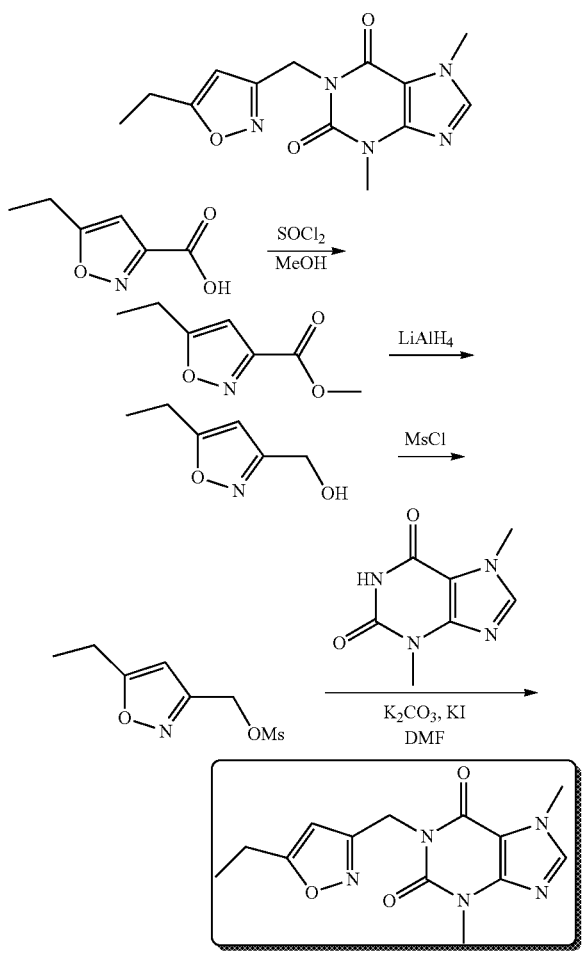

Step 1

Methyl 5-ethylisoxazole-3-carboxylate

5-Ethylisoxazole-3-carboxylic acid (500 mg, 3.54 mmol) was dissolved in methanol (4 mL) and thionyl chloride (631 mg, 5.31 mmol) was added at 0° C. to react for 0.5 h. The reaction was quenched by the addition of saturated sodium bicarbonate solution (20 mL). The reaction solution was extracted with ethyl acetate (10 mL×3), dried over anhydrous sodium sulfate, filtered and the filtrate was concentrated under reduced pressure to give methyl 5-ethylisoxazole-3-carboxylate (490 mg, as a yellow oil) with a yield of 89%. MS-ESI calcd. [M+H]$^+$ 156, found 156.

Step 2

(5-Ethyl-isoxazol-3-yl) methanol

Methyl 5-ethylisoxazole-3-carboxylate (100 mg, 0.645 mmol) was dissolved in tetrahydrofuran (5 mL), and lithium aluminum hydride (36.7 mg, 0.967 mmol) was added in batches at 0° C., followed by stirring under nitrogen atmosphere for 1 hour. The reaction solution was cooled to 0° C., followed by slowly adding water (0.04 mL), 15% sodium hydroxide (0.04 mL) and water (0.12 mL) successively, and then filtered. The filtrate was concentrated under reduced pressure to give the product (5-ethyl-isoxazol-3-yl) methanol (70.0 mg, as a yellow oil) with a yield of 85%.

$^1$H NMR: (400 MHz, CDCl$_3$) δ 6.04 (s, 1H), 4.71 (s, 2H), 2.76 (q, J=7.6 Hz, 2H), 2.57 (br, 1H), 1.29 (t, J=7.6 Hz, 3H).

Step 3

Methyl 5-ethyl-isoxazol-3-yl methanesulfonate (4,4-Difluoro-cyclohexyl)methanol (70.0 mg, 0.551 mmol) and triethylamine (167 mg, 1.65 mmol) were dissolved in dichloromethane (10 mL), and methanesulfonyl chloride (126 mg, 1.10 mmol) was slowly added at 0° C. The reaction solution was stirred at 0° C. for 4 hours. The reaction was quenched with water (10 mL) and extracted with dichloromethane (10 mL×2). The organic phases were combined, washed successively with saturated aqueous sodium bicarbonate solution (10 mL) and brine (10 mL), dried over anhydrous sodium sulfate, filtered and the filtrate was concentrated under reduced pressure to give methyl 5-ethyl-isoxazol-3-yl methanesulfonate (90.0 mg, as a yellow oil) with a yield of 80%.

$^1$H NMR: (400 MHz, CDCl$_3$) δ 6.17 (s, 1H), 5.28 (s, 2H), 3.08 (s, 3H), 2.82 (q, J=7.6 Hz, 2H), 1.33 (t, J=7.6 Hz, 3H). MS-ESI calcd. [M+H]$^+$ 206, found 206.

Step 4

1-(5-Ethyl-isoxazol-3-ylmethyl)-3,7-dimethyl-3,7-dihydro-purine-2,6-dione 3,7-Dimethyl-1H-purine-2,6(3H,7H)-dione (79.0 mg, 0.439 mmol) was dissolved in N,N-dimethylformamide (100 mL), and methyl 5-ethyl-isoxazol-3-yl methanesulfonate (90.0 mg, 0.439 mmol), potassium carbonate (121 mg, 0.876 mmol) and potassium iodide (87.3 mg, 0.526 mmol) were added. The reaction solution was heated to 120° C. and stirred for 3 hours, and then concentrated under reduced pressure. The residue was purified by preparative TLC plate (1:2 petroleum ether/ethyl acetate, R$_f$=0.2) to give 1-(5-ethyl-isoxazol-3-ylmethyl)-3,7-dimethyl-3,7-dihydro-purine-2,6-dione (48.0 mg) with a yield of 38%.

$^1$H NMR: (400 MHz, CDCl$_3$) δ 7.53 (s, 1H), 6.00 (s, 1H), 5.26 (s, 2H), 4.00 (s, 3H), 3.60 (s, 3H), 2.72 (q, J=7.6 Hz, 2H), 1.26 (t, J=7.6 Hz, 3H). MS-ESI calcd. [M+H]$^+$ 290, found 290.

Example 25

1-((3,5-Dimethylisoxazol-4-yl)methyl)-3,7-dimethyl-1H-purine-2,6(3H,7H)-dione

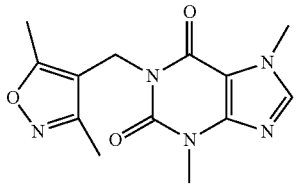

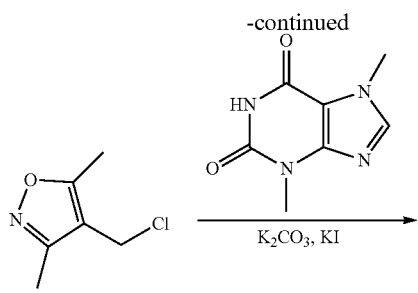

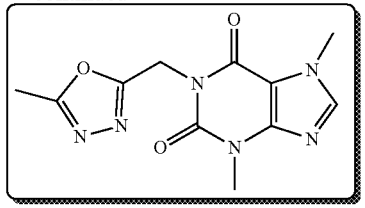

Step 1

1-((3,5-Dimethylisoxazol-4-yl)methyl)-3,7-dimethyl-1H-purine-2,6(3H,7H)-dione

4-Chloromethyl-3,5-dimethylisoxazole (100 mg, 0.689 mmol), 3,7-dimethyl-1H-purine-2,6(3H,7H)-dione (124 mg, 0.689 mmol), potassium iodide (10.9 mg, 0.0689 mmol) and potassium carbonate (190 mg, 1.38 mmol) were dissolved in anhydrous N,N-dimethylformamide (3 mL). The reaction was heated to 120° C. and reacted for 3 hours. The reaction solution was cooled to 20° C. and filtered, and then purified by preparative HPLC to give 1-((3,5-dimethylisoxazol-4-yl)methyl)-3,7-dimethyl-1H-purine-2,6(3H,7H)-dione (30.0 mg) with a yield of 15%.

$^1$H NMR: (400 MHz, Methanol-$d_4$) δ 7.73 (s, 1H), 4.94 (s, 2H), 4.03 (s, 3H), 3.60 (s, 3H), 2.50 (s, 3H), 2.32 (s, 3H). MS-ESI calcd. [M+H]$^+$ 290, found 290.

Example 26

3,7-Dimethyl-1-((5-methyl-1,3,4-oxadiazol-2-yl)methyl)-1H-purine-2,6(3H,7H)-dione

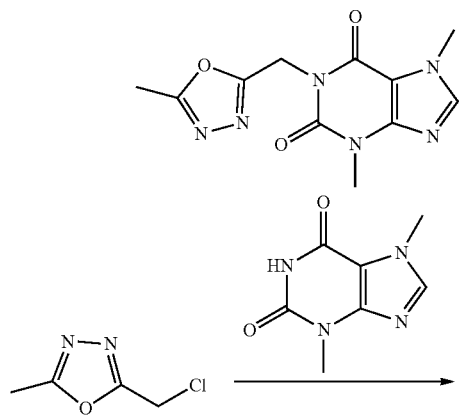

Step 1

3,7-Dimethyl-1-((5-methyl-1,3,4-oxadiazol-2-yl)methyl)-1H-purine-2,6(3H,7H)-dione 2-Chloromethyl-5-methyl-1,3,4-oxadiazole (100 mg, 0.758 mmol), 3,7-dimethyl-1H-purine-2,6(3H,7H)-dione (136 mg, 0.758 mmol), potassium iodide (12.0 mg, 0.0758 mmol) and potassium carbonate (209 mg, 1.52 mmol) were dissolved in anhydrous N,N-dimethylformamide (3 mL). The reaction was heated to 120° C. and reacted for 3 hours. The reaction solution was cooled to 20° C., filtered and purified by preparative HPLC to give 3,7-dimethyl-1-((5-methyl-1,3,4-oxadiazol-methyl)-1H-purine-2,6(3H,7H)-dione (30.0 mg) with a yield of 34%.

$^1$H NMR: (400 MHz, Methanol-$d_4$) δ 7.94 (s, 1H), 5.39 (s, 2H), 4.00 (s, 3H), 3.57 (s, 3H), 2.54 (s, 3H). MS-ESI calcd. [M+H]$^+$ 277, found 277.

Example 27

3,7-Dimethyl-1-(4-(3-methylisoxazol-5-yl)cyclohexyl)-1H-purine-2,6(3H,7H)-dione

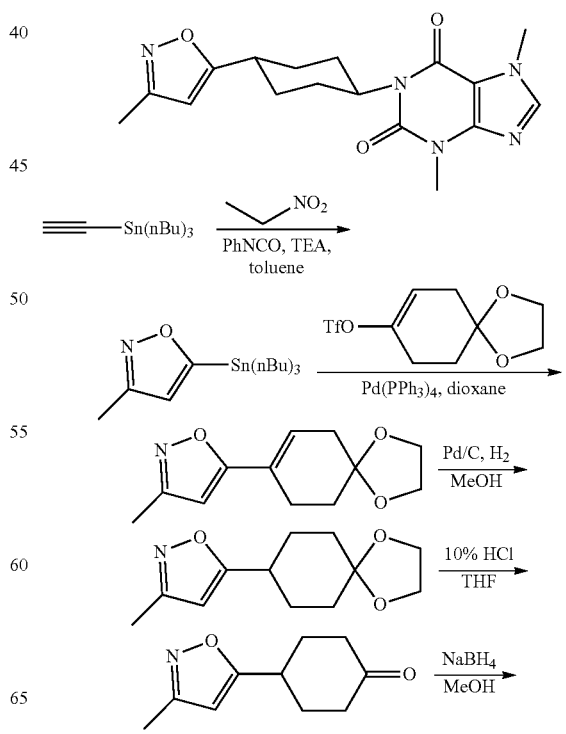

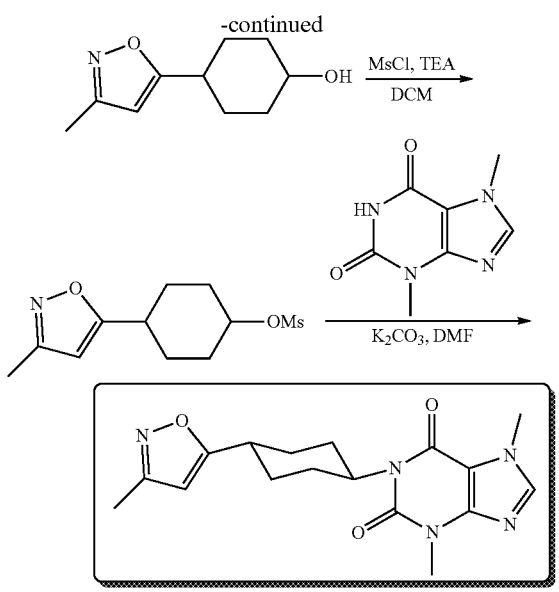

Step 1

3-Methyl-5-(tributylstannyl)isoxazole

Nitroethane (1.65 g, 22.0 mmol) and phenyl isocyanate (10.4 g, 87.7 mmol) were dissolved in dry toluene (20 mL), heated to 50° C. and stirred for 5 minutes, and tributylstannyl acetylene (6.30 g, 20.0 mmol) and triethylamine (3.7 mg, 0.0364 mmol) were added. The reaction solution was further stirred at 50° C. for 14 hours, and then diluted with ethyl acetate (70 mL). The organic phase was washed with water (50 mL×2), dried over anhydrous sodium sulfate, filtered and concentrated. The residue was purified by silica gel column chromatography (5:1 petroleum ether/ethyl acetate, $R_f$=0.5) to give 3-methyl-5-(tributylstannyl)isoxazole (6.35 g, as a yellow oil) with a yield of 85%.
$^1$H NMR: (400 MHz, CDCl$_3$) δ 6.19 (s, 1H), 2.31 (s, 3H), 1.55-1.53 (m, 5H), 1.35-1.29 (m, 7H), 1.15-1.11 (m, 5H), 0.90-0.87 (m, 10H). MS-ESI calcd. [M+H]$^+$ 374, found 374.

Step 2

3-Methyl-5-(1,4-dioxaspiro[4.5]dec-7-en-8-yl)isoxazole

3-Methyl-5-(tributylstannyl)isoxazole (4.00 g, 10.7 mmol) was dissolved in 1,4-dioxane (30 mL). 1,4-Dioxaspiro[4.5]dec-7-en-8-yl trifluoromethanesulfonate (2.57 g, 8.93 mmol) and tetrakis(triphenylphosphine)palladium(1.02 g, 0.883 mmol) were added to the reaction solution at 25° C. The reaction was heated to 120° C. and stirred for 2 hours. The reaction was cooled to 25° C., diluted with ethyl acetate (70 mL), washed with saturated sodium bicarbonate solution (30 mL×2), dried over anhydrous sodium sulfate, concentrated and purified by silica gel column chromatography (5:1 petroleum ether/ethyl acetate, $R_f$=0.3) to give 3-methyl-5-(1,4-dioxaspiro[4.5]dec-7-en-8-yl) isoxazole (1.21 g, as a yellow oil) with a yield of 62%. MS-ESI calcd. [M+H]+ 222, found 222.

Step 3

3-Methyl-5-(1,4-dioxaspiro[4.5]dec-8-yl)isoxazole

3-Methyl-5-(1,4-dioxaspiro[4.5]dec-7-en-8-yl)isoxazole (800 mg, 3.62 mmol) was dissolved in methanol (30 mL), and Pd/C (10%, 20.0 mg, 0.171 mmol) was added at 25° C. The reaction solution was stirred under hydrogen balloon for 2 hours, filtered and the filter cake was washed with methanol. The filtrates were combined and concentrated to give 3-methyl-5-(1,4-dioxaspiro[4.5]dec-8-yl)isoxazole (500 mg, as a colorless oil) with a yield of 62%. MS-ESI calcd. [M+H]$^+$ 224, found 224.

Step 4

4-(3-Methylisoxazol-5-yl)cyclohexanone

3-Methyl-5-(1,4-dioxaspiro[4.5]dec-8-yl)isoxazole (500 mg, 2.24 mmol) was dissolved in tetrahydrofuran (15 mL), and 10% hydrochloric acid (5 mL) was added at 25° C. The reaction solution was stirred at 50° C. for 1 hour, cooled to 25° C., diluted with ethyl acetate (20 mL), washed with saturated sodium bicarbonate solution (20 mL×2), dried over anhydrous sodium sulfate, filtered, and the filtrate was concentrated to give 4-(3-methylisoxazol-5-yl)cyclohexanone (220 mg, as a colorless oil) with a yield of 55%. MS-ESI calcd. [M+H]$^+$ 180, found 180.

Step 5

4-(3-Methylisoxazol-5-yl)cyclohexanol 4-(3-Methylisoxazol-5-yl)cyclohexanone (400 mg, 2.23 mmol) was dissolved in methanol (30 mL), and sodium borohydride (84.9 mg, 2.23 mmol) was added at 25° C. The reaction solution was stirred at 25° C. for 4 hours. The reaction was quenched by addition of water (10 mL) and extracted with ethyl acetate (30 mL). The organic phase was washed with saturated sodium bicarbonate solution (20 mL×2), dried over anhydrous sodium sulfate, filtered, and the filtrate was concentrated under reduced pressure. The residue was purified by silica gel column chromatography (2:1 petroleum ether/ethyl acetate, $R_f$=0.5) to give 4-(3-methylisoxazol-5-yl)cyclohexanol (200 mg, as a colorless oil) with a yield of 50%. MS-ESI calcd. [M+H]$^+$ 182, found 182.

Step 6

4-(3-Methylisoxazol-5-yl)cyclohexyl methanesulfonate 4-(3-Methylisoxazol-5-yl)cyclohexanol (100 mg, 0.552 mmol) and triethylamine (111 mg, 1.10 mmol) were dissolved in dichloromethane (20 mL), methanesulfonyl chloride (94.9 mg, 0.829 mmol) was added at 0° C. The reaction solution was stirred at 25° C. for 2 hours, diluted with dichloromethane (20 mL), washed with saturated sodium bicarbonate solution (30 mL×2), dried over anhydrous sodium sulfate, filtered and the filtrate was concentrated under reduced pressure, and then purified by silica gel column chromatography (4:1 petroleum ether/ethyl acetate, $R_f$=0.5) to give 4-(3-methylisoxazol-5-yl)cyclohexyl methanesulfonate (100 mg, as a colorless oil) with a yield of 50%. MS-ESI calcd. [M+H]$^+$ 260, found 260.

Step 7

3,7-Dimethyl-1-(4-(3-methylisoxazol-5-yl)cyclohexyl)-1H-purine-2,6(3H,7H)-dione 4-(3-Methylisoxazol-5-yl)cyclohexyl methanesulfonate was dissolved in N,N-dimethylformamide (10 mL), and 3,7-dimethyl-1H-purine-2,6(3H,7H)-dione (55.6 mg, 0.309 mmol) and cesium carbonate (110 mg, 0.309 mmol) were added into the reaction solution at 25° C. The reaction solution was heated to 100° C., reacted for 2 hours, diluted with ethyl acetate (20 mL). The organic phase was washed with saturated sodium bicarbonate solution (20 mL×2), dried over anhydrous sodium sulfate, filtered and the filtrate was concentrated under reduced pressure, and then purified by HPLC to give 3,7-dimethyl-1-(4-(3-methylisoxazol-5-yl) cyclohexyl)-1H-purine-2,6(3H,7H)-dione (4.0 mg) with a yield of 9%.

$^1$H NMR: (400 MHz, Methanol-d$_4$) δ 7.84 (s, 1H), 6.32 (s, 1H), 3.96 (s, 3H), 3.51 (s, 3H), 3.21 (m, 1H), 2.91-2.72 (m, 1H), 2.68-2.63 (m, 2H), 2.33 (s, 3H), 2.27 (m, 1H), 1.95-1.88 (m, 2H), 1.55-1.56 (m, 3H). MS-ESI calcd. [M+H]$^+$ 344, found 344.

Example 28

3,7-Dimethyl-1,3-(3-methylisoxazol-5-yl)methyl) cyclohexyl)-1H-purine-2,6(3H,7H)-dione

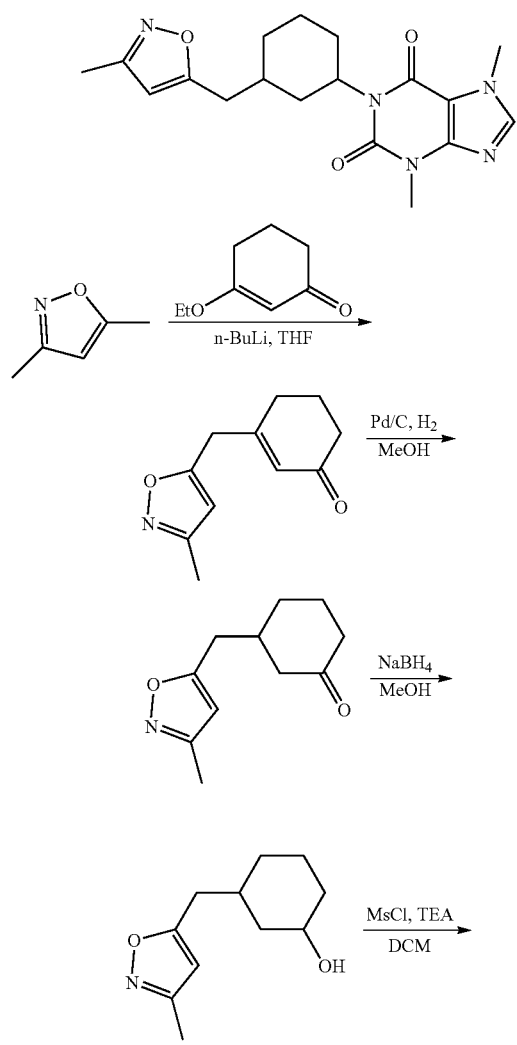

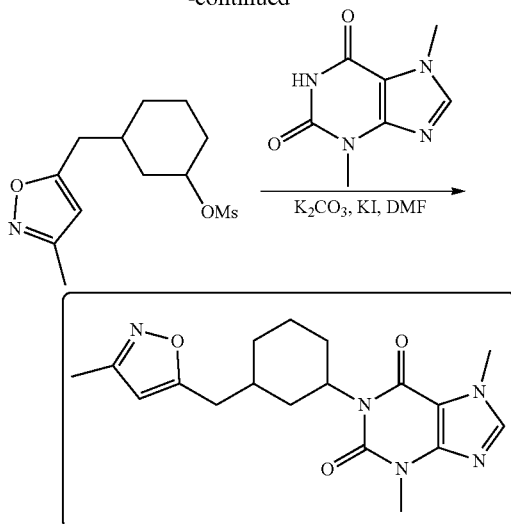

Step 1

3-((3-Methylisoxazol-5-yl)methyl)cyclohex-2-enone 3,5-Dimethylisoxazole (5.00 g, 51.5 mmol) was dissolved in anhydrous tetrahydrofuran (100 mL), n-butyllithium (62 mL, 3M n-hexane solution, 155 mmol) was added dropwise slowly at −78° C. under nitrogen atmosphere, and the reaction solution was stirred at −78° C. for 2 hours. 3-ethoxy-2-cyclohexen-1-one (7.22 g, 51.5 mmol) was slowly added and the stirring was continued for 1 hour. The reaction was quenched by the addition of water (100 mL), and extracted with ethyl acetate (30 mL×3). The organic phases were combined, washed successively with water (30 mL) and saturated sodium chloride solution (50 mL), dried over anhydrous magnesium sulfate, filtered and the filtrate was concentrated under reduced pressure, and purified by silica gel column chromatography (5:1 petroleum ether/ ethyl acetate, R$_f$=0.4) to give 3-((3-methylisoxazol-5-yl) methyl)cyclohex-2-enone (5.10 g, as a yellow oil) with a yield of 52%.

MS-ESI calcd. [M+H]$^+$ 192, found 192.

Step 2

3-((3-Methylisoxazol-5-yl)methyl)cyclohexanone 3-((3-Methylisoxazol-5-yl)methyl)cyclohex-2-enone (1.50 g, 7.84 mmol) was dissolved in methanol (30 mL), 10% Pd/C (20.0 mg, 0.171 mmol) was added at room temperature. The reaction solution was stirred under hydrogen ball (15 psi) for 1 hour, filtered and the filter cake was washed with methanol (10 mL). The filtrates were combined and concentrated to give 3-((3-methylisoxazol-5-yl)methyl) cyclohexanone (1.20 g, as a colorless oil) with a yield of 80%.

MS-ESI calcd. [M+H]$^+$ 194, found 194.

Step 3

3-((3-Methylisoxazol-5-yl)methyl)cyclohexanol 3-((3-Methylisoxazol-5-yl)methyl)cyclohexanone (2.00 g, 10.4 mmol) was dissolved in methanol (30 mL), sodium borohydride (0.790 g, 20.8 mmol) was added at room temperature, and the reaction solution was stirred at room temperature for 4 hours. The reaction was quenched by addition of water (20 mL) and extracted with ethyl acetate (30 mL×2). The organic phase was washed with saturated sodium bicarbonate solution (20 mL×2), dried over anhydrous sodium sulfate, filtered, and the filtrate was concentrated under reduced pressure. The residue was purified by silica gel column chromatography (2:1 petroleum ether/ethyl acetate, $R_f$=0.5) to give 3-((3-methylisoxazol-5-yl)methyl)cyclohexanol (1.21 g, as a colorless oil) with a yield of 60%.

MS-ESI calcd. [M+H]$^+$ 196, found 196.

Step 4

3-((3-Methylisoxazol-5-yl)methyl)cyclohexylmethyl methanesulfonate 3-((3-Methylisoxazol-5-yl)methyl)cyclohexanol (300 mg, 1.54 mmol) and triethylamine (311 mg, 3.08 mmol) were dissolved in dichloromethane (20 mL) and methanesulfonyl chloride (264 mg, 2.31 mmol) was added at 0° C. The reaction solution was stirred at room temperature for 2 hours, diluted with dichloromethane (20 mL), washed with saturated sodium bicarbonate solution (30 mL×2), dried over anhydrous sodium sulfate, filtered and the filtrate was concentrated under reduced pressure. The residue was purified by silica gel column chromatography (4:1 petroleum ether/ethyl acetate, $R_f$=0.5) to give 3-((3-methylisoxazol-5-yl)methyl)cyclohexylmethyl methanesulfonate (400 mg, as a colorless oil) with a yield of 96%.

MS-ESI calcd. [M+H]$^+$ 274, found 274.

Step 5

3,7-Dimethyl-1,3-(3-methylisoxazol-5-yl)methyl) cyclohexyl)-1H-purine-2,6(3H,7H)-dione 3-((3-Methylisoxazol-5-yl)methyl)cyclohexylmethyl methanesulfonate (100 mg, 0.366 mmol) was dissolved in N,N-dimethylformamide (15 mL). 3,7-Dimethyl-1H-purine-2,6(3H,7H)-dione (66.0 mg, 0.366 mmol), potassium iodide (6.1 mg, 0.037 mmol) and potassium carbonate (758 mg, 0.549 mmol) were added into the reaction solution at room temperature. The reaction solution was heated to 100° C., reacted for 2 hours, diluted with ethyl acetate (20 mL). The organic phase was washed with saturated sodium bicarbonate solution (20 mL×2), dried over anhydrous sodium sulfate, filtered and the filtrate was concentrated under reduced pressure. The residue was purified by HPLC to give 3,7-dimethyl-1,3-(3-methylisoxazol-5-yl)methyl)cyclohexyl)-1H-purine-2,6(3H,7H)-dione (20.0 mg) with a yield of 15%.

$^1$H NMR: (400 MHz, CDCl$_3$) δ 7.48 (s, 1H), 5.89 (s, 1H), 5.19-5.12 (m, 1H), 3.97 (s, 3H), 3.54 (s, 3H), 2.94 (d, J=8.0 Hz, 2H), 2.77-2.75 (m, 1H), 2.73-2.70 (m, 2H), 2.25 (s, 3H), 1.70-1.68 (m, 3H), 1.58-1.51 (m, 3H). MS-ESI calcd. [M+H]$^+$ 358, found 358.

Example 29

1-((2,4-Dimethylthiazol-5-yl)methyl)-3,7-dimethyl-1H-purine-2,6(3H,7H)-dione

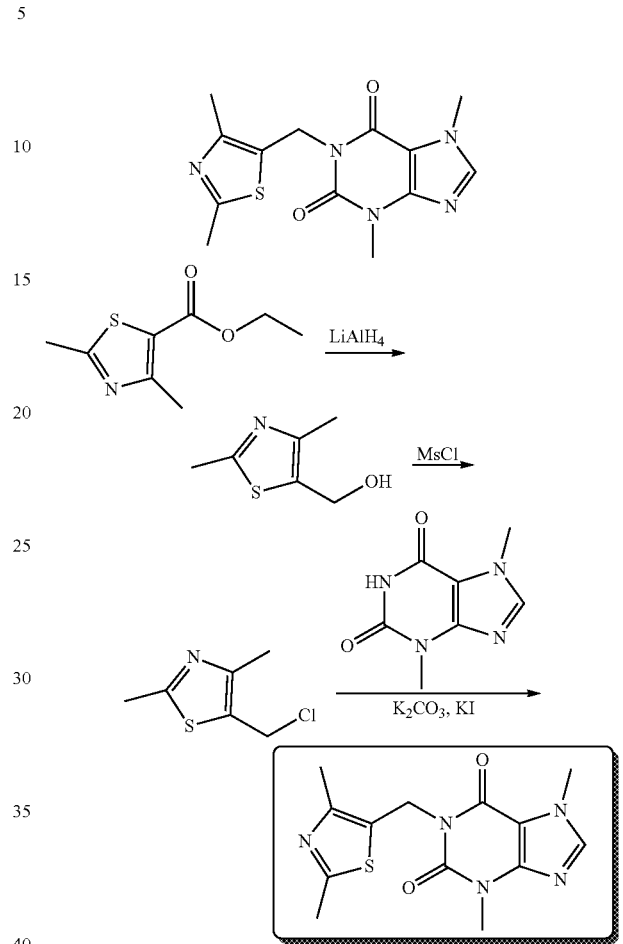

Step 1

(2,4-Dimethylthiazol-5-yl)methanol

Ethyl (2,4-dimethylthiazol-5-yl) formate (500 mg, 2.70 mmol) was dissolved in anhydrous tetrahydrofuran (10 mL), and lithium aluminum hydride (205 mg, 5.40 mmol) was added at 0° C. to react for 1 hour. The reaction was quenched by addition of water (10 mL), and the reaction solution was extracted with ethyl acetate (15 mL×3), dried over anhydrous sodium sulfate, concentrated under reduced pressure, and purified by preparative TLC plate (1:1 petroleum ether/ethyl acetate, $R_f$=0.4) to give (2,4-dimethylthiazol-5-yl) methanol (300 mg, as a yellow solid) with a yield of 77%.

$^1$H NMR: (400 MHz, Methanol-d$_4$) δ 4.68 (s, 2H), 2.64 (s, 3H), 2.33 (s, 3H).

Step 2

5-(Chloromethyl)-2,4-dimethylthiazole (2,4-Dimethylthiazol-5-yl)methanol (300 mg, 2.09 mmol) and triethylamine (635 mg, 6.29 mmol) were dissolved in anhydrous dichloromethane (10 mL). Methanesulfonyl chloride (468 mg, 4.18 mmol) was added at 0° C. The reaction solution was slowly warmed to 25° C. and stirred for 2 hours. The reaction was quenched by the addition of saturated aqueous sodium bicarbonate solution (10 mL) and extracted with dichloromethane (15 mL×3). The combined organic phases were combined, washed with saturated sodium chloride (30 mL), dried over anhydrous sodium sulfate and concentrated under reduced pressure to give 5-(chloromethyl)-2,4-dimethylthiazole (182 mg, as a yellow solid) with a yield of 54%.

$^1$H NMR: (400 MHz, Methanol-$d_4$) δ 4.86 (s, 2H), 2.65 (s, 3H), 2.73 (s, 3H).

Step 3

1-((2,4-Dimethylthiazol-5-yl)methyl)-3,7-dimethyl-1H-purine-2,6(3H,7H)-dione 5-(Chloromethyl)-2,4-dimethylthiazole (182 mg, 1.13 mmol), 3,7-dimethyl-1H-purine-2,6(3H,7H)-dione (203 mg, 1.13 mmol), potassium iodide (17.9 mg, 0.113 mmol) and potassium carbonate (312 mg, 2.26 mmol) were dissolved in anhydrous N,N-dimethylformamide (5 mL). The reaction was heated to 120° C. and reacted for 3 hours. The reaction solution was cooled to 20° C., filtered and purified by preparative HPLC to give 1-((2,4-dimethylthiazol-5-yl) methyl)-3,7-dimethyl-1H-purine-2,6(3H,7H)-dione (130 mg) with a yield of 38%.

$^1$H NMR: (400 MHz, Methanol-$d_4$) δ 7.88 (s, 1H), 5.23 (s, 2H), 3.99 (s, 3H), 3.54 (s, 3H), 2.58 (s, 3H), 2.52 (s, 3H). MS-ESI calcd. [M+H]$^+$ 306, found 306.

Example 30

3,7-Dimethyl-1,2-(2-methylthiazol-4-yl)ethyl)-1H-purine-2,6(3H,7H)-dione

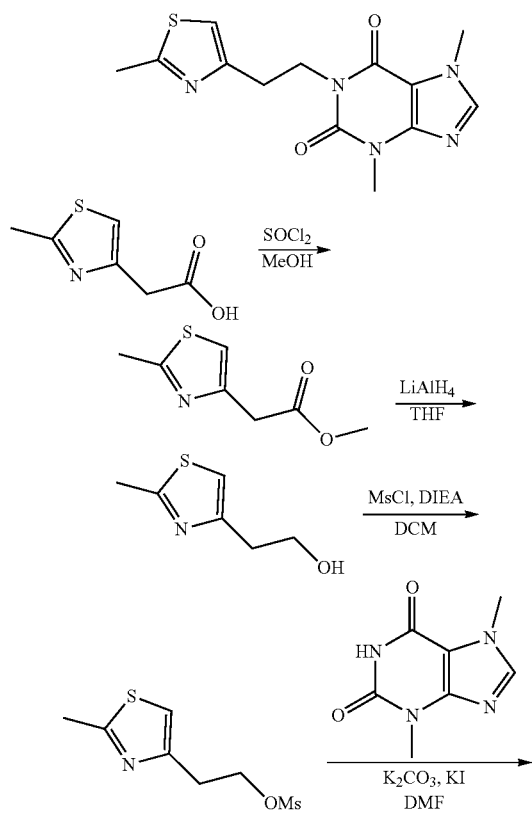

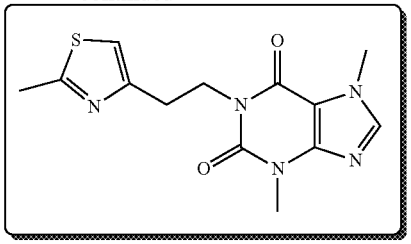

Step 1

Methyl 2-(2-methylthiazol-4-yl)acetate 2-(2-Methylthiazol-4-yl)acetic acid (50.0 mg, 0.270 mmol) was dissolved in methanol (2 mL), thionyl chloride (0.1 mL) was slowly added at 0° C. The reaction solution was slowly allowed to warm to room temperature and stirred for 2.5 hours. The reaction was quenched by addition of water (10 mL) and extracted with ethyl acetate (10 mL×3). The organic phase was dried over anhydrous sodium sulfate, filtered and the filtrate was concentrated under reduced pressure. The resulting product was purified by high performance preparative TLC plate (1:3 petroleum ether/ethyl acetate, $R_f$=0.4) to give methyl 2-(2-methylthiazol-4-yl) acetate (40.0 mg, as a yellow oil) with a yield of 87%.

$^1$H NMR: (400 MHz, Methanol-$d_4$) δ7.21 (s, 1H), 3.78 (s, 2H), 3.70 (s, 3H), 2.67 (s, 3H).

Step 2

2-(2-Methylthiazol-4-yl)ethanol

Lithium aluminum hydride (34.0 mg, 0.890 mmol) was slowly dissolved in tetrahydrofuran (20 mL) at 0° C. under nitrogen atmosphere, and a solution of methyl 2-(2-methyl-thiazol-4-yl) acetate (40.0 mg, 0.230 mmol) in tetrahydrofuran (3 mL) was slowly added. The reaction solution was slowly allowed to warm to room temperature and stirred for 1.5 hours. The reaction solution was cooled to 0° C. and water (0.1 mL), 15% sodium hydroxide solution (0.1 mL) and water (0.3 mL) were slowly added successively. The reaction was allowed to warm to room temperature, stirred for half an hour, filtered and the filter cake was washed with tetrahydrofuran (10 mL×3). The filtrate was concentrated under reduced pressure and purified by high performance preparative TLC plate (1:3 petroleum ether/ethyl acetate, $R_f$=0.5) to give 2-(2-methylthiazol-4-yl)ethanol (22.0 mg, as a yellow oil) with a yield of 67%.

$^1$H NMR: (400 MHz, Methanol-$d_4$) δ 7.04 (s, 1H), 3.83 (t, J=6.8 Hz, 2H), 2.92 (t, J=6.8 Hz, 2H), 2.67 (s, 3H).

Step 3

2-(2-Methylthiazol-4-yl)ethyl methanesulfonate 2-(2-Methylthiazol-4-yl) ethanol (22.0 mg, 0.150 mmol) and diisopropylethylamine (40.0 mg, 0.310 mmol) were dissolved in dichloromethane (5 mL), methanesulfonyl chloride (50.0 mg, 0.440 mmol) was slowly added at 0° C. The reaction was slowly allowed to warm to room temperature and stirred overnight. The reaction was quenched by addition of water (20 mL), and then extracted with ethyl acetate (30 mL×3). The organic phases were combined, dried over anhydrous sodium sulfate, filtered and the filtrate was concentrated under reduced pressure to give the product 2-(2-methylthiazol-4-yl)ethyl methanesulfonate (26.0 mg, as a yellow liquid) with a yield of 79%.

Step 4

3,7-Dimethyl-1,2-(2-methylthiazol-4-yl)ethyl)-1H-purine-2,6(3H,7H)-dione 2-(2-Methylthiazol-4-yl)ethyl methanesulfonate (218 mg, 1.00 mmol), 3,7-dimethyl-1H-purine-2,6(3H,7H)-dione (180 mg, 1.00 mmol) and potassium carbonate (414 mg, 3.00 mmol) were dissolved in N,N-dimethylformamide (3.3 mL), potassium iodide (17.0 mg, 0.100 mmol) was added and the reaction was heated to 130° C. and stirred for 3 hours. The reaction solution was cooled to room temperature, followed by adding brine (20 mL), and extracted with ethyl acetate (20 mL×3). The organic phases were combined, dried over anhydrous sodium sulfate, filtered, and the filtrate was concentrated under reduced pressure, and purified by preparative HPLC to give 3,7-dimethyl-1,2-(2-methylthiazol-4-yl)ethyl)-1H-purine-2,6(3H,7H)-dione (44.0 mg) with a yield of 15%.

$^1$H NMR: (400 MHz, Methanol-$d_4$) δ 7.86 (s, 1H), 7.04 (s, 1H), 4.29 (t, J=7.2 Hz, 2H), 3.95 (s, 3H), 3.51 (s, 3H), 3.04 (t, J=7.2 Hz, 2H), 2.65 (s, 3H). MS-ESI calcd. [M+H]$^+$ 306, found 306.

Example 31

1-(2-(2,4-Dimethylthiazol-5-yl)ethyl)-3,7-dimethyl-1H-purine-2,6(3H,7H)-dione

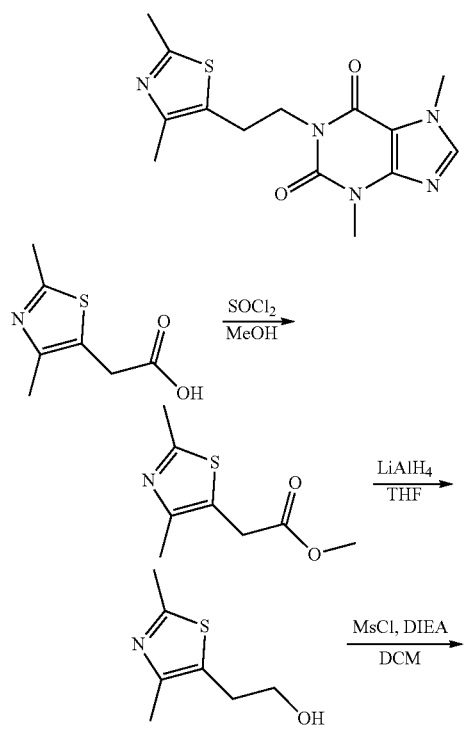

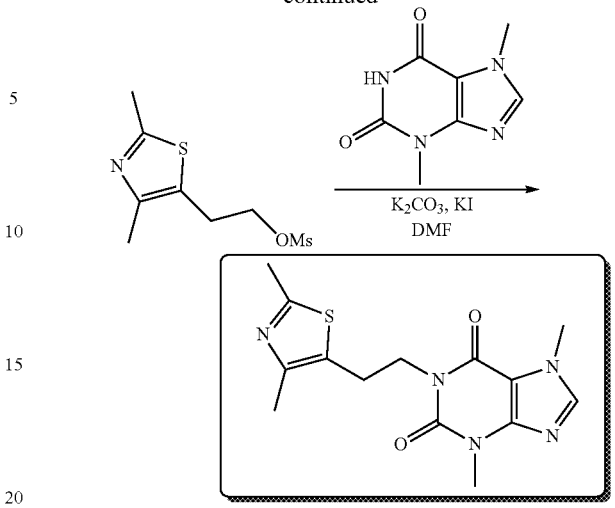

Step 1

Methyl 2-(2,4-dimethylthiazol-5-yl) acetate 2-(2,4-Dimethylthiazol-5-yl)acetic acid (50.0 mg, 0.250 mmol) was dissolved in methanol (2 mL) and thionyl chloride (0.1 mL) was slowly added at 0° C. The reaction solution was slowly allowed to warm to room temperature and stirred for 2.5 hours. The reaction was quenched by addition of water (20 mL) and the reaction solution was extracted with ethyl acetate (20 mL×3). The organic phases were combined, dried over anhydrous sodium sulfate, filtered, the filtrate was concentrated under reduced pressure, and purified by high performance preparation plate (1:3 petroleum ether/ethyl acetate, $R_f$=0.3) to give the product methyl 2-(2,4-dimethylthiazol-5-yl) acetate (32.0 mg, as a yellow liquid) with a yield of 70%.

$^1$H NMR: (400 MHz, Methanol-$d_4$) δ 3.79 (s, 2H), 3.71 (s, 3H), 2.61 (s, 3H), 2.27 (s, 3H).

Step 2

2-(2,4-Dimethylthiazol-5-yl)ethanol

Lithium aluminum hydride (47.0 mg, 1.20 mmol) was slowly dissolved in tetrahydrofuran (60 mL) at 0° C. under nitrogen atmosphere, and a solution of methyl 2-(2,4-dimethylthiazol-5-yl) acetate (159 mg, 0.820 mmol) in tetrahydrofuran (4 mL) was slowly added. The reaction was slowly warmed to room temperature and stirred for 1.5 hours. The reaction solution was cooled to 0° C. and water (0.1 mL), 15% sodium hydroxide solution (0.1 mL) and water (0.3 mL) were slowly added successively. The reaction solution was warmed to room temperature and stirred for half an hour, filtered and the filter cake was washed with tetrahydrofuran (10 mL×3). The filtrate was concentrated under reduced pressure and purified by high performance preparative TLC plate (1:3 petroleum ether/ethyl acetate, $R_f$=0.5) to give 2-(2,4-dimethylthiazol-5-yl)ethanol (61.0 mg, yellow liquid) with a yield of 48%.

$^1$H NMR: (400 MHz, Methanol-$d_4$) δ 3.69 (t, J=6.4 Hz, 2H), 2.90 (t, J=6.4 Hz, 2H), 2.59 (s, 3H), 2.28 (s, 3H).

Step 3

2-(2,4-Dimethylthiazol-5-yl)ethyl methanesulfonate 2-(2,4-Dimethylthiazol-5-yl)ethanol (61.0 mg, 0.400 mmol) and diisopropylethylamine (103 mg, 0.800 mmol) were dissolved in dichloromethane (1.8 mL), methanesulfonyl chloride (124 mg, 1.10 mmol) was slowly added at 0° C. The reaction was slowly allowed to warm to room temperature and stirred overnight. The reaction was quenched by addition of water (10 mL) and extracted with ethyl acetate (10 mL×3). The organic phases were combined, dried over anhydrous sodium sulfate, filtered and the filtrate was concentrated under reduced pressure to give the product 2-(2,4-dimethylthiazol-5-yl)ethyl methanesulfonate (70.0 mg, as a yellow liquid) with a yield of 75%.

Step 4

1-(2-(2,4-Dimethylthiazol-5-yl)ethyl)-3,7-dimethyl-1H-purine-2,6(3H,7H)-dione 2-(2,4-Dimethylthiazol-5-yl)ethyl methanesulfonate (70.0 mg, 0.300 mmol), 3,7-dimethyl-1H-purine-2,6(3H,7H)-dione (60.0 mg, 0.330 mmol) and potassium carbonate (124 mg, 0.900 mmol) were dissolved in N,N-dimethylformamide (3 mL) and potassium iodide (5.0 mg, 0.0300 mmol) was added. The reaction was heated to 130° C. and stirred for 3 hours. The reaction solution was cooled to room temperature, followed by adding brine (30 mL), and extracted with ethyl acetate (20 mL×3). The organic phases were combined, dried over anhydrous sodium sulfate, filtered, and the filtrate was concentrated under reduced pressure. The product was purified by preparative HPLC to give 1-(2-(2,4-dimethylthiazol-5-yl)ethyl)-3,7-dimethyl-1H-purine-2,6(3H,7H)-dione (20.0 mg) with a yield of 21%.

$^1$H NMR: (400 MHz, Methanol-$d_4$) δ 7.87 (s, 1H), 4.17-4.12 (m, 2H), 3.96 (s, 3H), 3.52 (s, 3H), 3.08-3.03 (m, 2H), 2.59 (s, 3H), 2.29 (s, 3H). MS-ESI calcd. [M+H]$^+$ 320, found 320.

Example 32

1-[2-(2,4-Dimethylthiazol-5-yl)ethyl]-3,7-dimethyl-purine-2,6-dione

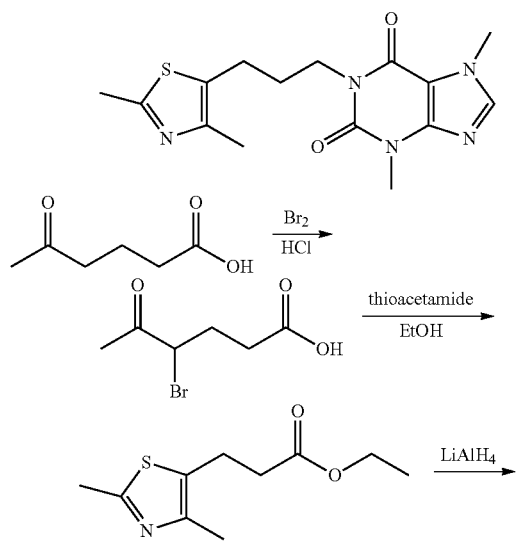

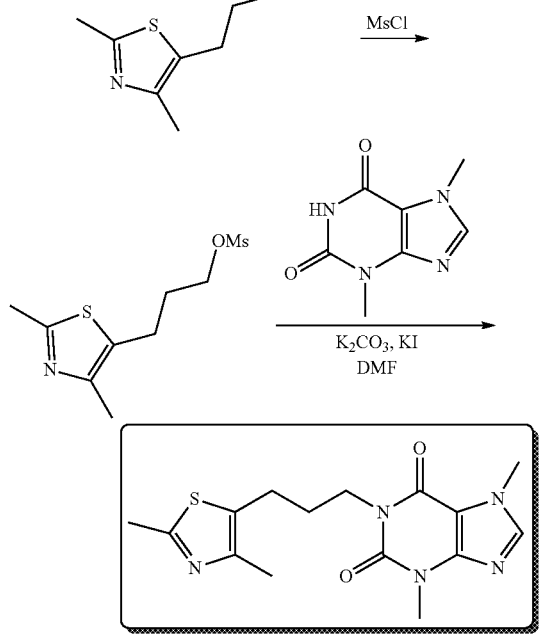

Step 1

4-Bromo-5-oxohexanoic acid

5-Oxohexanoic acid (2.00 g, 15.4 mmol) was dissolved in conc. hydrochloric acid (20 mL) and liquid bromine (2.46 g, 15.4 mmol) was added at 0° C., then reacted at room temperature for 2 hours. Water (10 mL) was added to quench the reaction. The reaction solution was extracted with ethyl acetate (10 mL×3), dried over anhydrous sodium sulfate, filtered, and the filtrate was concentrated under reduced pressure and purified by silica gel column chromatography (20:1 petroleum ether/ethyl acetate, $R_f$=0.5) to give 4-bromo-5-oxohexanoic acid (2.5 g, as a yellow oil) with a yield of 76%. MS-ESI calcd. [M+H]$^+$ 209 and 211, found 209 and 211.

Step 2

Ethyl 3-(2,4-dimethylthiazol-5-yl)propionate

A mixture of 4-bromo-5-oxohexanoic acid (2.50 g, 11.9 mmol) and thioacetamide (1.00 g, 13.3 mmol) was dissolved in ethanol (30 mL) and heated under reflux for 3 hours under nitrogen atmosphere. Water (10 mL) was added to quench the reaction. The reaction solution was extracted with ethyl acetate (10 mL×3), dried over anhydrous sodium sulfate, filtered, and the filtrate was concentrated under reduced pressure and purified by silica gel column chromatography (1:1 petroleum ether/ethyl acetate, $R_f$=0.6) to give ethyl 3-(2,4-dimethylthiazol-5-yl)propionate (120 mg, as a yellow oil) with a yield of 6%. MS-ESI calcd. [M+H]$^+$ 214, found 214.

Step 3

2-(2,4-Dimethylthiazol-5-yl)ethanol

Ethyl 3-(2,4-dimethylthiazol-5-yl)propionate (150 mg, 0.703 mmol) was dissolved in tetrahydrofuran (10 mL), lithium aluminum hydride (40.0 mg, 1.05 mmol) was added at 0° C. and reacted for 1 hour. Water (10 mL) was added to quench the reaction. The reaction solution was extracted with ethyl acetate (10 mL×3), dried over anhydrous sodium sulfate, filtered, and the filtrate was concentrated under reduced pressure and purified by preparative TLC plate (1:1 petroleum ether/ethyl acetate, $R_f$=0.1) to give 2-(2,4-dimethylthiazol-5-yl)ethanol (100 mg, as a colorless oil) with a yield of 83%. MS-ESI calcd. [M+H]$^+$ 172, found 172.

Step 4

2-(2,4-Dimethylthiazol-5-yl)ethyl methanesulfonate 2-(2,4-Dimethylthiazol-5-yl)ethanol (75.0 mg, 0.477 mmol) and triethylamine (96.0 mg, 0.949 mmol) were dissolved in dichloromethane (5 mL), methanesulfonyl chloride (54.6 mg, 0.477 mmol) was added at 0° C. The reaction solution was slowly allowed to warm to room temperature and stirred for 2 hours. The reaction was quenched by addition of aqueous sodium bicarbonate solution (10 mL), and extracted with dichloromethane (10 mL×3). The organic phases were combined, washed with brine, dried over anhydrous sodium sulfate, filtered and the filtrate was concentrated under reduced pressure to give 2-(2,4-dimethylthiazol-5-yl)ethyl methanesulfonate (100 mg, as a yellow oil) with a yield of 89%. MS-ESI calcd. [M+H]$^+$ 250, found 250.

Step 5

1-[2-(2,4-Dimethylthiazol-5-yl)ethyl]-3,7-dimethyl-purine-2,6-dione 2-(2,4-Dimethylthiazol-5-yl)ethyl methanesulfonate (100 mg, 0.425 mmol), 3,7-dimethyl-1H-purine-2,6(3H,7H)-dione (76.5 mg, 0.425 mmol), potassium iodide (7.0 mg, 0.042 mmol) and potassium carbonate (117 mg, 0.846 mmol) were dissolved in N,N-dimethylformamide (10 mL). The reaction was heated to 120° C. and stirred for 3 hours, then cooled to room temperature, filtered, and the filtrate was concentrated under reduced pressure and purified by preparative HPLC to give 1-[2-(2,4-dimethylthiazol-5-yl)ethyl]-3,7-dimethylpurine-2,6-dione (22.0 mg) with a yield of 16%.

$^1$H NMR: (400 MHz, Methanol-d$_4$) δ 7.86 (s, 1H), 4.06 (t, J=7.6 Hz, 2H), 3.96 (s, 3H), 3.51 (s, 3H), 2.80 (t, J=7.6 Hz, 2H), 2.53 (s, 3H), 2.26 (s, 3H), 2.00-1.91 (m, 2H). MS-ESI calcd. [M+H]$^+$ 334, found 334.

Example 33

3,7-Dimethyl-1-((5-(trifluoromethyl)-1,3,4-oxadi-azol-2-yl)methyl)-1H-purine-2,6(3H,7H)-dione

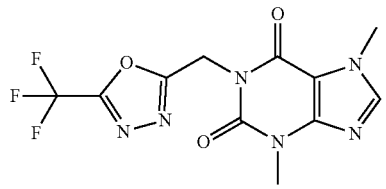

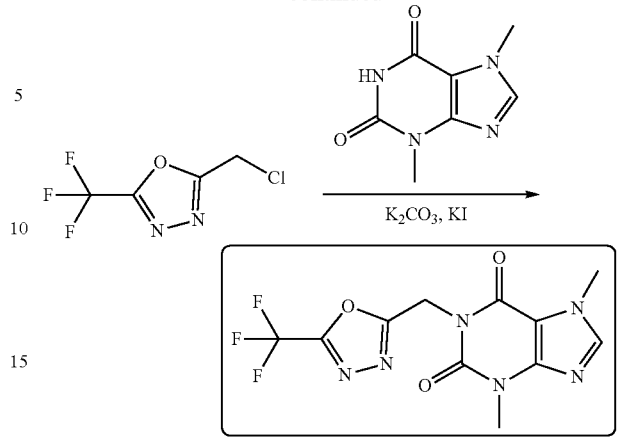

Step 1

3,7-Dimethyl-1-((5-(trifluoromethyl)-1,3,4-oxadi-azol-2-yl)methyl)-1H-purine-2,6(3H,7H)-dione 2-Chloromethyl-5-trifluoromethyl-1,3,4-oxadiazole (100 mg, 0.541 mmol), 3,7-dimethyl-1H-purine-2,6(3H,7H)-dione (97.3 mg, 0.541 mmol), potassium iodide (8.5 mg, 0.0541 mmol) and potassium carbonate (143 mg, 1.08 mmol) were dissolved in anhydrous N,N-dimethylformamide (3 mL). The reaction was heated to 120° C. and reacted for 3 hours. The reaction solution was cooled to 20° C., filtered and purified by preparative HPLC to give 3,7-dimethyl-1-((5-(trifluoromethyl)-1,3,4-oxadiazol-2-yl)methyl)-1H-purine-2,6(3H,7H)-dione (60.0 mg) with a yield of 34%.

$^1$H NMR: (400 MHz, Methanol-d$_4$) δ 7.95 (s, 1H), 5.53 (s, 2H), 4.00 (s, 3H), 3.57 (s, 3H). MS-ESI calcd. [M+H]$^+$ 331, found 331.

Example 34

1-(4-(2H-1,2,3-triazol-4-yl)butyl)-3,7-dimethyl-1H-purine-2,6(3H,7H)-dione

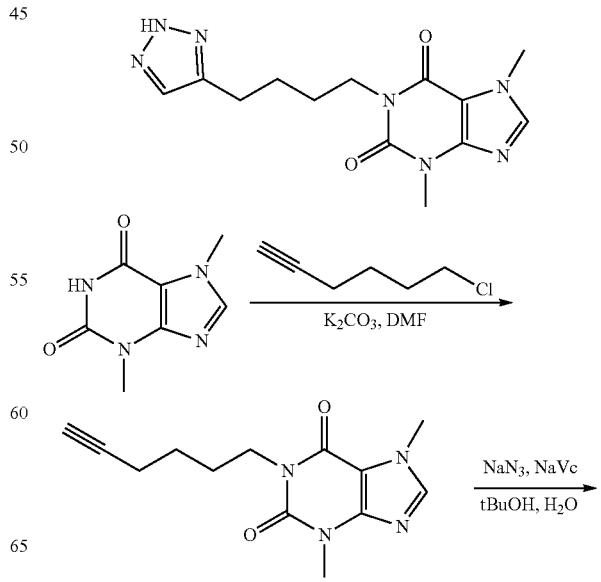

-continued

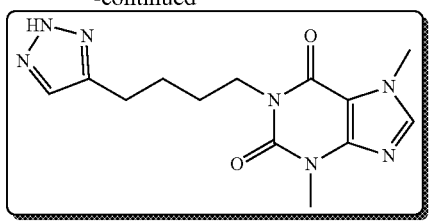

Step 1

1-(Hex-5-yn-1-yl)-3,7-dimethyl-1H-purine-2,6(3H,7H)-dione 3,7-Dimethyl-1H-purine-2,6(3H,7H)-dione (773 mg, 4.15 mmol) was dissolved in N,N-dimethylformamide (20 mL), 6-chlorohex-1-yne (500 mg, 4.15 mmol), potassium carbonate (859 mg, 6.23 mmol) and potassium iodide (103 mg, 0.623 mmol) were added at room temperature. The reaction solution was heated to 100° C. and stirred for 2 hours. The reaction solution was cooled to room temperature and diluted with ethyl acetate (30 mL). The organic phase was washed with saturated sodium bicarbonate solution (20 mL×2), dried over anhydrous sodium sulfate and concentrated under reduced pressure to give 1-(hex-5-yn-1-yl)-3,7-dimethyl-1H-purine-2,6(3H,7H)-dione (1.15 g, as a yellow oil) with a yield of 95%. MS-ESI [M+H]$^+$ calcd. 261, found 261.

Step 2

1-(4-(2H-1,2,3-triazol-4-yl)butyl)-3,7-dimethyl-1H-purine-2,6(3H,7H)-dione 1-(Hex-5-yn-1-yl)-3,7-dimethyl-1H-purine-2,6(3H,7H)-dione (1.00 g, 3.85 mmol) was dissolved in a mixture of tert-butyl alcohol (15 mL) and water (15 mL). Sodium azide (375 mg, 5.77 mmol), sodium ascorbate (305 mg, 1.54 mmol) and copper sulfate pentahydrate (96.3 mg, 0.385 mmol) were added at room temperature. The reaction was heated to 60° C. and stirred for 24 hours, then cooled to room temperature and diluted with ethyl acetate (30 mL). The organic phase was washed with saturated sodium bicarbonate solution (20 mL×2), dried over anhydrous sodium sulfate and concentrated under reduced pressure to give 1-(4-(2H-1,2,3-triazol-4-yl)butyl)-3,7-dimethyl-1H-purine-2,6(3H,7H)-dione (300 mg) with a yield of 19%.

$^1$H NMR: (400 MHz, Methanol-d$_4$) δ 7.88 (s, 1H), 7.61 (s, 1H), 4.04 (t, J=7.2 Hz, 2H), 3.98 (s, 3H), 3.54 (s, 3H), 2.80 (t, J=7.2 Hz, 2H), 1.71-1.73 (m, 4H). MS-ESI calcd. [M+H]$^+$ 304, found 304.

Example 35

3,7-Dimethyl-1-(4-(2-methyl-2H-1,2,3-triazol-4-yl)butyl)-1H-purine-(3H,7H)-dione

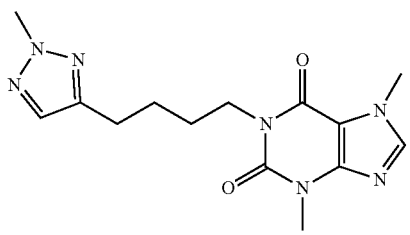

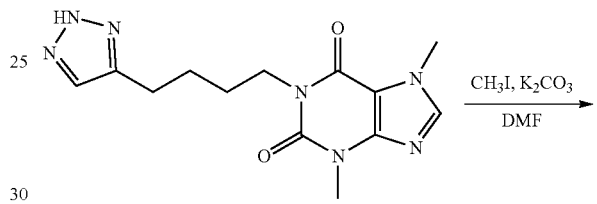

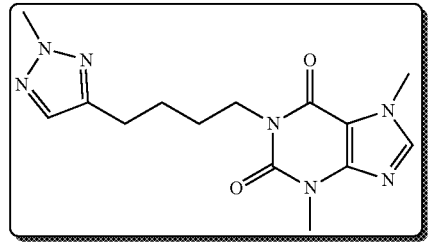

1-(4-(2H-1,2,3-triazol-4-yl)butyl)-3,7-dimethyl-1H-purine-2,6(3H,7H)-dione (300 mg, 0.990 mmol) was dissolved in N,N-dimethylformamide (20 mL). Iodomethane (281 mg, 2.00 mmol) and potassium carbonate (276 mg, 2.00 mmol) were added at room temperature. The reaction was stirred at room temperature for 2 hours. The organic phase was washed with saturated sodium bicarbonate solution (20 mL×2), dried over anhydrous sodium sulfate, concentrated under reduced pressure and purified by HPLC to give 3,7-dimethyl-1-(4-(2-methyl-2H-1,2,3-triazol-4-yl)butyl)-1H-purine-(3H,7H)-dione (15.0 mg) with a yield of 10%.

$^1$H NMR: (400 MHz, Methanol-d$_4$) δ 7.88 (s, 1H), 7.46 (s, 1H), 4.10 (s, 3H), 4.02 (t, J=7.2 Hz, 2H), 3.98 (s, 3H), 3.53 (s, 3H), 2.72 (t, J=7.2 Hz, 2H), 1.69-1.71 (m, 4H). MS-ESI calcd. [M+H]$^+$318, found 318.

Example 36

3,7-Dimethyl-1-(3-(1-methyl-2H-1,2,3-triazol-4-yl)propyl)-1H-purine-2,6(3H,7H)-dione 3,7-Dimethyl-1-(3-(1-methyl-1H-1,2,3-triazol-4-yl)propyl)-1H-purine-2,6(3H,7H)-dione 3,7,9-Trimethyl-1-(3-(2-methyl-1H-1,2,3-triazol-4-yl)propyl)-2,6-dioxo-2,3,6,7-tetrahydro-1H-purine-2,6(3H,7H)-dione

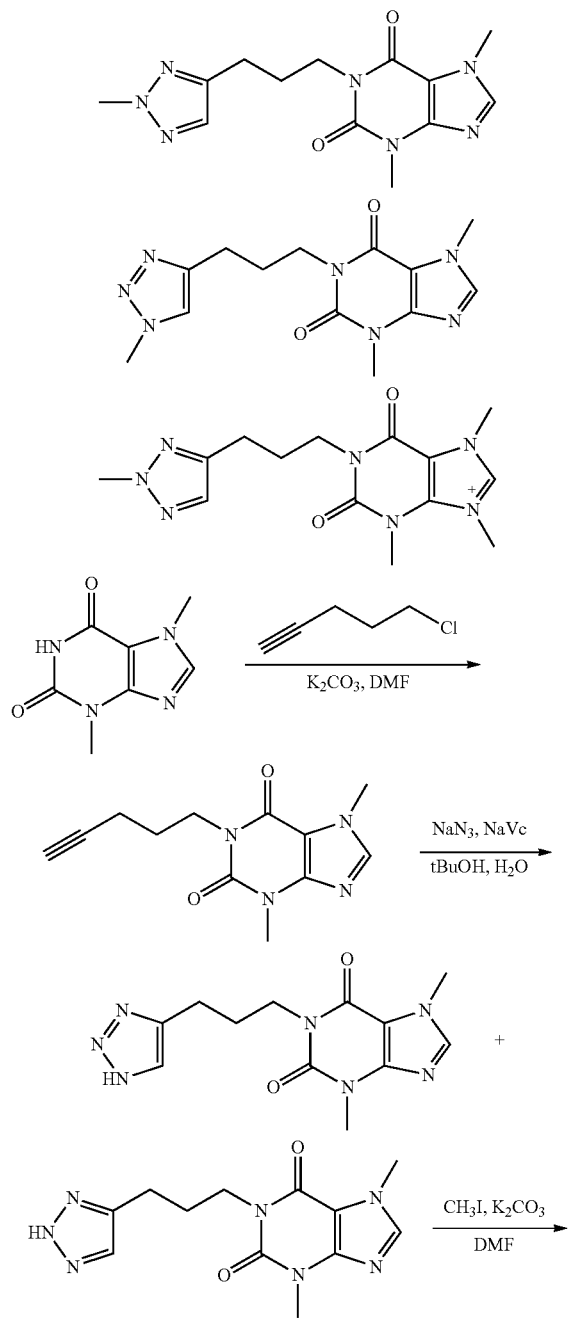

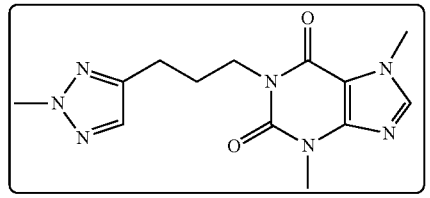

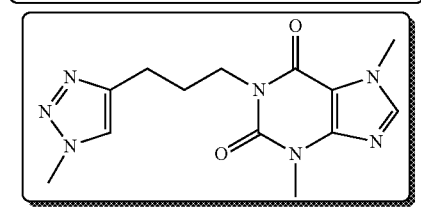

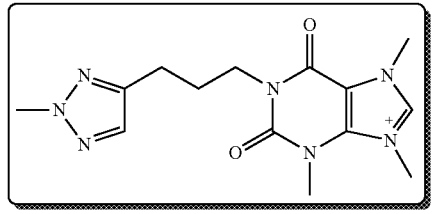

Step 1

3,7-dimethyl-1-(pent-4-yn-1-yl)-1H-purine-2,6(3H,7H)-dione 3,7-Dimethyl-1H-purine-2,6(3H,7H)-dione (965 mg, 5.37 mmol) was dissolved in N,N-dimethylformamide (20 mL). 5-Chloropent-1-yne (500 mg, 4.88 mmol), potassium carbonate (1.35 g, 9.76 mmol) and potassium iodide (162 mg, 0.976 mmol) were added at room temperature. The reaction was heated to 100° C. and stirred for 2 hours. The reaction solution was cooled to room temperature and diluted with ethyl acetate (30 mL). The organic phase was washed with saturated sodium bicarbonate solution (20 mL×2). The organic phases were combined, dried over anhydrous sodium sulfate, concentrated and evaporated to dryness to give the product 3,7-dimethyl-1-(pent-4-yn-1-yl)-1H-purine-2,6(3H,7H)-dione (1.02 g, as a yellow oil) with a yield of 94%. MS-ESI [M+H]+ calcd. 247, found 247.

Step 2

1-(3-(1H-1,2,3-triazol-4-yl)propyl)-3,7-dimethyl-1H-purine-2,6(3H,7H)-dione 1-(3-(1H-1,2,3-triazol-5-yl)propyl)-3,7-dimethyl-1H-purine-2,6(3H,7H)-dione 3,7-Dimethyl-1-(pent-4-yn-1-yl)-1H-purine-2,6(3H,7H)-dione (1.40 g, 5.69 mmol) was dissolved in the mixture of tert-butyl alcohol (20 mL) and water (20 mL). Sodium azide (444 mg, 6.83 mmol), sodium ascorbate (450 mg, 2.28 mmol) and copper sulfate pentahydrate (142 mg, 0.569 mmol) were added at room temperature. The reaction was heated to 60° C. and stirred for 24 hours, then cooled to room temperature and diluted with ethyl acetate (30 mL). The organic phase was washed with saturated sodium bicarbonate solution (20 mL×2). The combined organic phases were dried over anhydrous sodium sulfate and concentrated to dryness to give a mixture of 1-(3-(1H-1,2,3-triazol-4-yl)

propyl)-3,7-dimethyl-1H-purine-2,6(3H,7H)-dione and 1-(3-(1H-1,2,3-triazol-5-yl)propyl)-3,7-dimethyl-1H-purine-2,6(3H,7H)-dione (300 mg, as a yellow oil) with a yield of 19%. MS-ESI [M+H]$^+$ calcd. 290, found 290.

Step 3

3,7-Dimethyl-1-(3-(1-methyl-2H-1,2,3-triazol-4-yl)propyl)-1H-purine-2,6(3H,7H)-dione 3,7-Dimethyl-1-(3-(1-methyl-1H-1,2,3-triazol-4-yl)propyl)-1H-purine-2,6(3H,7H)-dione 3,7,9-trimethyl-1-(3-(2-methyl-1H-1,2,3-triazol-4-yl)propyl)-2,6-dioxo-2,3,6,7-tetrahydro-1H-purine-2,6(3H,7H)-dione A mixture of 1-(3-(1H-1,2,3-triazol-4-yl)propyl)-3,7-dimethyl-1H-purine-2,6(3H,7H)-dione and 1-(3-(1H-1,2,3-triazol-5-yl)propyl)-3,7-dimethyl-1H-purine-2,6(3H,7H)-dione (300 mg, 1.04 mmol) was dissolved in N,N-dimethylformamide (20 mL) and methyl iodide (295 mg, 2.08 mmol) and potassium carbonate (287 mg, 2.08 mmol) were added at room temperature. The reaction was stirred at room temperature for 2 hours and diluted with ethyl acetate (40 mL). The organic phases were washed with saturated sodium bicarbonate solution (20 mL×2). The combined organic phase were dried over anhydrous sodium sulfate, concentrated and evaporated to dryness and purified by HPLC to give two substituted isomeric products and one trisubstituted quaternary ammonium salt: 3,7-dimethyl-1-(3-(1-methyl-2H-1,2,3-triazol-4-yl)propyl)-1H-purine-2,6(3H,7H)-dione (20.0 mg) (isomer 1, first peak) with a yield of 10%; 3,7-dimethyl-1-(3-(1-methyl-1H-1,2,3-triazol-4-yl)propyl)-1H-purine-2,6(3H,7H)-dione (8.0 mg) (isomer 2, second peak) with a yield of 3%; 3,7,9-trimethyl-1-(3-(2-methyl-1H-1,2,3-triazol-4-yl)propyl)-2,6-dioxo-2,3,6,7-tetrahydro-1H-purine-2,6(3H,7H)-dione (10.0 mg) (isomer 3, third peak) with a yield of 6%.

3,7-Dimethyl-1-(3-(1-methyl-2H-1,2,3-triazol-4-yl)propyl)-1H-purine-2,6(3H,7H)-dione: $^1$H NMR: (400 MHz, Methanol-d$_4$) δ 7.87 (s, 1H), 7.48 (s, 1H), 4.07 (t, J=7.2 Hz, 2H), 4.04 (s, 3H), 3.98 (s, 3H), 3.52 (s, 3H), 2.74 (t, J=7.2 Hz, 2H), 2.02-2.07 (m, 2H). MS-ESI calcd. [M+H]$^+$ 304, found 304.

3,7-Dimethyl-1-(3-(1-methyl-1H-1,2,3-triazol-4-yl)propyl)-1H-purine-2,6(3H,7H)-dione: $^1$H NMR: (400 MHz, Methanol-d$_4$) δ 7.90 (s, 1H), 7.76 (s, 1H), 4.09 (t, J=7.2 Hz, 2H), 4.05 (s, 3H), 3.99 (s, 3H), 3.53 (s, 3H), 2.77 (t, J=7.2 Hz, 2H), 2.03 (m, 2H). MS-ESI calcd. [M+H]$^+$ 304, found 304.

3,7,9-Trimethyl-1-(3-(2-methyl-1H-1,2,3-triazol-4-yl)propyl)-2,6-dioxo-2,3,6,7-tetrahydro-1H-purine-2,6(3H,7H)-dione: $^1$H NMR: (400 MHz, Methanol-d$_4$) δ 8.64 (s, 1H), 7.91 (s, 1H), 4.33 (s, 3H), 4.24 (s, 3H), 4.10 (t, J=7.2 Hz, 2H), 4.00 (s, 3H), 3.56 (s, 3H), 2.96 (t, J=7.2 Hz, 2H), 2.13-2.19 (m, 2H). MS-ESI calcd. [M+H]$^+$ 319, found 319.

Example 37

1-(4-(2H-tetrazol-5-yl)butyl)-3,7-dimethyl-1H-purine-2,6(3H,7H)-dione

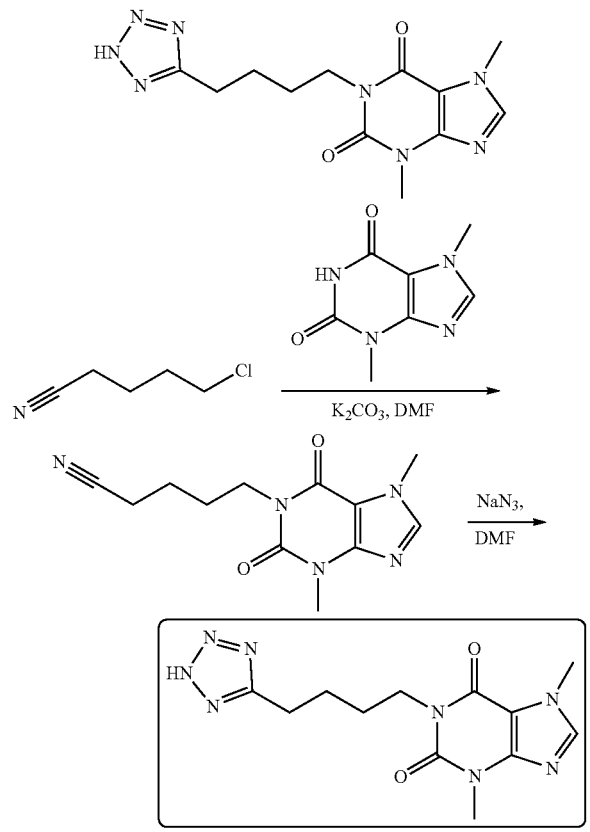

Step 1

5-(3,7-Dimethyl-2,6-dioxo-2,3,6,7-tetrahydro-1H-purin-1-yl)pentanenitrile

6-Chloropentanenitrile (1.00 g, 8.56 mmol) was dissolved in anhydrous N,N-dimethylformamide (15 mL), and potassium carbonate (2.40 g, 17.1 mmol), potassium iodide (142 mg, 0.850 mmol), 2,6-hydroxy-3,7-dimethylpurine (1.85 g, 10.3 mmol) were added. The reaction was heated to 130° C. and stirred for 3 hours, cooled to room temperature, and then quenched by addition of water (100 mL). The reaction mixture was extracted with ethyl acetate (30 mL×3). The organic phases were combined, washed with saturated sodium chloride solution (30 mL×3), dried over anhydrous magnesium sulfate, filtered and the filtrate was concentrated under reduced pressure to give 5-(3,7-dimethyl-2,6-dioxo-2,3,6,7-tetrahydro-1H-purin-1-yl)pentanenitrile (2.3 g, as a yellow oil) with a yield of 100%. MS-ESI [M+H]$^+$ calcd. 262, found 262.

Step 2

1-(4-(2H-tetrazol-5-yl)butyl)-3,7-dimethyl-1H-purine-2,6(3H,7H)-dione 5-(3,7-Dimethyl-2,6-dioxo-2,3,6,7-tetrahydro-1H-purin-1-yl)pentanenitrile (400 mg, 1.53 mmol) was dissolved in N,N-dimethylformamide (5 mL), sodium azide (299 mg, 4.60 mmol) and ammonium chloride (244 mg, 0.740 mmol) were added. The reaction solution was heated to 130° C. and stirred for 80 hours, then cooled to room temperature. Saturated sodium bicarbonate solution (30 mL) was added, and the solution was extracted with dichloromethane (30 mL×2), and the organic phases were combined. The organic phase was dried over anhydrous sodium sulfate and filtered. The filtrate was concentrated under reduced pressure and purified by preparative HPLC to give 1-(4-(2H-tetrazol-5-yl)butyl)-3,7-dimethyl-1H-purine-2,6(3H,7H)-dione (250 mg) with a yield of 54%.

$^1$H NMR: (400 MHz, Methanol-$d_4$) δ 7.88 (s, 1H), 4.07-4.04 (m, 2H), 3.98 (s, 3H), 3.54 (s, 3H), 3.05-3.01 (m, 2H), 1.87-1.81 (m, 2H), 1.77-1.71 (m, 2H). MS-ESI calcd. [M+H]$^+$ 305, found 305.

Example 38

3,7-Dimethyl-1-(4-(2-methyl-2H-tetrazol-5-yl)butyl)-1H-purine-(3H,7H)-dione 3,7-Dimethyl-1-(4-(1-methyl-1H-tetrazol-5-yl)butyl)-1H-purine-(3H,7H)-dione 1-(4-(2H-tetrazol-5-yl)butyl)-3,7-dimethyl-1H-purine-2,6(3H,7H)-dione (200 mg, 0.658 mmol) was dissolved in N,N-dimethylformamide (5 mL), iodomethane (280 mg, 1.97 mmol) and potassium carbonate (272 mg, 1.97 mmol) were added and the reaction solution was stirred at 20° C. for 12 hours. Water (30 mL) was added to the reaction solution and the reaction solution was extracted with ethyl acetate (30 mL×3). The organic phases were combined, dried over anhydrous sodium sulfate, filtered, the filtrate was concentrated under reduced pressure and purified by preparative HPLC to obtain two substituted isomeric products: 3,7-dimethyl-1-(4-(2-methyl-2H-tetrazol-5-yl)butyl)-1H-purine-(3H,7H)-dione (70.0 mg) (isomer 1, first peak) with a yield of 33%; and 3,7-dimethyl-1-(4-(2-methyl-2H-tetrazol-5-yl)butyl)-1H-purine-(3H,7H)-dione (70.0 mg) (isomer 2, second peak) with a yield of 33%.

3,7-Dimethyl-1-(4-(2-methyl-2H-tetrazol-5-yl)butyl)-1H-purine-(3H,7H)-dione: $^1$H NMR: (400 MHz, Methanol-$d_4$) δ 7.88 (s, 1H), 4.32 (s, 3H), 4.04-4.02 (m, 2H), 3.99 (s, 3H), 3.54 (s, 3H), 2.93-2.91 (m, 2H), 1.82-1.73 (m, 4H). MS-ESI calcd. [M+H]$^+$ 319, found 319.

3,7-Dimethyl-1-(4-(1-methyl-1H-tetrazol-5-yl)butyl)-1H-purine-(3H,7H)-dione: $^1$H NMR: (400 MHz, Methanol-$d_4$) δ 7.88 (s, 1H), 4.08 (s, 3H), 4.06-4.04 (m, 2H), 3.98 (s,

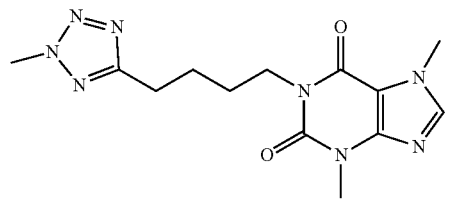
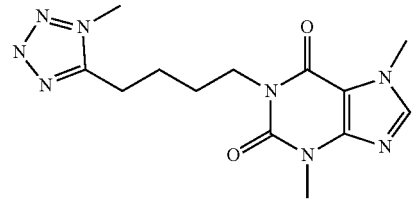

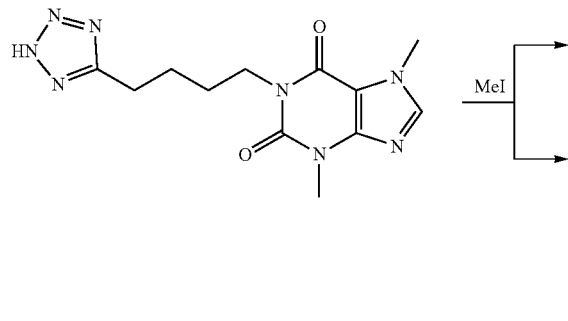
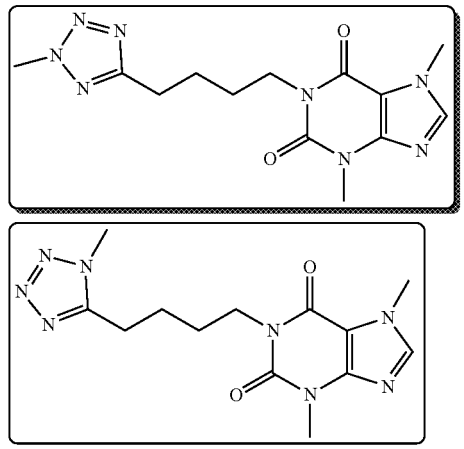

3H), 3.53 (s, 3H), 3.03-2.99 (m, 2H), 1.88-1.76 (m, 4H). MS-ESI calcd. [M+H]⁺ 319, found 319.

Example 39

1-(5-(2H-tetrazol-5-yl)pentyl)-3,7-dimethyl-1H-purine-2,6(3H,7H)-dione

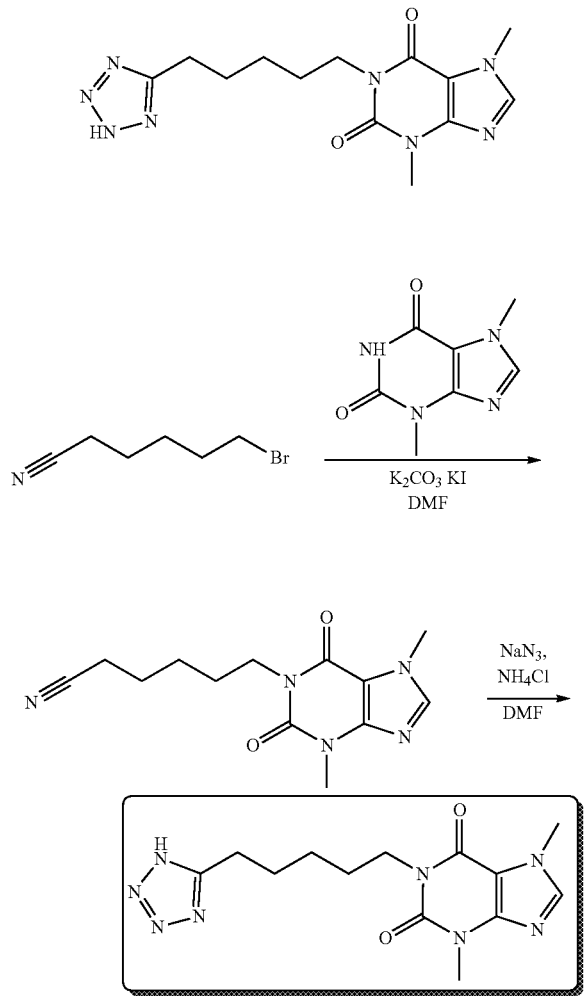

Step 1

6-(3,7-Dimethyl-2,6-dioxo-2,3,6,7-tetrahydro-1H-purin-1-yl)hexanenitrile

6-Bromohexanenitrile (1.00 g, 5.70 mmol) was dissolved in anhydrous N,N-dimethylformamide (15 mL) and potassium carbonate (1.60 g, 11.7 mmol), potassium iodide (94.0 mg, 0.570 mmol), 2,6-hydroxy-3,7-dimethylpurine (1.20 g, 6.80 mmol) were added successively at room temperature under nitrogen atmosphere. The reaction solution was heated to 130° C. and stirred for 3 hours. The reaction mixture was slowly cooled to room temperature and quenched by the addition of water (60 mL). The mixture was extracted with ethyl acetate. The organic phases were combined, washed successively with water, saturated sodium chloride solution, dried over anhydrous magnesium sulfate and filtered. The filtrate was concentrated under reduced pressure to give the crude product 6-(3,7-dimethyl-2,6-dioxo-2,3,6,7-tetrahydro-1H-purin-1-yl)hexanenitrile (1.80 g, as a yellow oil). MS-ESI calcd. [M+H]⁺ calcd. 276, found 276.

Step 2

1-(5-(2H-tetrazol-5-yl)pentyl)-3,7-dimethyl-1H-purine-2,6(3H,7H)-dione 6-(3,7-Dimethyl-2,6-dioxo-2,3,6,7-tetrahydro-1H-purin-1-yl)hexanenitrile (300 mg, 1.09 mmol) was dissolved in anhydrous N,N-dimethylformamide (10 mL), and sodium azide (355 mg, 5.45 mmol) and ammonium chloride (300 mg, 5.45 mmol) were added at room temperature under nitrogen atmosphere. The reaction solution was heated to 130° C. and stirred for 10 hours. The reaction mixture was slowly cooled to room temperature and quenched by the addition of water (60 mL). The mixture was extracted with ethyl acetate (30 mL×2). The organic phases were combined, washed with saturated sodium chloride solution (30 mL×2), dried over anhydrous magnesium sulfate, filtered, and the filtrate was concentrated under reduced pressure. The product was purified by preparative HPLC to give 1-(5-(2H-tetrazol-5-yl)pentyl)-3,7-dimethyl-1H-purine-2,6(3H,7H)-dione (80.0 mg) with a yield of 23%.

¹H NMR: (400 MHz, CDCl₃) δ 7.60 (s, 1H), 4.17 (t, J=6.0 Hz, 2H), 4.12 (s, 3H), 3.67 (s, 3H), 3.13 (t, J=6.0 Hz, 2H), 2.11-2.07 (m, 2H), 1.87-1.82 (m, 2H), 1.33-1.29 (m, 2H). MS-ESI calcd. [M+H]⁺ 319, found 319.

Example 40

3,7-Dimethyl-1-(5-(1-methyl-1H-tetrazol-5-yl)pentyl)-1H-purine-(3H,7H)-dione 3,7-Dimethyl-1-(5-(1-methyl-2H-tetrazol-5-yl)pentyl)-1H-purine-(3H,7H)-dione

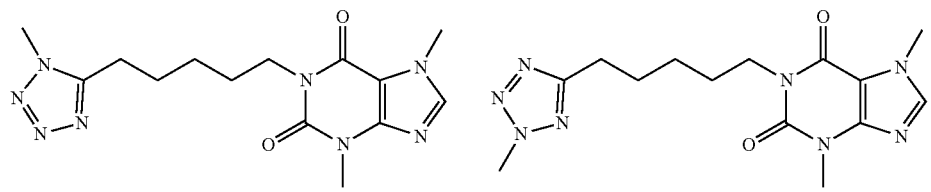

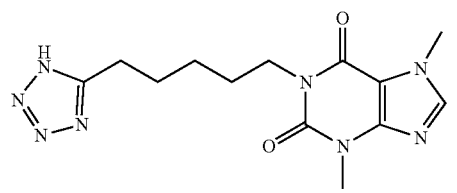

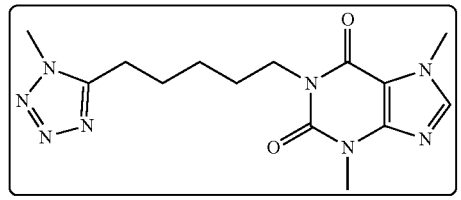

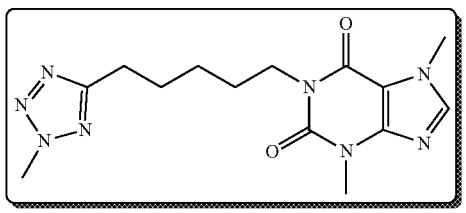

1-(5-(2H-tetrazol-5-yl)pentyl)-3,7-dimethyl-1H-purine-2,6(3H,7H)-dione (80.0 mg, 0.250 mmol) was dissolved in anhydrous N,N-dimethylformamide (3 mL), iodomethane (72.0 mg, 0.500 mmol) and potassium carbonate (69.0 mg, 0.500 mmol) were added at room temperature under nitrogen atmosphere. The reaction solution was stirred at room temperature for 3 hours. The reaction was quenched by addition of water (40 mL) and the mixture was extracted with ethyl acetate (30 mL×2). The organic phases were combined, washed with saturated sodium chloride solution (30 mL×2), dried over anhydrous magnesium sulfate and filtered. The filtrate was concentrated under reduced pressure and purified by preparative HPLC to give two substituted isomeric products: 3,7-dimethyl-1-(5-(1-methyl-1H-tetrazol-5-yl)pentyl)-1H-purine-(3H,7H)-dione (10.0 mg) (isomer 1, first peak): $^1$H NMR: (400 MHz, Methanol-d$_4$) δ 7.87 (s, 1H), 4.06 (s, 3H), 4.02-4.00 (m, 2H), 3.97 (s, 3H), 3.52 (s, 3H), 2.94 (t, J=7.6 Hz, 2H), 1.89-1.85 (m, 2H), 1.74-1.70 (m, 2H), 1.47-1.42 (m, 2H). MS-ESI calcd. [M+H]$^+$ 333, found 333.

3,7-Dimethyl-1-(5-(1-methyl-2H-tetrazol-5-yl)pentyl)-1H-purine-(3H,7H)-dione (10.0 mg) (isomer 2, second peak) with a yield of 23%. $^1$H NMR: (400 MHz, Methanol-d$_4$) δ 7.88 (s, 1H), 4.32 (s, 3H), 4.02-3.99 (m, 2H), 3.98 (s, 3H), 3.54 (s, 3H), 2.89 (t, J=7.6 Hz, 2H), 1.85-1.82 (m, 2H), 1.72-1.68 (m, 2H), 1.48-1.42 (m, 2H). MS-ESI calcd. [M+H]$^+$ 333, found 333.

Example 41

1-(3-(1H-indole-3)propyl-3,7-dimethyl-1H-purine-2,6(3H,7H)-dione

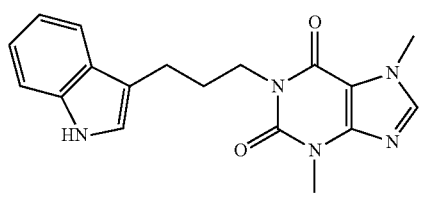

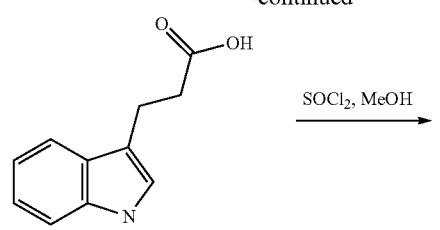

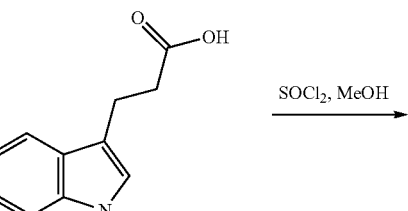

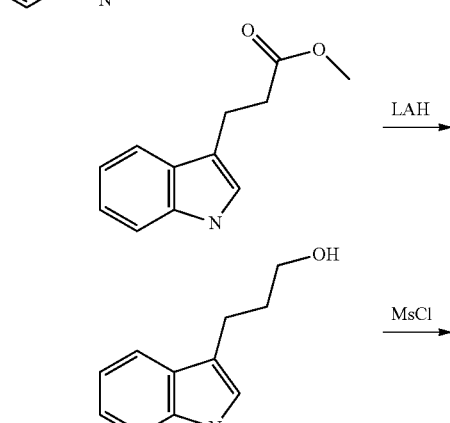

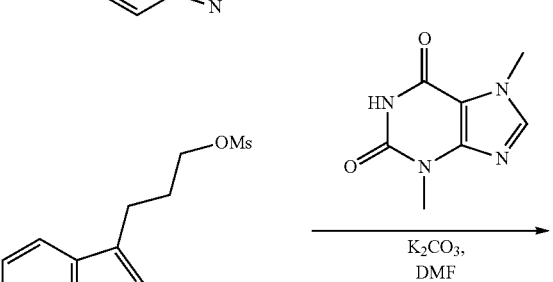

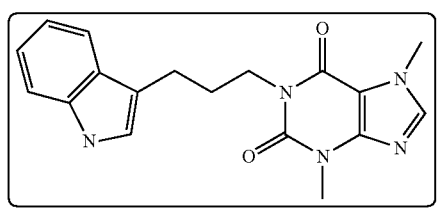

Step 1

Methyl 3-(1H-indole-3-yl)propionate 3-(1H-indol-3-yl)propionic acid (200 mg, 1.06 mmol) was dissolved in anhydrous methanol (3 mL), and thionyl chloride (249 mg, 2.12 mmol) was added at 0° C. to react for 0.5 h. Water (10 mL) was added to quench the reaction. The reaction solution was extracted with ethyl acetate (10 mL×3). The organic phases were combined, dried over anhydrous sodium sulfate, concentrated under reduced pressure and purified by preparative TLC plate (3:1 petroleum ether/ethyl acetate, $R_f$=0.5) to give methyl 3-(1H-indole-3-yl)propionate (180 mg, as a green solid) with a yield of 85%. MS-ESI [M+H]$^+$ calcd. 204, found 204.

Step 2

3-(1H-indole-3-yl)propan-1-ol

Methyl 3-(1H-indole-3-yl)-propionate (180 mg, 0.890 mmol) was dissolved in anhydrous tetrahydrofuran (10 mL), and lithium aluminum hydride (67.0 mg, 1.70 mmol) was added at 0° C. to react for 1 hour. Water (10 mL) was added to quench the reaction. The reaction solution was extracted with ethyl acetate (10 mL×3), dried over anhydrous sodium sulfate, concentrated under reduced pressure and purified by preparative TLC plate (1:1 petroleum ether/ethyl acetate, $R_f$=0.5) to give 3-(1H-indole-3-yl)propan-1-ol (100 mg, as a green solid) with a yield of 65%. MS-ESI [M+H]$^+$ calcd. 176, found 176.

Step 3

3-(1H-indole-3-yl)propyl methanesulfonic Acid 3-(1H-indole-3-yl)propan-1-ol (100 mg, 0.570 mmol) and triethylamine (173 mg, 1.71 mmol) were dissolved in anhydrous dichloromethane (5 mL). Methanesulfonyl chloride (128 mg, 1.14 mmol) was added at 0° C. The reaction solution was slowly heated to room temperature and stirred for 2 hours. The reaction was quenched by the addition of saturated aqueous sodium bicarbonate solution (10 mL) and extracted with dichloromethane (30 mL×3). The organic phases were combined, washed with saturated sodium chloride solution (30 mL×2), dried over anhydrous sodium sulfate and concentrated under reduced pressure to give 3-(1H-indole-3-yl) propyl methanesulfonic acid (100 mg, as a green solid) with a yield of 69%. MS-ESI [M+H]$^+$ calcd. 254, found 254.

Step 4

1-(3 (1H-indole-3-yl)propyl-3,7-dimethyl-1H-purine-2,6(3H,7H)-dione 3-(1H-indole-3-yl)propyl methanesulfonic acid (100 mg, 0.395 mmol), 3,7-dimethyl-1H-purine-2,6(3H,7H)-dione (71.1 mg, 0.395 mmol), potassium iodide (7.1 mg, 0.039 mmol) and potassium carbonate (109 mg, 0.790 mmol) were dissolved in anhydrous N,N-dimethylformamide (3 mL). The reaction solution was heated to 120° C. and reacted for 3 hours. The reaction solution was cooled to 20° C., filtered and purified by preparative HPLC to give 1-(3 (1H-indole-3-yl)propyl-3,7-dimethyl-1H-purine-2,6(3H,7H)-dione (40.0 mg) with a yield of 30%.

$^1$H NMR: (400 MHz, Methanol-d$_4$) δ 8.05 (s, 1H), 7.50 (d, J=3.8 Hz, 1H), 7.01 (d, J=4.0 Hz, 1H), 7.01-6.97 (m, 3H), 4.17-4.13 (m, 2H), 3.92 (s, 3H), 3.40 (s, 3H), 2.88-2.84 (m, 2H), 2.19-2.16 (m, 2H). MS-ESI calcd. [M+H]$^+$ 338, found 338.

Example 42

1-(4-(Benzofuran-2-yl)butyl)-3,7-dimethyl-1H-purine-2,6(3H,7H)-dione

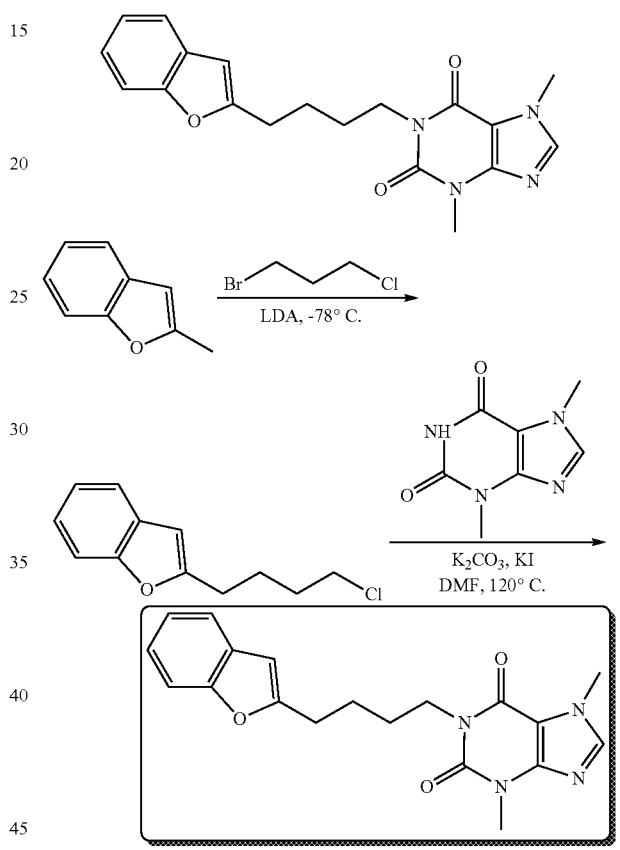

Step 1

2-(4-Chlorobutyl)benzofuran

2-Methylbenzofuran (400 mg, 3.03 mmol) was dissolved in tetrahydrofuran (15 mL), cooled to −78° C., and lithium diisopropylamide (2 M tetrahydrofuran solution, 1.7 mL, 3.33 mmol) was added dropwise. The reaction solution was stirred at −78° C. for 1 hour, and 1-bromo-3-chloropropane (525 mg, 3.33 mmol) was added and the mixture was stirred at −78° C. for another 2 hours. The reaction was quenched by the addition of saturated ammonium chloride solution (30 mL). The mixture was extracted with ethyl acetate (30 mL×2). The organic phases were combined, washed with brine (20 mL), dried over anhydrous sodium sulfate, filtered and the filtrate was concentrated under reduced pressure to give 2-(4-chlorobutyl)benzofuran (500 mg, as a yellow oil). MS-ESI M+H]$^+$ calcd. 209, found 209.

Step 2

1-(4-(Benzofuran-2-yl)butyl)-3,7-dimethyl-1H-purine-2,6(3H,7H)-dione 2-(4-Chlorobutyl)benzofuran (500 mg, 2.40 mmol) was dissolved in N,N-dimethylformamide (10 mL), potassium carbonate (662 mg, 4.80 mmol), 3,7-dimethyl-1H-purine-2,6(3H,7H)-dione (432 mg, 2.40 mmol) and potassium iodide (478 mg, 2.88 mmol) were added. The reaction was heated to 120° C. and stirred for 16 hours, then cooled to room temperature, followed by adding water (30 mL) to quench the reaction. The reaction mixture was extracted with ethyl acetate (30 mL×2). The organic phase was combined, dried over anhydrous sodium sulfate, filtered and the filtrate was concentrated under reduced pressure. The residue was purified by silica gel column chromatography (1:1 petroleum ether/ethyl acetate, $R_f$=0.5) to give 1-(4-(benzofuran-2-yl)butyl)-3,7-dimethyl-1H-purine-2,6(3H,7H)-dione (200 mg) with a yield of 24%.

$^1$H NMR: (400 MHz, CDCl$_3$) δ 7.50 (m, 1H), 7.47 (d, J=7.2 Hz, 1H), 7.38 (d, J=7.2 Hz, 1H), 7.23-7.12 (m, 2H), 6.39 (s, 1H), 4.07 (t, J=7.2 Hz, 2H), 3.98 (s, 3H), 3.57 (s, 3H), 2.83 (t, J=7.2 Hz, 2H), 1.88-1.71 (m, 4H). MS-ESI calcd. [M+H]$^+$ 353, found 353.

Example 43

1-(3-(Benzo[d]thiazol-2-yl)propyl)-3,7-dimethyl-1H-purine 2,6(3H,7H)-dione

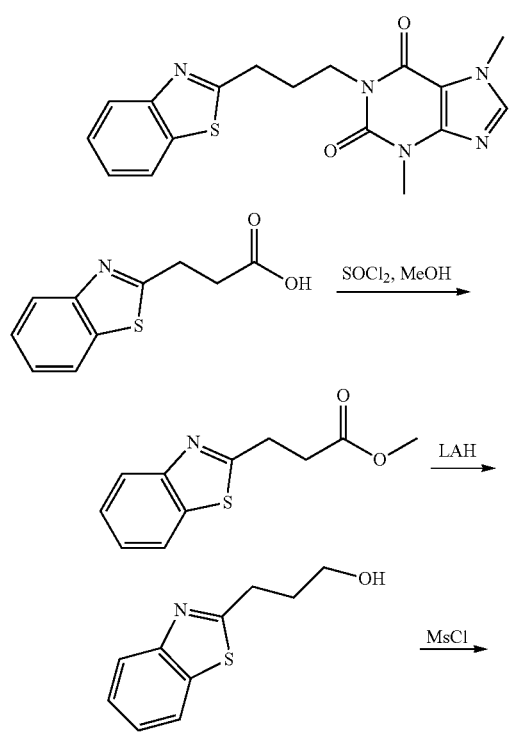

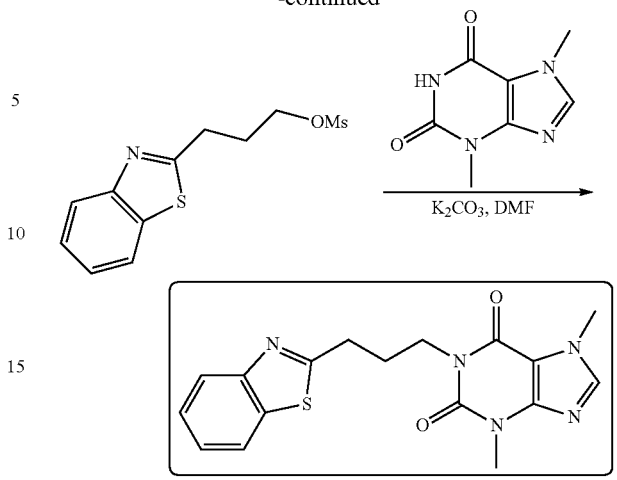

Step 1

3-Benzothiazole-2-methyl propionate 3-(Benzo[d]thiazol-2-yl)propionic acid (200 mg, 0.970 mmol) was dissolved in methanol (3 mL). Thionyl chloride (229 mg, 1.96 mmol) was added at 0° C. and reacted under nitrogen atmosphere for 0.5 hour. The reaction was quenched with water (10 mL), extracted with ethyl acetate (10 mL×3), dried over anhydrous sodium sulfate and concentrated under reduced pressure. The residue was purified by preparative TLC plate (3:1 petroleum ether/ethyl acetate, $R_f$=0.5) to give 3-benzothiazole-2-methyl propionate (150 mg, as a yellow solid) with a yield of 70%. MS-ESI [M+H]$^+$ calcd. 222, found 222.

Step 2

3-(Benzo[d]thiazole-2-yl)propan-1-ol

3-Benzothiazole-2-methyl propionate (150 mg, 0.680 mmol) was dissolved in tetrahydrofuran (10 mL). Lithium aluminum hydride (52.0 mg, 1.36 mmol) was added 0° C. and reacted for 1 hour. The reaction was quenched with water (10 mL), extracted with ethyl acetate (10 mL×3), dried over anhydrous sodium sulfate and concentrated under reduced pressure. The residue was purified by preparative TLC plate (1:1 petroleum ether/ethyl acetate, $R_f$=0.4) to give 3-(benzo[d]thiazole-2-yl)propan-1-ol (100 mg, as a yellow solid) with a yield of 52%. MS-ESI [M+H]$^+$ calcd. 194, found 194.

Step 3

3-(Benzo[d]thiazole-2-yl)propyl methanesulfonate 3-(Benzo[d]thiazole-2-yl)propan-1-ol (100 mg, 0.520 mmol) and triethylamine (173 mg, 1.71 mmol) were dissolved in dichloromethane (5 mL). Methanesulfonyl chloride (128 mg, 1.14 mmol) was added at 0° C. The reaction solution was slowly allowed to warm to room temperature and stirred for 2 hours. The reaction was quenched by the addition of aqueous sodium bicarbonate solution (10 mL) and extracted with dichloromethane (10 mL×3). The combined organic phases were washed with saturated sodium chloride solution (10 mL), dried over anhydrous sodium sulfate and concentrated under reduced pressure to give 3-(benzo[d]thiazole-2-yl)propyl methanesulfonate (100 mg, as a yellow solid) with a yield of 71%. MS-ESI [M+H]+ calcd. 272, found 272.

Step 4

1-(3-(Benzo[d]thiazol-2-yl)propyl)-3,7-dimethyl-1H-purine 2,6(3H,7H)-dione 3-(Benzo[d]thiazole-2-yl)propyl methanesulfonate (100 mg, 0.370 mmol), 3,7-dimethyl-1H-purine-2,6(3H,7H)-dione (66.4 mg, 0.370 mmol), potassium iodide (7.1 mg, 0.037 mmol) and potassium carbonate (109 mg, 0.790 mmol) were dissolved in anhydrous N,N-dimethylformamide (3 mL). The reaction was heated to 120° C. and stirred for 3 hours. The reaction solution was cooled to 20° C., filtered and purified by preparative HPLC to give 1-(3-(benzo[d]thiazol-2-yl) propyl)-3,7-dimethyl-1H-purine 2,6(3H,7H)-dione (40.0 mg) with a yield of 30%.

$^1$H NMR: (400 MHz, Methanol-d$_4$) δ 8.15 (d, J=4.0 Hz, 1H), 8.06 (s, 1H), 7.98 (d, J=4.0 Hz, 1H), 7.75-7.72 (m, 1H), 7.67-7.65 (m, 1H), 4.23-4.20 (m, 2H), 3.99 (s, 3H), 3.50 (s, 3H), 3.48-3.46 (m, 2H), 2.40-2.37 (m, 2H). MS-ESI calcd. [M+H]+ 356, found 356.

Example 44

3,7-Dimethyl-1-(3-(4,5,6,7-tetrahydro-2H-indol-3-yl)propyl)-1H-purine-2,6(3H,7H)-dione

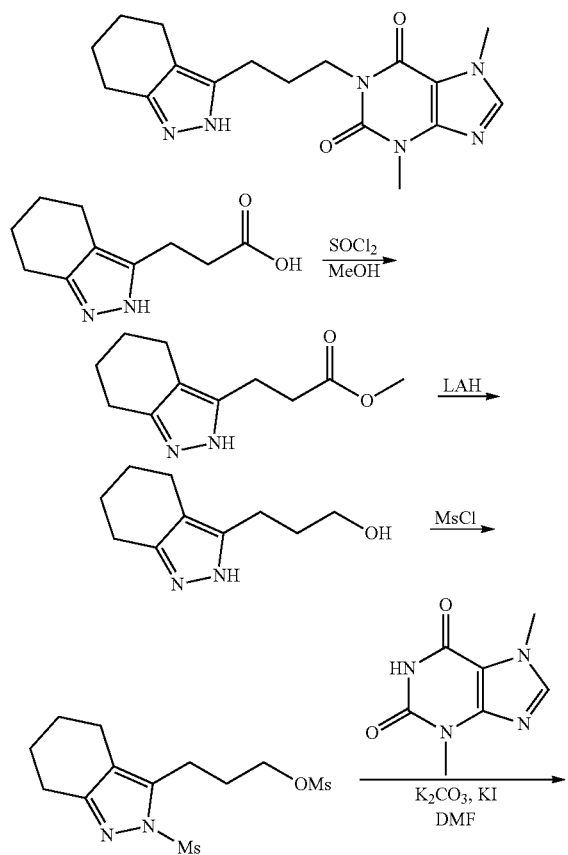

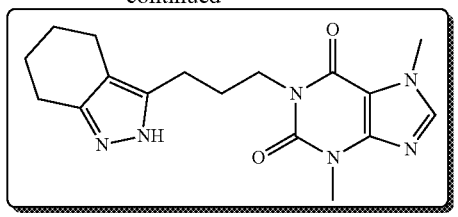

Step 1

3-(4,5,6,7-tetrahydro-2H-indol-3-yl)-methyl propionate 3-(4,5,6,7-Tetrahydro-2H-indol-3-yl)-propionic acid (150 mg, 0.770 mmol) was dissolved in anhydrous methanol (7 mL). Thionyl chloride (0.1 mL) was added at room temperature, the reaction solution was stirred at room temperature for 4 hours. The reaction was quenched with water (10 mL), extracted with ethyl acetate (10 mL×3), and the combined organic phases were dried over anhydrous sodium sulfate and concentrated under reduced pressure to give 3-(4,5,6,7-tetrahydro-2H-indol-3-yl)-methyl propionate (150 mg, as a white solid) with a yield of 94%. MS-ESI [M+H]+ calcd. 209, found 209.

Step 2

3-(4,5,6,7-Tetrahydro-2H-indol-3-yl)-propanol 3-(4,5,6,7-Tetrahydro-2H-indol-3-yl)-methyl propionate (150 mg, 0.720 mmol) was dissolved in anhydrous tetrahydrofuran (5 mL). Lithium aluminum hydride (41.0 mg, 1.08 mmol) was added at 0° C. and the reaction was slowly allowed to warm to room temperature and stirred for 3 hours. Water (0.04 mL), 15% sodium hydroxide solution (0.04 mL) and water (0.12 mL) were added sequentially. The solution was filtered and the filtrate was concentrated under reduced pressure to give 3-(4,5,6,7-tetrahydro-2H-indol-3-yl)-propanol (110 mg, as a yellow liquid) with a yield of 85%. MS-ESI [M+H]+ calcd. 181, found 181.

Step 3

3-(2-(Methylsulfonyl)-4,5,6,7-tetrahydro-2H-indol-3-yl)-propyl methanesulfonic acid 3-(4,5,6,7-Tetrahydro-2H-indol-3-yl)-propanol (110 mg, 0.610 mmol) and diisopropylethylamine (236 mg, 1.83 mmol) were dissolved in anhydrous dichloromethane (3 mL). Methanesulfonyl chloride (139 mg, 1.22 mmol) was added at 0° C. The reaction solution was slowly allowed to warm to room temperature and stirred for 0.5 hour. The reaction was quenched by the addition of water (10 mL) and extracted with dichloromethane (30 mL×3). The organic phases were combined, washed with saturated sodium chloride solution (30 mL×2), dried over anhydrous sodium sulfate, and concentrated to give 3-(2-(methylsulfonyl)-4,5,6,7-tetrahydro-2H-indol-3-yl)-propylmethanesulfonic acid (50 mg, yellow oil) with a yield of 25%. MS-ESI [M+H]+ calcd. 337, found 337.

Step 4

3,7-Dimethyl-1-(3-(4,5,6,7-tetrahydro-2H-indol-3-yl)propyl)-1H-purine-2,6(3H,7H)-dione 3-(2-(Methylsulfonyl)-4,5,6,7-tetrahydro-2H-indol-3-yl)-propyl methanesulfonic acid (50.0 mg, 0.150 mmol), 3,7-dimethyl-1H-purine-2,6(3H,7H)-dione (32.0 mg, 0.180 mmol), potassium iodide (2.5 mg, 0.015 mmol) and potassium carbonate (41.0 mg, 0.300 mmol) were dissolved in anhydrous N,N-dimethylformamide (2 mL). The reaction was heated to 130° C. and reacted for 3 hours. The reaction solution was cooled to 20° C. and filtered, and purified by preparative HPLC to give 3,7-dimethyl-1-(3-(4,5,6,7-tetrahydro-2H-indol-3-yl)propyl)-1H-purine-2,6(3H,7H)-dione (40.0 mg) with a yield of 32%.

$^1$H NMR (400 MHz, Methanol-$d_4$) δ 7.84 (s, 1H), 4.02 (t, J=7.2 Hz, 2H), 3.96 (s, 3H), 3.49 (s, 3H), 2.66-2.59 (m, 2H), 2.52 (t, J=5.4 Hz, 2H), 2.43 (t, J=5.4 Hz, 2H), 2.02-1.95 (m, 2H), 1.78-1.66 (m, 4H). MS-ESI calcd. [M+H]$^+$ 343, found 343.

Example 45

3,7-Dimethyl-1-[4-(3-methylisoxazol-5-yl)-benzyl]-3,7-dihydro-purine-2,6-dione

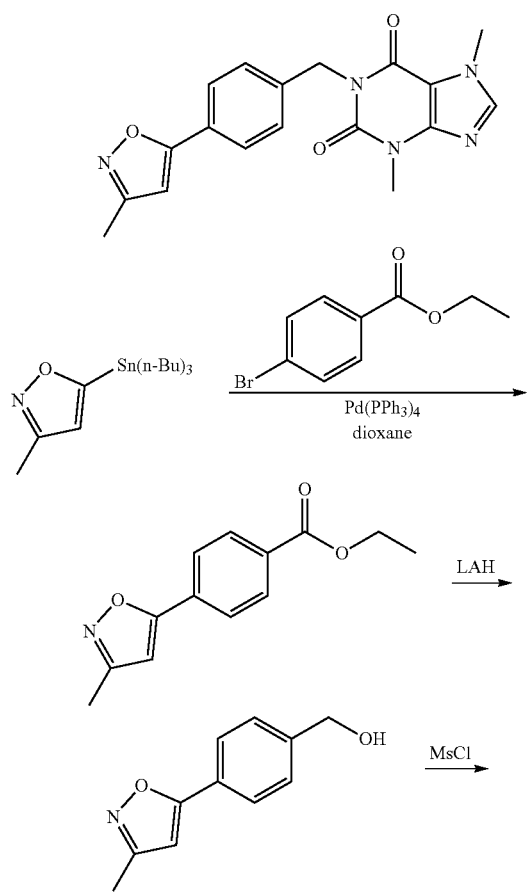

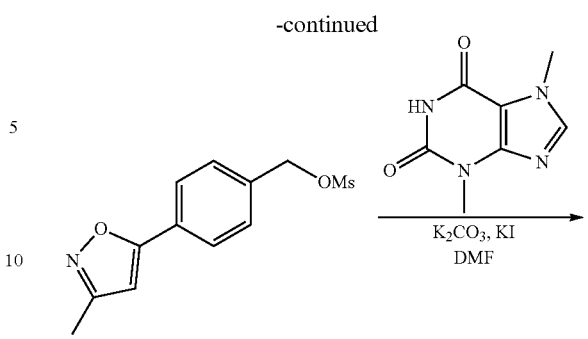

Step 1

Ethyl 4-(3-methylisoxazole-5-yl)-benzoate

3-Methyl-5-(tri-n-butylmethoxy)isoxazole (200 mg, 0.540 mmol) and ethyl 4-bromo-benzoate (122 mg, 0.540 mmol) were dissolved in anhydrous dioxane (3 mL) and tetrakis(triphenylphosphine)palladium (15.0 mg, 0.0141 mmol) was added under nitrogen atmosphere, and the reaction solution was heated to 100° C. and stirred for 2 hours. The reaction was cooled to 20° C., quenched with water (10 mL), extracted with ethyl acetate (10 mL×3), dried over anhydrous sodium sulfate, filtered, concentrated under reduced pressure and purified by preparative TLC plate (5:1 petroleum ether/ethyl acetate, $R_f$=0.5) to give ethyl 4-(3-methylisoxazole-5)-benzoate (100 mg, as a yellow solid) with a yield of 80%. MS-ESI [M+H]$^+$ calcd. 232, found 232.

Step 2

[4-(3 Methylisoxazol-5-yl)-phenyl]-methanol

Ethyl 4-(3-methylisoxazole-5-yl)-benzoate (100 mg, 0.430 mmol) was dissolved in anhydrous tetrahydrofuran (2 mL). Lithium aluminum hydride (33.0 mg, 0.860 mmol) was added at 0° C., the temperature was warmed to 25° C. and stirred for 1 hour. The reaction was quenched with water (10 mL), extracted with ethyl acetate (10 mL×3), dried over anhydrous sodium sulfate, filtered and concentrated under reduced pressure. The residue was purified by preparative TLC plate (3:1 petroleum ether/ethyl acetate, $R_f$=0.4) to give [4-(3-methylisoxazol-5-yl)-phenyl]-methanol (70.0 mg, as a yellow solid) with a yield of 86%. MS-ESI [M+H]$^+$ calcd. 190, found 190.

Step 3

4-(3-Methylisoxazol-5-yl)benzyl methanesulfonate

[4-(3-Methylisoxazol-5-yl)-phenyl]-methanol (70.0 mg, 0.370 mmol) and triethylamine (112 mg, 1.11 mmol) were dissolved in anhydrous dichloromethane (5 mL). Methanesulfonyl chloride (83.0 mg, 0.740 mmol) was added at 0° C. The reaction solution was slowly warmed to 25° C. and stirred for 2 hours. The reaction was quenched with aqueous sodium bicarbonate solution (10 mL), extracted with dichloromethane (10 mL×3), the combined organic phases were washed with saturated sodium chloride solution, dried over anhydrous sodium sulfate, filtered and concentrated under reduced pressure to give 4-(3-methylisoxazol-5-yl)benzyl methanesulfonate (80.0 mg, as a yellow oil) with a yield of 82%. MS-ESI [M+H]$^+$ calcd. 268, found 268.

Step 4

3,7-Dimethyl-1-[4-(3-methylisoxazol-5-yl)-benzyl]-3,7-dihydro-purine-2,6-dione 4-(3-Methylisoxazol-5-yl)benzyl methanesulfonate (80.0 mg, 0.300 mmol), 3,7-dimethyl-3,7-dihydro-purine-2,6-dione (55.0 mg, 0.300 mmol), potassium iodide (7.0 mg, 0.0300 mmol) and potassium carbonate (109 mg, 0.790 mmol) were dissolved in anhydrous N,N-dimethylformamide (3 mL) and the reaction was warmed to 120° C. and stirred for 3 hours. The reaction solution was cooled to 20° C., filtered and purified by preparative HPLC to give 3,7-dimethyl-1-[4-(3-methylisoxazol-5-yl)-benzyl]-3,7-dihydro-purine-2,6-dione (40.0 mg) with a yield of 30%.

$^1$H NMR: (400 MHz, Methanol-d$_4$) δ 8.04 (s, 1H), 7.73 (d, J=8.4 Hz, 2H), 7.41 (d, J=8.4 Hz, 2H), 6.81 (s, 1H), 5.07 (s, 2H), 3.87 (s, 3H), 3.41 (s, 3H), 2.25 (s, 3H). MS-ESI calcd. [M+H]$^+$ 352, found 352.

Example 46

3,7-Dimethyl-1-(3-(pyridin-4-yl)propyl)-1H-purine-2,6(3H,7H)-dione

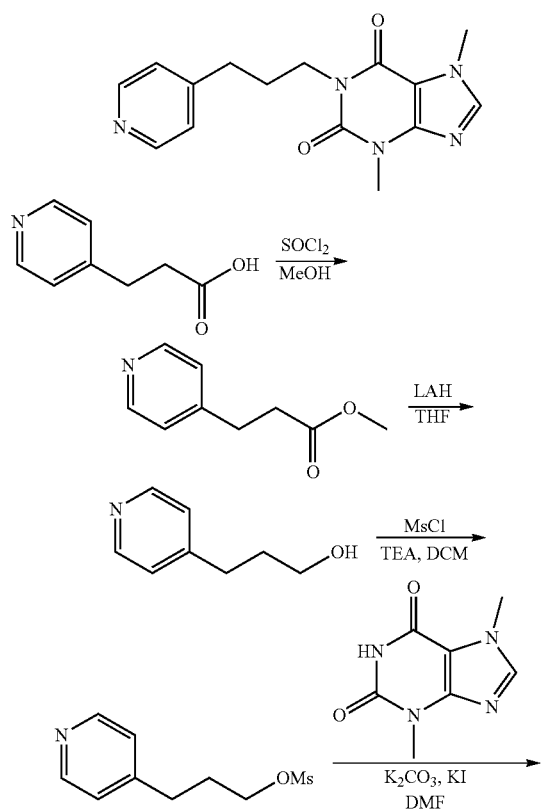

-continued

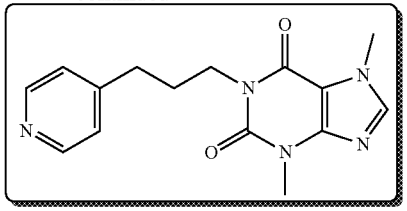

Step 1

Methyl 3-(pyridin-4-yl) propionate 3-(Pyridin-4-yl)propionic acid (200 mg, 1.32 mmol) was dissolved in methanol (5 mL), and thionyl chloride (471 mg, 3.96 mmol) was slowly added at 0° C. The reaction solution was stirred at 25° C. for 3 hours and concentrated under reduced pressure to give methyl 3-(pyridin-4-yl)propionate (311 mg, as a yellow solid). $^1$H NMR: (400 M Hz, Methonal-d$_4$) δ 8.75 (d, J=6.4 Hz, 2H), 8.02 (d, J=6.4 Hz, 2H), 3.66 (s, 3H), 3.26 (t, J=7.2 Hz, 2H), 2.89 (t, J=7.2 Hz, 2H).

Step 2

3-(Pyridin-4-yl)propan-1-ol

Lithium aluminum hydride (107 mg, 2.82 mmol) was added slowly to a solution of methyl 3-(pyridin-4-yl)propionate (310 mg, 1.88 mmol) in tetrahydrofuran (10 mL) at 0° C. under nitrogen atmosphere. The reaction solution was stirred at 25° C. for 4 hours, and then cooled to 0° C. in an ice-water bath, followed by slowly adding water (107 mg, 5.94 mmol), 15% sodium hydroxide (107 mg, 2.68 mmol) and water (321 mg, 17.8 mmol) successively. The reaction solution was heated to 25° C. and stirred for half an hour, and then filtered. The filter cake was washed with tetrahydrofuran (8 mL×3) and the filtrate was concentrated under reduced pressure to give 3-(pyridin-4-yl)propan-1-ol (182 mg, as a yellow solid) with a yield of 71%. $^1$H NMR: (400 M Hz, Methanol-d$_4$) δ 8.44-8.41 (m, 2H), 7.33 (d, J=6.0 Hz, 2H), 3.60 (t, J=6.4 Hz, 2H), 2.79-2.74 (m, 2H), 1.92-1.85 (m, 2H).

Step 3

3-(Pyridin-4-yl)propyl methanesulfonate 3-(Pyridin-4-yl)propan-1-ol (180 mg, 1.31 mmol) and triethylamine (398 mg, 3.93 mmol) were dissolved in dichloromethane (8 mL), methanesulfonyl chloride (300 mg, 2.62 mmol) was added slowly at 0° C. The reaction solution was stirred at 25° C. overnight, followed by adding water, and extracted with ethyl acetate (50 mL×3). The organic phase was dried over anhydrous sodium sulfate, filtered and the filtrate was concentrated under reduced pressure to give the crude product 3-(pyridin-4-yl)propyl methanesulfonate (741 mg, as a red solid).

Step 4

3,7-Dimethyl-1-(3-(pyridin-4-yl)propyl)-1H-purine-2,6(3H,7H)-dione 3-(Pyridin-4-yl)propyl methanesulfonate (1.20 g, 5.57 mmol), 3,7-dimethyl-1H-purine-2,6(3H,7H)-dione (502 mg, 2.79 mmol) and potassium iodide (92.5 mg, 0.53 mmol) were dissolved in N,N-dimethylformamide (20 mL), potassium carbonate (847 mg, 6.13 mmol) was added and the reaction was heated to reflux at 130° C. for 3 hours. The reaction solution was cooled to 25° C., filtered and the filtrate was concentrated under reduced pressure. The resulting product was purified by preparative HPLC to give 3,7-dimethyl-1-(3-(pyridin-4-yl)propyl)-1H-purine-2,6(3H,7H)-dione (163 mg) with a yield of 10%. $^1$H NMR: (400 MHz, Methanol-$d_4$) δ 8.36 (d, J=6.0 Hz, 2H), 7.85 (s, 1H), 7.32 (d, J=6.0 Hz, 2H), 4.05 (t, J=7.2 Hz, 2H), 3.96 (s, 3H), 3.50 (s, 3H), 2.76 (t, J=7.2 Hz, 2H), 2.09-2.00 (m, 2H). MS-ESI calcd. [M+H]$^+$ 300, found 300.

Example 47

1-(2-(4,6-Dimethylpyridin-2-yl)ethyl)-3,7-dimethyl-1H-purine-2,6(3H,7H)-dione

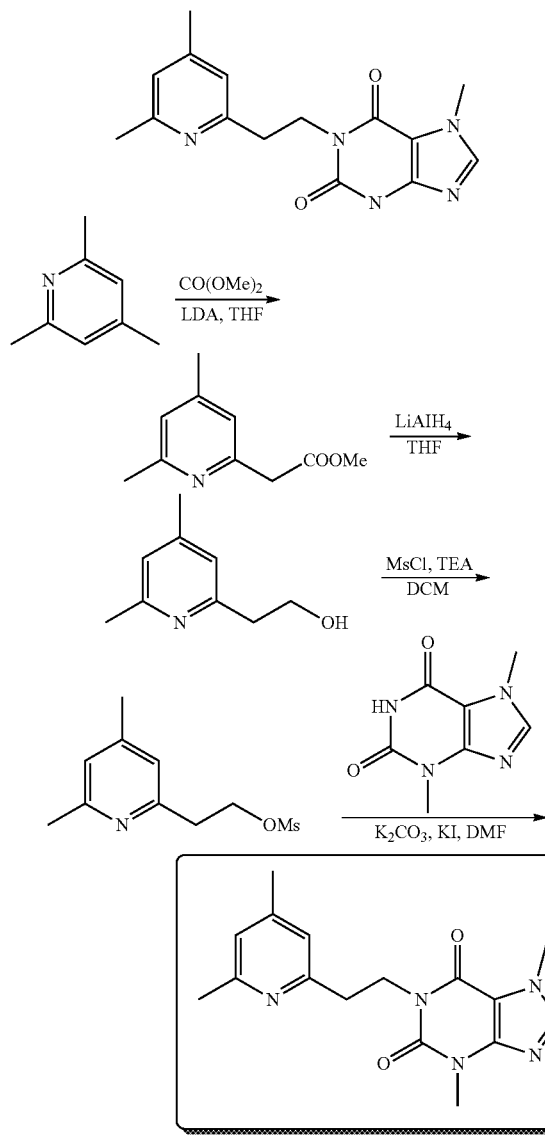

Step 1

Methyl 2-(4,6-dimethylpyridin-2-yl) acetate 2,4,6-Trimethylpyridine (1.00 g, 8.25 mmol) was dissolved in tetrahydrofuran (30 mL), lithium diisopropylamide (8.2 mL, 2 M tetrahydrofuran solution, 16.5 mmol) was added at 0° C. under nitrogen atmosphere. The reaction solution was stirred at 0° C. for 0.5 hour. Dimethyl carbonate (743 mg, 8.25 mmol) was added to the reaction mixture and then slowly heated to 20° C. The stirring was continued for 2 hours. The reaction solution was quenched by the addition of saturated ammonium chloride solution (100 mL). The mixture was extracted with ethyl acetate (20 mL×3). The organic phase was washed with brine (20 mL×3), dried over anhydrous sodium sulfate and concentrated under reduced pressure. The residue was purified by silica gel column chromatography (2:1 petroleum ether/ethyl acetate, $R_f$=0.5) to give methyl 2-(4,6-dimethylpyridin-2-yl)acetate (1.20 g, as a yellow oil) with a yield of 81%.
$^1$H NMR: (400 MHz, CDCl$_3$) δ 6.91 (s, 1H), 6.87 (s, 1H), 3.77 (s, 2H), 3.70 (s, 3H), 2.48 (s, 3H), 2.28 (s, 3H). MS-ESI calcd. [M+H]$^+$ 180, found 180.

Step 2

2-(4,6-Dimethylpyridin-2-yl)ethanol

Methyl 2-(4,6-dimethylpyridin-2-yl)acetate (500 mg, 2.79 mmol) was dissolved in tetrahydrofuran (20 mL), lithium aluminum hydride (211 mg, 5.58 mmol) was added at 0° C. and reacted for 1 hour. The reaction was quenched by adding water (10 mL), extracted with ethyl acetate (20 mL×3), dried over anhydrous sodium sulfate, filtered and concentrated under reduced pressure. The residue was purified by silica gel column chromatography (2:1 petroleum ether/ethyl acetate, $R_f$=0.3) to give 2-(4,6-dimethylpyridin-2-yl)ethanol (410 mg, as a yellow oil) with a yield of 92%.
MS-ESI calcd. [M+H]$^+$ 152, found 152.

Step 3

2-(4,6-Dimethylpyridin-2-yl)ethyl methanesulfonate 2-(4,6-Dimethylpyridin-2-yl)ethanol (421 mg, 3.07 mmol) and triethylamine (1.18 g, 11.6 mmol) were dissolved in dichloromethane (20 mL), methanesulfonyl chloride (794 mg, 6.94 mmol) was added at 0° C. The reaction solution was stirred at room temperature for 2 hours, diluted with dichloromethane (20 mL), washed with saturated sodium bicarbonate solution (30 mL×2), dried over anhydrous sodium sulfate, filtered and the filtrate was concentrated under reduced pressure, and purified by silica gel column chromatography (4:1 petroleum ether/ethyl acetate, $R_f$=0.5) to give 2-(4,6-dimethylpyridin-2-yl)ethyl methanesulfonate (400 mg, as a colorless oil) with a yield of 61%.
MS-ESI calcd. [M+H]$^+$ 230, found 230.

Step 4

1-(2-(4,6-Dimethylpyridin-2-yl)ethyl)-3,7-dimethyl-1H-purine-2,6(3H,7H)-dione 2-(4,6-Dimethylpyridin-2-yl)ethyl methanesulfonate (200 mg, 0.929 mmol) was dissolved in N,N-dimethylformamide (15 mL), and 3,7-dimethyl-1H-purine-2,6(3H,7H)-dione (167 mg, 0.929 mmol), potassium carbonate (192 mg, 1.39 mmol) and potassium iodide (184 mg, 1.11 mmol) were added at room temperature. The reaction solution was heated to 100° C., reacted for 2 hours, diluted with ethyl acetate (20 mL). The organic phase was washed with saturated sodium bicarbonate solution (20 mL×2), dried over anhydrous sodium sulfate, filtered and the filtrate was concentrated under reduced pressure, and purified by HPLC to give 1-(2-(4,6-dimethylpyridin-2-yl)ethyl)-3,7-dimethyl-1H-purine-2,6(3H,7H)-dione (120 mg) with a yield of 43%.

$^1$H NMR: (400 MHz, CDCl$_3$) δ 7.53 (s, 1H), 6.99 (s, 1H), 6.91 (s, 1H), 4.33 (t, J=7.6 Hz, 2H), 3.97 (s, 3H), 3.56 (s, 3H), 3.13 (t, J=7.6 Hz, 2H), 2.52 (s, 3H), 2.32 (s, 3H). MS-ESI calcd. [M+H]$^+$ 314, found 314.

Example 48

1-((6-Methoxypyridin-3-yl)methyl)-3,7-dimethyl-1H-purine-2,6(3H,7H)-dione

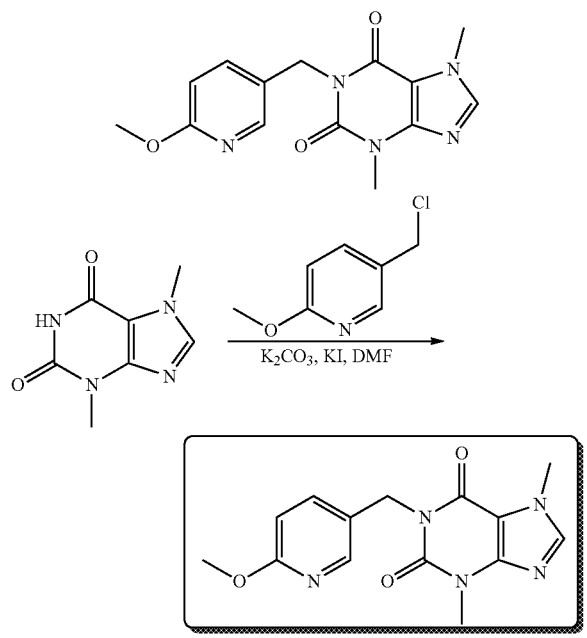

Step 1

1-((6-Methoxypyridin-3-yl)methyl)-3,7-dimethyl-1H-purine-2,6(3H,7H)-dione 3,7-Dimethyl-1H-purine-2,6(3H,7H)-dione (300 mg, 1.67 mmol) was dissolved in N,N-dimethylformamide (10 mL), and 5-(chloromethyl)-2-methoxypyridine (263 mg, 1.67 mmol), potassium iodide (332 mg, 2.00 mmol) and potassium carbonate (461 mg, 3.34 mmol) were added. The reaction solution was heated to 120° C., stirred for 3 hours and concentrated under reduced pressure. The residue was purified by silica gel column chromatography (1:1 petroleum ether/ethyl acetate, R$_f$=0.2) to give 1-((6-methoxypyridin-3-yl)methyl)-3,7-dimethyl-1H-purine-2,6(3H,7H)-dione (20.0 mg) with a yield of 4%.

$^1$H NMR: (400 MHz, CDCl$_3$) δ 8.28 (s, 1H), 7.78 (d, J=8.0 Hz, 1H), 7.51 (s, 1H), 6.67 (d, J=8.0 Hz, 1H), 5.12 (s, 2H), 3.99 (s, 3H), 3.91 (s, 3H), 3.57 (s, 3H). MS-ESI calcd. [M+H]$^+$ 302, found 302.

Example 49

7-(Difluoromethyl)-3-methyl-1-(4-(3-methylisoxazol-5-yl)butyl)-1H-purine-2,6(3H,7H)-dione 9-(Difluoromethyl)-3-methyl-1-(4-(3-methylisoxazol-5-yl)butyl)-1H-purine-2,6(3H,7H)-dione

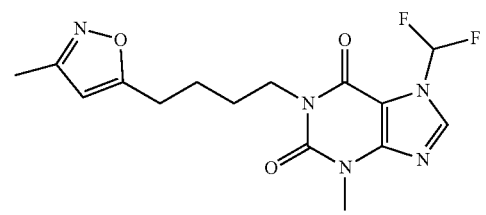

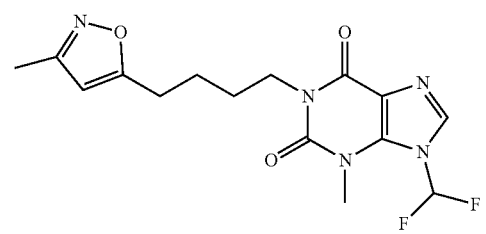

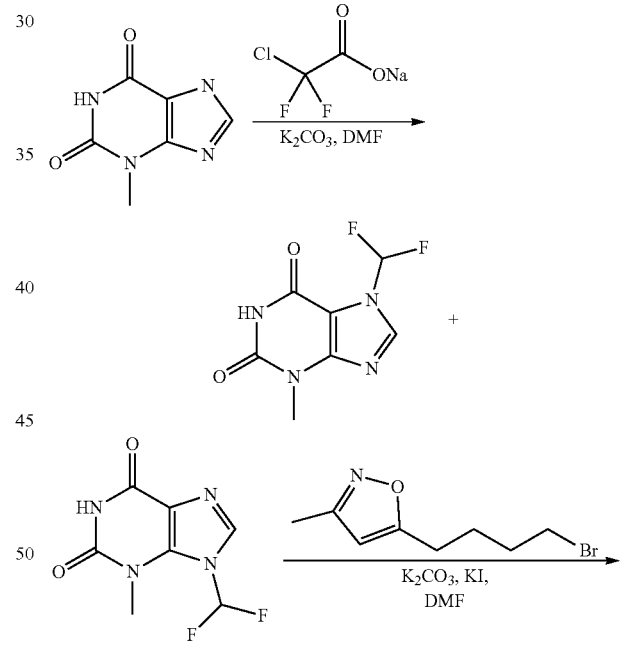

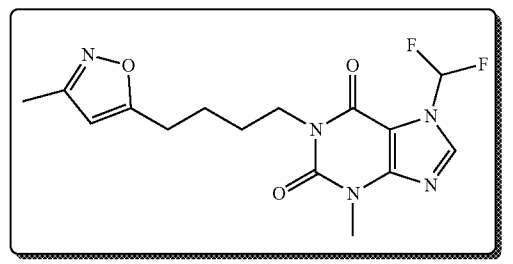

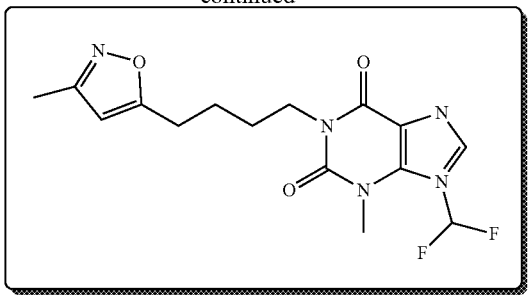

Step 1

7-(Difluoromethyl)-3-methyl-1H-purine-2,6(3H,7H)-dione 9-(Difluoromethyl)-3-methyl-1H-purine-2,6(3H,7H)-dione 3-Methyl-1H-purine-2,6(3H,7H)-dione (1.00 g, 6.02 mmol) was dissolved in N,N-dimethylformamide (40 mL), 2-chloro-2,2-difluoroacetate (1.84 g, 12.0 mmol) and potassium carbonate (1.66 g, 12.0 mmol) were added into the reaction solution at room temperature. The reaction solution was heated to 95° C. After reacting for 8 hours, the reaction solution was cooled to room temperature, and concentrated to dryness, diluted with ethyl acetate (80 mL) and the organic phase was washed with saturated sodium bicarbonate solution (50 mL×2), dried over anhydrous sodium sulfate, filtered, and the filtrate was concentrated under reduced pressure. The residue was purified by silica gel column chromatography (1:1 petroleum ether/ethyl acetate, $R_f$=0.3) to give a mixture of 7-(difluoromethyl)-3-methyl-1H-purine-2,6(3H,7H)-dione and 9-(difluoromethyl)-3-methyl-1H-purine-2,6(3H,7H)-dione (300 mg, as a yellow solid) with a yield of 23%.

MS-ESI calcd. [M+H]$^+$ 217, found 217.

Step 2

7-(Difluoromethyl)-3-methyl-1-(4-(3-methylisoxazol-5-yl)butyl)-1H-purine-2,6(3H,7H)-dione 9-(Difluoromethyl)-3-methyl-1-(4-(3-methylisoxazol-5-yl)butyl)-1H-purine-2,6(3H,7H)-dione A mixture of 7-(difluoromethyl)-3-methyl-1H-purine-2,6(3H,7H)-dione and 9-(difluoromethyl)-3-methyl-1H-purine-2,6(3H,7H)-dione (200 mg, 0.917 mmol) was dissolved in N,N-dimethylformamide (20 mL). 5-(4-Bromobutyl)-3-methylisoxazole (200 mg, 0.917 mmol), potassium carbonate (190 mg, 1.38 mmol) and potassium iodide (86.3 mg, 0.520 mmol) were added to the reaction solution at room temperature. The reaction solution was heated to 100° C., reacted for 2 hours, diluted with ethyl acetate (20 mL). The organic phase was washed with saturated sodium bicarbonate solution (20 mL×2), dried over anhydrous sodium sulfate, filtered and the filtrate was concentrated under reduced pressure. The residue was purified by HPLC to give 7-(difluoromethyl)-3-methyl-1-(4-(3-methylisoxazol-5-yl)butyl)-1H-purine-2,6(3H,7H)-dione (isomer 1, 50.0 mg) with a yield of 15%, $^1$H NMR: (400 MHz, CDCl$_3$) δ 8.07 (s, 1H), 7.93-7.63 (m, 1H), 5.83 (s, 1H), 4.02 (m, 2H), 3.58 (s, 3H), 2.73 (m, 2H), 2.23 (s, 3H), 1.71 (m, 4H). MS-ESI calcd. [M+H]$^+$ 354, found 354.

9-(Difluoromethyl)-3-methyl-1(4-(3-methylisoxazol-5-yl)butyl)-1H-purine-2,6(3H,7H)-dione (isomer 2, 20.0 mg) with a yield of 6%, $^1$H NMR: (400 MHz, CDCl$_3$) δ 7.86 (s, 1H), 7.73-7.43 (m, 1H), 5.84 (s, 1H), 4.06 (m, 2H), 3.75 (s, 3H), 2.74 (m, 2H), 2.24 (s, 3H), 1.72 (m, 4H). MS-ESI calcd. [M+H]$^+$ 354, found 354.

Example 50

7-Ethyl-3-methyl-1-(4-(3-methylisoxazol-5-yl)butyl)-1H-purine-2,6(3H,7H)-dione

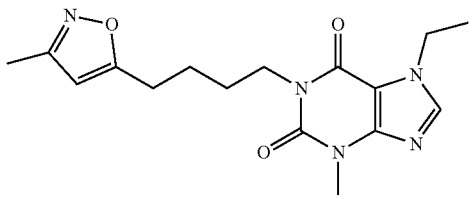

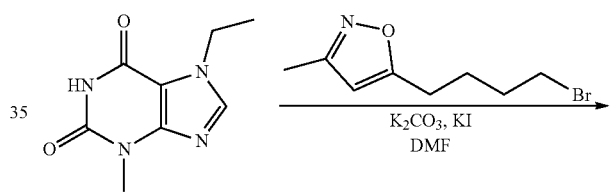

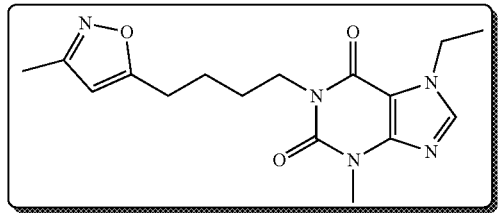

7-Ethyl-3-methyl-1H-purine-2,6(3H,7H)-dione (50.0 mg, 0.260 mmol), 5-(4-bromobutyl)-3-methylisoxazole (60.0 mg, 0.335 mmol), potassium carbonate (70.0 mg, 0.520 mmol) and potassium iodide (4.0 mg, 0.0260 mmol) were dissolved in N,N-dimethylformamide (10 mL). The reaction was heated to 110° C. and reacted for 2 hours. The reaction solution was poured into water and extracted with ethyl acetate (20 mL×3). The organic phases were combined, dried over anhydrous sodium sulphate, filtered, concentrated and purified by preparative TLC plate to give 7-ethyl-3-methyl-1-(4-(3-methylisoxazol-5-yl)butyl)-1H-purine-2,6(3H,7H)-dione (30.0 mg) with a yield of 39%.

$^1$H NMR: (400 MHz, CDCl$_3$): δ 7.94 (s, 1H), 6.03 (s, 1H), 4.39-4.33 (m, 2H), 4.04-4.02 (m, 2H), 3.53 (s, 3H), 2.81-2.78 (m, 2H), 2.23 (s, 3H), 1.73-1.71 (m, 4H), 1.48 (t, J=7.0 Hz, 3H). MS-ESI calcd. [M+H]$^+$ 332, found 332.

Example 51

3-Methyl-1-(4-(3-methylisoxazol-5-yl)butyl)-7-(2,2,2-trifluoroethyl)-1H-purine-2,6(3H,7H)-dione

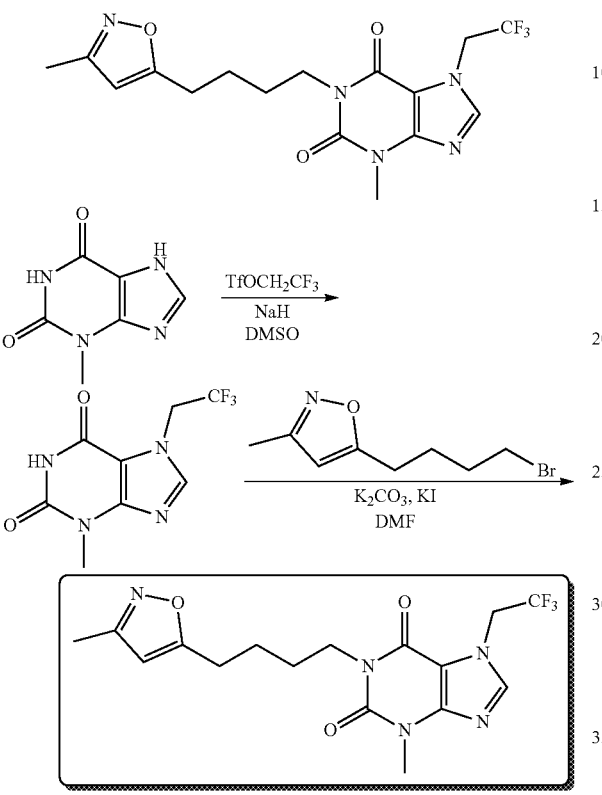

Step 1

3-Methyl-7-(2,2,2-trifluoroethyl)-1H-purine-2,6(3H,7H)-dione

3-Methyl-1H-purine-2,6(3H,7H)-dione (3.00 g, 1.81 mmol) was dissolved in methanol (50 mL), sodium hydride (760 mg, 19.0 mmol) was added in batches at room temperature. The reaction was heated to 40° C. and stirred for 1.5 hours. 2,2,2-Trifluoroethyl trifluoromethanesulfonate (5.45 g, 23.5 mmol) was added and the reaction was stirred at 40° C. for 16 hours. The reaction solution was cooled to room temperature, filtered, and the filter cake was washed successively with water (30 mL) and methanol (20 mL), and dried to give 3-methyl-7-(2,2,2-trifluoroethyl)-1H-purine-2,6(3H,7H)-dione (1.90 g, as a white solid) with a yield of 42%.

$^1$H NMR: (400 Hz, DMSO-$d_6$) δ 11.32 (s, 1H), 8.19 (s, 1H), 5.23 (q, J=4.2 Hz, 2H), 3.36 (s, 3H). MS-ESI calcd. [M+H]$^+$ 249, found 249.

Step 2

3-Methyl-1-(4-(3-methylisoxazol-5-yl)butyl)-7-(2,2,2-trifluoroethyl)-1H-purine-2,6(3H,7H)-dione 5-(4-Bromobutyl)-3-methylisoxazole (130 mg, 0.600 mmol) was dissolved in N,N-dimethylformamide (10 mL). Potassium carbonate (166 mg, 1.20 mmol), 3-methyl-7-propyl-1H-purine-2,6(3H,7H)-dione (150 mg, 0.60 mmol) and potassium iodide (119 mg, 0.720 mmol) were added. The reaction was heated to 120° C. and stirred for 16 hours. The reaction solution was concentrated under reduced pressure and purified by preparative HPLC to give 3-methyl-1-(4-(3-methylisoxazol-5-yl)butyl)-7-(2,2,2-trifluoroethyl)-1H-purine-2,6(3H,7H)-dione (60.0 mg) with a yield of 26%.

$^1$H NMR: (400 MHz, CDCl$_3$) δ 7.70 (s, 1H), 5.83 (s, 1H), 5.05 (q, J=8.4 Hz, 2H), 4.12-3.98 (m, 2H), 3.60 (s, 3H), 2.77-2.70 (m, 2H), 2.25 (s, 3H), 1.80-1.66 (m, 4H). MS-ESI calcd. [M+H]$^+$ 386, found 386.

Example 52

3-Methyl-1-(4-(3-methylisoxazol-5-yl)butyl)-7-propyl-1H-purine-2,6(3H,7H)-dione

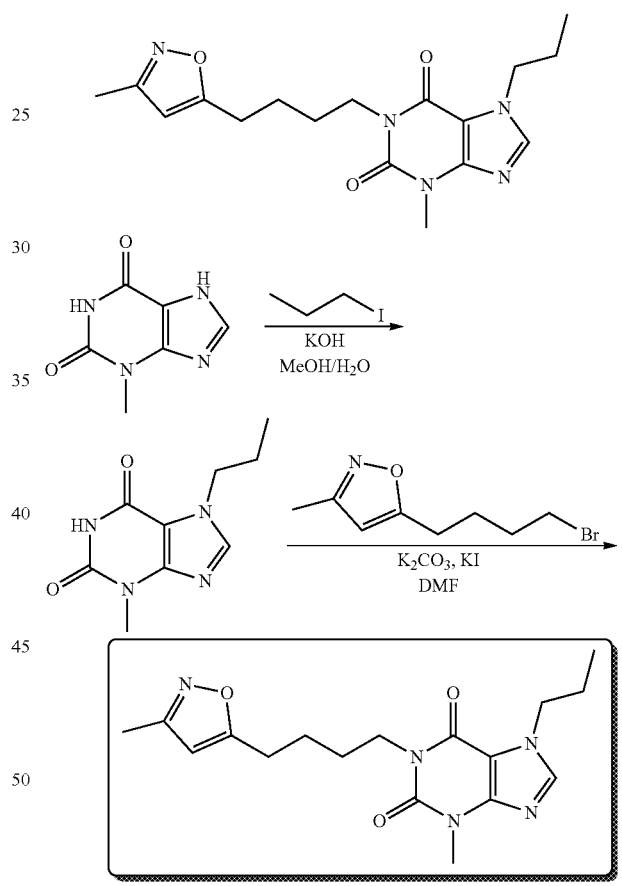

Step 1

3-Methyl-7-propyl-1H-purine-2,6(3H,7H)-dione

3-Methyl-1H-purine-2,6(3H,7H)-dione (4.00 g, 24.1 mmol) was dissolved in methanol (30 mL). An aqueous solution (15 mL) of potassium hydroxide (1.48 g, 26.5 mmol) was added and the mixture was heated to 80° C. and stirred for 1.5 hours. After cooling to 50° C., 1-iodopropane (5.33 g, 31.3 mmol) was added and the reaction solution was stirred at 50° C. for 24 hours, then cooled to room temperature and filtered. The filter cake was washed successively with water (30 mL) and methanol (30 mL), and dried to give 3-methyl-7-propyl-1H-purine-2,6(3H,7H)-dione (2.30 g, as a white solid) with a yield of 46%.

$^1$H NMR: (400 Hz, DMSO-d$_6$) δ 11.12 (s, 1H), 8.05 (s, 1H), 4.16 (t, J=7.2 Hz, 2H), 3.34 (s, 3H), 1.83-1.68 (m, 2H), 0.81 (t, J=7.2 Hz, 3H). MS-ESI calcd. [M+H]$^+$ 209, found 209.

Step 2

3-Methyl-1-(4-(3-methylisoxazol-5-yl)butyl)-7-propyl-1H-purine-2,6(3H,7H)-dione 5-(4-Bromobutyl)-3-methylisoxazole (218 mg, 1.00 mmol) was dissolved in N,N-dimethylformamide (10 mL). Potassium carbonate (276 mg, 2.00 mmol), 3-methyl-7-propyl-1H-purine-2,6(3H,7H)-dione (208 mg, 1.00 mmol) and potassium iodide (199 mg, 1.20 mmol) were added. The reaction was heated to 120° C. and stirred for 16 hours. The reaction solution was concentrated under reduced pressure and purified by preparative HPLC to give 3-methyl-1-(4-(3-methylisoxazol-5-yl)butyl)-7-propyl-1H-purine-2,6(3H, 7H)-dione (60.0 mg) with a yield of 17%.

$^1$H NMR: (400 MHz, CDCl$_3$) δ 7.54 (s, 1H), 5.82 (s, 1H), 4.24 (t, J=7.2 Hz, 2H), 4.10-3.97 (m, 2H), 3.58 (s, 3H), 2.82-2.70 (m, 2H), 2.25 (s, 3H), 1.97-1.84 (m, 2H), 1.81-1.65 (m, 4H), 0.95 (t, J=7.2 Hz, 3H). MS-ESI calcd. [M+H]$^+$ 346, found 346.

Example 53

7-Cyclopropyl-3-methyl-1-(4-(5-methylisoxazol-3-yl)butyl)-1H-purine-2,6(3H,7H)-dione

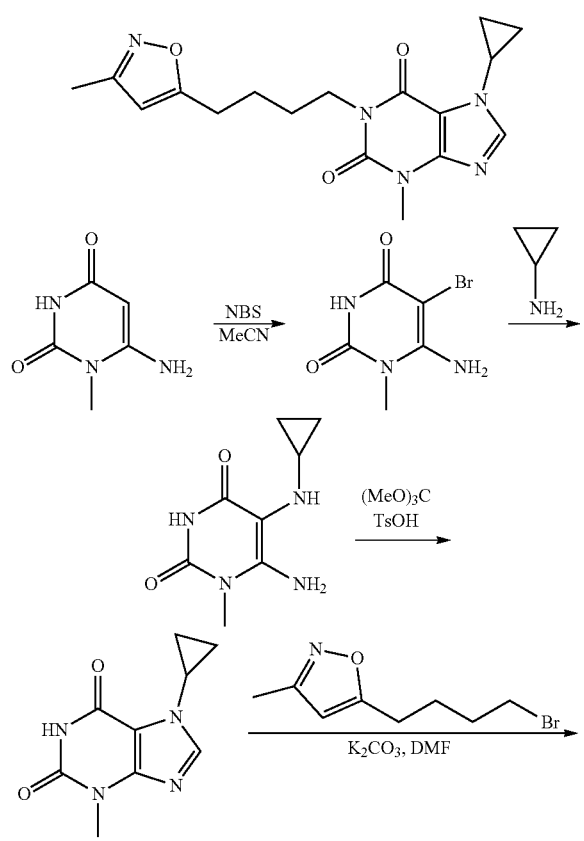

-continued

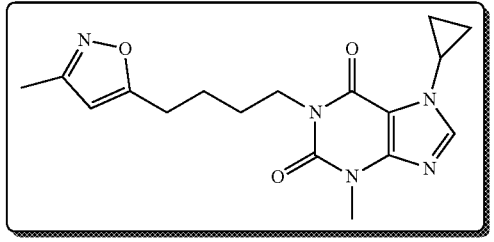

Step 1

6-Amino-5-bromo-1-methylpyrimidine-2,4(1H,3H)-dione

A mixture of 6-amino-1-methylpyrimidine-2,4(1H,3H)-dione (5.46 g, 40.0 mmol) and bromosuccinimide (7.56 g, 42.0 mmol) in acetonitrile (100 mL) and was heated to reflux under nitrogen atmosphere for 1.5 hours. The reaction solution was cooled to room temperature, filtered and the solvent was removed. The resulting solid was washed with water (20 mL) and dried to give 6-amino-5-bromo-1-methylpyrimidine-2,4(1H,3H)-dione (8.6 g, as a white solid) with a yield of 98%. $^1$H NMR: (400 MHz, DMSO-d6) δ 10.90 (s, 1H), 7.04 (s, 2H), 3.28 (s, 3H).

Step 2

6-Amino-5-(cyclopropylamine)-1-methylpyrimidine-2,4(1H,3H)-dione

6-Amino-5-bromo-1-methylpyrimidine-2,4(1H,3H)-dione (2.19 g, 10.0 mmol) was dissolved in a mixed solvent of cyclopropylamine (20 mL) and water (5 mL). The reaction solution was heated to reflux for 5 hours. The reaction solution was filtered to remove the solvent to give the crude product 6-amino-5-(cyclopropylamine)-1-methylpyrimidine-2,4(1H,3H)-dione directly used for the next step.

Step 3

7-cyclopropyl-3-methyl-1H-purine-2,6(3H,7H)-dione

6-Amino-5-(cyclopropylamine)-1-methylpyrimidine-2,4 (1H,3H)-dione (1.96 g, 10.0 mmol), trimethyl orthoformate (2.12 g, 20.0 mmol) and p-toluenesulfonic acid (86.0 mg, 0.500 mmol) were dissolved in anhydrous N,N-dimethylformamide (20 mL) under nitrogen atmosphere. The reaction was heated to 100° C. and reacted overnight. The reaction solution was filtered and the solvent was removed to give the crude product 7-cyclopropyl-3-methyl-1H-purine-2,6(3H,7H)-dione directly used for the next step.

Step 4

7-Cyclopropyl-3-methyl-1-(4-(5-methylisoxazol-3-yl)butyl)-1H-purine-2,6(3H,7H)-dione 7-Cyclopropyl-3-methyl-1H-purine-2,6(3H,7H)-dione (96.0 mg, 0.470 mmol), 3-(4-bromobutyl)-5-methylisoxazole (152 mg, 0.700 mmol) and potassium carbonate (130 mg, 0.940 mmol) were dissolved in N,N-dimethylformamide (5 mL) under nitrogen atmosphere. The reaction was heated to 120° C. and reacted for 3 hours, and then cooled to room temperature, diluted with water (20 mL) and extracted with ethyl acetate (30 mL×2). The organic phase was dried over anhydrous sodium sulfate, filtered, concentrated and purified by HPLC to give 7-cyclopropyl-3-methyl-1-(4-(5-methylisoxazol-3-yl)butyl)-1H-purine-2,6(3H,7H)-dione (100 mg, with a yield of 63%).

$^1$H NMR: (400 MHz, Methanol-$d_4$) δ 7.95 (s, 1H), 6.05 (s, 1H), 4.04 (t, J=6.8 Hz, 2H), 3.75-3.69 (m, 1H), 3.53 (s, 3H), 2.81 (t, J=6.8 Hz, 2H), 2.25 (s, 3H), 1.75-1.34 (m, 4H), 1.19-1.10 (m, 4H). MS-ESI calcd. [M+H]$^+$ 344, found 344.

Example 54

7-Isopropyl-3-methyl-1-(4-(3-methylisoxazol-5-yl)butyl)-1H-purine-2,6(3H,7H)-dione

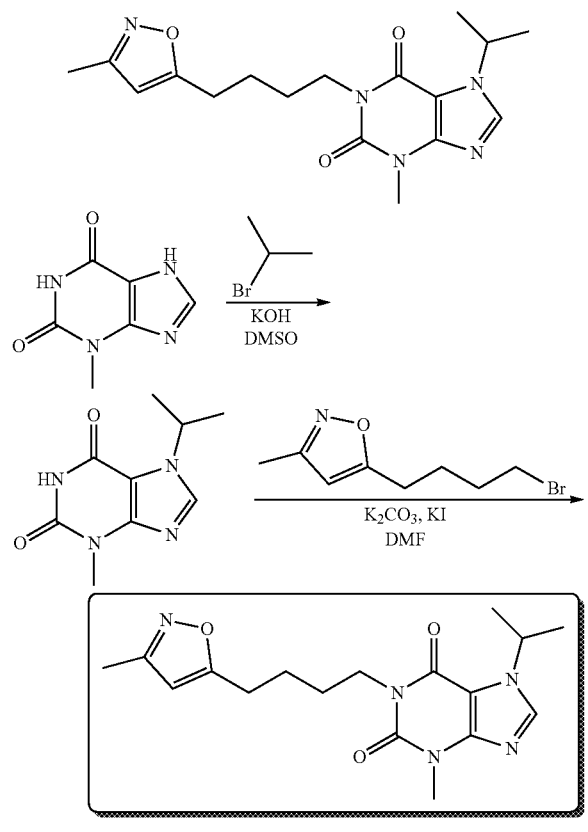

Step 1

7-Isopropyl-3-methyl-1H-purine-2,6(3H,7H)-dione

3-Methyl-1H-purine-2,6(3H,7H)-dione (3.00 g, 1.81 mmol) was dissolved in dimethyl sulfoxide (50 mL). Sodium hydrogen (760 mg, 19.0 mmol) was added in batches at room temperature. The reaction was heated to 40° C. and stirred for 1.5 hours. 2-Iodopropane (4.00 g, 23.5 mmol) was added. The reaction solution was stirred at 40° C. for 16 hours, cooled to room temperature, filtered, and the filter cake was washed successively with water (30 mL) and methanol (30 mL), and then dried to give 7-isopropyl-3-methyl-1H-purine-2,6(3H,7H)-dione (2.20 g, as a white solid) with a yield of 59%.

$^1$H NMR: (400 Hz, DMSO-$d_6$) δ 11.11 (s, 1H), 8.15 (s, 1H), 4.90-4.75 (m, 1H), 3.35 (s, 3H), 1.48 (d, J=6.8 Hz, 6H). MS-ESI calcd. [M+H]$^+$ 209, found 209.

Step 2

7-Isopropyl-3-methyl-1-(4-(3-methylisoxazol-5-yl)butyl)-1H-purine-2,6(3H,7H)-dione 4-Bromobutyl-3-methylisoxazole (91.1 mg, 0.424 mmol), 7-isopropyl-3-methyl-1H-purine-2,6(3H,7H)-dione (100 mg, 0.466 mmol), potassium iodide (7.4 mg, 0.047 mmol) and potassium carbonate (109 mg, 0.790 mmol) were dissolved in anhydrous N,N-dimethylformamide (3 mL). The reaction was heated to 120° C. and stirred for 3 hours. The reaction was cooled to 20° C. and filtered, and the filtrate was separated and purified by preparative HPLC to give 7-isopropyl-3-methyl-1-(4-(3-methylisoxazol-5-yl)butyl)-1H-purine-2,6(3H,7H)-dione (80.0 mg) with a yield of 55%.

$^1$H NMR: (400 MHz, Methanol-$d_4$) δ 8.89 (s, 1H), 6.06 (s, 1H), 5.21-5.16 (m, 1H), 4.08-4.04 (m, 2H), 3.58 (s, 3H), 2.83-2.79 (m, 2H), 2.24 (s, 3H), 1.75-1.72 (m, 4H), 1.65 (d, J=3.4 Hz, 6H). MS-ESI calcd. [M+H]$^+$ 346, found 346.

Example 55

7-Butyl-3-methyl-1-(4-(3-methylisoxazol-5-yl)butyl)-1H-purine-2,6(3H,7H)-dione

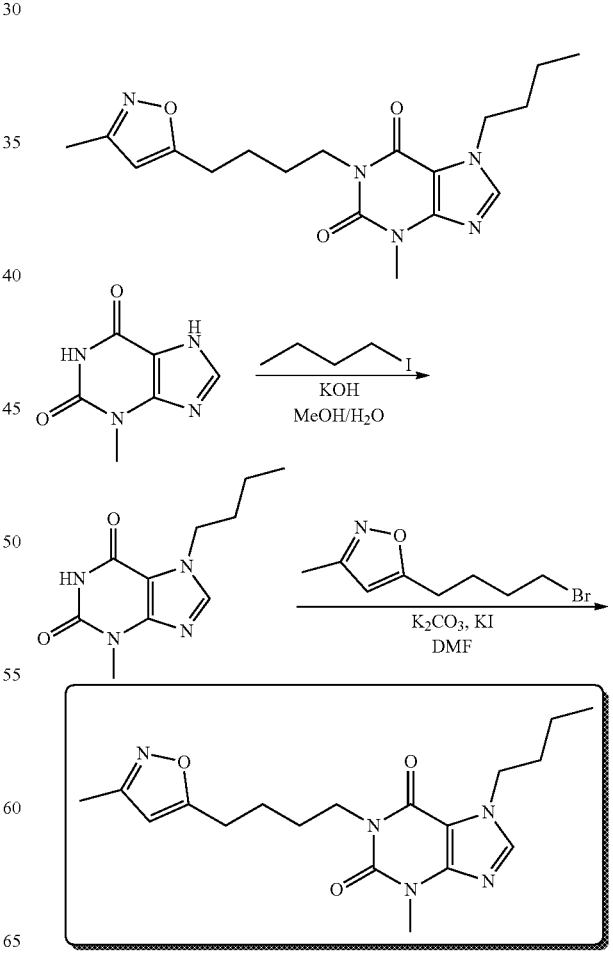

131

Step 1

7-Butyl-3-methyl-1H-purine-2,6(3H,7H)-dione

3-Methyl-1H-purine-2,6(3H,7H)-dione (4.00 g, 24.1 mmol) was dissolved in methanol (30 mL). An aqueous solution (15 mL) of potassium hydroxide (1.48 g, 26.5 mmol) was added and the mixture was heated to 80° C. and stirred for 1.5 hours. After cooling to 50° C., 1-iodobutane (5.76 g, 31.3 mmol) was added and the reaction was stirred at 50° C. for 24 hours. Then the reaction was cooled to room temperature, filtered, and the filter cake was washed successively with water (30 mL) and methanol (30 mL), and dried to give 7-butyl-3-methyl-1H-purine-2,6(3H,7H)-dione (2.80 g, as a white solid) with a yield of 52%.

$^1$H NMR: (400 Hz, DMSO-$d_6$) δ 11.11 (s, 1H), 8.05 (s, 1H), 4.20 (t, J=6.8 Hz, 2H), 3.37 (s, 3H), 1.81-1.67 (m, 2H), 1.30-1.12 (m, 2H), 0.87 (t, J=7.2 Hz, 3H). MS-ESI calcd. [M+H]$^+$ 223, found 223.

Step 2

7-Butyl-3-methyl-1-(4-(3-methylisoxazol-5-yl)butyl)-1H-purine-2,6(3H,7H)-dione 5-(4-bromobutyl)-3-methylisoxazole (218 mg, 1.00 mmol) was dissolved in N,N-dimethylformamide (10 mL). Potassium carbonate (276 mg, 2.00 mmol), 7-butyl-3-methyl-1H-purine-2,6(3H,7H)-dione (222 mg, 1.00 mmol) and potassium iodide (199 mg, 1.20 mmol) were added. The reaction was heated to 120° C. and stirred for 16 hours. The reaction solution was concentrated under reduced pressure and purified by preparative HPLC to give 7-butyl-3-methyl-1-(4-(3-methylisoxazol-5-yl)butyl)-1H-purine-2,6(3H,7H)-dione (60.0 mg) with a yield of 17%.

$^1$H NMR: (400 MHz, CDCl$_3$) δ 7.53 (s, 1H), 5.82 (s, 1H), 4.28 (t, J=7.2 Hz, 2H), 4.10-3.99 (m, 2H), 3.58 (s, 3H), 2.81-2.70 (m, 2H), 2.25 (s, 3H), 1.91-1.80 (m, 2H), 1.79-1.67 (m, 4H), 1.42-1.28 (m, 2H), 0.96 (t, J=7.2 Hz, 3H). MS-ESI calcd. [M+H]$^+$ 360, found 360.

Example 56

7-(Cyclopropylmethyl)-3-methyl-1-(4-(3-methylisoxazol-5-yl)butyl)-1H-purine-2,6(3H,7H)-dione

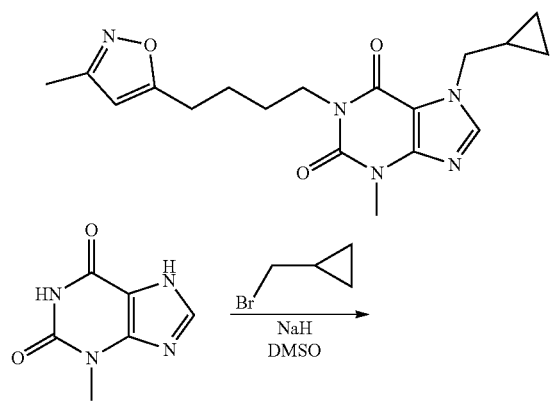

132

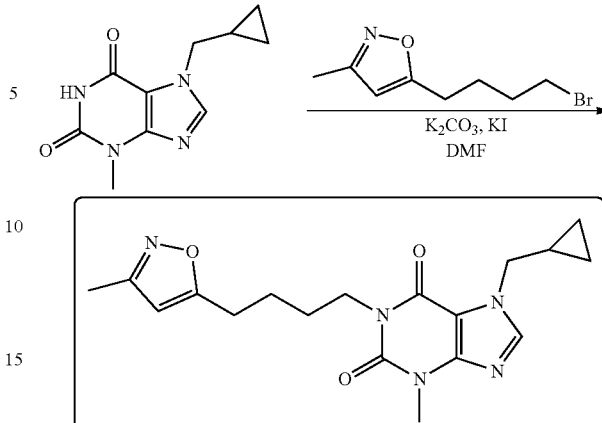

Step 1

7-(Cyclopropylmethyl)-3-methyl-1H-purine-2,6(3H,7H)-dione

3-Methyl-1H-purine-2,6(3H,7H)-dione (3.00 g, 1.81 mmol) was dissolved in dimethyl sulfoxide (50 mL), sodium hydrogen (760 mg, 19.0 mmol) was added in batches at room temperature. The reaction was heated to 40° C. and stirred for 1.5 hours. Bromomethyl cyclopropane (3.17 g, 23.5 mmol) and potassium iodide (3.60 g, 2.17 mmol) were added and the reaction was stirred at 40° C. for 16 hours, then cooled to room temperature, filtered, and the filter cake was washed successively with water (30 mL) and methanol (30 mL), and dried to give 7-(cyclopropylmethyl)-3-methyl-1H-purine-2,6(3H,7H)-dione (1.70 g, as a white solid) with a yield of 43%.

$^1$H NMR: (400 Hz, DMSO-$d_6$) δ 11.14 (s, 1H), 8.08 (s, 1H), 4.06 (d, J=7.2 Hz, 2H), 3.35 (s, 3H), 1.37-1.20 (m, 1H), 0.55-0.34 (m, 4H). MS-ESI calcd. [M+H]$^+$ 221, found 221.

Step 2

7-(Cyclopropylmethyl)-3-methyl-1-(4-(3-methylisoxazol-5-yl)butyl)-1H-purine-2,6(3H,7H)-dione 5-(4-Bromobutyl)-3-methylisoxazole (91.1 mg, 0.424 mmol), 7-(cyclopropylmethyl)-3-methyl-1H-purine-2,6(3H,7H)-dione (102 mg, 0.466 mmol), potassium iodide (7.4 mg, 0.047 mmol) and potassium carbonate (109 mg, 0.790 mmol) were dissolved in anhydrous N,N-dimethylformamide (3 mL). The reaction was heated to 120° C. and stirred for 3 hours. The reaction was cooled to 20° C. and filtered and the filtrate was purified by preparative HPLC to give 7-(cyclopropylmethyl)-3-methyl-1-(4-(3-methylisoxazol-5-yl)butyl)-H-purine-2,6(3H,7H)-dione (80.0 mg) with a yield of 53%.

$^1$H NMR: (400 MHz, Methanol-$d_4$) δ 8.56 (s, 1H), 6.05 (s, 1H), 4.30-4.29 (m, 2H), 4.07-4.04 (m, 2H), 3.57 (s, 3H), 2.83-2.79 (m, 2H), 2.24 (s, 3H), 1.75-1.72 (m, 4H), 1.47-1.44 (m, 1H), 0.67-0.65 (m, 2H), 0.54-0.51 (m, 2H). MS-ESI calcd. [M+H]$^+$ 358, found 358.

Example 57

7-(Cyclopropylmethyl)-1-((3,5-dimethylisoxazol-4-yl)methyl)-3-methyl-1H-purine-2,6-(3H,7H)-dione

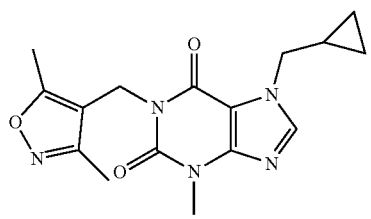

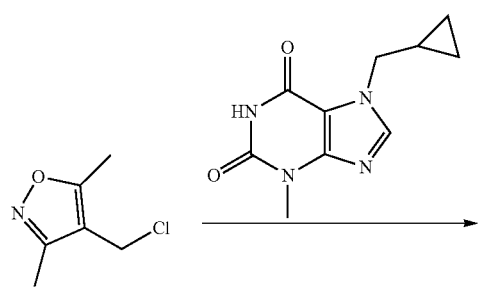

Step 1

7-(Cyclopropylmethyl)-1-((3,5-dimethylisoxazol-4-yl)methyl)-3-methyl-1H-purine-2,6(3H,7H)-dione 4-Chloromethyl-3,5-dimethylisoxazole (200 mg, 1.37 mmol), 7-(cyclopropylmethyl)-3-methyl-1H-purine-2,6(3H,7H)-dione (332 mg, 1.51 mmol), potassium iodide (22.7 mg, 0.137 mmol) and potassium carbonate (568 mg, 4.11 mmol) were dissolved in anhydrous N,N-dimethylformamide (5 mL). The reaction was heated to 120° C. and reacted for 3 hours. The reaction solution was cooled to 20° C. and filtered, and purified by preparative HPLC to give 7-(cyclopropylmethyl)-1-((3,5-dimethylisoxazol-4-yl)methyl)-3-methyl-1H-purine-2,6(3H,7H)-dione (200 mg) with a yield of 44%.

$^1$H NMR: (400 MHz, Methanol-$d_4$) δ 8.01 (s, 1H), 4.98 (s, 2H), 4.22 (d, J=3.2 Hz, 2H), 3.54 (s, 3H), 2.47 (s, 3H), 2.29 (s, 3H), 1.44-1.39 (m, 1H), 0.64-0.60 (m, 2H), 0.50-0.47 (m, 2H). MS-ESI calcd. [M+H]$^+$ 330, found 330.

Example 58

7-(Cyclopropylmethyl)-1-(5-isopropylisoxazol-4-yl)methyl)-3-methyl-1H-purine-2,6(3H,7H)-dione

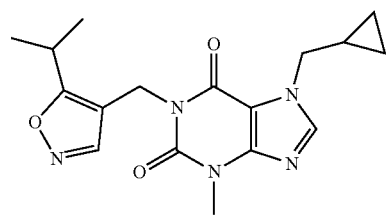

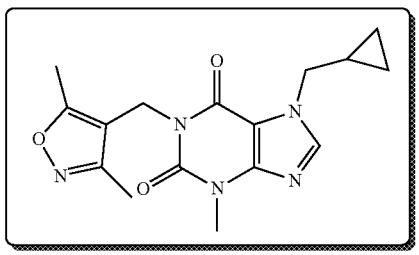

Step 1

7-(Cyclopropylmethyl)-1-(5-isopropylisoxazol-4-yl)methyl)-3-methyl-1H-purine-2,6(3H,7H)-dione 4-(Chloromethyl)-5-isopropylisoxazole (100 mg, 0.627 mmol), 7-(cyclopropylmethyl)-3-methyl-1H-purine-2,6(3H,7H)-dione (138 mg, 0.627 mmol), potassium iodide (10.4 mg, 0.0627 mmol) and potassium carbonate (260 mg, 1.88 mmol) were dissolved in anhydrous N,N-dimethylformamide (5 mL). The reaction was heated to 120° C. and reacted for 3 hours. The reaction solution was cooled to 20° C., filtered and purified by preparative HPLC to give 7-(cyclopropylmethyl)-1-(5-isopropylisoxazol-4-yl)methyl)-3-methyl-1H-purine-2,6(3H,7H)-dione (80.0 mg) with a yield of 37%.

$^1$H NMR: (400 MHz, Methanol-$d_4$) δ 8.34 (s, 1H), 8.08 (s, 1H), 5.00 (s, 2H), 4.23 (d, J=3.6 Hz, 2H), 3.68-3.65 (m, 1H), 3.56 (s, 3H), 1.44-1.41 (m, 1H), 1.32 (d, J=3.4 Hz, 6H), 0.63-0.61 (m, 2H), 0.49-0.48 (m, 2H).

MS-ESI calcd. [M+H]$^+$ 344, found 344.

Example 59

7-(Cyclopropylmethyl)-1-((3-isopropylisoxazol-5-yl)methyl)-3-methyl-1H-purine-2,6(3H,7H)-dione

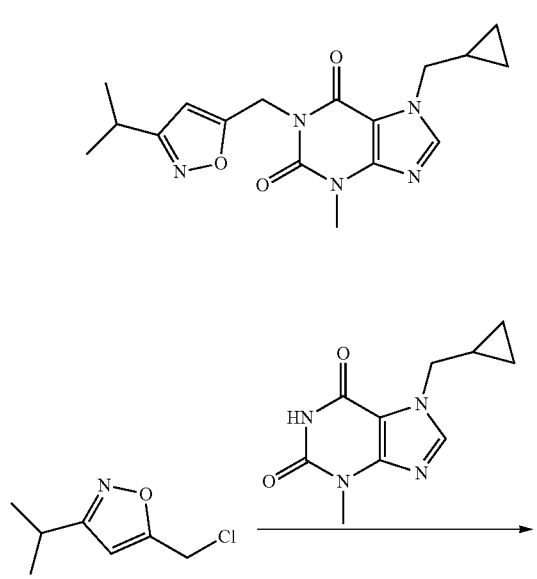

Step 1

7-(Cyclopropylmethyl)-1-((3-isopropylisoxazol-5-yl)methyl)-3-methyl-1H-purine-2,6(3H,7H)-dione 5-(Chloromethyl)-3-isopropylisoxazole (72.5 mg, 0.456 mmol), 7-(cyclopropylmethyl)-3-methyl-1H-purine-2,6(3H,7H)-dione (94.0 mg, 0.456 mmol), potassium iodide (7.5 mg, 0.046 mmol) and potassium carbonate (189 mg, 1.37 mmol) were dissolved in anhydrous N,N-dimethylformamide (5 mL). The reaction was heated to 120° C. and reacted for 3 hours. The reaction solution was cooled to 20° C., filtered and purified by preparative HPLC to give 7-(cyclopropylmethyl)-1-((3-isopropylisoxazol-5-yl)methyl)-3-methyl-1H-purine-2,6(3H,7H)-dione (50.0 mg) with a yield of 31%.

$^1$H NMR: (400 MHz, Methanol-$d_4$) δ 8.04 (s, 1H), 6.27 (s, 1H), 5.27 (s, 2H), 4.21 (d, J=3.6 Hz, 2H), 3.57 (s, 3H), 3.03-2.96 (m, 1H), 1.44-1.41 (m, 1H), 1.25 (d, J=3.4 Hz, 6H), 0.64-0.59 (m, 2H), 0.50-0.47 (m, 2H). MS-ESI calcd. [M+H]$^+$ 344, found 344.

Example 60

7-Isobutyl-3-methyl-1-(4-(3-methylisoxazol-5-yl)butyl)-1H-purine-2,6(3H,7H)-dione

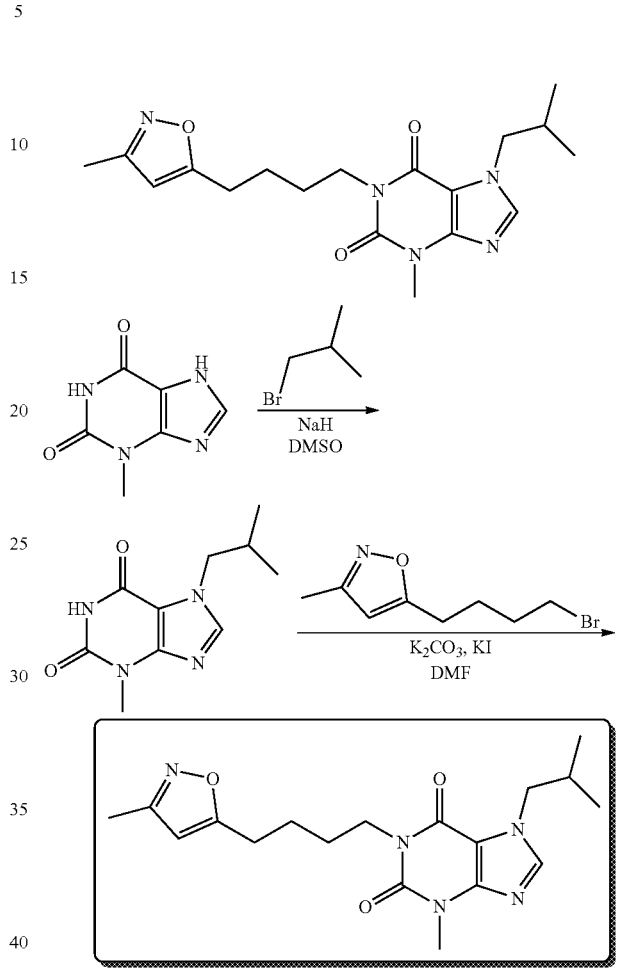

Step 1

7-isobutyl-3-methyl-1H-purine-2,6(3H, 7H)-dione

3-Methyl-1H-purine-2,6(3H,7H)-dione (3.00 g, 1.81 mmol) was dissolved in dimethyl sulfoxide (50 mL). Sodium hydrogen (760 mg, 19.0 mmol) was added in batches at room temperature. The reaction was heated to 40° C. and stirred for 1.5 hours. 1-Bromo-2-methylpropane (3.22 g, 23.5 mmol) was added and the reaction was stirred at 40° C. for 16 hours, and cooled to room temperature, filtered, and the filter cake was washed successively with water (30 mL) and methanol (30 mL), and dried to give 7-isobutyl-3-methyl-1H-purine-2,6(3H,7H)-dione (1.80 g, as a white solid) with a yield of 45%. MS-ESI calcd. [M+H]$^+$ 223, found 223.

Step 2

7-Isobutyl-3-methyl-1-(4-(3-methylisoxazol-5-yl)butyl)-1H-purine-2,6(3H,7H)-dione 5-(4-Bromobutyl)-3-methylisoxazole (196 mg, 0.900 mmol) was dissolved in N,N-dimethylformamide (10 mL), potassium carbonate (248 mg, 1.50 mmol), 7-isobutyl-3-methyl-1H-purine-2,6(3H,7H)-dione (200 mg, 0.90 mmol) and potassium iodide (179 mg, 1.08 mmol) were added. The reaction was heated to 120° C. and stirred for 16 hours. The reaction solution was concentrated under reduced pressure and purified by preparative HPLC to give 7-isobutyl-3-methyl-1-(4-(3-methylisoxazol-5-yl)butyl)-1H-purine-2,6(3H,7H)-dione (70.0 mg) with a yield of 33%.

$^1$H NMR: (400 MHz, CDCl$_3$) δ 7.50 (s, 1H), 5.81 (s, 1H), 4.12-3.95 (m, 4H), 3.57 (s, 3H), 2.80-2.67 (m, 2H), 2.28-2.12 (m, 4H), 1.80-1.65 (m, 4H), 0.92 (d, J=6.8 Hz, 6H). MS-ESI calcd. [M+H]$^+$ 360, found 360.

Example 61

3-Methyl-1-(4-(3-methylisoxazol-5-yl)butyl)-7-((3-methyloxetan-3-yl)methyl)-1H-purine-2,6(3H,7H)-dione

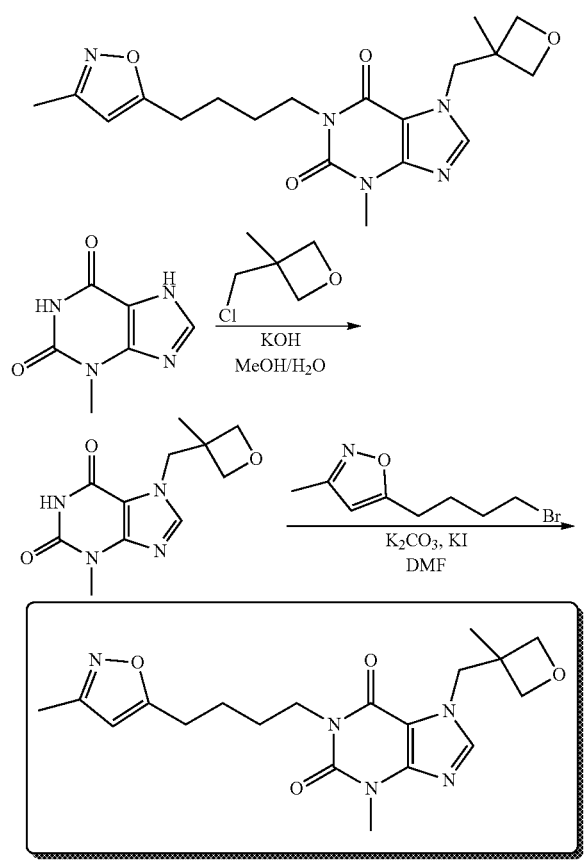

Step 1

3-Methyl-7-((3-methyloxetan-3-yl)methyl)-1H-purine-2,6(3H,7H)-dione

3-Methyl-1H-purine-2,6(3H,7H)-dione (4.00 g, 24.1 mmol) was dissolved in methanol (30 mL). An aqueous solution (15 mL) of potassium hydroxide (1.48 g, 26.5 mmol) was added and the mixture was heated to 80° C. and stirred for 1.5 hours, and then cooled to 50° C. 3-(Chloromethyl)-3-methyloxetane (3.77 g, 31.3 mmol) and potassium iodide (4.80 g, 28.9 mmol) were added and the reaction was stirred at 50° C. for 24 hours. The reaction solution was cooled to room temperature, filtered, and the filter cake was washed successively with water (30 mL) and methanol (30 mL), and dried to give 3-methyl-7-((3-methyloxetan-3-yl)methyl)-1H-purine-2,6(3H,7H)-dione (2.40 g, as a white solid) with a yield of 40%.

$^1$H NMR: (400 Hz, DMSO-d$_6$) δ 11.18 (s, 1H), 8.14 (s, 1H), 4.58-4.40 (m, 4H), 4.19 (d, J=6.0 Hz, 2H), 3.36 (s, 3H), 1.20 (s, 3H). MS-ESI calcd. [M+H]$^+$ 251, found 251.

Step 2

3-Methyl-1-(4-(3-methylisoxazol-5-yl)butyl)-7-((3-methyloxetan-3-yl)methyl)-1H-purine-2,6(3H,7H)-dione 5-(4-Bromobutyl)-3-methylisoxazole (174 mg, 0.80 mmol) was dissolved in N,N-dimethylamide (10 mL). Potassium carbonate (220 mg, 1.60 mmol), 3-methyl-7-propyl-1H-purine-2,6(3H,7H)-dione (200 mg, 0.80 mmol) and potassium iodide (159 mg, 0.96 mmol) were added. The reaction was heated to 120° C. and stirred for 16 hours. The reaction solution was concentrated under reduced pressure and purified by preparative HPLC to give 3-methyl-1-(4-(3-methylisoxazol-5-yl)butyl)-7-((3-methyloxetan-3-yl)methyl)-1H-purine-2,6(3H, 7H)-dione (40.0 mg) with a yield of 13%.

$^1$H NMR: (400 MHz, CDCl$_3$) δ 7.57 (s, 1H), 5.82 (s, 1H), 4.64-4.52 (m, 4H), 4.39 (d, J=6.0 Hz, 2H), 4.12-3.97 (m, 2H), 3.59 (s, 3H), 2.82-2.68 (m, 2H), 2.25 (s, 3H), 1.80-1.65 (m, 4H), 1.35 (s, 3H). MS-ESI calcd. [M+H]$^+$ 388, found 388.

Example 62

7-(Cyclobutylmethyl)-3-methyl-1-(4-(3-methylisoxazol-5-yl)butyl)-1H-purine-2,6(3H,7H)-dione

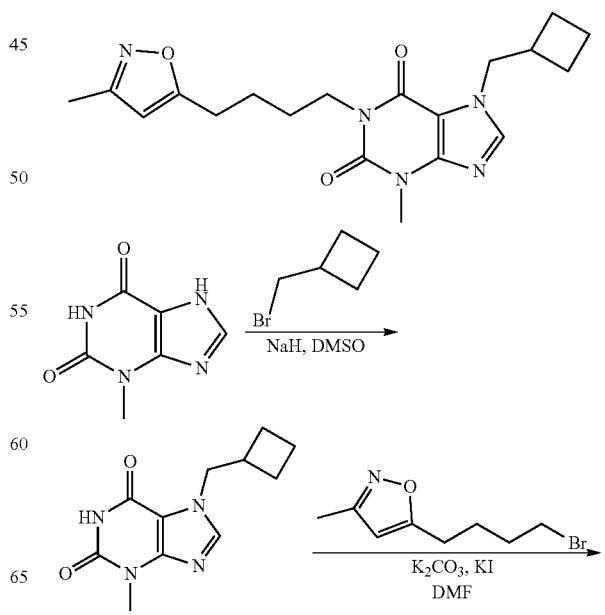

-continued

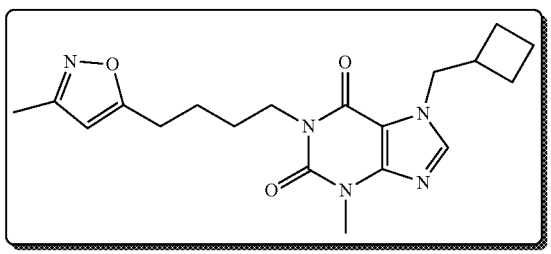

Step 1

7-(Cyclobutylmethyl)-3-methyl-1H-purine-2,6(3H,7H)-dione

3-Methyl-1H-purine-2,6(3H,7H)-dione (2.00 g, 12.0 mmol) was dissolved in dimethyl sulfoxide (15 mL). Sodium hydride (530 mg, 13.2 mmol, 600%) was slowly added at 0° C. The reaction was warmed to 80° C. and stirred for 30 minutes, and then (bromomethyl) cyclobutane (1.97 g, 13.2 mmol) was slowly added under nitrogen atmosphere. The reaction solution was stirred at 80° C. for 12 hours. The reaction was cooled to 25° C., filtered after adding water (150 mL), and the filter cake was rinsed with water (10 mL×2). The solid was dried under reduced pressure by oil pump to give 7-(cyclobutylmethyl)-3-methyl-1H-purine-2,6(3H,7H)-dione (1.29 g, as a yellow solid) with a yield of 46%.

$^1$H NMR: (400 Hz, DMSO-$d_6$) δ 11.10 (s, 1H), 8.05 (s, 1H), 4.22 (d, J=7.2 Hz, 2H), 3.32 (s, 3H), 2.79-2.70 (m, 1H), 1.97-1.61 (m, 6H). MS-ESI calcd. [M+H]$^+$ 235, found 235.

Step 2

7-(Cyclobutylmethyl)-3-methyl-1-(4-(3-methylisoxazol-5-yl)butyl)-1H-purine-2,6(3H,7H)-dione 7-(Cyclobutylmethyl)-3-methyl-1H-purine-2,6(3H,7H)-dione (100 mg, 0.427 mmol), 5-(4-bromobutyl)-3-methylisoxazole (93.1 mg, 0.427 mmol) and potassium iodide (7.1 mg, 0.043 mmol) were dissolved in N,N-dimethylformamide (5 mL), potassium carbonate (118 mg, 0.854 mmol) was added at 25° C. The reaction was heated to reflux at 130° C. for 3 hours. The reaction solution was cooled to 25° C., filtered and the filtrate was concentrated under reduced pressure. The resulting product was purified by preparative HPLC to give 7-(cyclobutylmethyl)-3-methyl-1-(4-(3-methylisoxazol-5-yl)butyl)-1H-purine-2,6(3H,7H)-dione (64.0 mg) with a yield of 40%.

$^1$H NMR: (400 MHz, Methanol-$d_4$) δ 7.94 (s, 1H), 6.02 (s, 1H), 4.34 (d, J=7.6 Hz, 2H), 4.02 (t, J=6.0 Hz, 2H), 3.52 (s, 3H), 2.90-2.77 (m, 3H), 2.22 (s, 3H), 2.04-1.98 (m, 2H), 1.95-1.77 (m, 4H), 1.76-1.73 (m, 4H). MS-ESI calcd. [M+H]$^+$ 372, found 372.

Example 63

7-(Cyclopentylmethyl)-3-methyl-1-(4-(3-methylisoxazol-5-yl)butyl)-1H-purine-2,6(3H,7H)-dione

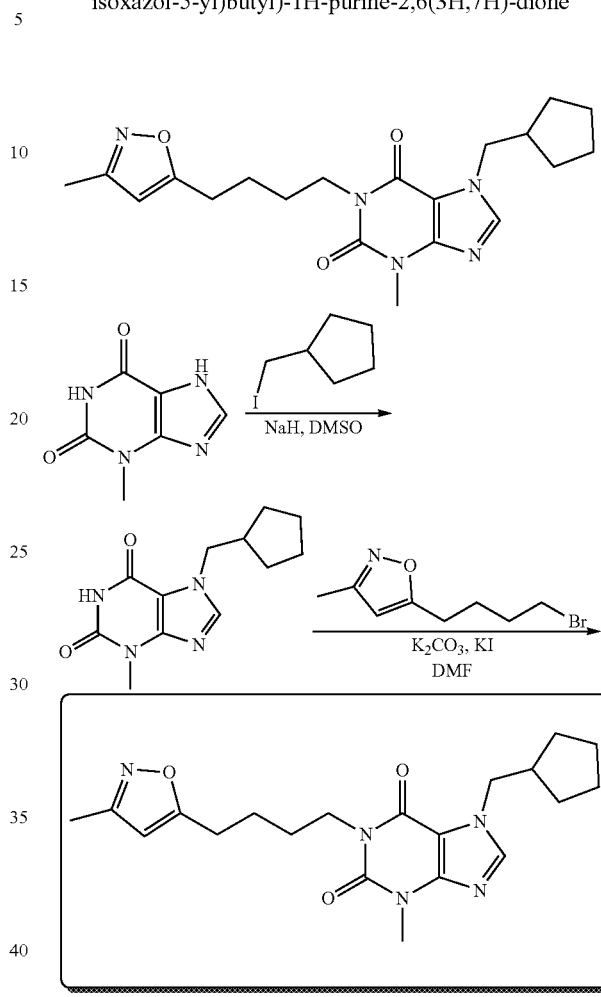

Step 1

7-(Cyclopentylmethyl)-3-methyl-1H-purine-2,6(3H,7H)-dione

3-Methyl-1H-purine-2,6(3H,7H)-dione (350 mg, 2.11 mmol) was dissolved in dimethyl sulfoxide (5 mL), sodium hydride (92.7 mg, 2.32 mmol, 600%) was slowly added at 0° C. The reaction was warmed to 80° C. and stirred for 30 minutes, and then (iodomethyl) cyclopentane (487 mg, 2.32 mmol) was slowly added under nitrogen atmosphere. The reaction solution was stirred at 80° C. for 12 hours, and then cooled to 25° C. The reaction solution was filtered after adding water (50 mL), and the filter cake was rinsed with water (5 mL×2). The solid was dried under reduced pressure by oil pump to give 7-(cyclopentylmethyl)-3-methyl-1H-purine-2,6(3H,7H)-dione (125 mg, as a yellow solid) with a yield of 24%.

$^1$H NMR: (400 MHz, DMSO-$d_6$) δ 11.11 (s, 1H), 8.07 (s, 1H), 4.11 (d, J=7.6 Hz, 2H), 3.33 (s, 3H), 2.43-2.31 (m, 1H), 1.60-1.46 (m, 6H), 1.24-1.18 (m, 2H). MS-ESI calcd. [M+H]$^+$ 249, found 249.

Step 2

7-(Cyclopentylmethyl)-3-methyl-1-(4-(3-methyl-isoxazol-5-yl)butyl)-1H-purine-2,6(3H,7H)-dione 7-(Cyclopentylmethyl)-3-methyl-1H-purine-2,6(3H,7H)-dione (100 mg, 0.403 mmol), 5-(4-bromobutyl)-3-methyl-isoxazole (87.8 mg, 0.403 mmol) and potassium iodide (6.7 mg, 0.40 mmol) were dissolved in N,N-dimethylformamide (5 mL), potassium carbonate (111 mg, 0.806 mmol) was added at 25° C. The reaction was heated to reflux at 130° C. for 3 hours. The reaction solution was cooled to 25° C., filtered and the filtrate was concentrated under reduced pressure. The resulting product was purified by preparative HPLC to give 7-(cyclopentylmethyl)-3-methyl-1-(4-(3-methylisoxazol-5-yl)butyl)-1H-purine-2,6(3H,7H)-dione (41.0 mg) with a yield of 26%.

$^1$H NMR: (400 MHz, Methanol-$d_4$) δ 7.98 (s, 1H), 6.05 (s, 1H), 4.27 (d, J=7.6 Hz, 2H), 4.05 (t, J=6.4 Hz, 2H), 3.55 (s, 3H), 2.83-2.79 (m, 2H), 2.54-2.44 (m, 1H), 2.25 (s, 3H), 1.76-1.68 (m, 8H), 1.37-1.31 (m, 4H). MS-ESI calcd. [M+H]$^+$ 386, found 386.

Example 64

7-(Cyclohexylmethyl)-3-methyl-1-(4-(3-methylisoxazol-5-yl)butyl)-1H-purine-2,6(3H,7H)-dione

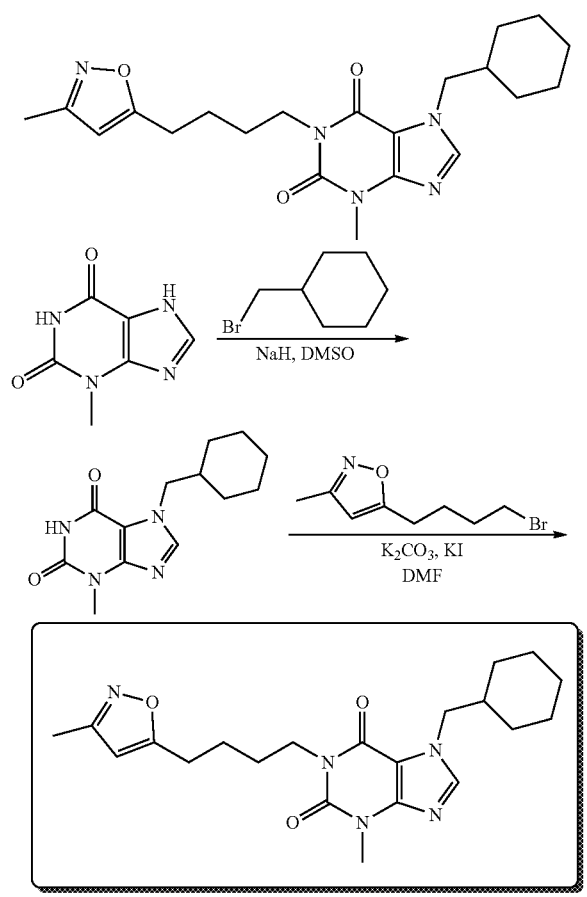

Step 1

7-(Cyclohexylmethyl)-3-methyl-1H-purine-2,6(3H,7H)-dione

3-Methyl-1H-purine-2,6(3H,7H)-dione (2.00 g, 12.0 mmol) was dissolved in dimethyl sulfoxide (15 mL), sodium hydride (530 mg, 13.2 mmol, 600%) was slowly added at 0° C. The reaction was warmed to 80° C. and stirred for 30 minutes, and then (bromomethyl)cyclohexane (2.34 g, 13.2 mmol) was slowly added under nitrogen atmosphere. The reaction solution was stirred at 80° C. for 12 hours, and then cooled to 25° C. The reaction solution was filtered after adding water (150 mL), and the filter cake was rinsed with water (10 mL×2). The solid was dried under reduced pressure by oil pump to give 7-(cyclohexylmethyl)-3-methyl-1H-purine-2,6(3H,7H)-dione (2.8 g, as a yellow solid) with a yield of 89%.

$^1$H NMR: (400 MHz, DMSO-$d_6$) δ 11.09 (s, 1H), 8.00 (s, 1H), 4.04 (d, J=7.2 Hz, 2H), 3.33 (s, 3H), 1.67-1.55 (m, 4H), 1.18-1.09 (m, 4H), 0.95-0.79 (m, 3H). MS-ESI calcd. [M+H]$^+$ 263, found 263.

Step 2

7-(Cyclohexylmethyl)-3-methyl-1-(4-(3-methylisoxazol-5-yl)butyl)-1H-purine-2,6(3H,7H)-dione 7-(Cyclohexylmethyl)-3-methyl-1H-purine-2,6(3H,7H)-dione (100 mg, 0.381 mmol), 5-(4-bromobutyl)-3-methyl-isoxazole (83.0 mg, 0.381 mmol) and potassium iodide (6.3 mg, 0.038 mmol) were dissolved in N,N-dimethylformamide (5 mL), potassium carbonate (105 mg, 0.763 mmol) was added at 25° C. The reaction was heated to reflux at 130° C. for 3 hours. The reaction solution was cooled to 25° C., filtered and the filtrate was concentrated under reduced pressure. The resulting product was purified by preparative HPLC to give 7-(cyclohexylmethyl)-3-methyl-1-(4-(3-methylisoxazol-5-yl)butyl)-1H-purine-2,6(3H,7H)-dione (75.0 mg) with a yield of 49%.

$^1$H NMR: (400 MHz, Methanol-$d_4$) δ 7.90 (s, 1H), 6.03 (s, 1H), 4.15 (d, J=7.2 Hz, 2H), 4.09-4.01 (m, 2H), 3.53 (s, 3H), 2.82-2.76 (m, 2H), 2.23 (s, 3H), 1.92-1.80 (m, 1H), 1.72-1.61 (m, 7H), 1.59 (d, J=12.8 Hz, 2H), 1.26-1.16 (m, 3H), 1.08-0.96 (m, 2H). MS-ESI calcd. [M+H]$^+$ 400, found 400.

Example 65

7-Benzyl-3-methyl-1-(4-(3-methylisoxazol-5-yl)butyl)-1H-purine-2,6(3H,7H)-dione

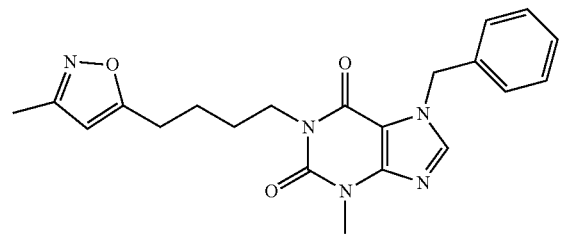

143

-continued

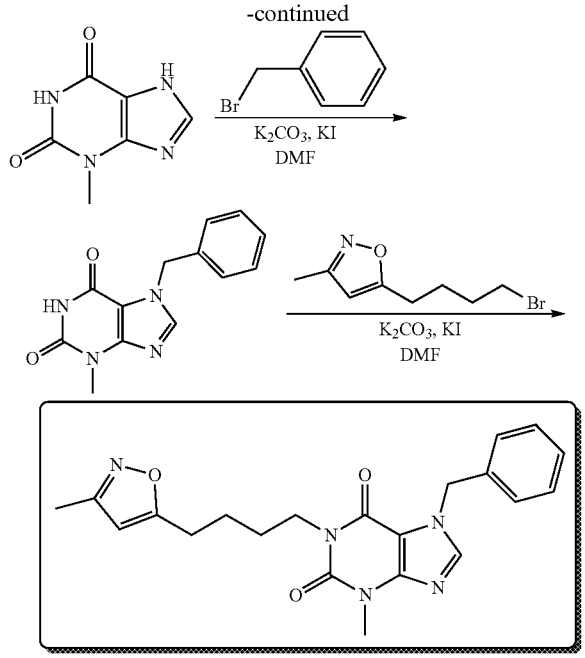

Step 1

7-Benzyl-3-methyl-1H-purine-2,6(3H,7H)-dione

3-Methyl-1H-purine-2,6(3H,7H)-dione (200 mg, 1.20 mmol), benzyl bromide (153 mg, 1.20 mmol) and potassium iodide (19.9 mg, 0.120 mmol) were dissolved in N,N-dimethylformamide (10 mL), potassium carbonate (182 mg, 1.32 mmol) was added. The reaction was heated to reflux at 60° C. for 12 hours, and then cooled to 25° C. The reaction solution was filtered after adding water (50 mL), and the filter cake was rinsed with water (5 mL×2). The solid was dried under reduced pressure by oil pump to give 7-benzyl-3-methyl-1H-purine-2,6(3H,7H)-dione (271 mg, as a yellow solid) with a yield of 88%.

$^1$H NMR: (400 M Hz, DMSO-$d_6$) δ 8.22 (s, 1H), 7.95 (s, 1H), 7.37-7.27 (m, 5H), 5.45 (s, 2H), 3.34 (s, 3H).

Step 2

7-Benzyl-3-methyl-1-(4-(3-methylisoxazol-5-yl)butyl)-1H-purine-2,6(3H,7H)-dione 7-Benzyl-3-methyl-1H-purine-2,6(3H,7H)-dione (270 mg, 1.05 mmol), 5-(4-bromobutyl)-3-methyl (230 mg, 1.05 mmol) and potassium iodide (17.4 mg, 0.105 mmol) were dissolved in N,N-dimethylformamide (8 mL) and potassium carbonate (290 mg, 2.10 mmol) was added at 25° C. The reaction was heated at 130° C. for 3 hours. The reaction solution was cooled to 25° C., filtered and the filtrate was concentrated under reduced pressure. The resulting product was purified by preparative HPLC to give 7-benzyl-3-methyl-1-(4-(3-methylisoxazol-5-yl)butyl)-1H-purine-2,6 (3H,7H)-dione (92.0 mg) with a yield of 22%.

$^1$H NMR: (400 M Hz, Methanol-$d_4$) δ 8.05 (s, 1H), 7.38-7.27 (m, 5H), 6.02 (s, 1H), 5.54 (s, 2H), 4.04-3.08 (m, 2H), 3.53 (s, 3H), 2.79-2.75 (m, 2H), 2.23 (s, 3H), 1.73-1.67 (m, 4H). MS-ESI calcd. [M+H]$^+$ 394, found 394.

144

Example 66

1-Methyl-3-(3-(3-methylisoxazol-5-yl)butyl)-1H-pyrrolo[2,3-d]pyrimidine-2,4(3H,7H)-dione

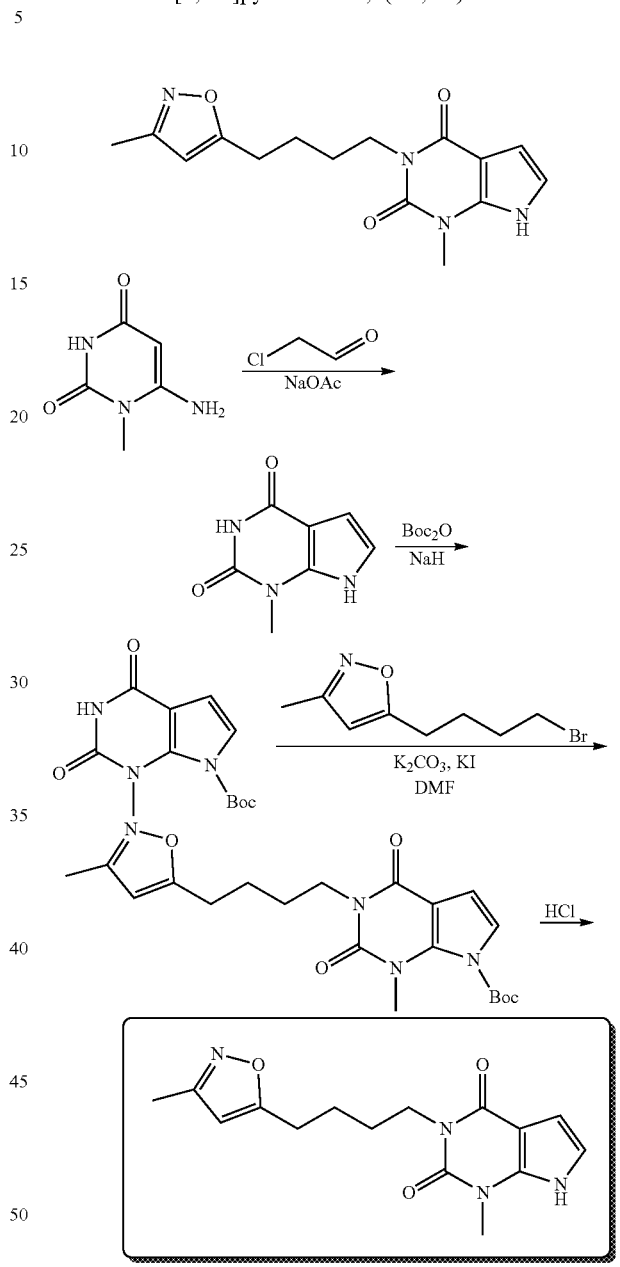

Step 1

1-Methyl-1H-pyrrolo[2,3-d]pyrimidine-2,4(3H,7H)-dione

A mixture of 6-amino-1-methylpyrimidine-2,4(1H,3H)-dione (2.00 g, 15.7 mmol), sodium acetate (1.30 g, 15.7 mmol) and an aqueous solution (7 mL) of 2-chloroacetaldehyde (3.70 g, 47.2 mmol) was heated to 70° C. and the reaction was stirred for 2 hours, cooled to room temperature, filtered and the filter cake was dried to give 1-methyl-1H-pyrrolo[2,3-d]pyrimidine-2,4(3H,7H)-dione (400 mg, as a light brown solid) with a yield of 15%.

¹H NMR: (400 MHz, DMSO-d₆) δ 11.66 (s, 1H), 10.70 (s, 1H), 6.74 (d, J=3.2 Hz, 1H), 6.30 (d, J=3.2 Hz, 1H), 3.34 (s, 3H). MS-ESI calcd. [M+H]⁺ 166, found 166.

Step 2

Tert-butyl 1-methyl-2,4-dioxo-3,4-dihydro-1H-pyrrolo[2,3-d]pyrimidine-7(2H)-carboxylate 1-Methyl-1H-pyrrolo[2,3-d]pyrimidine-2,4(3H,7H)-dione (396 mg, 2.40 mmol) and di-tert-butyl dicarbonate (785 mg, 3.60 mmol) were added successively into a suspension of sodium hydride (96.0 mg, 2.40 mmol) in dimethylsulfoxide (10 mL) at 15° C. The reaction was heated to 30° C. and stirred overnight, and then quenched by pouring into ice water (20 mL). The reaction solution was filtered, and the filter cake was dried to give tert-butyl 1-methyl-2,4-dioxo-3,4-dihydro-1H-pyrrolo[2,3-d]pyrimidine-7(2H)-carboxylate (400 mg, as a light brown solid) with a yield of 62%.
¹H NMR: (400 MHz, DMSO-d₆) δ 11.29 (s, 1H), 7.10 (d, J=3.2 Hz, 1H), 6.50 (d, J=3.2 Hz, 1H), 3.32 (s, 3H), 1.57 (s, 9H). MS-ESI calcd. [M+H]⁺ 266, found 266.

Step 3

Tert-butyl-1-methyl-3-(4-(3-methylisoxazol-5-yl)-2,4-dioxo-3,4-dihydro-1H-pyrrolo[2,3-d]pyrimidine-7(2H)-carboxy late Tert-butyl 1-methyl-2,4-dioxo-3,4-dihydro-1H-pyrrolo[2,3-d]pyrimidine-7(2H)-carboxylate (196 mg, 0.734 mmol) was dissolved in N,N-dimethylformamide (5 mL), 5-(4-bromobutyl)-3-methylisoxazole (200 mg, 0.917 mmol), potassium iodide (15.0 mg, 0.0917 mmol) and potassium carbonate (253 mg, 1.83 mmol) were added. The reaction was stirred at 20° C. for 72 hours. The reaction mixture was extracted with water (30 mL) and extracted with ethyl acetate (30 mL×2). The organic phase was dried over anhydrous sodium sulfate and filtered. The filtrate was concentrated under reduced pressure and purified by high performance plate (3:1 petroleum ether/ethyl, R_f=0.4) to give tert-butyl-1-methyl-3-(4-(3-methylisoxazol-5-yl)-2,4-dioxo-3,4-dihydro-1H-pyrrolo[2,3-d]pyrimidine-7(2H)-carboxylate (200 mg, as a yellow solid) with a yield of 54%. MS-ESI calcd. [M+H]⁺ 403, found 403.

Step 4

1-Methyl-3-(3-methylisoxazol-5-yl)butyl)-1H-pyrrolo[2,3-d]pyrimidine-2,4(3H,7H)-dione Tert-butyl-1-methyl-3-(4-(3-methylisoxazol-5-yl)butyl)-2,4-dioxo-3,4-dihydro-1H-pyrrolo[2,3-d]pyrimidine-7(2H)-carboxylate (200 mg, 0.497 mmol) was dissolved in ethyl acetate (2 mL) at 0° C., hydrochloric acid/ethyl acetate solution (5 mL) was added and the reaction was stirred at 0° C. for 5 hours. The reaction solution was concentrated under reduced pressure directly and purified by preparative HPLC to give 1-methyl-3-(3-methylisoxazol-5-yl)butyl)-1H-pyrrolo[2,3-d]pyrimidine-2,4(3H,7H)-dione (60.0 mg) with a yield of 40%.
¹H NMR: (400 MHz, Methanol-d₄) δ 6.75 (d, J=3.2 Hz, 1H), 6.49 (d, J=3.2 Hz, 1H), 6.05 (s, 1H), 4.07-4.03 (m, 2H), 3.54 (s, 3H), 2.82-2.79 (m, 2H), 2.24 (s, 3H), 1.74-1.72 (m, 4H). MS-ESI calcd. [M+H]⁺ 303, found 303.

Example 67

1,7-Dimethyl-3-(4-(3-methylisoxazol-5-yl)butyl)-1H-pyrrolo[2,3-d]pyrimidine-2,4(3H,7H)-dione

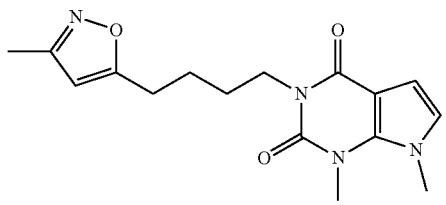

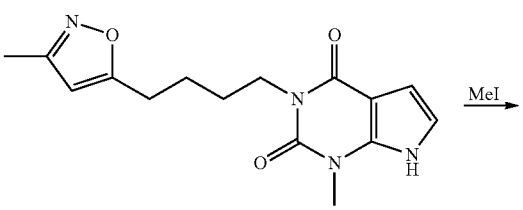

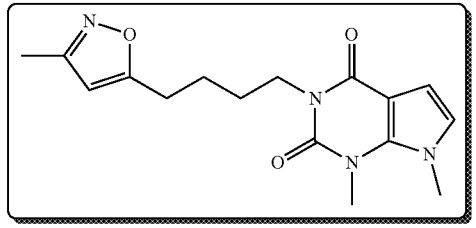

Step 1

1,7-Dimethyl-3-(4-(3-methylisoxazol-5-yl)butyl)-1H-pyrrolo[2,3-d]pyrimidine-2,4(3H,7H)-dione 1-Methyl-3-(4-(3-methylisoxazol-5-yl)butyl)-1H-pyrrolo[2,3-d]pyrimidine-2,4(3H,7H)-dione (60.0 mg, 0.199 mmol) was dissolved in N,N-dimethylformamide (3 mL), sodium hydride (24.0 mg, 0.596 mmol) was added and stirred for 30 minutes at 0° C. The reaction solution was stirred at 25° C. for 12 hours, and quenched by addition of water (30 mL) and extracted with ethyl acetate (30 mL×3). The organic phase was dried over anhydrous sodium sulfate and filtered. The filtrate was concentrated under reduced pressure and purified by preparative HPLC to give 1,7-dimethyl-3-(4-(3-methylisoxazol-5-yl)butyl)-1H-pyrrolo[2,3-d]pyrimidine-2,4(3H,7H)-dione (20.0 mg) with a yield of 32%.
¹H NMR: (400 MHz, Methanol-d₄) δ 6.59 (d, J=3.2 Hz, 1H), 6.41 (d, J=3.2 Hz, 1H), 6.02 (s, 1H), 4.03-4.00 (m, 2H), 3.94 (s, 3H), 3.79 (s, 3H), 2.79-2.76 (m, 2H), 2.21 (s, 3H), 1.70-1.68 (m, 4H). MS-ESI calcd. [M+H]⁺ 317, found 317.

Example 68

1,4-Dimethyl-6-[4-(3-methylisoxazol-5-yl)-butyl]-1,4-dihydro-pyrazolo[4,3-d]pyrimidine-5,7-dione

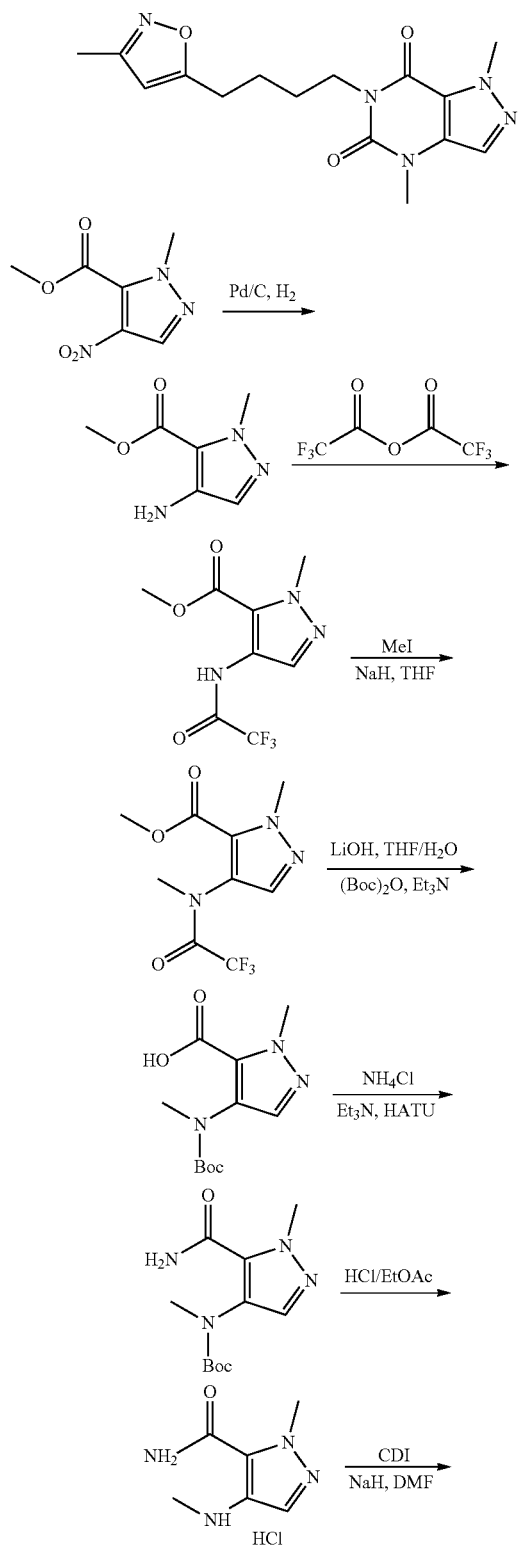

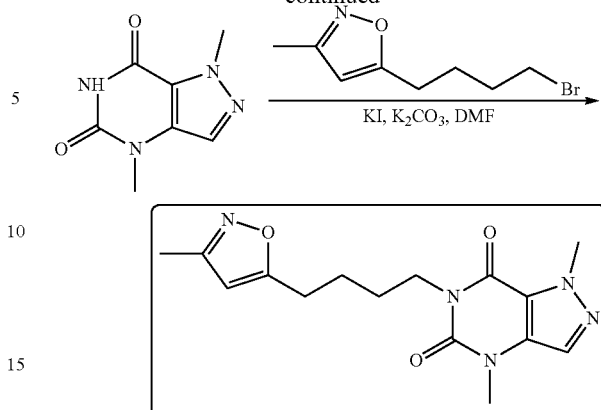

Step 1

Methyl 4-amino-2-methyl-2H-pyrazole-3-carboxylate

Methyl 2-methyl-4-nitro-2H-pyrazole-3-carboxylate (4.00 g, 21.6 mmol) was dissolved in methanol (120 mL), dry palladium on carbon (10% palladium, 1% water, 400 mg) was added. The reaction solution was allowed to react under 30 psi hydrogen pressure for 5 hours at room temperature. The reaction solution was filtered, and the filtrate was concentrated under reduced pressure to give methyl 4-amino-2-methyl-2H-pyrazole-3-carboxylate (3.00 g, as an off-white solid) with a yield of 90%.

$^1$H NMR: (400 MHz, CDCl$_3$) δ 7.10 (s, 1H), 4.09 (s, 2H), 4.02 (s, 3H), 3.90 (s, 3H). MS-ESI calcd. [M+H]$^+$ 156, found 156.

Step 2

Methyl 2-methyl-4-(2,2,2-trifluoro-acetamido)-2H-pyrazole-3-carboxylate

Methyl 4-amino-2-methyl-2H-pyrazole-3-carboxylate (3.00 g, 19.3 mmol) was dissolved in dichloromethane (50 mL), trifluoroacetic anhydride (4.47 g, 21.3 mmol) was added dropwise under nitrogen atmosphere. The reaction solution was stirred at room temperature for 20 minutes, and quenched with saturated sodium bicarbonate solution (30 mL), and extracted with dichloromethane (50 mL×2). The organic phases were combined, washed with brine (50 mL), dried over anhydrous sodium sulfate and concentrated under reduced pressure to give methyl 2-methyl-4-(2,2,2-trifluoro-acetamido)-2H-pyrazole-3-carboxylate (4.2 g, as a yellow oil) with a yield of 86%. MS-ESI calcd. [M+H]$^+$ 252, found 252.

Step 3

Methyl 2-methyl-4-[methyl-(2,2,2-trifluoro-acetyl)-amino]-2H-pyrazole-3-carboxylate Methyl 2-methyl-4-(2,2,2-trifluoro-acetamido)-2H-pyrazole-3-carboxylate (4.20 g, 16.7 mmol) was dissolved in tetrahydrofuran (50 mL), sodium hydride (736 mg, 18.4 mmol) was added in batches at 0° C., and the reaction solution was stirred for 40 minutes at 0° C. under nitrogen atmosphere. Methyl iodide (3.56 g, 25.1 mmol) was added and the reaction was stirred at room temperature for 18 hours. Water (50 mL) was added to the reaction solution, and the reaction solution was extracted with ethyl acetate (100 mL×2), the organic phases were combined, washed with brine (20 mL), dried over anhydrous sodium sulfate, filtered and concentrated under reduced pressure to give methyl 2-methyl-4-[methyl-(2,2,2-trifluoro-acetyl)-amino]-2H-pyrazole-3-carboxylate (3.60 g, as a yellow oil) with a yield of 85%.

$^1$H NMR: (400 MHz, CDCl$_3$) δ 7.49 (s, 1H), 4.20 (s, 3H), 3.90 (s, 3H), 3.27 (s, 3H). MS-ESI calcd. [M+H]$^+$ 266, found 266.

Step 4

4-(Tert-butoxycarbonyl-methyl-amino)-2-methyl-2H-pyrazole-3-carboxylic acid

Methyl 2-Methyl-4-[methyl-(2,2,2-trifluoro-acetyl)-amino]-2H-pyrazole-3-carboxylate (2.90 g, 10.9 mmol) was dissolved in tetrahydrofuran (30 mL) and water (30 mL), lithium hydroxide monohydrate (1.84 g, 43.8 mmol), triethylamine (2.21 g, 21.9 mmol) and di-tert-butyl dicarbonate (7.16 g, 32.8 mmol) were added successively and the reaction was allowed to react at room temperature for 24 hours. The reaction solution was concentrated under reduced pressure, adjusted to pH=4 with 2 N aqueous hydrochloric acid (20 mL), extracted with ethyl acetate (50 mL×2), the organic phases were combined, washed with brine (30 mL), dried over anhydrous sodium sulfate, filtered and the filtrate was concentrated under reduced pressure. The residue was purified by silica gel column chromatography (5:1 petroleum ether/ethyl acetate, $R_f$=0.5) to give 4-(tert-butoxycarbonyl-methyl-amino)-2-methyl-2H-pyrazole-3-carboxylic acid (2.20 g, as a yellow oil) with a yield of 79%.

$^1$H NMR: (400 MHz, CDCl$_3$) δ 7.47 (s, 1H), 4.15 (s, 3H), 3.20 (s, 3H), 1.46 (s, 9H). MS-ESI calcd. [M+H]$^+$ 256, found 256.

Step 5

Tert-butyl (5-carbamoyl-1-methyl-1H-pyrazol-4-yl)-methyl-carbamate 4-(Tert-butoxycarbonyl-methyl-amino)-2-methyl-2H-pyrazole-3-carboxylic acid (1.60 g, 6.27 mmol), 2-(7-azobenzotriazole)-tetramethyluronium hexafluorophosphate (7.15 g, 18.8 mmol) and ammonium chloride (671 mg, 12.5 mmol) were dissolved in dichloromethane (100 mL). Triethylamine (952 mg, 9.40 mmol) was added dropwise at room temperature. The reaction was stirred at room temperature for 18 hours. Water (200 mL) was added to the reaction solution, and the reaction solution was extracted with dichloromethane (100 mL×2). The organic phases were combined, washed with brine (50 mL), dried over anhydrous sodium sulfate, filtered and concentrated under reduced pressure. The residue was purified by silica gel column chromatography (1:1 petroleum ether/ethyl acetate, $R_f$=0.6) to give tert-butyl (5-carbamoyl-1-methyl-1H-pyrazol-4-yl)-methyl-carbamate (600 mg, as a yellow oil) with a yield of 38%.

$^1$H NMR: (400 MHz, CDCl$_3$) δ 7.38 (s, 1H), 4.10 (s, 3H) 3.19 (s, 3H), 1.47 (s, 9H). MS-ESI calcd. [M+H]$^+$ 255, found 255.

Step 6

2-Methyl-4-methylamino-2H-pyrazole-3-carboxamide hydrochloride

Tert-butyl (5-Carbamoyl-1-methyl-1H-pyrazol-4-yl)-methyl-carbamate (550 mg, 2.16 mmol) was dissolved in 4 N hydrochloric acid/ethyl acetate solution (15 mL) and the reaction was stirred at room temperature for 18 hours. The reaction solution was concentrated under reduced pressure to give 2-methyl-4-methylamino-2H-pyrazole-3-carboxamide hydrochloride (300 mg, as a white solid) with a yield of 73%.

$^1$H NMR: (400 MHz, DMSO-d$_6$) δ 8.19 (br, 2H), 7.67 (s, 1H), 3.96 (s, 3H), 2.88 (s, 3H). MS-ESI calcd. [M+H]$^+$ 155, found 155.

Step 7

1,4-dimethylpyrazolo[4,3-d]pyrimidine-5,7-dione

2-Methyl-4-methylamino-2H-pyrazole-3-carboxamide hydrochloride (300 mg, 1.57 mmol) was dissolved in N,N-dimethylformamide (10 mL). Sodium hydride (378 mg, 9.44 mmol) was added in batches at 0° C. The reaction was stirred at 0° C. for 0.5 hour under nitrogen atmosphere. 1,1-Carbonyldiimidazole (766 mg, 4.72 mmol) was added and the reaction was heated to 75° C. to react for 3 hours. The reaction was quenched by the addition of water (30 mL), filtered and the filter cake was washed with ethanol (5 mL) to give 1,4-dimethylpyrazolo[4,3-d]pyrimidine-5,7-dione (210 mg, as an off-white solid) with a yield of 73%.

$^1$H NMR: (400 MHz, DMSO-d$_6$) δ 11.35 (s, 1H), 7.69 (s, 1H), 4.07 (s, 3H), 3.30 (s, 3H). MS-ESI calcd. [M+H]$^+$ 181, found 181.

Step 8

1,4-Dimethyl-6-[4-(3-methylisoxazol-5-yl)-butyl]-pyrazolo[4,3-d]pyrimidine-5,7-dione 1,4-Dimethylpyrazolo[4,3-d]pyrimidine-5,7-dione (50.0 mg, 0.278 mmol) was dissolved in N,N-dimethylformamide (2 mL). 5-(4-Bromobutyl)-3-methylisoxazole (60.5 mg, 0.278 mmol), potassium carbonate (76.7 mg, 0.555 mmol) and potassium iodide (55.3 mg, 0.333 mmol) were added. The reaction solution was heated to 120° C. and stirred for 3 hours, and then concentrated under reduced pressure, the residue was purified by HPLC to give 1,4-dimethyl-6-[4-(3-methylisoxazol-5-yl)-butyl]-pyrazolo[4,3-d]pyrimidine-5,7-dione (30.0 mg) with a yield of 34%.

$^1$H NMR: (400 MHz, CDCl$_3$) δ 7.36 (s, 1H), 5.82 (s, 1H), 4.22 (s, 3H), 4.12-3.97 (m, 2H), 3.47 (s, 3H), 2.82-2.70 (m, 2H), 2.25 (s, 3H), 1.85-1.60 (m, 4H). MS-ESI calcd. [M+H]$^+$ 318, found 318.

Example 69

2,4-Dimethyl-6-[4-(3-methylisoxazol-5-yl)-butyl]-2,4-dihydro-pyrazolo[4,3-d]pyrimidine-5,7-dione

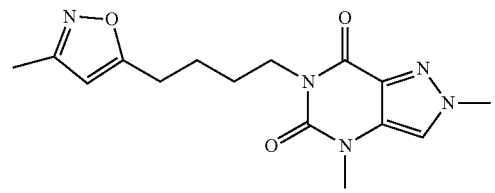

-continued

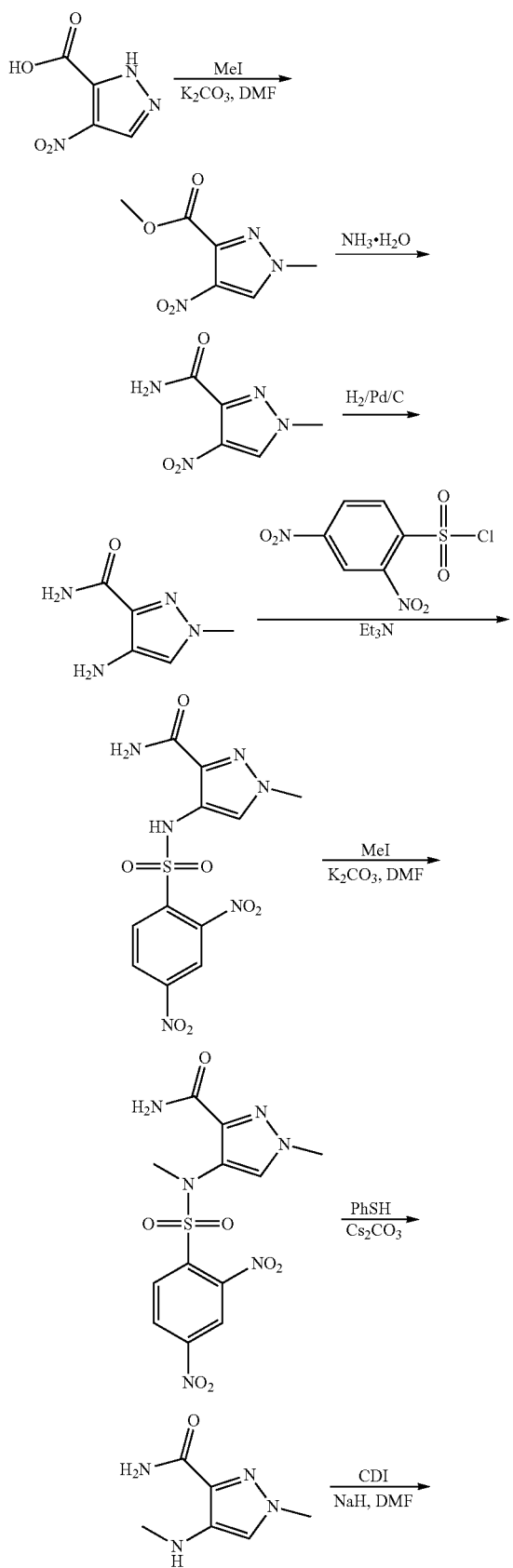

-continued

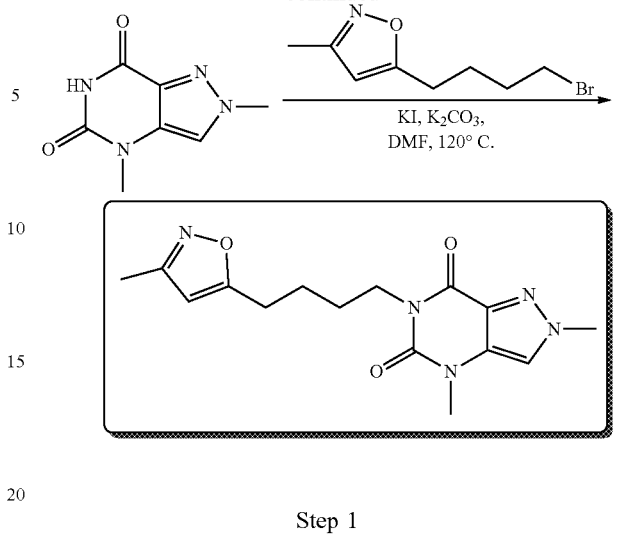

Step 1

Methyl 1-methyl-4-nitro-pyrazole-3-carboxylate

4-Nitropyrazole-3-carboxylic acid (27.5 g, 175 mmol) was dissolved in N,N-dimethylformamide (800 mL) and K$_2$CO$_3$ (53.2 g, 385 mmol) was added at room temperature. The reaction was heated to 80° C. and stirred for 3 hours. After cooling to room temperature, iodomethane (74.6 g, 525 mmol) was added and the reaction was allowed to react at room temperature for 15 hours. The reaction solution was diluted with water (2.5 L) and extracted with ethyl acetate (1 L×2). The organic phases were combined, washed with saturated aqueous sodium chloride solution (800 mL), dried over anhydrous sodium sulfate, filtered and the filtrate was concentrated under reduced pressure. The residue was purified by silica gel column chromatography (1:1 petroleum ether/ethyl acetate, R$_{f1}$=0.5, R$_{f2}$=0.3) to give methyl 2-methyl-4-nitro-2H-pyrazole-3-carboxylate (6.00 g, as a yellow liquid) with a yield of 19%, and methyl 1-methyl-4-nitro-pyrazole-3-carboxylate (11.0 g, as a white solid) with a yield of 34%.

$^1$H NMR: (400 MHz, CDCl$_3$) δ 8.15 (s, 1H), 4.01 (s, 3H), 4.00 (s, 3H). MS-ESI calcd. [M+H]$^+$ 186, found 186.

Step 2

1-Methyl-4-nitro-pyrazole-3-carboxamide

Methyl 1-methyl-4-nitro-pyrazole-3-carboxylate (5.00 g, 27.0 mmol) was dissolved in aqueous ammonia (30 mL) and the reaction was heated to 80° C. and stirred for 18 hours. The reaction solution was cooled to room temperature and concentrated under reduced pressure. The residue was washed with ethanol (10 mL) and filtered to give 1-methyl-4-nitro-pyrazole-3-carboxamide (2.30 g, as a white solid) with a yield of 50%. MS-ESI calcd. [M+H]$^+$ 171, found 171.

Step 3

4-Amino-1-methyl-pyrazole-3-carboxamide

1-Methyl-4-nitro-pyrazole-3-carboxamide (2.30 g, 13.5 mmol) was dissolved in methanol (50 mL), dry palladium on carbon (palladium 10%, water 1%, 230 mg) was added. The reaction was allowed to react under 30 psi hydrogen pressure for 18 hours at room temperature, and then filtered. The filtrate was concentrated under reduced pressure to give 4-amino-1-methyl-pyrazole-3-carboxamide (2.00 g, as a white solid) with a yield of 96%. MS-ESI calcd. [M+H]+ 141, found 141.

Step 4

4-(2,4-Dinitro-benzenesulfonylamino)-1-methyl-pyrazole-3-carboxamide

4-Amino-1-methyl-pyrazole-3-carboxamide (140 mg, 0.999 mmol) was dissolved in tetrahydrofuran (15 mL). Triethylamine (152 mg, 1.50 mmol) and 2,4-dinitro-benzenesulfonyl chloride (200 mg, 1.05 mmol) were added at room temperature. The reaction was stirred at room temperature for 1.5 hours. The reaction solution was filtered and the filter cake was washed with water (5 mL) and filtered to give 4-(2,4-dinitro-benzenesulfonylamino)-1-methyl-pyrazole-3-carboxamide (200 mg, as a yellow solid) with a yield of 54%. MS-ESI calcd. [M+H]+ 371, found 371.

Step 5

4-[(2,4-Dinitro-benzenesulfonyl)-methyl-amino]-1-methyl-pyrazole-3-carboxamide 4-(2,4-Dinitro-benzenesulfonylamino)-1-methyl-pyrazole-3-carboxamide (100 mg, 0.270 mmol) was dissolved in N,N-dimethylformamide (5 mL), potassium carbonate (56.0 mg, 0.405 mmol) was added and the reaction was heated to 80° C. and stirred for 2 hours. The reaction solution was cooled to room temperature, methyl iodide (57.5 mg, 0.405 mmol) was added, and the reaction was stirred at room temperature for 16 hours. The reaction solution was diluted with water (15 mL) and filtered. The filter cake was washed with ethanol (1 mL) and filtered to give 4-[(2,4-dinitro-benzenesulfonyl)-methyl-amino]-1-methyl-pyrazole-3-carboxamide (90.0 mg, as a yellow oil) with a yield of 87%. $^1$H NMR: (400 MHz, DMSO-$d_6$) δ 8.93 (d, J=2.4 Hz, 1H), 8.49 (dd, J=8.8, 2.4 Hz, 1H), 8.03 (d, J=8.8 Hz, 1H), 7.97 (s, 1H), 7.35-7.30 (br, 1H), 7.15-7.10 (br, 1H), 3.88 (s, 3H), 3.33 (s, 3H). MS-ESI calcd. [M+H]+ 385, found 385.

Step 6

1-Methyl-4-methylamino-pyrazole-3-carboxamide

4-[(2,4-Dinitro-benzenesulfonyl)-methyl-amino]-1-methyl-pyrazole-3-carboxamide (110 mg, 0.286 mmol) was dissolved in acetonitrile (10 mL). Cesium carbonate (280 mg, 0.859 mmol) and thiophenol (34.7 mg, 0.315 mmol) were added. The reaction was stirred at room temperature for 3 hours. The reaction was diluted with dichloromethane (20 mL), filtered and the filtrate was concentrated under reduced pressure. The residue was purified by silica gel column chromatography (1:1 petroleum ether/ethyl acetate, $R_f$=0.2) to give 1-methyl-4-methylamino-pyrazole-3-carboxamide (42.0 mg, as a yellow solid) with a yield of 95%. MS-ESI calcd. [M+H]+ 155, found 155.

Step 7

2,4-Dimethyl-pyrazolo[4,3-d]pyrimidine-5,7-dione

1-Methyl-4-methylamino-pyrazole-3-carboxamide (670 mg, 4.35 mmol) was dissolved in N,N-dimethylformamide (15 mL). Sodium hydride (365 mg, 9.14 mmol) was added in batches at 0° C., the reaction was stirred at 0° C. for 0.5 hour under nitrogen atmosphere. 1,1-Carbonyldiimidazole (1.41 g, 8.70 mmol) was added and the reaction was heated to 75° C. to react for 3 hours. The reaction was quenched by the addition of water (45 mL), filtered and the filter cake was washed with ethanol (5 mL) to give 2,4-dimethyl-pyrazolo[4,3-d]pyrimidine-5,7-dione (640 mg, as a off-white solid) with a yield of 82%.
$^1$H NMR: (400 MHz, DMSO-$d_6$) δ 11.01 (s, 1H), 7.93 (s, 1H), 3.97 (s, 3H), 3.25 (s, 3H). MS-ESI calcd. [M+H]+ 181, found 181.

Step 8

2,4-Dimethyl-6-[4-(3-methylisoxazol-5-yl)-butyl]-pyrazolo[4,3-d]pyrimidine-5,7-dione 2,4-Dimethyl-pyrazolo[4,3-d]pyrimidine-5,7-dione (100 mg, 0.555 mmol) was dissolved in N,N-dimethylformamide (2 mL). 5-(4-Bromobutyl)-3-methylisoxazole (133 mg, 0.611 mmol), potassium carbonate (153 mg, 1.11 mmol) and potassium iodide (111 mg, 0.611 mmol) were added. The reaction solution was heated to 120° C. and stirred for 3 hours. And the residue was purified by HPLC to give 2,4-dimethyl-6-[4-(3-methylisoxazol-5-yl)-butyl]-pyrazolo[4,3-d]pyrimidine-5,7-dione (40.0 mg) with a yield of 23%.
$^1$H NMR: (400 MHz, DMSO-$d_6$) δ 7.26 (s, 1H), 5.84 (s, 1H), 4.15-4.00 (m, 5H), 3.42 (s, 3H), 2.82-2.69 (m, 2H), 2.25 (s, 3H), 1.83-1.60 (m, 4H). MS-ESI calcd. [M+H]+ 318, found 318.

Example 70

6-((3-Isopropylisoxazol-5-yl)methyl)-4-methyl-1-(2,2,2-trifluoroethyl)-pyrazolo[4,3-d]pyrimidine-5,7-dione

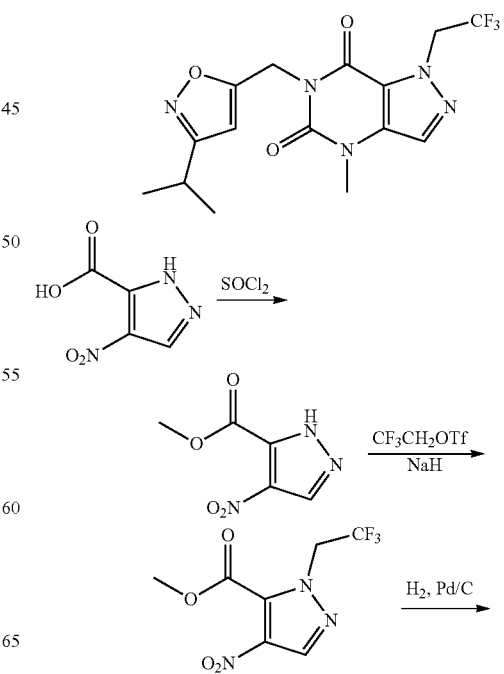

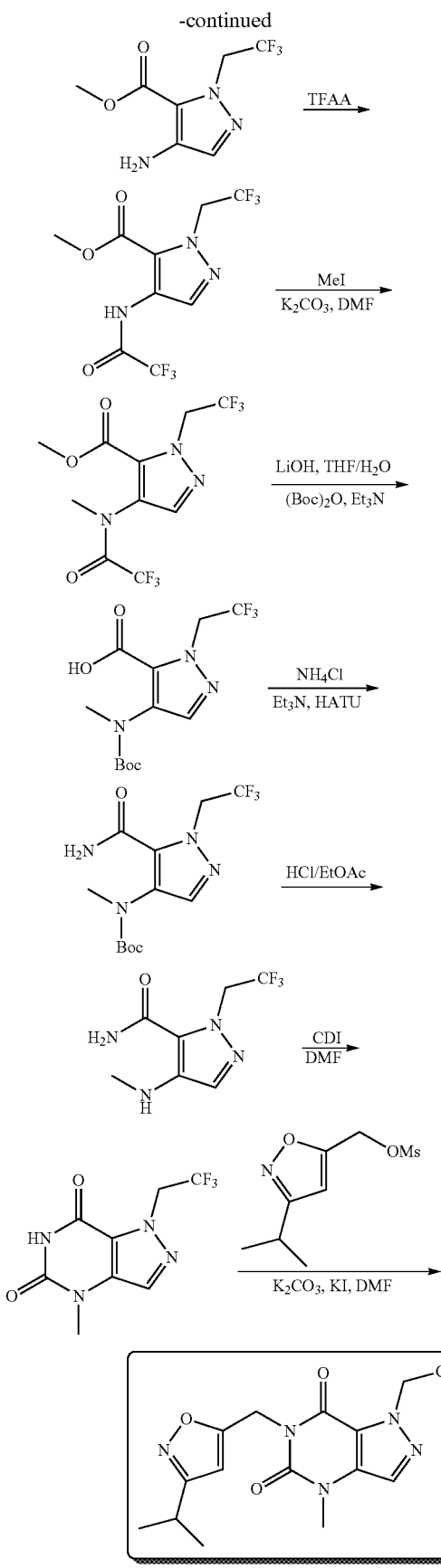

Step 1

Methyl 4-nitro-pyrazole-5-carboxylate

4-Nitro-pyrazole-5-carboxylic acid (45.0 g, 286 mmol) was dissolved in methanol (700 mL) and thionyl chloride (102 g, 859 mmol) was added dropwise at 0° C. The reaction was stirred at 25° C. for 18 hours. The reaction mixture was concentrated under reduced pressure to give methyl 4-nitro-pyrazole-5-carboxylate (49.0 g, as a white solid) with a yield of 100%. $^1$H NMR: (400 MHz, CDCl$_3$) δ 8.53 (s, 1H), 4.06 (s, 3H). MS-ESI calcd. [M+H]$^+$ 172, found 172.

Step 2

Methyl 4-Nitro-1-(2,2,2-trifluoroethyl)-pyrazole-5-carboxylate

Methyl 4-nitro-pyrazole-5-carboxylate (25.0 g, 146 mmol) was dissolved in N,N-dimethylformamide (350 mL) and sodium hydride (6.43 g, 161 mmol) was added in batches at 0° C. The reaction was stirred at 0° C. for 1 hour, and 2,2,2-trifluoroethyl trifluoromethanesulfonate (33.9 g, 146 mmol) was added dropwise. The reaction was stirred at 25° C. for 18 hours. The reaction solution was added with water (1.2 L) and extracted with ethyl acetate (300 mL×2). The organic phases were combined, washed with brine (500 mL), dried over anhydrous sodium sulfate, filtered and concentrated under reduced pressure. The residue was purified by silica gel column chromatography (5:1 petroleum ether/ethyl acetate, R$_f$=0.3) to give methyl 4-nitro-1-(2,2,2-trifluoroethyl)-pyrazole-5-carboxylate (8.00 g, as a colorless oil) with a yield of 22%. $^1$H NMR: (400 MHz, CDCl$_3$) δ 8.13 (s, 1H), 5.06 (q, J=8.0 Hz, 2H), 4.04 (s, 3H). MS-ESI calcd. [M+H]$^+$ 254, found 254.

Step 3

Methyl 4-amino-1-(2,2,2-trifluoroethyl)-pyrazole-5-carboxylate

Methyl 4-nitro-1-(2,2,2-trifluoroethyl)-pyrazole-5-carboxylate (7.50 g, 29.6 mmol) was dissolved in methanol (100 mL). Dry palladium on carbon (10% palladium, 1% water, 750 mg) was added and the reaction was stirred at 40 psi of hydrogen pressure for 3 hours at room temperature. The reaction was filtered and the filtrate was concentrated under reduced pressure to give methyl 4-amino-1-(2,2,2-trifluoroethyl)-pyrazole-5-carboxylate (6.30 g, as an off white solid) with a yield of 95%. $^1$H NMR: (400 MHz, CDCl$_3$) δ 7.25 (s, 1H), 5.10 (q, J=8.4 Hz, 2H), 4.21 (s, 2H), 3.94 (s, 3H). MS-ESI calcd. [M+H]$^+$ 224, found 224.

Step 4

Methyl 4-(2,2,2-trifluoroacetamide)-1-(2,2,2-trifluoroethyl)-pyrazole-5-carboxylate Methyl 4-amino-1-(2,2,2-trifluoroethyl)-pyrazole-5-carboxylate (6.30 g, 28.2 mmol) was dissolved in dichloromethane (100 mL). Trifluoroacetic anhydride (8.89 g, 42.4 mmol) was added dropwise under nitrogen atmosphere and the reaction was stirred at room temperature for 2 hours. The reaction was quenched with saturated sodium bicarbonate aqueous solution (100 mL), extracted with dichloromethane (100 mL), and the organic phase was washed with brine (50 mL), dried over anhydrous sodium sulfate and concentrated under reduced pressure to give methyl 4-(2,2,2-trifluoroacetamide)-1-(2,2,2-trifluoroethyl)-pyrazole-5-carboxylate (crude product, 9.20 g, as a yellow oil). $^1$H NMR: (400 MHz, CDCl$_3$) δ 9.66 (s, 1H), 8.45 (s, 1H), 5.18 (q, J=8.0 Hz, 2H), 4.06 (s, 3H). MS-ESI calcd. [M+H]$^+$ 320, found 320.

Step 5

Methyl 4-(2,2,2-trifluoro-N-methylacetamide)-1-(2,2,2-trifluoroethyl)-pyrazole-5-carboxylate Methyl 4-(2,2,2-trifluoroacetamide)-1-(2,2,2-trifluoroethyl)-pyrazole-5-carboxylate (9.20 g, 28.8 mmol) was dissolved in N,N-dimethylformamide (50 mL) and potassium carbonate (5.98 g, 43.3 mmol) was added. The reaction was heated to 80° C. to react for 1 hour, and cooled to room temperature and methyl iodide (6.14 g, 43.2 mmol) was added. The reaction was stirred at room temperature for 18 hours. The reaction solution was added with water (300 mL) and extracted with ethyl acetate (100 mL×3). The organic phases were combined, washed with brine (100 mL), dried over anhydrous sodium sulfate, filtered and concentrated under reduced pressure to give methyl 4-(2,2,2-trifluoro-N-methylacetamide)-1-(2,2,2-trifluoroethyl)-pyrazole-5-carboxylate (crude product, 9.80 g, as a yellow oil). $^1$H NMR: (400 MHz, CDCl$_3$) δ 7.65 (s, 1H), 5.45-5.15 (m, 2H), 3.93 (s, 3H), 3.29 (s, 3H). MS-ESI calcd. [M+H]$^+$ 334, found 334.

Step 6

4-[(Tert-butoxycarbonyl)(methyl) amino]-1-(2,2,2-trifluoroethyl)-pyrazole-5-carboxylic Acid Methyl 4-(2,2,2-trifluoro-N-methylacetamide)-1-(2,2,2-trifluoroethyl)-pyrazole-5-carboxylate (9.90 g, 29.7 mmol) was dissolved in tetrahydrofuran (40 mL) and water (40 mL), lithium hydroxide monohydrate (6.23 g, 148.6 mmol) was added and the reaction was stirred at room temperature for 18 hours. Di-tert-butyl dicarbonate (13.0 g, 59.4 mmol) was added and the reaction was continued for 6 hours at room temperature. The reaction mixture was concentrated under reduced pressure, adjusted to pH 4 with 2 N aqueous hydrochloric acid, filtered and the filter cake was dried to give 4-[(tert-butoxycarbonyl)(methyl)amino]-1-(2,2,2-trifluoroethyl)-pyrazole-5-carboxylic acid (8.00 g, as a white solid) with a yield of 83%. $^1$H NMR: (400 MHz, CDCl$_3$) δ 7.58 (s, 1H), 5.25 (q, J=8.0 Hz, 2H), 3.27 (s, 3H), 1.42 (s, 9H). MS-ESI calcd. [M+H]$^+$ 324, found 324.

Step 7

4-[(Tert-butoxycarbonyl)(methyl)amino]-1-(2,2,2-trifluoroethyl)-pyrazole-5-carboxamide 4-[Tert-butoxycarbonyl(methyl)amino]-2-(2,2,2-trifluoroethyl)pyrazole-5-carboxylic acid, 2-(7-azobenzotriazole)-tetramethyluronium hexafluorophosphate (13.8 g, 36.2 mmol) and ammonium chloride (2.98 g, 55.7 mmol) were dissolved in dichloromethane (120 mL). Triethylamine (4.23 g, 41.8 mmol) was added dropwise at room temperature. The reaction mixture was stirred at room temperature for 18 hours. Water (100 mL) was added to the reaction mixture and the mixture was extracted with dichloromethane (100 mL×2). The organic phases were combined and washed sequentially with saturated sodium bicarbonate solution (50 mL) and brine (50 mL), dried over anhydrous sodium sulfate, filtered and concentrated under reduced pressure. The residue was treated with ethanol (20 mL) to give 4-[(tert-butoxycarbonyl)(methyl)amino]-1-(2,2,2-trifluoroethyl)-pyrazole-5-carboxamide (6.00 g, as a white solid) with a yield of 67%. $^1$H NMR: (400 MHz, CDCl$_3$) δ 7.54 (s, 1H), 5.25 (q, J=8.0 Hz, 2H), 3.22 (s, 3H), 1.48 (s, 9H). MS-ESI calcd. [M+H]$^+$ 323, found 323.

Step 8

4-(Methylamino)-2-(2,2,2-trifluoroethyl)pyrazole-5-carboxamide

4-[(Tert-butoxycarbonyl)(methyl)amino]-1-(2,2,2-trifluoroethyl)-pyrazole-5-carboxamide (5.00 g, 15.51 mmol) was dissolved in hydrochloride/ethyl acetate (50 mL). The reaction was stirred at room temperature for 18 hours and concentrated under reduced pressure. The residue was dissolved in methanol (50 mL), added with potassium carbonate (5.36 g, 38.8 mmol) and stirred at room temperature for 2 hours. The mixture was concentrated under reduced pressure and the residue was extracted with dichloromethane (100 mL), filtered and the filtrate was evaporated to give 4-(methylamino)-2-(2,2,2-trifluoroethyl)pyrazole-5-carboxamide (2.90 g, as a white solid) with a yield of 84%. $^1$H NMR: (400 MHz, Methanol-d$_4$) δ 7.93 (s, 1H), 5.26 (q, J=8.4 Hz, 2H), 3.13 (s, 3H). MS-ESI calcd. [M+H]$^+$ 223, found 223.

Step 9

4-Methyl-1-(2,2,2-trifluoroethyl)-pyrazolo[4,3-d]pyrimidine-5,7-dione 4-(Methylamino)-2-(2,2,2-trifluoroethyl)pyrazole-5-carboxamide (2.70 g, 12.2 mmol) and 1,1-carbonyldiimidazole (3.94 g, 24.3 mmol) were dissolved in N,N-dimethylformamide (20 mL) and the reaction was heated to 140° C. for 1 hour. After cooling to room temperature, water (100 mL) was added to the reaction mixture, and the solid was precipitated and was collected by filtration and dried to give 4-methyl-1-(2,2,2-trifluoroethyl)-pyrazolo[4,3-d]pyrimidine-5,7-dione (1.80 g, as a white solid) with a yield of 60%. $^1$H NMR: (400 MHz, DMSO-d$_6$) δ 11.56 (s, 1H), 7.95 (s, 1H), 5.35 (q, J=8.8 Hz, 2H), 3.33 (s, 3H). MS-ESI calcd. [M+H]$^+$ 249, found 249.

Step 10

6-((3-Isopropylisoxazol-5-yl)methyl)-4-methyl-1-(2,2,2-trifluoroethyl)-pyrazolo[4,3-d]pyrimidine-5,7-dione 4-Methyl-1-(2,2,2-trifluoroethyl)pyrazolo[4,3-d]pyrimidine-5,7-dione (30.0 mg, 0.120 mmol), (3-isopropylisoxazol-5-yl)methyl methanesulfonate (39.7 mg, 0.181 mmol), potassium carbonate (33.4 mg, 0.242 mmol) and potassium iodide (4.0 mg, 0.024 mmol) were dissolved in N,N-dimethylformamide (10 mL). The reaction was heated to 120° C. and stirred for 3 hours. The reaction was cooled to room temperature, poured into water (30 mL) and extracted with ethyl acetate (20 mL×3). The organic phases were combined, dried over anhydrous sodium sulfate, filtered and the filtrate was concentrated, and purified by preparative HPLC to give 6-((3-isopropylisoxazol-5-yl)methyl)-4-methyl-1-(2,2,2-trifluoroethyl)-pyrazolo[4,3-d]pyrimidine-5,7-dione with a yield of 22%. $^1$H NMR: (400 MHz, Methanol-d$_4$) δ

7.83 (s, 1H), 6.26 (s, 1H), 5.33-5.27 (m, 4H), 3.50 (s, 3H), 3.00-2.92 (m, 1H), 1.22 (d, J=7.2 Hz, 6H). MS-ESI calcd. [M+H]⁺ 372, found 372.

Example 71

(2-(2,4-Dimethylthiazol-5-yl)ethyl)-4-methyl-1-(2,2, 2-trifluoroethyl)-pyrazolo[4,3-d]pyrimidine-5,7-dione

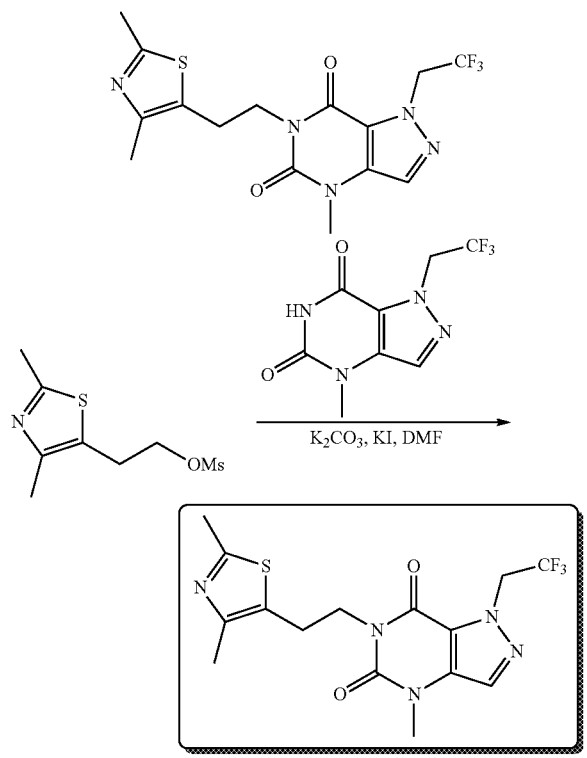

Step 1

6-(2-(2,4-Dimethylthiazol-5-yl)ethyl)-4-methyl-1-(2, 2,2-trifluoroethyl)-pyrazolo[4,3-d]pyrimidine-5,7-dione 2-(2,4-Dimethylthiazol-5-yl)ethyl methanesulfonate (30.0 mg, 0.127 mmol), 4-methyl-1-(2,2,2-trifluoroethyl) pyrazolo[4,3-d]pyrimidine-5,7-dione, potassium carbonate (35.2 mg, 0.255 mmol) and potassium iodide (4.2 mg, 0.026 mmol) were dissolved in N,N-dimethylformamide (5 mL). The reaction was heated to 120° C. and stirred for 3 hours. The reaction was cooled to room temperature, poured into water (20 mL) and extracted with ethyl acetate (20 mL×3). The organic phases were combined, dried over anhydrous sodium sulfate, filtered and the filtrate was concentrated and purified by preparative HPLC to give 6-(2-(2,4-dimethylthiazol-5-yl)ethyl)-4-methyl-1-(2,2,2-trifluoroethyl)-pyrazolo [4,3-d]pyrimidine-5,7-dione (10.0 mg) with a yield of 20%. ¹H NMR: (400 MHz, Methanol-d₄) δ 7.86 (s, 1H), 5.34-5.25 (m, 2H), 4.29 (t, J=6.8 Hz, 2H), 3.51 (s, 3H), 3.26 (t, J=6.8 Hz, 2H), 2.90 (s, 3H), 2.31 (s, 3H). MS-ESI calcd. [M+H]⁺ 388, found 388.

Example 72

6-(4-(Benzofuran-2-yl)butyl)-4-methyl-1-(2,2,2-trifluoroethyl)-pyrazolo[4,3-d]pyrimidine-5,7-dione

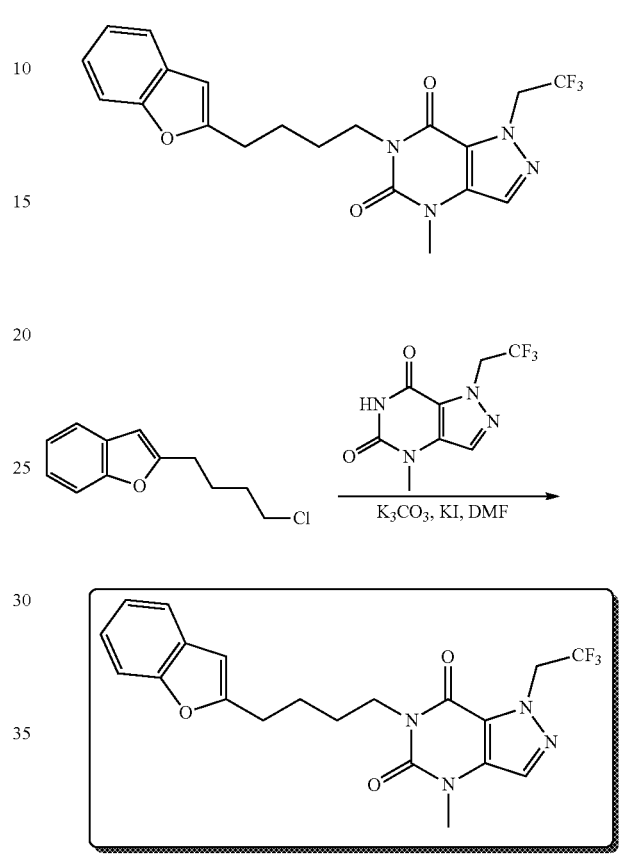

Step 1

6-(4-(Benzofuran-2-yl)butyl)-4-methyl-1-(2,2,2-trifluoroethyl)-pyrazolo[4,3-d]pyrimidine-5,7-dione 2-(4-Chlorobutyl)benzofuran (30.0 mg, 0.143 mmol), 4-methyl-1-(2,2,2-trifluoroethyl)pyrazolo[4,3-d]pyrimidine-5,7-dione (35.7 mg, 0.143 mmol), potassium carbonate (39.7 mg, 0.287 mmol) and potassium iodide (4.7 mg, 0.029 mmol) were dissolved in N,N-dimethylformamide (5 mL). The reaction was heated to 120° C. and stirred for 3 hours. The reaction was cooled to room temperature, poured into water (20 mL) and extracted with ethyl acetate (20 mL×3). The organic phases were combined, dried over anhydrous sodium sulfate, filtered and the filtrate was concentrated and purified by preparative HPLC to give 6-(4-(benzofuran-2-yl)butyl)-4-methyl-1-(2,2,2-trifluoroethyl)-pyrazolo[4,3-d] pyrimidine-5,7-dione (10.0 mg) with a yield of 17%. ¹H NMR: (400 MHz, Methanol-d₄) δ 7.79 (s, 1H), 7.34 (d, J=7.6 Hz, 1H), 7.18 (d, J=6.8 Hz, 1H), 7.16-7.12 (m, 2H), 6.46 (s, 1H), 5.34-5.28 (m, 2H), 4.07 (t, J=6.8 Hz, 2H), 3.47 (s, 3H), 2.84 (t, J=6.8 Hz, 2H), 1.83-1.75 (m, 4H). MS-ESI calcd. [M+H]⁺421, found 421.

Example 73

6-(3-(1H-indol-3-yl)propyl)-4-methyl-1-(2,2,2-trifluoroethyl)-pyrazolo[4,3-d]pyrimidine-5,7-dione

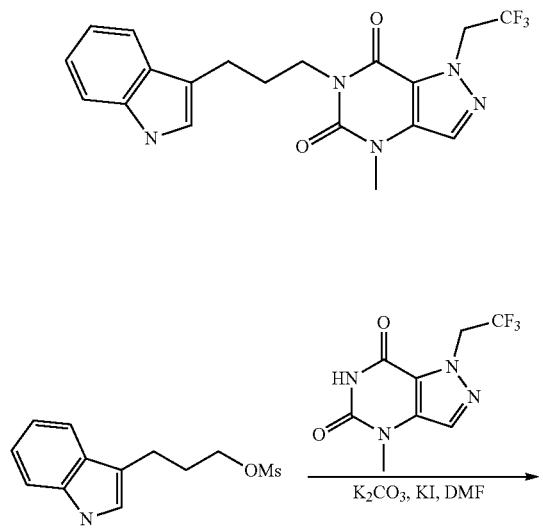

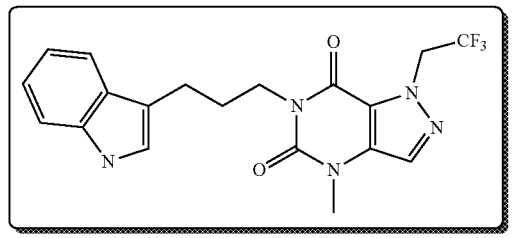

Step 1

6-(3-(1H-indol-3-yl)propyl)-4-methyl-1-(2,2,2-trifluoroethyl)-pyrazolo[4,3-d]pyrimidine-5,7-dione 3-(1H-indol-3-yl)propyl methanesulfonate (30.0 mg, 0.118 mmol), 4-methyl-1-(2,2,2-trifluoroethyl)-pyrazolo[4,3-d]pyrimidine-5,7-dione (29.4 mg, 0.118 mmol), potassium carbonate (32.7 mg, 0.236 mmol) and potassium iodide (3.9 mg, 0.024 mmol) were dissolved in N,N-dimethylformamide (5 mL). The reaction was heated to 120° C. and stirred for 3 hours. The reaction was cooled to room temperature, poured into water (20 mL) and extracted with ethyl acetate (20 mL×3). The organic phases were combined, dried over anhydrous sodium sulfate, filtered and the filtrate was concentrated and purified by preparative HPLC to give 6-(3-(1H-indol-3-yl)propyl)-4-methyl-1-(2,2,2-trifluoroethyl)-pyrazolo[4,3-d]pyrimidine-5,7-dione (15.0 mg) with a yield of 31%. $^1$H NMR: (400 MHz, Methanol-$d_4$) δ 7.70 (s, 1H), 7.50 (d, J=7.6 Hz, 1H), 7.23 (d, J=7.6 Hz, 1H), 7.05-6.97 (m, 3H), 5.22 (q, J=8.4 Hz, 2H), 4.16 (t, J=7.2 Hz, 2H), 3.39 (s, 3H), 2.86 (t, J=7.2 Hz, 2H), 2.19-2.12 (m, 2H). MS-ESI calcd. [M+H]$^+$ 406, found 406.

Example 74

4-Methyl-6-(3-(3-methylisoxazol-5-yl)propyl)-1-(2,2,2-trifluoroethyl)-pyrazolo[4,3-d]pyrimidine-5,7-dione

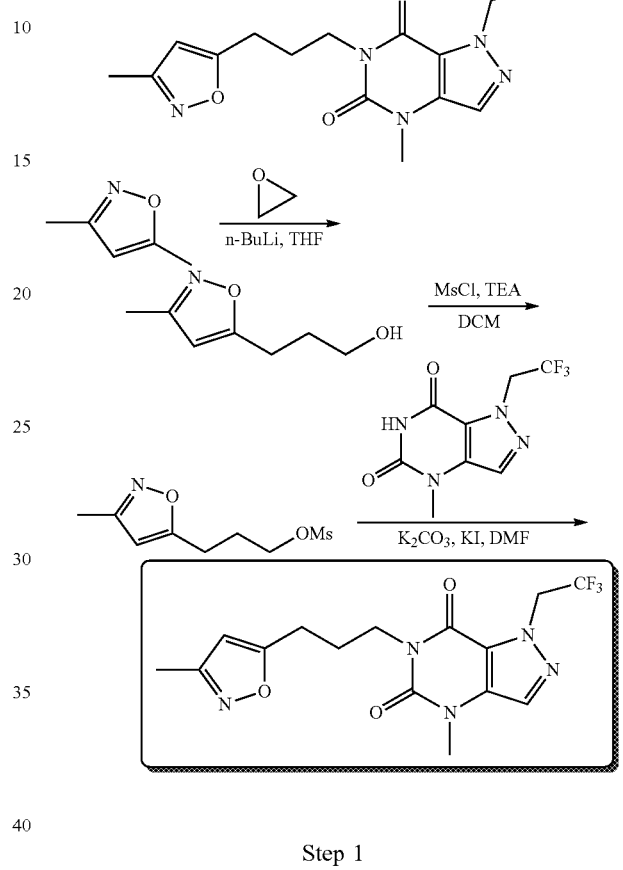

Step 1

3-(3-Methylisoxazol-5-yl)propan-1-ol 3,5-Dimethylisoxazole (4.00 g, 41.2 mmol) was dissolved in anhydrous tetrahydrofuran (50 mL). Under nitrogen atmosphere, n-butyllithium (16.5 mL, 2.5 M in n-heptane, 41.2 mmol) was slowly added at −78° C. The reaction was stirred at −78° C. for 2 hours, and added with ethylene oxide (1.81 g, 41.2 mmol) to continue to react for 1 hour. The reaction was quenched by addition of saturated ammonium chloride solution (50 mL) and extracted with ethyl acetate (20 mL×2). The organic phases were combined, washed with saturated sodium chloride solution (50 mL×2), dried over anhydrous magnesium sulfate, filtered and the filtrate was concentrated under reduced pressure to give 3-(3-methylisoxazol-5-yl)propan-1-ol (5.00 g, as a yellow oil) with a yield of 86%. $^1$H NMR: (400 MHz, Methanol-$d_4$) δ 6.05 (s, 1H), 3.63-3.55 (m, 2H), 2.85-2.81 (m, 2H), 2.27 (s, 3H), 1.95-1.87 (m, 2H). MS-ESI calcd. [M+H]$^+$ 142, found 142.

Step 2

3-(3-Methylisoxazol-5-yl)propyl methanesulfonate 3-(3-Methylisoxazol-5-yl)propan-1-ol (5.00 g, 35.4 mmol) and triethylamine (7.17 g, 70.8 mmol) were dissolved in anhydrous dichloromethane (20 mL). Methanesulfonyl chloride (6.09 g, 53.1 mmol) was slowly added at 0° C. under nitrogen atmosphere. The reaction solution was stirred at 0° C. for 1 hour. The reaction was quenched by addition of saturated sodium bicarbonate solution (50 mL) and extracted with dichloromethane (20 mL×2). The organic phases were combined, washed with saturated sodium chloride solution (50 mL×2), dried over anhydrous magnesium sulfate, filtered and the filtrate was concentrated under reduced pressure to give 3-(3-methylisoxazol-5-yl)propyl methanesulfonate (6.50 g, as a yellow oil) with a yield of 84%. MS-ESI calcd. [M+H]$^+$ 220, found 220.

Step 3

4-Methyl-6-(3-(3-methylisoxazol-5-yl)propyl)-1-(2,2,2-trifluoroethyl)-pyrazolo[4,3-d]pyrimidine-5,7-dione 3-(3-Methylisoxazol-5-yl)propyl methanesulfonate (30.0 mg, 0.136 mmol), 4-methyl-1-(2,2,2-trifluoroethyl)-pyrazolo[4,3-d]pyrimidine-5,7-dione (33.9 mg, 0.136 mmol), potassium carbonate (37.8 mg, 0.273 mmol) and potassium iodide (4.5 mg, 0.027 mmol) were dissolved in N,N-dimethylformamide (5 mL). The reaction was heated to 120° C. and stirred for 3 hours. The reaction was cooled to room temperature, poured into water (20 mL) and extracted with ethyl acetate (20 mL×3). The organic phases were combined, dried over anhydrous sodium sulfate, filtered and the filtrate was concentrated. The residue was purified by preparative HPLC to give 4-Methyl-6-(3-(3-methylisoxazol-5-yl)propyl)-1-(2,2,2-trifluoroethyl)-pyrazolo[4,3-d]pyrimidine-5,7-dione (20.0 mg) with a yield of 39%. $^1$H NMR: (400 MHz, Methanol-d$_4$) δ 7.81 (s, 1H), 6.06 (s, 1H), 5.35-5.29 (m, 2H), 4.13-4.07 (m, 2H), 3.50 (s, 3H), 2.82 (t, J=7.4 Hz, 2H), 2.18 (s, 3H), 2.12-2.05 (m, 2H). MS-ESI calcd. [M+H]$^+$ 372, found 372.

Example 75

4-Methyl-6-(4-(3-methylisoxazol-5-yl)butyl)-1-(2,2,2-trifluoroethyl)-pyrazolo[4,3-d]pyrimidine-5,7-dione

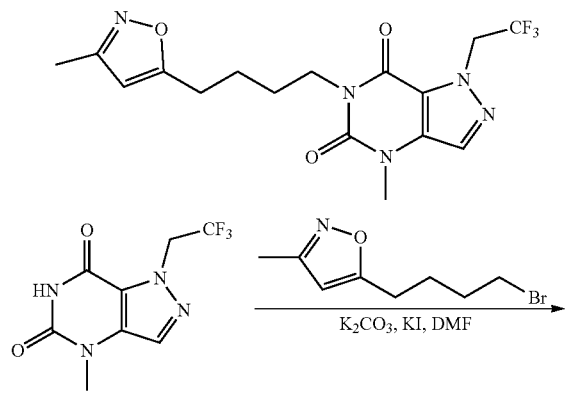

-continued

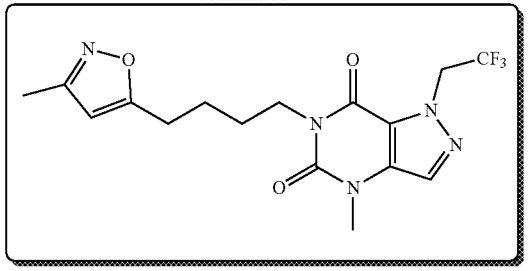

Step 1

4-Methyl-6-(4-(3-methylisoxazol-5-yl)butyl)-1-(2,2,2-trifluoroethyl)-pyrazolo[4,3-d]pyrimidine-5,7-dione 4-Methyl-1-(2,2,2-trifluoroethyl)pyrazolo[4,3-d]pyrimidine-5,7-dione (70.0 mg, 0.282 mmol) was dissolved in N,N-dimethylformamide (2 mL). 5-(4-Bromobutyl)-3-methylisoxazole (73.8 mg, 0.338 mmol), potassium carbonate (78.0 mg, 0.564 mmol) and potassium iodide (56.2 mg, 0.338 mmol) were added. The reaction was heated to 120° C. and stirred for 1 hour. The reaction was cooled to room temperature and filtered. The filtrate was concentrated under reduced pressure and the residue was purified by HPLC to give 4-methyl-6-(4-(3-methylisoxazol-5-yl)butyl)-1-(2,2,2-trifluoroethyl)-pyrazolo[4,3-d]pyrimidine-5,7-dione (44.0 mg) with a yield of 40%. $^1$H NMR: (400 MHz, CDCl$_3$) δ 7.55 (s, 1H), 5.83 (s, 1H), 5.22 (q, J=8.0 Hz, 2H), 4.14-4.00 (m, 2H), 3.51 (s, 3H), 2.83-2.70 (m, 2H), 2.26 (s, 3H), 1.83-1.67 (m, 4H). MS-ESI calcd. [M+H]$^+$ 386, found 386.

Example 76

1-(Cyclopropylmethyl)-6-((3-isopropylisoxazol-5-yl)methyl)-4-methyl-pyrazolo[4,3-d]pyrimidine-5,7-dione

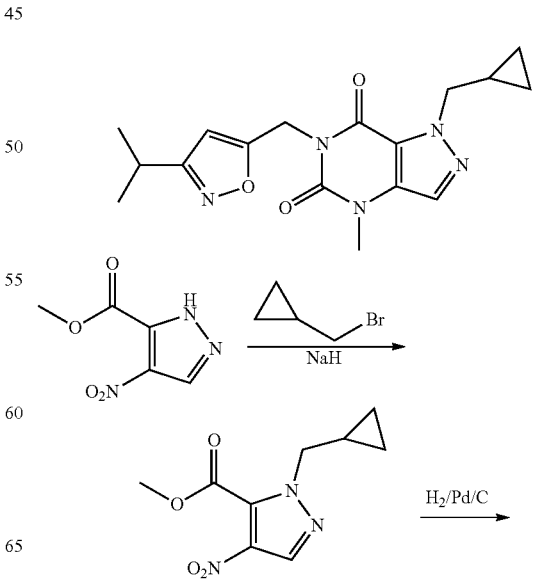

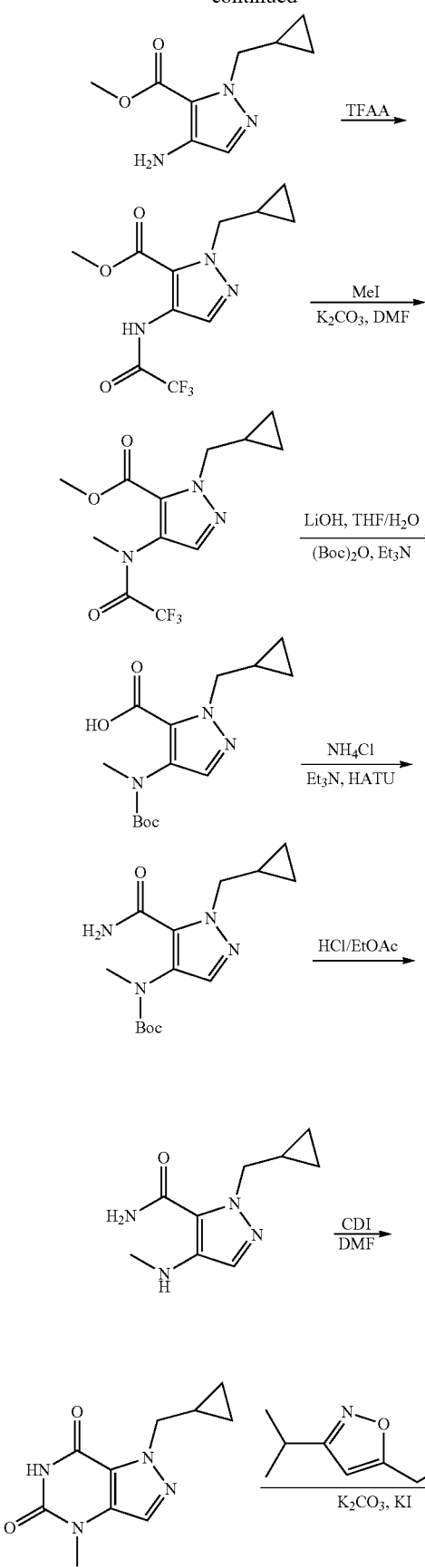

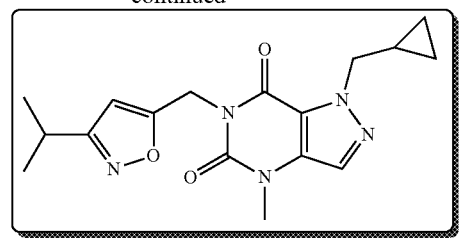

Step 1

Methyl 1-(cyclopropylmethyl)-4-nitro-pyrazole-5-carboxylate

Methyl 4-nitro-pyrazole-5-carboxylate (22.0 g, 129 mmol) was dissolved in N,N-dimethylformamide (350 mL) and sodium hydride (5.66 g, 141 mmol) was added in batches at 0° C. The reaction was stirred at 0° C. for 1 hour, sodium iodide (21.2 g, 141 mmol) was added and bromomethyl cyclopropane (19.1 g, 141 mmol) was added dropwise. The reaction solution was stirred at 25° C. for 18 hours, and extracted with ethyl acetate (300 mL×2) after adding with water (1.2 L). The organic phases were combined, washed with brine (500 mL), dried over anhydrous sodium sulfate, filtered and concentrated under reduced pressure. The residue was purified by silica gel column chromatography (5:1 petroleum ether/ethyl acetate, $R_f$=0.3) to give methyl 1-(cyclopropylmethyl)-4-nitro-pyrazole-5-carboxylate (5.00 g, as a colorless oil) with a yield of 17%. $^1$H NMR: (400 MHz, $CDCl_3$) δ 8.04 (s, 1H), 4.14 (d, J=7.6 Hz, 2H), 4.03 (s, 3H), 1.40-1.23 (m, 1H), 0.75-0.55 (m, 2H), 0.47-0.34 (m, 2H). MS-ESI calcd. $[M+H]^+$ 226, found 226.

Step 2

Methyl 4-amino-1-(cyclopropylmethyl)-pyrazole-5-carboxylate

Methyl 1-(cyclopropylmethyl)-4-nitro-pyrazole-5-carboxylate (5.00 g, 22.2 mmol) was dissolved in methanol (70 mL), dry palladium on carbon (10% palladium, 1% water, 500 mg) was added. The reaction was allowed to react under 40 psi of hydrogen pressure for 3 hours at room temperature. The reaction was filtered and the filtrate was concentrated under reduced pressure to give methyl 4-amino-1-(cyclopropylmethyl)-pyrazole-5-carboxylate (4.30 g, as an off white solid) with a yield of 99%. $^1$H NMR: (400 MHz, $CDCl_3$) δ 7.11 (s, 1H), 4.27 (d, J=7.6 Hz, 2H), 4.11 (s, 2H), 3.91 (s, 3H), 1.46-1.21 (m, 1H), 0.53-0.43 (m, 2H), 0.41-0.32 (m, 2H). MS-ESI calcd. $[M+H]^+$ 196, found 196.

Step 3

Methyl 1-(cyclopropylmethyl)-4-(2,2,2-trifluoroacetamido)-pyrazole-5-carboxylate Methyl 4-amino-1-(cyclopropylmethyl)-pyrazole-5-carboxylate (4.30 g, 22.0 mmol) was dissolved in dichloromethane (40 mL), trifluoroacetic anhydride (6.94 g, 33.1 mmol) was added dropwise under nitrogen atmosphere and the reaction solution was stirred at room temperature for 2 hours. The reaction was quenched with saturated sodium bicarbonate solution (50 mL), extracted with dichloromethane (40 mL), washed with brine (50 mL), dried over sodium sulfate and concentrated under reduced pressure to give methyl 1-(cyclopropylmethyl)-4-(2,2,2-trifluoroacetamido)-pyrazole-5-carboxylate (6.30 g, as a colorless oil) with a yield of 98%. $^1$H NMR: (400 MHz, CDCl$_3$) δ 9.72 (s, 1H), 8.28 (s, 1H), 4.37 (d, J=7.6 Hz, 2H), 4.09 (s, 3H), 1.39-1.23 (m, 1H), 0.60-0.48 (m, 2H), 0.45-0.37 (m, 2H). MS-ESI calcd. [M+H]$^+$292, found 292.

Step 4

Methyl 1-(cyclopropylmethyl)-4-(2,2,2-trifluoro-N-methylacetamido)-pyrazole-5-carboxylate Methyl 1-(cyclopropylmethyl)-4-(2,2,2-trifluoroacetamido)-pyrazole-5-carboxylate (6.20 g, 21.3 mmol) was dissolved in N,N-dimethylformamide (50 mL) and potassium carbonate (4.41 g, 31.9 mmol) was added. The reaction solution was heated to 80° C. to react for 1 hour, and then cooled to room temperature and added with methyl iodide (4.53 g, 31.9 mmol). The reaction solution was stirred at room temperature for 18 hours, and extracted with ethyl acetate (100 mL×2) after adding with water (300 mL). The organic phases were combined, washed with brine (100 mL), dried over anhydrous sodium sulfate, filtered and concentrated under reduced pressure to give methyl 1-(cyclopropylmethyl)-4-(2,2,2-trifluoro-N-methylacetamido)-pyrazole-5-carboxylate (6.44 g, as a yellow oil) with a yield of 98%. $^1$H NMR: (400 MHz, CDCl$_3$) δ 7.50 (s, 1H), 4.43 (d, J=7.6 Hz, 2H), 3.90 (s, 3H), 3.28 (s, 3H), 1.43-1.27 (m, 1H), 0.60-0.47 (m, 2H), 0.45-0.33 (m, 2H). MS-ESI calcd. [M+H]$^+$ 306, found 306.

Step 5

4-[(Tert-butoxycarbonyl)(methyl)amino] 1-(cyclopropylmethyl)-pyrazole-5-carboxylic Acid Methyl 1-(cyclopropylmethyl)-4-(2,2,2-trifluoro-N-methylacetamido)-pyrazole-5-carboxylate (6.40 g, 21.0 mmol) was dissolved in tetrahydrofuran (30 mL) and water (30 mL). Lithium hydroxide monohydrate (4.40 g, 105 mmol) was added and the reaction was stirred at room temperature for 16 hours. Di-tert-butyl dicarbonate (9.15 g, 41.9 mmol) was added and the reaction was continued for 16 hours at room temperature. The reaction solution was concentrated under reduced pressure, adjusted to pH 4 with 2 N aqueous hydrochloric acid, filtered and the filter cake was dried to give 4-[(tert-butoxycarbonyl)(methyl)amino]1-(cyclopropylmethyl)-pyrazole-5-carboxylic acid (4.50 g, as a white solid) with a yield of 73%. $^1$H NMR: (400 MHz, CDCl$_3$) δ 7.46 (s, 1H), 4.38 (d, J=7.6 Hz, 2H), 3.21 (s, 3H), 1.58-1.25 (m, 10H), 0.60-0.47 (m, 2H), 0.45-0.37 (m, 2H). MS-ESI calcd. [M+H]$^+$ 296, found 296.

Step 6

Tert-butyl 5-carbamoyl-1-(cyclopropylmethyl)-pyrazol-4-yl)(methyl)carbamate

4-[(Tert-butoxycarbonyl)(methyl)amino]1-(cyclopropylmethyl)-pyrazole-5-carboxylic acid (3.40 g, 11.5 mmol), 2-(7-azobenzotriazole)-tetramethyluronium hexafluorophosphate (5.69 g, 15.0 mmol) and ammonium chloride (1.23 g, 23.0 mmol) were dissolved in dichloromethane (120 mL). Triethylamine (1.75 g, 17.3 mmol) was added dropwise at room temperature. The reaction solution was stirred at room temperature for 18 hours, added with water (50 mL) and extracted with dichloromethane (500 mL×2). The organic phases were combined and washed sequentially with saturated sodium bicarbonate solution (50 mL) and brine (50 mL), dried over anhydrous sodium sulfate, filtered and concentrated under reduced pressure. The residue was treated with ethanol (20 mL) to give tert-butyl 5-carbamoyl-1-(cyclopropylmethyl)-pyrazol-4-yl)(methyl)carbamate (3.00 g, crude product, as a yellow oil). MS-ESI calcd. [M+H]$^+$ 295, found 295.

Step 7

1-(Cyclopropylmethyl)-4-(methylamino)-pyrazole-5-carboxamide

Tert-butyl 5-carbamoyl-1-(cyclopropylmethyl)-pyrazol-4-yl)(methyl)carbamate (3.30 g, 11.2 mmol) was dissolved in hydrochloride/ethyl acetate (25 mL). The reaction was stirred at room temperature for 18 hours, concentrated under reduced pressure and the residue was dissolved in methanol (40 mL). Potassium carbonate (3.10 g, 22.4 mmol) was added and stirred at room temperature for 2 hours. The reaction solution was filtered, concentrated under reduced pressure and the residue was extracted with dichloromethane (60 mL), filtered and the filtrate was evaporated to dryness. The residue was slurried with dichloromethane (15 mL) and filtered to give 1-(cyclopropylmethyl)-4-(methylamino)-pyrazole-5-carboxamide (1.45 g, as a white solid) with a yield of 67%. $^1$H NMR: (400 MHz, CDCl$_3$) δ 7.34 (br, 2H), 7.17 (s, 1H), 4.62-4.47 (q, J=5.6 Hz, 1H), 4.21 (d, J=7.6 Hz, 2H), 2.65 (d, J=5.6 Hz, 3H), 1.22-1.10 (m, 1H), 0.43-0.34 (m, 2H), 0.31-0.23 (m, 2H). MS-ESI calcd. [M+H]$^+$ 195, found 195.

Step 8

1-(Cyclopropylmethyl)-4-methyl-pyrazolo[4,3-d]pyrimidine-5,7-dione 1-(Cyclopropylmethyl)-4-(methylamino)-pyrazole-5-carboxamide (1.45 g, 7.47 mmol) was dissolved in N,N-dimethylformamide (10 mL). Sodium hydride (627 mg, 15.7 mmol) was added in batches at 0° C. Under nitrogen atmosphere, the reaction was stirred at 0° C. for 1 hour. 1,1-Carbonyldiimidazole (1.82 g, 11.2 mmol) was added and the reaction solution was heated to 75° C. to react for 2 hours. The reaction solution was cooled to room temperature, quenched by the addition of water (80 mL), filtered and the filter cake was dried to give 1-(cyclopropylmethyl)-4-methyl-pyrazolo[4,3-d]pyrimidine-5,7-dione (1.60 g, as a white solid) with a yield of 97%. $^1$H NMR: (400 MHz, DMSO-d$_6$) δ 11.35 (s, 1H), 7.72 (s, 1H), 4.29 (d, J=7.6 Hz, 2H), 3.32 (s, 3H), 1.17-1.07 (m, 1H), 0.54-0.32 (m, 4H). MS-ESI calcd. [M+H]$^+$ 221, found 221.

Step 9

1-(Cyclopropylmethyl)-6-(3-isopropylisoxazol-5-yl)methyl)-4-methyl-pyrazolo[4,3-d]pyrimidine-5,7-dione 3-Isopropylisoxazole-5-methyl methanesulfonate (29.9 mg, 0.136 mmol), 1-(cyclopropylmethyl)-4-methyl-pyrazolo[4,3-d]pyrimidine-5,7-dione (30.0 mg, 0.136 mmol), potassium iodide (2.3 mg, 0.014 mmol) and potassium carbonate (56.5 mg, 0.408 mmol) were dissolved in N,N- dimethylformamide (3 mL). The reaction solution was warmed to 120° C. and stirred for 3 hours, and then cooled to room temperature, filtered and the filtrate was concentrated under reduced pressure. The residue was purified by preparative HPLC to give 1-(cyclopropylmethyl)-6-(3-isopropylisoxazol-5-yl)methyl)-4-methyl-pyrazolo[4,3-d]pyrimidine-5,7-dione (8.0 mg) with a yield of 17%. $^1$H NMR: (400 MHz, CDCl$_3$) δ 7.43 (s, 1H), 6.14 (s, 1H), 5.32 (s, 2H), 4.44 (d, J=7.6 Hz, 2H), 3.52 (s, 3H), 3.07-3.00 (m, 1H), 1.43-1.40 (m, 1H), 1.26 (d, J=7.2 Hz, 6H), 0.56-0.47 (m, 4H). MS-ESI calcd. [M+H]$^+$ 344, found 344.

Example 77

1-(Cyclopropylmethyl)-6-(2-(2,4-dimethylthiazol-5-yl)ethyl)-4-methyl-pyrazolo[4,3-d]pyrimidine-5,7-dione

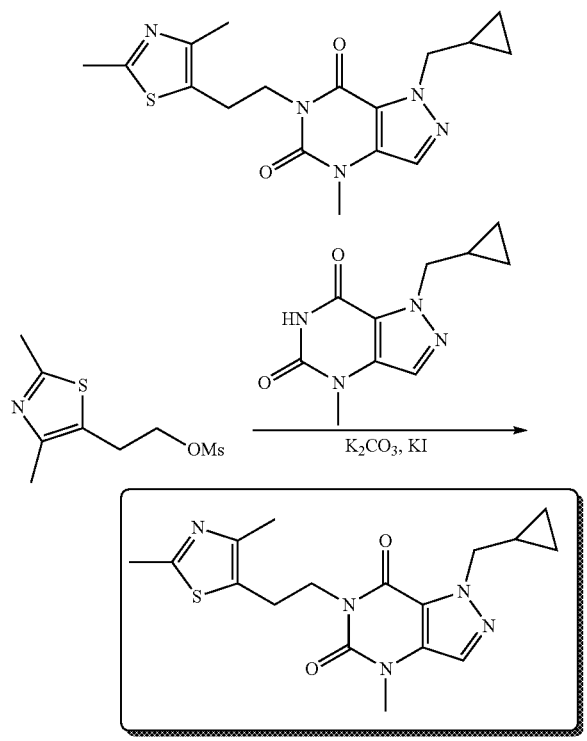

Step 1

1-(Cyclopropylmethyl)-6-(2-(2,4-dimethylthiazol-5-yl)ethyl)-4-methyl-pyrazolo[4,3-d]pyrimidine-5,7-dione 2-(2,4-Dimethylthiazol-5-yl)ethyl methanesulfonate (80.1 mg, 0.340 mmol), 1-(cyclopropylmethyl)-4-methyl-pyrazolo[4,3-d]pyrimidine-5,7-dione (50.0 mg, 0.227 mmol), potassium iodide (3.8 mg, 0.0227 mmol) and potassium carbonate (94.1 mg, 0.681 mmol) were dissolved in N,N-dimethylformamide (5 mL). The reaction solution was heated to 120° C. and stirred for 3 hours. The mixture was cooled to room temperature, filtered and the filtrate was concentrated under reduced pressure. The residue was purified by preparative HPLC to give 1-(cyclopropylmethyl)-6-(2-(2,4-dimethylthiazol-5-yl)ethyl)-4-methyl-pyrazolo[4,3-d]pyrimidine-5,7-dione (20.0 mg) with a yield of 25%. $^1$H NMR: (400 MHz, Methanol-d$_4$) δ 7.68 (s, 1H), 4.39 (d, J=7.6 Hz, 2H), 4.26 (t, J=6.8 Hz, 2H), 3.50 (s, 3H), 3.33 (t, J=6.8 Hz, 2H), 2.95 (s, 3H), 2.46 (s, 3H), 1.36-1.31 (m, 1H), 0.55-0.42 (m, 4H). MS-ESI calcd. [M+H]$^+$ 360, found 360.

Example 78

6-(3-(1H-indol-3-yl)propyl)-1-(cyclopropylmethyl)-4-methyl-pyrazolo[4,3-d]pyrimidine-5,7-dione

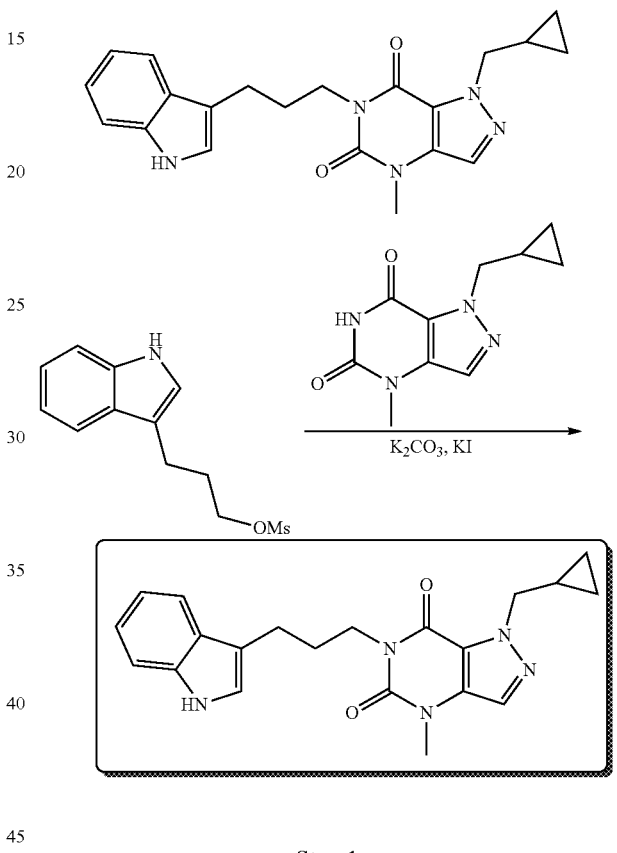

Step 1

6-(3-(1H-indol-3-yl)propyl)-1-(cyclopropylmethyl)-4-methyl-pyrazolo[4,3-d]pyrimidine-5,7-dione 3-(1H-indol-3-yl)propyl methanesulfonate (80.6 mg, 0.318 mmol), 1-(cyclopropylmethyl)-4-methyl-pyrazolo[4,3-d]pyrimidine-5,7-dione (50.0 mg, 0.227 mmol), potassium iodide (3.8 mg, 0.0227 mmol) and potassium carbonate (88.0 mg, 0.636 mmol) were dissolved in N,N-dimethylformamide (5 mL). The reaction solution was warmed to 120° C. and stirred for 3 hours. The mixture was cooled to room temperature, filtered and the filtrate was concentrated under reduced pressure. The residue was purified by preparative HPLC to give 6-(3-(1H-indol-3-yl)propyl)-1-(cyclopropylmethyl)-4-methyl-pyrazolo[4,3-d]pyrimidine-5,7-dione (20.0 mg) with a yield of 25%. $^1$H NMR: (400 MHz, Methanol-d$_4$) δ 7.54-7.50 (m, 2H), 7.24 (d, J=8.4 Hz, 1H), 7.05-6.96 (m, 3H), 4.35 (d, J=7.6 Hz, 2H), 4.15 (t, J=7.2 Hz, 2H), 3.40 (s, 3H), 2.85 (t, J=7.2 Hz, 2H), 2.17-2.10 (m, 2H), 1.35-1.31 (m, 1H), 0.55-0.45 (m, 4H). MS-ESI calcd. [M+H]$^+$ 378, found 378.

Example 79

6-(4-(Benzofuran-2-yl)butyl)-1-(cyclopropylmethyl)-4-methyl-pyrazolo[4,3-d]pyrimidine-5,7-dione

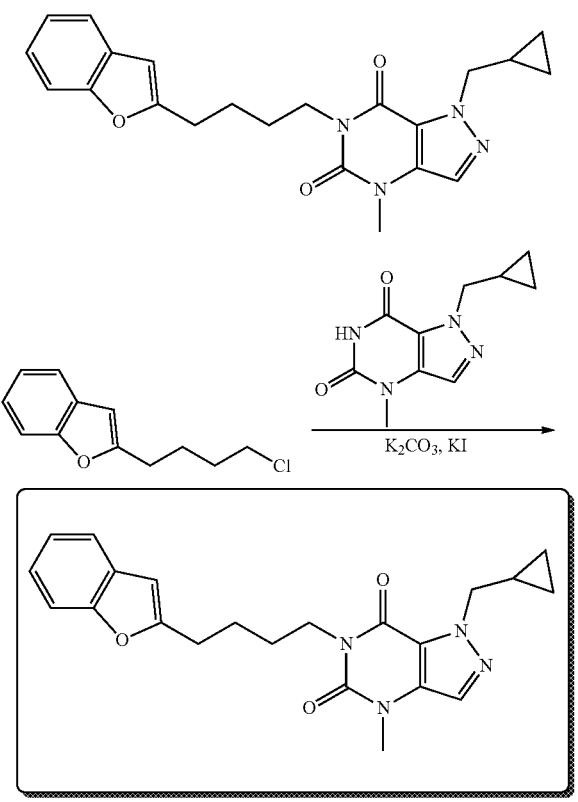

Step 1

6-(4-(Benzofuran-2-yl)butyl)-1-(cyclopropylmethyl)-4-methyl-pyrazolo[4,3-d]pyrimidine-5,7-dione 2-(4-Chlorobutyl)benzofuran (37.0 mg, 0.177 mmol), 1-(cyclopropylmethyl)-4-methyl-pyrazolo[4,3-d]pyrimidine-5,7-dione (30.0 mg, 0.136 mmol), potassium iodide (2.3 mg, 0.0136 mmol) and potassium carbonate (24.5 mg, 0.177 mmol) were dissolved in N,N-dimethylformamide (5 mL). The reaction solution was heated to 120° C. and stirred for 3 hours. The mixture was cooled to room temperature, filtered and the filtrate was concentrated under reduced pressure. The residue was purified by preparative HPLC to give 6-(4-(Benzofuran-2-yl)butyl)-1-(cyclopropylmethyl)-4-methyl-pyrazolo[4,3-d]pyrimidine-5,7-dione (20.0 mg) with a yield of 37%. $^1$H NMR: (400 MHz, Methanol-$d_4$) δ 7.59 (s, 1H), 7.44 (d, J=7.6 Hz, 1H), 7.33 (d, J=7.6 Hz, 1H), 7.16-7.12 (m, 2H), 6.44 (m, 1H), 4.38 (d, J=7.6 Hz, 2H), 4.04 (t, J=6.8 Hz, 2H), 3.44 (s, 3H), 2.82 (t, J=6.8 Hz, 2H), 1.81-1.73 (m, 4H), 1.34-1.31 (m, 1H), 0.50-0.44 (m, 4H). MS-ESI calcd. [M+H]$^+$ 393, found 393.

Example 80

1-(Cyclopropylmethyl)-4-methyl-6-(3-(3-methylisoxazol-5-yl)propyl)-pyrazolo[4,3-d]pyrimidin-5,7-dione

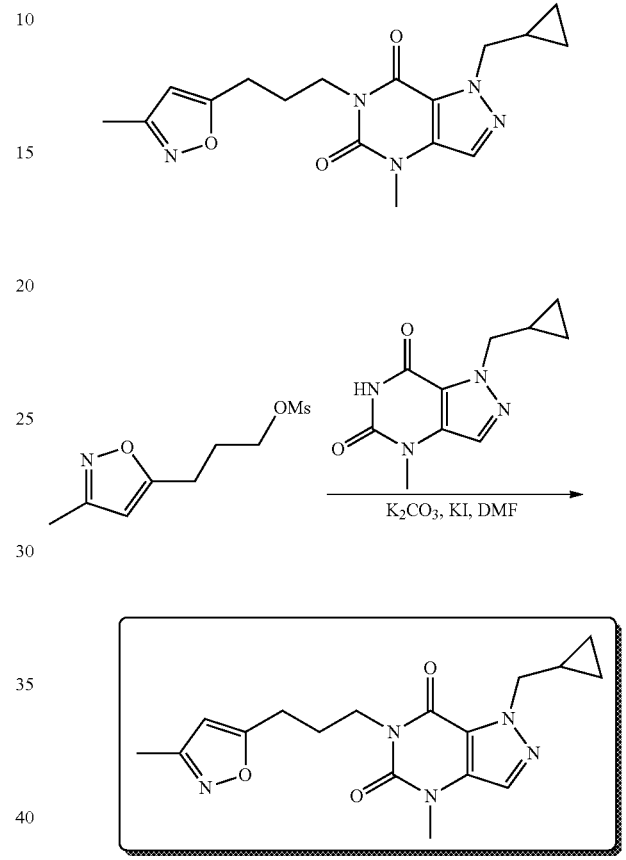

Step 1

1-(Cyclopropylmethyl)-4-methyl-6-(3-(3-methylisoxazol-5-yl)propyl)-pyrazolo[4,3-d]pyrimidin-5,7-dione 3-(3-Methylisoxazol-5-yl)propyl methanesulfonate (50.0 mg, 0.228 mmol), 1-(cyclopropylmethyl)-4-methyl-pyrazolo[4,3-d]pyrimidine-5,7-dione (38.6 mg, 0.175 mmol) and potassium carbonate (72.7 mg, 0.526 mmol) were dissolved in N,N-dimethylformamide (5 mL). Potassium iodide (3.8 mg, 0.023 mmol) was added and the reaction stirred at 120° C. for 3 hours. The reaction solution was filtered and the filtrate was concentrated under reduced pressure. The crude product was purified by preparative HPLC to give 1-(cyclopropylmethyl)-4-methyl-6-(3-(3-methylisoxazol-5-yl)propyl)-pyrazolo[4,3-d]pyrimidin-5,7-dione (26.0 mg) with a yield of 43%. $^1$H NMR: (400 MHz, Methanol-$d_4$) δ 7.63 (s, 1H), 6.07 (s, 1H), 4.41 (d, J=7.6 Hz, 2H), 4.12 (t, J=7.2 Hz, 2H), 3.48 (s, 3H), 2.83 (t, J=7.2 Hz, 2H), 2.18 (s, 3H), 2.12-2.05 (m, 2H), 1.40-1.35 (m, 1H), 0.55-0.47 (m, 4H). MS-ESI calcd. [M+H]$^+$ 344, found 344.

Example 81

1-(Cyclopropylmethyl)-4-methyl-6-(4-(3-methyl-isoxazol-5-yl)butyl)-pyrazolo[4,3-d]pyrimidin-5,7-dione

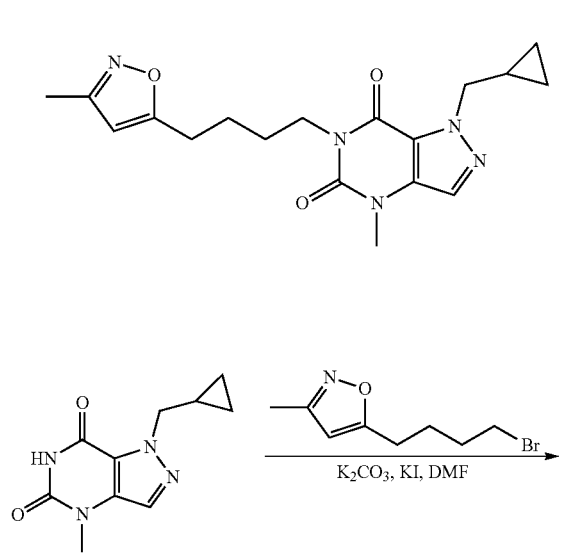

Step 1

1-(Cyclopropylmethyl)-4-methyl-6-(4-(3-methylisoxazol-5-yl)butyl)-pyrazolo[4,3-d]pyrimidin-5,7-dione 1-(Cyclopropylmethyl)-4-methyl-pyrazolo[4,3-d]pyrimidine-5,7-dione (62.1 mg, 0.282 mmol) was dissolved in N,N-dimethylformamide (2 mL). 5-(4-Bromobutyl)-3-methylisoxazole (73.8 mg, 0.338 mmol), potassium carbonate (78.0 mg, 0.564 mmol) and potassium iodide (56.2 mg, 0.338 mmol) were added. The reaction was heated to 120° C. and stirred for 1 hour. The reaction was cooled to room temperature and filtered. The filtrate was concentrated under reduced pressure and the residue was purified by HPLC to give 1-(cyclopropylmethyl)-4-methyl-6-(4-(3-methylisoxazol-5-yl)butyl)-pyrazolo[4,3-d]pyrimidin-5,7-dione (24.0 mg) with a yield of 24%. $^1$H NMR: (400 MHz, CDCl$_3$) δ 7.40 (s, 1H), 5.83 (s, 1H), 4.43 (d, J=7.6 Hz, 2H), 4.13-3.98 (m, 2H), 3.49 (s, 3H), 2.83-2.75 (m, 2H), 2.25 (s, 3H), 1.82-1.67 (m, 4H), 1.44-1.31 (m, 1H), 0.60-0.50 (m, 2H), 0.49-0.40 (m, 2H). MS-ESI calcd. [M+H]$^+$ 358, found 358.

Example 82

5-Isobutyl-3-(4-(3-methylisoxazol-5-yl)butyl)imidazo[5,1-f][1,2,4]triazin-4-one

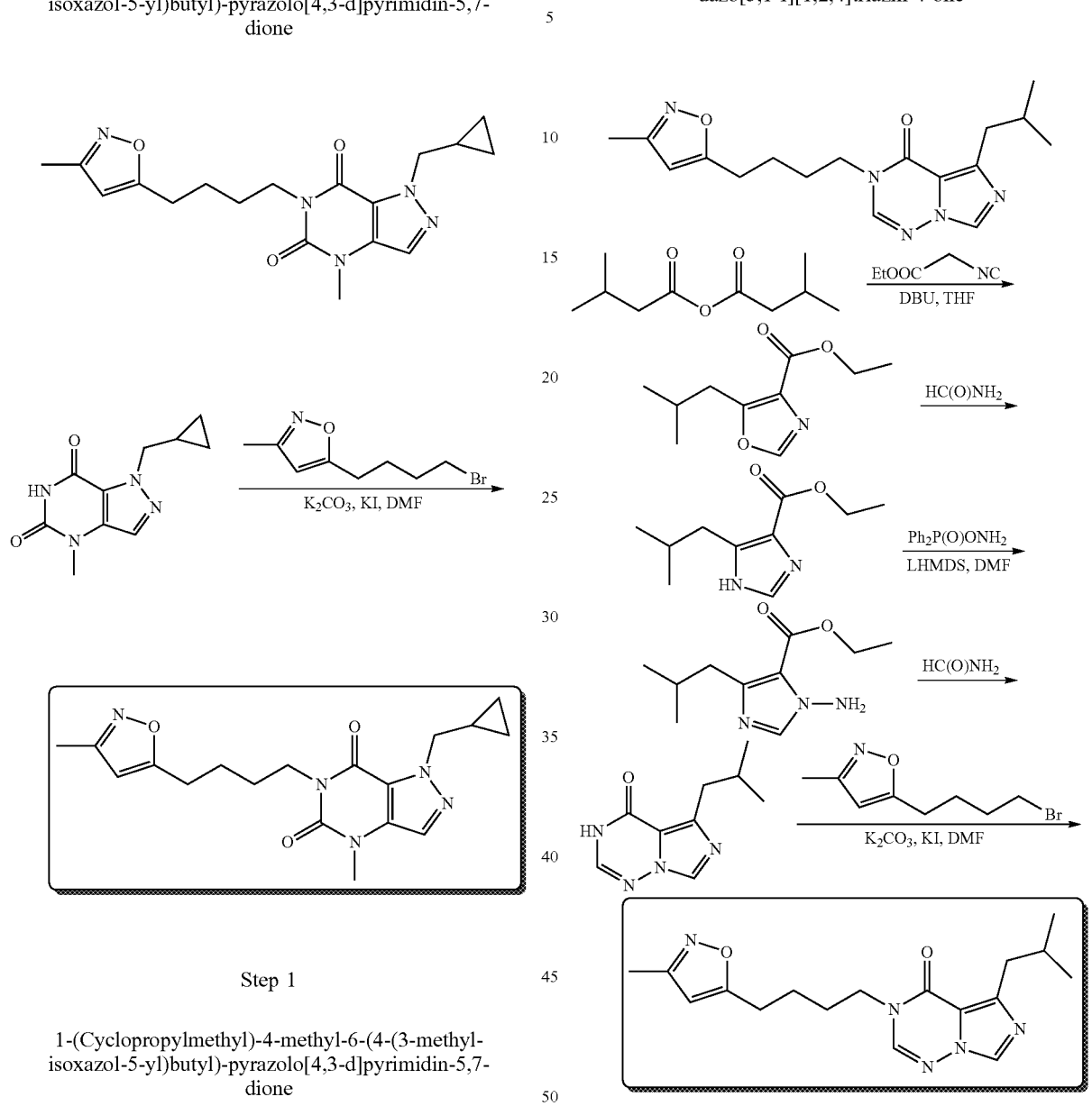

Step 1

Ethyl 5-isobutyl-oxazole-4-carboxylate

Isovaleric anhydride (4.50 g, 24.1 mmol) and ethyl 2-isocyanatoacetate (2.73 g, 24.1 mmol) were dissolved in tetrahydrofuran (50 mL) and 1,8-diazabicycloundec-7-ene (3.68 g, 24.1 mmol) was added and stirred for 12 hours at room temperature. The reaction solution was diluted with water (20 mL) and extracted with ethyl acetate (20 mL×3). The organic phases were combined and washed with saturated sodium chloride solution (20 mL×2), dried over anhydrous sodium sulfate, filtered and the filtrate was concentrated under reduced pressure and purified by silica gel column chromatography (30:1 petroleum ether/ethyl acetate, $R_f=0.6$) to give ethyl 5-isobutyl oxazole-4-carboxylate (2.50 g, as a yellow oil) with a yield of 57%. $^1$H NMR: (400 MHz, CDCl$_3$) δ 7.76 (s, 1H), 4.36 (q, J=7.2 Hz, 2H), 2.93 (d, J=7.6 Hz, 2H), 2.11-2.03 (m, 1H), 1.39 (t, J=7.2 Hz, 3H), 0.94 (d, J=6.4 Hz, 6H). MS-ESI calcd. [M+H]$^+$ 198, found 198.

Step 2

Ethyl 5-isobutyl-1H-imidazole-4-carboxylate

Ethyl 5-isobutyl oxazole-4-carboxylate (1.50 g, 7.61 mmol) was dissolved in formamide (15 mL) and heated at 150° C. to react for 12 hours. The reaction solution was cooled to room temperature and diluted with water (20 mL), extracted with ethyl acetate (20 mL×3). The organic phases were combined and washed with saturated sodium chloride solution (20 mL×2), dried over anhydrous sodium sulfate, filtered and the filtrate was concentrated under reduced pressure. The residue was purified by silica gel column chromatography (20:1 petroleum ether/ethyl acetate, $R_f=0.2$) to give ethyl 5-isobutyl-1H-imidazole-4-carboxylate (1.20 g, as a yellow solid) with a yield of 80%. MS-ESI calcd. [M+H]$^+$ 197, found 197.

Step 3

Ethyl 1-amino-4-isobutyl-1H-imidazole-5-carboxylate

Ethyl 5-isobutyl-1H-imidazole-4-carboxylate (1.00 g, 5.10 mmol) and O-diphenylphosphinylhydroxylamine (1.43 g, 6.12 mmol) were dissolved in N,N-dimethylformamide (60 mL). The reaction solution was added with lithium hexamethyldisilazide (6.12 mL, 1 M n-hexane solution, 6.12 mmol) at −10° C. and reacted at room temperature for 12 hours. The reaction was concentrated, diluted with water (20 mL) and extracted with ethyl acetate (20 mL×3). The organic phases were combined, and washed with saturated sodium chloride solution (20 mL×2), dried over anhydrous sodium sulfate, filtered and the filtrate was concentrated under reduced pressure to give ethyl 1-amino-4-isobutyl-1H-imidazole-5-carboxylate (800 mg, as a yellow oil) with a yield of 74%, which was directly used in the next step. MS-ESI calcd. [M+H]$^+$ 212, found 212.

Step 4

5-Isobutylimidazo[5,1-f][1,2,4]triazin-4-one 1-amino-4-isobutyl-1H-imidazole-5-carboxylate (1.00 g, 4.73 mmol) was dissolved in formamide (10 mL) and heated at 150° C. to react for 4 hours. The reaction solution was cooled to room temperature and purified by HPLC to give 5-isobutylimidazo[5,1-f][1,2,4]triazin-4-one (500 mg, as a yellow oil) with a yield of 55% $^1$H NMR: (400 MHz, Methanol-d$_4$) δ 8.23 (s, 1H), 7.68 (s, 1H), 2.85 (d, J=7.2 Hz, 2H), 2.15-2.05 (m, 1H), 0.95 (d, J=6.8 Hz, 6H). MS-ESI calcd. [M+H]$^+$ 193, found 193.

Step 5

5-Isobutyl-3-(4-(3-methylisoxazol-5-yl)butyl)imidazo[5,1-j][1,2,4]triazin-4-one

5-Isobutyl imidazo[5,1-f][1,2,4]triazin-4-one (50.0 mg, 0.260 mmol), 5-(4-bromobutyl)-3-methylisoxazole (85.1 mg, 0.390 mmol) and potassium iodide (12.9 mg, 0.0780 mmol) were dissolved in N,N-dimethylformamide (8 mL). Potassium carbonate (71.9 mg, 0.520 mmol) was added and the reaction was stirred at 120° C. for 2 hours. The reaction solution was cooled to room temperature, filtered and the filtrate was concentrated under reduced pressure. The resulting product was purified by preparative HPLC to give 5-isobutyl-3-(4-(3-methylisoxazol-5-yl)butyl)imidazo[5,1-F] [1,2,4]triazin-4-one (24.0 mg) with a yield of 28%. $^1$H NMR: (400 MHz, CDCl$_3$) δ 8.00 (s, 1H), 7.38 (s, 1H), 5.83 (s, 1H), 3.87 (t, J=6.8 Hz, 2H), 2.90 (d, J=7.2 Hz, 2H), 2.79 (t, J=6.8 Hz, 2H), 2.28 (s, 3H), 2.20-2.13 (m, 1H), 1.83-1.74 (m, 4H), 0.98-0.94 (m, 6H). MS-ESI calcd. [M+H]$^+$ 330, found 330.

Example 83

1-Methyl-3-(4-(3-methylisoxazol-5-yl)butyl)quinazoline-2,4(1H,3H)-dione

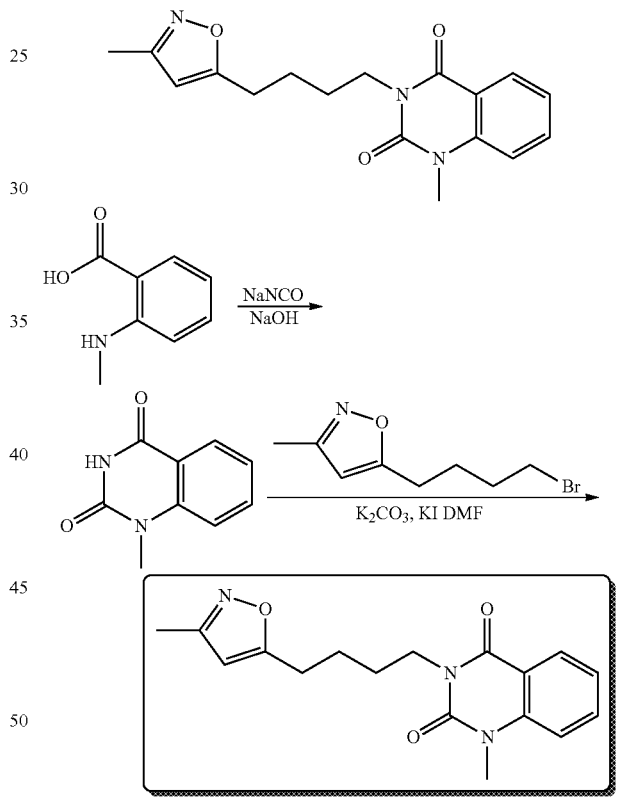

Step 1

1-Methylquinazoline-2,4-dione 2-(Methylamino)benzoic acid (4.50 g, 0.0300 mol) and acetic acid (0.3 mL) were dissolved in water (158 mL), a solution of sodium isocyanate (2.76 g, 42.0 mmol) in water (54 mL) was added slowly at room temperature. The reaction mixture was heated to 40° C. and added with sodium hydroxide (34.8 g, 0.870 mol). The temperature was raised to 75° C. and the reaction solution was stirred for 4 hours, cooled to room temperature, filtered and the filter cake was dissolved in boiling water (10 mL). The system was adjusted to pH 1-2 with 50% sulfuric acid solution (15 mL), filtered and the filter cake was washed with a small amount of water (3 mL) and dried under reduced pressure to give 1-methylquinazoline-2,4-dione (3.64 g, as a yellow solid) with a yield of 69%. $^1$H NMR: (400 MHz, DMSO-$d_6$) δ 11.55 (s, 1H), 8.00 (d, J=8.0 Hz, 1H), 7.78 (t, J=8.0 Hz, 1H), 7.42 (d, J=8.0 Hz, 1H), 7.28 (t, J=8.0 Hz, 1H), 3.44 (s, 3H). MS-ESI calcd. [M+H]$^+$ 177, found 177.

Step 2

1-Methyl-3-(4-(3-methylisoxazol-5-yl)butyl)quinazoline-2,4(1H,3H)-dione

1-Methylquinazoline-2,4-dione (50.0 mg, 0.280 mmol), 5-(4-bromobutyl)-3-methylisoxazole (98.0 mg, 0.420 mmol), potassium iodide (5.0 mg, 0.030 mmol) and potassium carbonate (83.0 mg, 0.600 mmol) were dissolved in N,N-dimethylformamide (1 mL). The reaction was heated to 130° C. to react for 2.5 hours. The reaction was cooled to room temperature and quenched by addition of brine (50 mL), extracted with ethyl acetate (50 mL×3) and the organic phases were combined, dried over anhydrous sodium sulfate, filtered and the filtrate was concentrated under reduced pressure. The residue was purified by preparative HPLC to give (4-(3-methylisoxazol-5-yl)butyl)quinazoline-2,4(1H,3H)-dione (41.0 mg) with a yield of 47%. $^1$H NMR: (400 MHz, Methanol-$d_4$) δ 8.16-8.13 (m, 1H), 7.77-7.75 (m, 1H), 7.44 (d, J=8.0 Hz, 1H), 7.31 (t, J=8.0 Hz, 1H), 6.04 (s, 1H), 4.13-4.08 (m, 2H), 3.61 (s, 3H), 2.80 (t, J=6.8 Hz, 2H), 2.23 (s, 3H), 1.77-1.73 (m, 4H). MS-ESI calcd. [M+H]$^+$ 314, found 314.

Example 84

3-((3-Isopropylisoxazol-5-yl)methyl)-1-methylpyrido[2,3-d]pyrimidine-2,4-dione

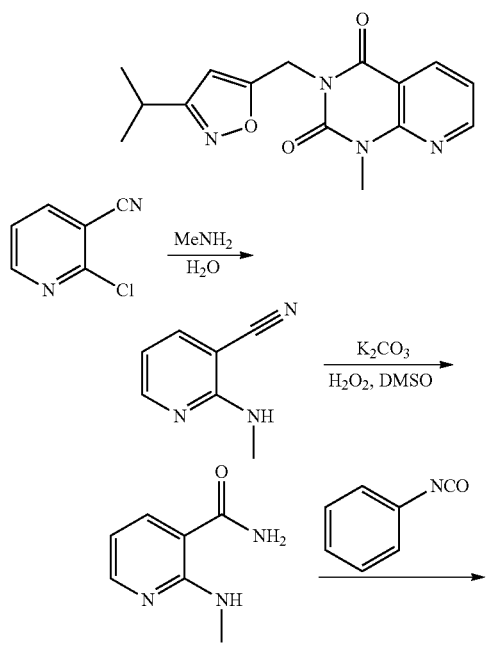

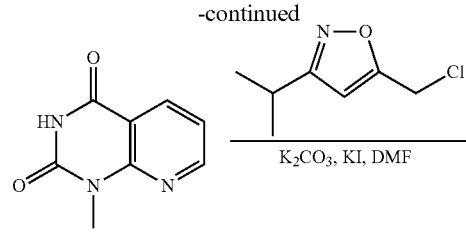

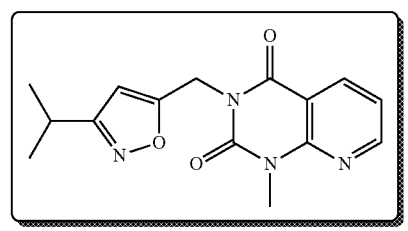

Step 1

2-(Methylamino)nicotinonitrile

2-Chloro-3-cyanopyridine (30.0 g, 216 mmol) was added to 40% aqueous methylamine solution (300 mL) and stirred for 2 hours after heating to 80° C. The reaction solution was concentrated under reduced pressure and filtered. The resulting solid was washed with water (30 mL×3) and dried to give 2-(methylamino)nicotinamide (22.3 g, as a pale yellow solid) with a yield of 76%. $^1$H NMR: (400 MHz, Methanol-$d_4$) δ 8.25-8.22 (m, 1H), 7.79-7.74 (m, 1H), 6.65-6.59 (m, 1H), 2.96 (s, 3H).

Step 2

2-(Methylamino)pyridine-3-carboxamide 2-(Methylamino)nicotinonitrile (600 mg, 4.51 mmol), potassium carbonate (1.87 mg, 0.130 mmol) and hydrogen peroxide (0.1 mL) were dissolved in dimethylsulfoxide (10 mL), reacted for 1 hour at room temperature and quenched by the addition of water (10 mL). The reaction solution was extracted with ethyl acetate (10 mL×3), dried over anhydrous sodium sulfate, filtered, and the filtrate was concentrated under reduced pressure, and purified on a silica gel plate (1:1 petroleum ether/ethyl acetate, $R_f$=0.2) to give 2-(methylamino)pyridine-3-carboxamide (500 mg, white solid) with a yield of 73%. $^1$H NMR: (400 MHz, DMSO-$d_6$) δ 8.45-8.40 (br, 1H), 8.28 (d, J=2.0 Hz, 1H), 7.95-7.93 (m, 2H), 7.35-7.30 (br, 1H), 6.53 (dd, J=7.6, 2.0 Hz, 1H), 3.03 (d, J=4.8 Hz, 3H). MS-ESI calcd. [M+H]$^+$ 152, found 152.

Step 3

1-Methylpyrido[2,3-d]pyrimidine-2,4(1H,3H)-dione 2-(Methylamino)pyridine-3-carboxamide (100 mg, 0.661 mmol) and phenylisocyanate (157 mg, 1.32 mmol) were dissolved in toluene (10 mL) and stirred at 110° C. for 12 hours. The reaction was quenched by adding water (10 mL) and filtered to give 1-methylpyrido[2,3-d]pyrimidine-2,4 (1H,3H)-dione (20.0 mg, as a yellow solid) with a yield of 17%. $^1$H NMR: (400 MHz, DMSO-$d_6$) δ 11.72 (s, 1H), 8.72 (d, J=2.0 Hz, 1H), 8.31 (d, J=7.6 Hz, 1H), 7.29 (dd, J=7.6, 2.0 Hz, 1H), 3.48 (s, 3H). MS-ESI calcd. [M+H]$^+$ 178, found 178.

Step 4

3-((3-Isopropylisoxazol-5-yl)methyl)-1-methylpyrido[2,3-d]pyrimidine-2,4-dione 5-(Chloromethyl)-3-isopropylisoxazole (25.0 mg, 0.157 mmol), 1-methylpyrido[2,3-d]pyrimidine-2,4-dione (30.5 mg, 0.172 mmol) and potassium iodide (7.8 mg, 0.055 mmol) were dissolved in N,N-dimethylformamide (5 mL) and potassium carbonate (64.9 mg, 0.470 mmol) was added and the reaction was heated to reflux for 2 hours at 120° C. The reaction solution was cooled to room temperature, filtered, and the filtrate was concentrated under reduced pressure. The resulting crude product was separated and purified by preparative high performance liquid chromatography to 3-((3-isopropylisoxazol-5-yl)methyl)-1-methylpyrido[2,3-d]pyrimidine-2,4-dione (8.0 mg) with a yield of 17%. $^1$H NMR: (400 MHz, Methanol-$d_4$) δ 8.74 (d, J=2.0 Hz, 1H), 8.47 (d, J=7.6 Hz, 1H), 7.36-7.31 (m, 1H), 6.32 (s, 1H), 5.33 (s, 2H), 3.71 (s, 3H), 3.04-2.93 (m, 1H), 1.24 (d, J=8.0 Hz, 6H). MS-ESI calcd. [M+H]$^+$ 301, found 301.

Example 85

3-(2-(2,4-Dimethyl-5-yl)ethyl)-1-methylpyrido[2,3-d]pyrimidine-2,4-dione

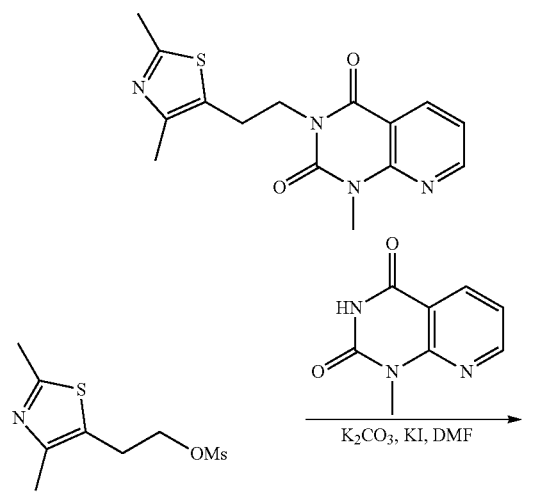

Step 1

3-(2-(2,4-Dimethyl-5-yl)ethyl)-1-methylpyrido[2,3-d]pyrimidine-2,4-dione 2-(2,4-Dimethylthiazol-5-yl)ethyl methanesulfonate (30.0 mg, 0.127 mmol), 1-methylpyrido[2,3-d]pyrimidine-2,4-dione (22.6 mg, 0.127 mmol), potassium carbonate (35.2 mg, 0.255 mmol) and potassium iodide (4.2 mg, 0.026 mmol) were dissolved in N,N-dimethylformamide (5 mL). The reaction was heated to 120° C. and stirred for 3 hours. The reaction solution was cooled to room temperature, poured into water (20 mL) and extracted with ethyl acetate (20 mL×3). The organic phases were combined, dried over anhydrous sodium sulfate, filtered and the filtrate was concentrated. The residue was purified by preparative HPLC to give 3-(2-(2,4-dimethyl-5-yl)ethyl)-1-methylpyrido[2,3-d]pyrimidine-2,4-dione (10.0 mg) with a yield of 25%. $^1$H NMR: (400 MHz, Methanol-$d_4$) δ 8.76-8.74 (m, 1H), 8.52-8.45 (m, 1H), 7.37-7.34 (m, 1H), 4.34-4.30 (m, 2H), 3.71 (s, 3H), 3.26 (t, J=6.8 Hz, 2H), 2.93 (s, 3H), 2.49 (s, 3H). MS-ESI calcd. [M+H]$^+$ 317, found 317.

Example 86

3-[3-(1H-indol-3-yl)propyl]-1-methylpyrido[2,3-d]pyrimidine-2,4-dione

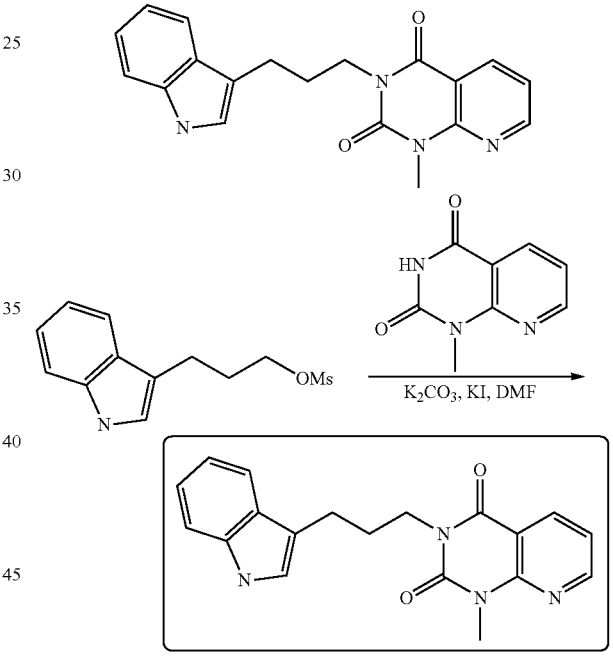

Step 1

3-[3-(1H-indol-3-yl)propyl]-1-methylpyrido[2,3-d]pyrimidine-2,4-dione 3-(1H-indol-3-yl)propyl methanesulfonate (30.0 mg, 0.118 mmol), 1-methylpyrido[2,3-d]pyrimidine-2,4-dione (21.0 0.118 mmol), potassium carbonate (32.7 mg, 0.237 mmol) and potassium iodide (3.9 mg, 0.024 mmol) were dissolved in N,N-dimethylformamide (5 mL). The reaction was heated to 120° C. and stirred for 3 hours. The reaction solution was cooled to room temperature, poured into water (20 mL) and extracted with ethyl acetate (20 mL×3). The organic phases were combined, dried over anhydrous sodium sulfate, filtered and the filtrate was concentrated. The residue was purified by preparative HPLC to give 3-[3-(1H-indol-3-yl)propyl]-1-methylpyrido[2,3-d]pyrimidine-2,4-dione (10.0 mg) with a yield of 25%. ¹H NMR: (400 MHz, Methanol-d₄) δ 8.65-8.63 (m, 1H), 8.37-8.35 (m, 1H), 7.50 (d, J=7.6 Hz, 1H), 7.28-7.26 (m, 1H), 7.19 (d, J=7.6 Hz, 1H), 7.04 (s, 1H), 7.00-6.95 (m, 2H), 4.23-4.19 (m, 2H), 3.60 (s, 3H), 2.88 (t, J=7.2 Hz, 2H), 2.22-2.15 (m, 2H). MS-ESI calcd. [M+H]⁺ 335, found 335.

Example 87

3-(4-(Benzofuran-2-yl)butyl)-1-methylpyrido[2,3-d]pyrimidine-2,4-dione

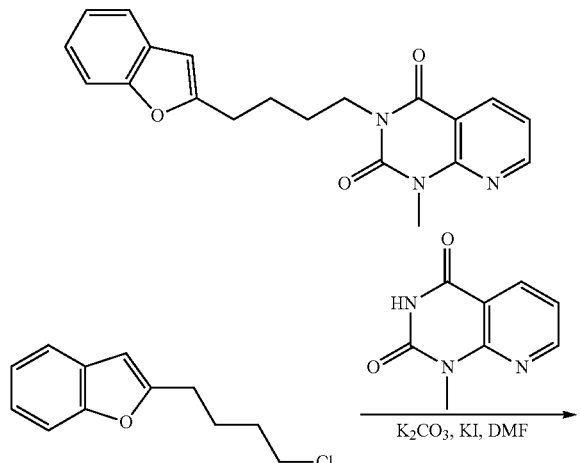

Example 88

1-Methyl-3-(3-(3-methylisoxazol-5-yl)propyl)pyrido[2,3-d]pyrimidine-2,4-dione

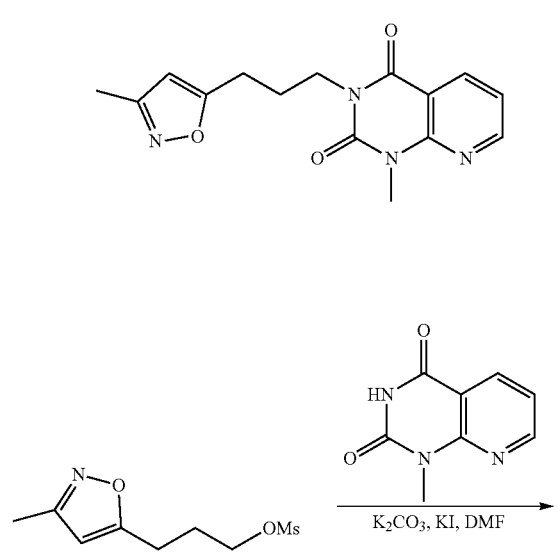

Step 1

3-(4-(Benzofuran-2-yl)butyl)-1-methylpyrido[2,3-d]pyrimidine-2,4-dione

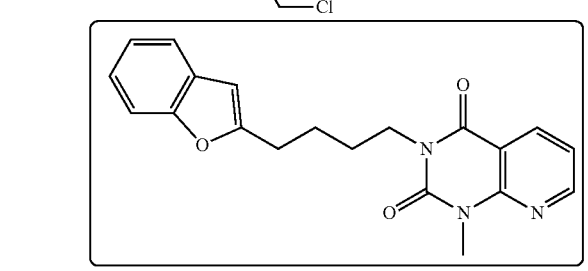

2-(4-Chlorobutyl)benzofuran (30.0 mg, 0.143 mmol), 1-methylpyrido[2,3-d]pyrimidine-2,4-dione (35.7 mg, 0.143 mmol), potassium carbonate (39.7 mg, 0.287 mmol) and potassium iodide (4.8 mg, 0.029 mmol) were dissolved in N,N-dimethylformamide (5 mL). The reaction was heated to 120° C. and stirred for 3 hours. The reaction solution was cooled to room temperature, poured into water (20 mL) and extracted with ethyl acetate (20 mL×3). The organic phases were combined, dried over anhydrous sodium sulfate, filtered and the filtrate was concentrated. The residue was purified by preparative HPLC to give 3-(4-(benzofuran-2-yl)butyl)-1-methylpyrido[2,3-d]pyrimidine-2,4-dione (10.0 mg) with a yield of 17%. ¹H NMR: (400 MHz, Methanol-d₄) δ 8.72-8.71 (m, 1H), 8.37-8.35 (m, 1H), 7.49 (d, J=6.8 Hz, 1H), 7.44 (d, J=7.6 Hz, 1H), 7.34-7.32 (m, 1H), 7.19-7.15 (m, 2H), 6.56 (s, 1H), 3.97 (t, J=6.8 Hz, 2H), 3.54 (s, 3H), 2.80 (t, J=6.8 Hz, 2H), 1.71-1.66 (m, 4H). MS-ESI calcd. [M+H]⁺ 350, found 350.

Step 1

1-Methyl-3-(3-(3-methylisoxazol-5-yl)propyl)pyrido[2,3-d]pyrimidine-2,4-dione

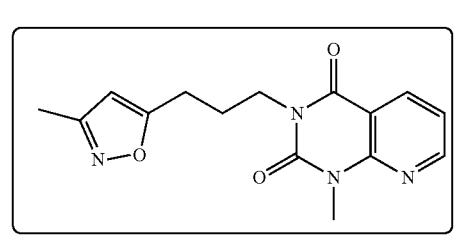

3-(3-Methylisoxazol-5-yl)propyl methanesulfonate (30.0 mg, 0.136 mmol), 1-methylpyrido[2,3-d]pyrimidine-2,4-dione (24.2 mg, 0.136 mmol), potassium carbonate (37.8 mg, 0.273 mmol) and potassium iodide (4.5 mg, 0.027 mmol) were dissolved in N,N-dimethylformamide (5 mL). The reaction was heated to 120° C. and stirred for 3 hours. The reaction solution was cooled to room temperature, poured into water (20 mL) and extracted with ethyl acetate (20 mL×3). The organic phases were combined, dried over anhydrous sodium sulfate, filtered and the filtrate was concentrated to give 1-methyl-3-(3-(3-methylisoxazol-5-yl)propyl)pyrido[2,3-d]pyrimidine-2,4-dione (20.0 mg) with a yield of 49%. ¹H NMR: (400 MHz, Methanol-d₄) δ 8.72-8.69 (m, 1H), 8.44-8.41 (m, 1H), 7.37-7.29 (m, 1H), 6.07 (s, 1H), 4.19-4.11 (m, 2H), 3.70 (s, 3H), 2.84 (t, J=7.2 Hz, 2H), 2.15 (s, 3H), 2.13-2.07 (m, 2H). MS-ESI calcd. [M+H]⁺ 301, found 301.

Example 89

1-Methyl-3-[4-(3-methylisoxazol-5-yl)butyl]pyrido[2,3-d]pyrimidine-2,4-dione

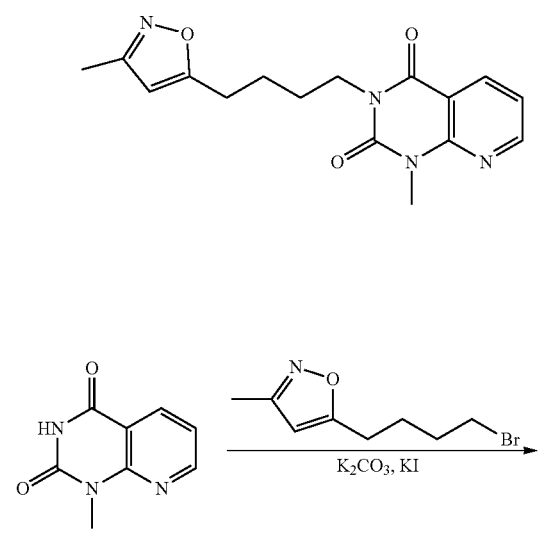

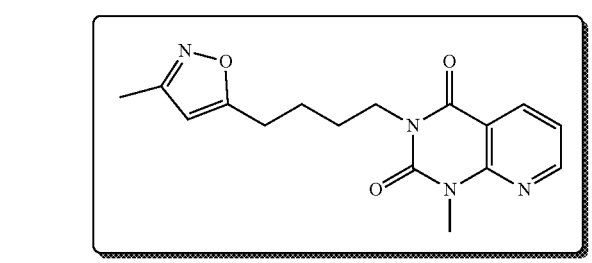

Step 1

1-Methyl-3-[4-(3-methylisoxazol-5-yl)butyl]pyrido[2,3-d]pyrimidine-2,4-dione 1-Methylpyrido[2,3-d]pyrimidine-2,4(1H,3H)-dione (20.0 mg, 0.112 mmol), 5-(4-bromobutyl)-3-methyl-isoxazole (30.5 mg, 0.139 mmol), potassium iodide (2.1 mg, 0.124 mmol) and potassium carbonate (31.5 mg, 0.228 mmol) were dissolved in N,N-dimethylformamide (10 mL). The reaction solution was warmed to 120° C. and stirred for 3 hours. The reaction solution was cooled to room temperature, filtered and the filtrate was concentrated under reduced pressure. The residue was purified by preparative HPLC to give 1-methyl-3-[4-(3-methylisoxazol-5-yl)butyl]pyrido[2,3-d]pyrimidine-2,4-dione (10.0 mg) with a yield of 28%. $^1$H NMR: (400 MHz, Methanol-$d_4$) δ 8.69 (d, J=2.0 Hz, 1H), 8.42 (d, J=7.6 Hz, 1H), 7.29 (dd, J=7.6, 2.0 Hz, 1H), 6.04 (s, 1H), 4.08 (t, J=6.8 Hz, 2H), 3.67 (s, 3H), 2.80 (t, J=6.8 Hz, 2H), 2.23 (s, 3H), 1.79-1.72 (m, 4H). MS-ESI calcd. [M+H]$^+$ 315, found 315.

Example 90

1-Methyl-3-(3-(3-methylisoxazol-5-yl)propyl)pyrido[3,4-d]pyrimidine-2,4-dione

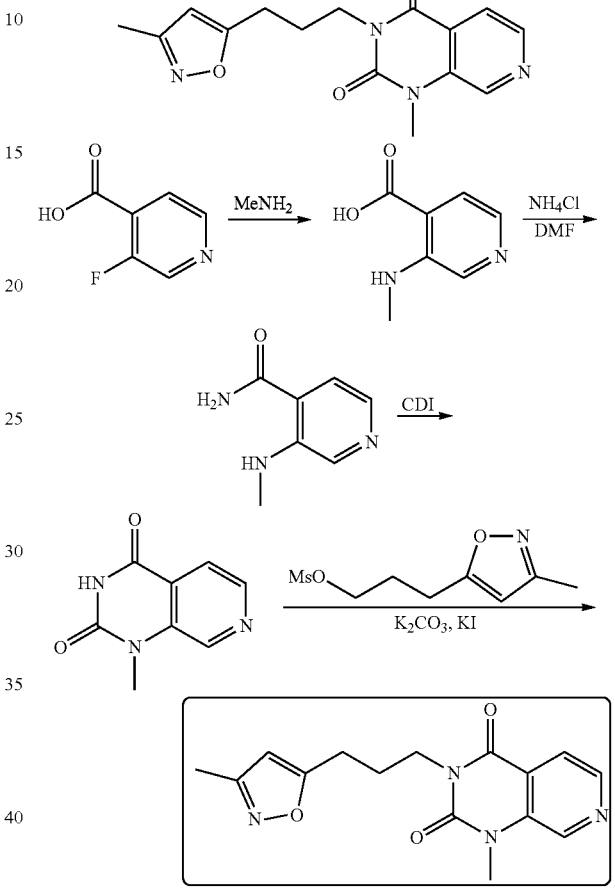

Step 1

3-(Methylamino)isonicotinic acid

3-Fluoroisonicotinic acid (3.00 g, 21.3 mmol) was dissolved in dioxane (6 mL) and 30% aqueous methylamine solution (22.0 g, 213 mmol) was added. The reaction solution was heated to 140° C. and stirred for 14 hours. Conc. hydrochloric acid (12 N, 3 mL) was added and the pH was adjusted to 3, filtered and the filter cake was dried to give 3-(methylamino)isonicotinic acid (3.00 g, as a yellow solid) with a yield of 93%. $^1$H NMR: (400 MHz, DMSO-$d_6$) δ 8.46 (br, 1H), 7.89 (s, 1H), 7.69 (d, J=5.2 Hz, 1H), 7.50 (d, J=5.2 Hz, 1H), 2.80 (s, 3H).

Step 2

3-(Methylamino)isonicotinamide 3-(Methylamino)isonicotinic acid (4.00 g, 26.3 mmol), 1-hydroxybenzotriazole (10.7 g, 78.9 mmol), 1-(3-dimethylaminopropyl)-3-ethylcarbodiimide (15.1 g, 78.9 mmol)

and ammonium chloride (5.63 g, 105 mmol) were dissolved in N,N-dimethylformamide (5 mL). The reaction solution was stirred at 25° C. for 24 hours. The reaction was quenched by adding water (100 mL). The mixture was extracted with isopropanol/chloroform (1:3) (50 mL×2). The organic phases were combined and concentrated under reduced pressure. The residue was added with dichloromethane/methanol (10:1, 30 mL), stirred for 10 minutes, filtered and the filter cake was dried to give 3-(methylamino)isonicotinamide (3.50 g, as a yellow solid) with a yield of 88%. $^1$H NMR: (400 MHz, DMSO-$d_6$) δ 8.12-8.06 (m, 2H), 7.80 (d, J=5.2 Hz, 1H), 7.62-7.61 (br, 1H), 7.52-7.48 (br, 1H), 7.43 (d, J=5.2 Hz, 1H), 2.84 (d, J=5.2 Hz, 3H).

Step 3

1-Methylpyrido[3,4-d]pyrimidine-2,4-dione

Sodium hydride (1.80 g, 45.0 mmol) was added to a solution of 3-(methylamino)isonicotinamide (3.40 g, 22.5 mmol) in N,N-dimethylformamide (50 mL) at 0° C. The reaction was stirred at 0° C. for 1 hour. Carbonyldiimidazole (5.47 g, 33.7 mmol) was added. The reaction mixture was reacted at room temperature for 1 hour. The reaction was cooled to 0° C. and quenched with water (20 mL). A white solid was precipitated, filtered and the filter cake was dried to give 1-methylpyrido[3,4-d]pyrimidine-2,4-dione (3.50 g, as a yellow solid) with a yield of 95%. $^1$H NMR: (400 MHz, DMSO-$d_6$) δ 11.83 (s, 1H), 8.86 (s, 1H), 8.48 (d, J=4.8 Hz, 1H), 7.82 (d, J=4.8 Hz, 1H), 3.49 (s, 3H).

Step 4

1-Methyl-3-(3-(3-methylisoxazol-5-yl)propyl)pyrido[3,4-d]pyrimidine-2,4-dione 3-(3-Methylisoxazol-5-yl)propyl methanesulfonate (48.4 mg, 0.221 mmol), 1-methylpyrido[3,4-d]pyrimidine-2,4-dione (30.0 mg, 0.169 mmol), potassium iodide (2.8 mg, 0.017 mmol) and potassium carbonate (46.8 mg, 0.338 mmol) were dissolved in N,N-dimethylformamide (5 mL). The reaction was warmed to 120° C. and stirred for 3 hours. After cooling to room temperature and filtration, the filtrate was concentrated under reduced pressure and the residue was purified by preparative HPLC to give 1-methyl-3-(3-(3-methylisoxazol-5-yl)propyl)[3,4-d]pyrimidine-2,4-dione (10.0 mg) with a yield of 18%. $^1$H NMR: (400 MHz, Methanol-$d_4$) δ 8.85 (s, 1H), 8.51 (d, J=4.8 Hz, 1H), 8.01 (d, J=4.8 Hz, 1H), 6.08 (s, 1H), 4.18 (t, J=7.0 Hz, 2H), 3.67 (s, 3H), 2.83 (t, J=7.2 Hz, 2H), 2.16-2.11 (m, 5H). MS-ESI calcd. [M+H]$^+$ 301, found 301.

Example 91

3-(2-(2,4-Dimethylthiazol-5-yl)ethyl)-1-methylpyrido[3,4-d]pyrimidine-2,4-dione

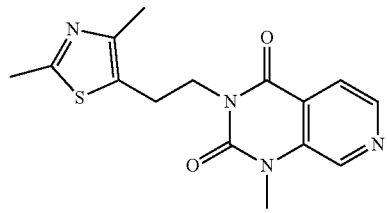

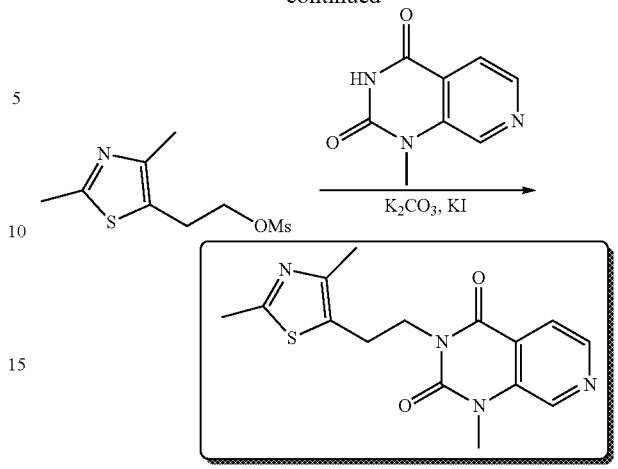

Step 1

3-(2-(2,4-Dimethylthiazol-5-yl)ethyl)-1-methylpyrido[3,4-d]pyrimidine-2,4-dione 2-(2,4-Dimethylthiazol-5-yl)ethyl methanesulfonate (43.8 mg, 0.186 mmol), 1-methylpyrido[3,4-d] pyrimidine-2,4-dione (30.0 mg, 0.169 mmol), potassium iodide (2.8 mg, 0.017 mmol) and potassium carbonate (46.8 mg, 0.338 mmol) were dissolved in N,N-dimethylformamide (5 mL). The reaction solution was warmed to 120° C. and stirred for 3 hours. The reaction solution was cooled to room temperature, filtered and the filtrate was concentrated under reduced pressure. The residue was purified by preparative HPLC to give 3-(2-(2,4-dimethylthiazol-5-yl)ethyl)-1-methylpyrido[3,4-d]pyrimidine-2,4-dione (21.0 mg) with a yield of 38%. $^1$H NMR: (400 MHz, Methanol-$d_4$) δ 8.87 (s, 1H), 8.52 (d, J=4.8 Hz, 1H), 8.01 (d, J=4.8 Hz, 1H), 4.24 (t, J=6.8 Hz, 2H), 3.69 (s, 3H), 3.11 (t, J=6.8 Hz, 2H), 2.60 (s, 3H), 2.31 (s, 3H). MS-ESI calcd. [M+H]$^+$ 317, found 317.

Example 92

3-(3-(1H-indol-3-yl)propyl)-1-methylpyrido[3,4-d]pyrimidine-2,4-dione

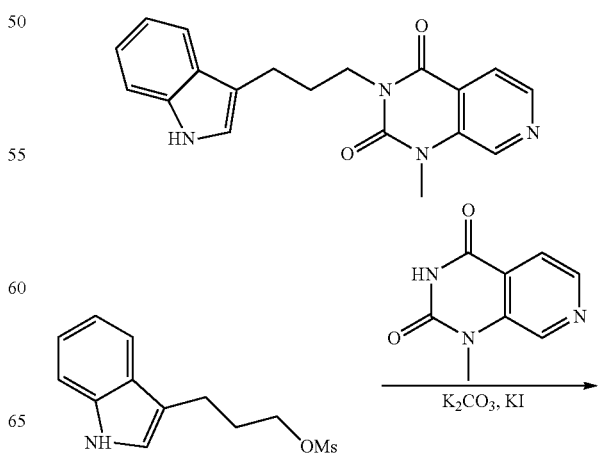

-continued

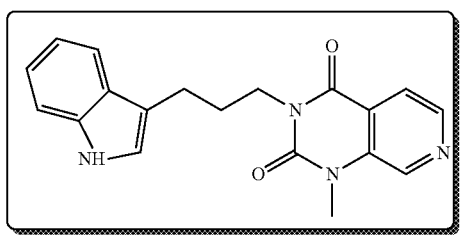

Step 1

3-(3-(1H-indol-3-yl)propyl)-1-methylpyrido[3,4-d]pyrimidine-2,4-dione 3-(1H-indol-3-yl)propyl methanesulfonate (47.2 mg, 0.186 mmol), 1-methylpyrido[3,4-d]pyrimidine-2,4-dione (30.0 mg, 0.169 mmol), potassium iodide (2.8 mg, 0.017 mmol) and potassium carbonate (46.8 mg, 0.338 mmol) were dissolved in N,N-dimethylformamide (5 mL). The reaction solution was warmed to 120° C. and stirred for 3 hours. The reaction solution was cooled to room temperature, filtered and the filtrate was concentrated under reduced pressure. The residue was purified by preparative HPLC to give 3-(3-(1H-indol-3-yl)propyl)-1-methylpyrido[3,4-d]pyrimidine-2,4-dione (10.0 mg) with a yield of 18%. $^1$H NMR: (400 MHz, CDCl$_3$) δ 8.70 (s, 1H), 8.57 (d, J=5.2 Hz, 1H), 7.99 (d, J=5.2 Hz, 1H), 7.73 (br, 1H), 7.62 (d, J=7.6 Hz, 1H), 7.32-7.28 (m, 1H), 7.19-7.11 (m, 3H), 4.28-4.24 (m, 2H), 3.63 (s, 3H), 2.93-2.89 (m, 2H), 2.24-2.17 (m, 2H). MS-ESI calcd. [M+H]$^+$ 335, found 335.

Example 93

3-(4-(Benzofuran-3-yl)butyl)-1-methylpyrido[3,4-d]pyrimidine-2,4-dione

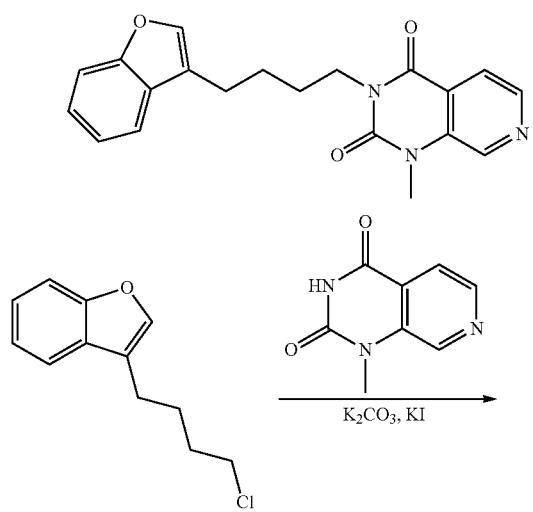

-continued

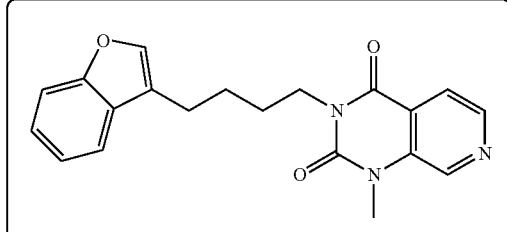

Step 1

3-(4-(Benzofuran-3-yl)butyl)-1-methylpyrido[3,4-d]pyrimidine-2,4-dione 3-(4-Chlorobutyl)benzofuran (38.9 mg, 0.186 mmol), 1-methylpyridino[3,4-d]pyrimidine-2,4-dione (30.0 mg, 0.169 mmol), potassium iodide (2.8 mg, 0.017 mmol) and potassium carbonate (46.8 mg, 0.338 mmol) were dissolved in N,N-dimethylformamide (5 mL). The reaction was allowed to warm to 120° C. and stirred for 3 hours, cooled to room temperature, filtered and the filtrate was concentrated under reduced pressure. The residue was purified by preparative HPLC to give 3-(4-(benzofuran-3-yl)butyl)-1-methylpyrido[3,4-d]pyrimidine-2,4-dione (11.0 mg) with a yield of 17%. $^1$H NMR: (400 MHz, Methanol-d$_4$) δ 8.87 (s, 1H), 8.50 (d, J=4.8 Hz, 1H), 8.01 (d, J=4.8 Hz, 1H), 7.45 (d, J=8.0 Hz, 1H), 7.34 (d, J=8.0 Hz, 1H), 7.18-7.15 (m, 2H), 6.48 (s, 1H), 4.16-4.12 (m, 2H), 3.65 (s, 3H), 2.88-2.85 (m, 2H), 1.86-1.80 (m, 4H). MS-ESI calcd. [M+H]$^+$ 350, found 350.

Example 94

1-Methyl-3-(4-(3-methylisoxazol-5-yl)butyl)pyrido[3,4-d]pyrimidine-2,4-dione

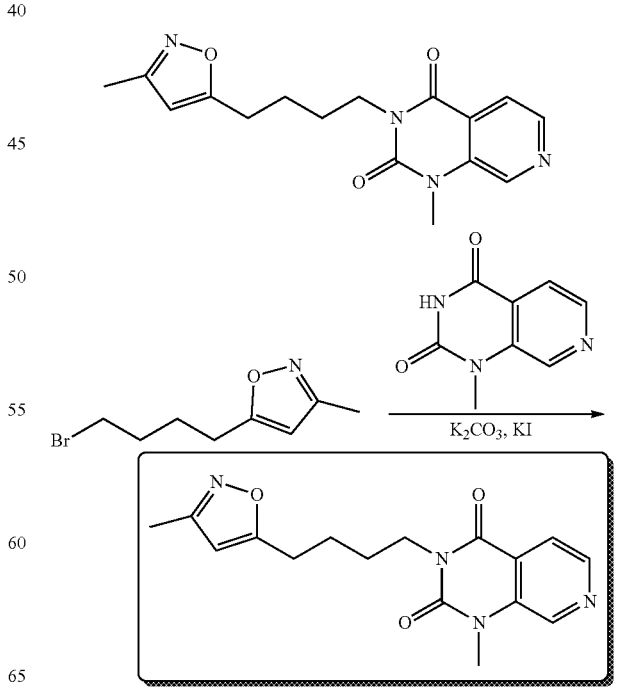

Step 1

1-Methyl-3-(4-(3-methylisoxazol-5-yl)butyl)pyrido[3,4-d]pyrimidine-2,4-dione 5-(4-Bromobutyl)-3-methylisoxazole (40.6 mg, 0.186 mmol), 1-methylpyrido[3,4-d]pyrimidine-2,4-dione (30.0 mg, 0.169 mmol), potassium iodide (2.8 mg, 0.017 mmol) and potassium carbonate (46.8 mg, 0.338 mmol) were dissolved in N,N-dimethylformamide (5 mL). The reaction was allowed to warm to 120° C. and stirred for 3 hours, cooled to room temperature, filtered and the filtrate was concentrated under reduced pressure. The residue was purified by preparative HPLC to give 1-methyl-3-(4-(3-methylisoxazol-5-yl) butyl)pyrido[3,4-d]pyrimidine-2,4-dione (10.0 mg) with a yield of 19%. $^1$H NMR: (400 MHz, Methanol-$d_4$) δ 8.84 (s, 1H), 8.50 (d, J=5.2 Hz, 1H), 8.00 (d, J=5.2 Hz, 1H), 6.05 (s, 1H), 4.11-4.08 (m, 2H), 3.67 (s, 3H), 2.81 (t, J=6.8 Hz, 2H), 2.23 (s, 3H), 1.77-1.74 (m, 4H). MS-ESI calcd. [M+H]$^+$ 315, found 315.

Example 95

1-Methyl-3-(4-(3-methylisoxazol-5-yl)butyl)pyrido[4,3-d]pyrimidine-2,4-dione

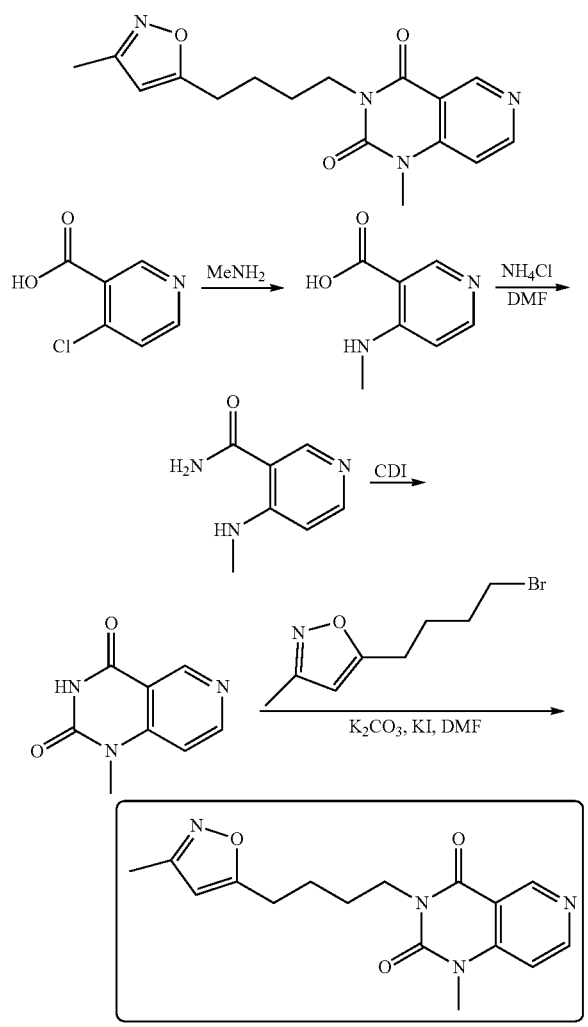

Step 1

4-(Methylamino)nicotinic acid

4-Chloronicotinic acid (7.00 g, 44.3 mmol) was dissolved in dioxane (14 mL) and 30% methylamine aqueous solution (55.2 g, 444 mmol) was added. The reaction solution was warmed to 100° C. in a microwave and stirred for 50 minutes. Hydrochloric acid aqueous solution (4 N, 5 mL) was added to adjust pH value to 3. The reaction solution was filtered and the filter cake was dried to give 4-(methylamino) nicotinic acid (5.00 g, white solid) with a yield of 74%.
$^1$H NMR: (400 MHz, DMSO-$d_6$) δ 8.52 (s, 1H), 8.13 (d, J=6.8 Hz, 1H), 6.78 (d, J=6.8 Hz, 1H), 2.95 (d, J=4.4 Hz, 3H).

Step 2

4-(methylamino) nicotinamide 4-(Methylamino)nicotinic acid (5.20 g, 34.2 mmol), 1-hydroxybenzotriazole (27.7 g, 205 mmol), 1-ethyl-(3-dimethylaminopropyl)carbodiimide hydrochloride (39.3 g, 205 mmol) and ammonium chloride (14.6 g, 273 mmol) were dissolved in N,N-dimethylformamide (50 mL). The reaction was stirred at 25° C. for 8 hours. Water (100 mL) was added to quench the reaction. The mixture was extracted with isopropanol/chloroform (1:3) (30 mL×5). The organic phases were combined and concentrated under reduced pressure. The residue was added to dichloromethane/methanol (10:1, 150 mL), stirred for 10 minutes, filtered and the filter cake was dried to give 4-(methylamino)nicotinamide (4.70 g, as a white solid) with a yield of 91%. $^1$H NMR: (400 MHz, DMSO-$d_6$) δ 9.67 (br, 1H), 8.77 (s, 1H), 8.52 (br, 1H), 8.29 (d, J=7.6 Hz, 1H), 7.87 (br, 1H), 7.01 (d, J=7.6 Hz, 1H), 3.01 (s, 3H).

Step 3

1-Methylpyrido[4,3-d]pyrimidine-2,4-dione

Sodium hydride (1.52 g, 63.5 mmol) was added to a solution of 4-(methylamino)nicotinamide (4.80 g, 31.8 mmol) in N,N-dimethylformamide (50 mL) at 0° C. The reaction was stirred at 0° C. for 1 hour. Carbonyl diimidazole (7.72 g, 47.6 mmol) was added. The reaction mixture was reacted at 75° C. for 2 hours. The reaction solution was cooled to room temperature and quenched with water (50 mL). Hydrochloric acid aqueous solution (12 N, 5 mL) was added to adjust the pH value to 3 to generate a white solid precipitate. The reaction solution was filtered, and the filter cake was dried to give 1-methylpyrido[4,3-d]pyrimidine-2,4-dione (3.50 g, as a yellow solid) with a yield of 95% yield. $^1$H NMR: (400 MHz, DMSO-$d_6$) δ 11.76 (s, 1H), 8.97 (s, 1H), 8.69 (d, J=6.0 Hz, 1H), 7.38 (d, J=6.0 Hz, 1H), 3.39 (s, 3H).

Step 4

1-Methyl-3-(4-(3-methylisoxazol-5-yl)butyl)pyrido[4,3-d]pyrimidine-2,4-dione 5-(4-Bromobutyl)-3-methylisoxazole (48.0 mg, 0.220 mmol), 1-methylpyrido[4,3-d]pyrimidine-2,4-dione (30.0 mg, 0.169 mmol) and potassium carbonate (70.2 mg, 0.508 mmol) were dissolved in N,N-dimethylformamide (3 mL), potassium iodide (2.8 mg, 0.017 mmol) was added and the reaction was stirred at 120° C. for 3 hours. The reaction solution was directly filtered and the filtrate was concentrated under reduced pressure. The crude product was purified by preparative HPLC to give 1-methyl-3-(4-(3-methyl-isoxazol-5-yl)butyl)pyrido[4,3-d]pyrimidine-2,4-dione (21.0 mg) with a yield of 39%. $^1$H NMR: (400 MHz, Methanol-$d_4$) δ 9.10 (s, 1H), 8.68 (d, J=6.0 Hz, 1H), 7.41 (d, J=6.0 Hz, 1H), 6.05 (s, 1H), 4.08 (t, J=6.6 Hz, 2H), 3.59 (s, 3H), 2.80 (t, J=6.6 Hz, 2H), 2.23 (s, 3H), 1.77-1.74 (m, 4H). MS-ESI calcd. [M+H]$^+$ 315, found 315.

Example 96

3-(2-(2,4-Dimethyl-5-yl)ethyl)-1-methylpyrido[4,3-d]pyrimidine-2,4-dione

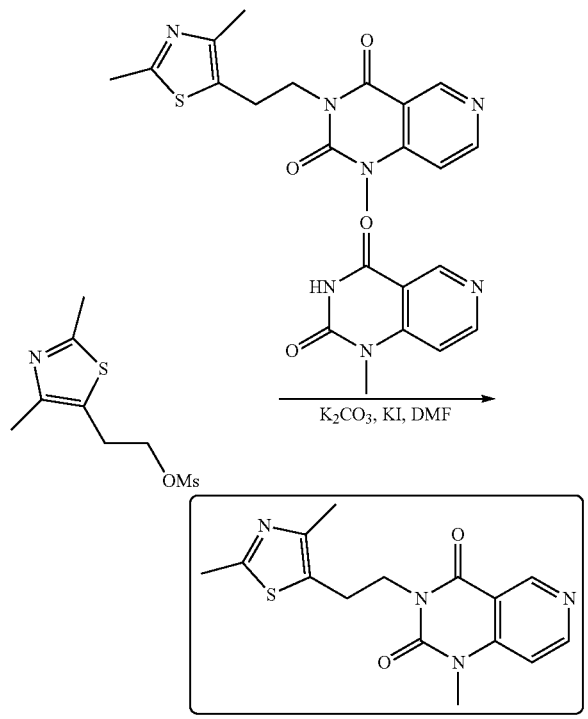

Step 1

3-(2-(2,4-Dimethyl-5-yl)ethyl)-1-methylpyrido[4,3-d]pyrimidine-2,4-dione 2-(2,4-Dimethylthiazol-5-yl)ethyl methanesulfonate (51.8 mg, 0.220 mmol), 1-methylpyrido[4,3-d]pyrimidine-2,4-dione (30 mg, 0.169 mmol) and potassium carbonate (70.2 mg, 0.508 mmol) were dissolved in N,N-dimethylformamide (3 mL), potassium iodide (2.8 mg, 0.0169 mmol) was added and the reaction was stirred at 120° C. for 3 hours. The reaction solution was directly filtered and the filtrate was concentrated under reduced pressure. The crude product was purified by preparative HPLC to give 3-(2-(2,4-dimethyl-5-yl)ethyl)-1-methylpyrido[4,3-d]pyrimidine-2,4-dione (8.0 mg) with a yield of 15%. $^1$H NMR: (400 MHz, CDCl$_3$) δ 9.31 (s, 1H), 8.76 (d, J=6.0 Hz, 1H), 7.08 (d, J=6.0 Hz, 1H), 4.24 (t, J=7.8 Hz, 2H), 3.59 (s, 3H), 3.08 (t, J=7.8 Hz, 2H), 2.63 (s, 3H), 2.36 (s, 3H). MS-ESI calcd. [M+H]$^+$ 317, found 317.

Example 97

3-(3-(1H-indol-2-yl)propyl)-1-methylpyrido[4,3-d]pyrimidine-2,4-dione

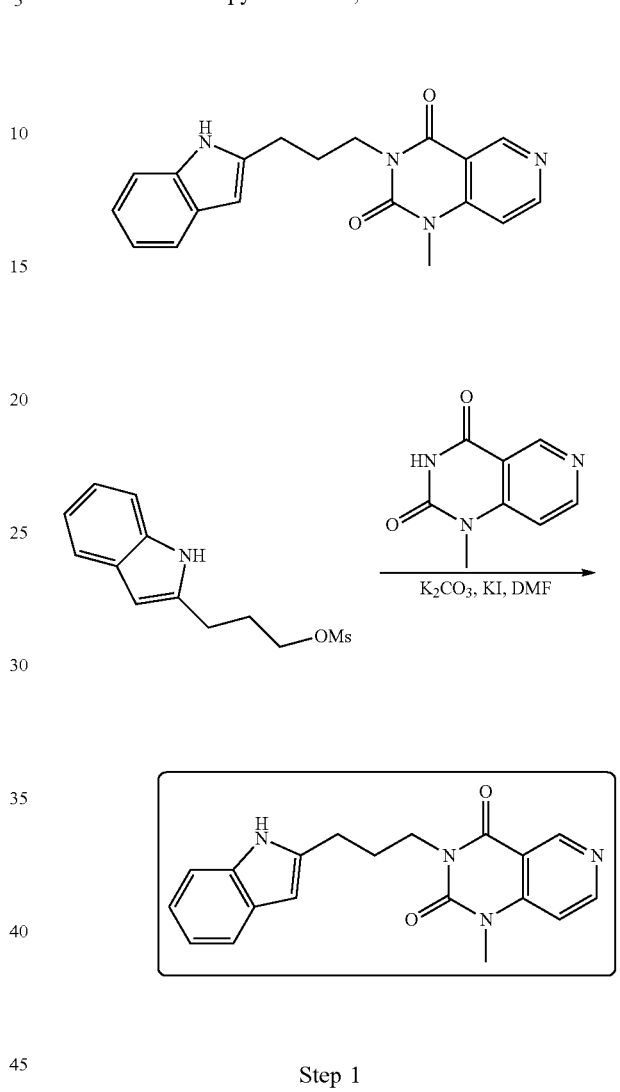

Step 1

3-(3-(1H-indol-2-yl)propyl)-1-methylpyrido[4,3-d]pyrimidine-2,4-dione 2-(4-Chlorobutyl)benzofuran (42.9 mg, 0.169 mmol), 1-methylpyrido[4,3-d]pyrimidine-2,4-dione (30.0 mg, 0.169 mmol), potassium carbonate (70.2 mg, 0.508 mmol) were dissolved in N,N-dimethylformamide (3 mL) and potassium iodide (2.8 mg, 0.017 mmol) was added and the reaction was stirred at 120° C. for 3 hours. The reaction solution was directly filtered and the filtrate was concentrated under reduced pressure. The crude product was purified by preparative HPLC to give 3-(3-(1H-indol-2-yl)propyl)-1-methylpyrido[4,3-d]pyrimidine-2,4-dione (37.0 mg) with a yield of 65%. $^1$H NMR: (400 MHz, Methanol-$d_4$) δ 8.99 (s, 1H), 8.60 (d, J=6.0 Hz, 1H), 8.26 (br, 1H), 7.50 (d, J=7.6 Hz, 1H), 7.26 (d, J=6.0 Hz, 1H), 7.16 (d, J=7.6 Hz, 1H), 7.02 (s, 1H), 6.99-6.92 (m, 2H), 4.20 (d, J=7.2 Hz, 2H), 3.44 (s, 3H), 2.89 (d, J=6.8 Hz, 2H), 2.24-2.17 (m, 2H). MS-ESI calcd. [M+H]$^+$ 335, found 335.

Example 98

3-(4-(Benzofuran-2-yl)butyl)-1-methylpyrido[4,3-d]pyrimidine-2,4-dione

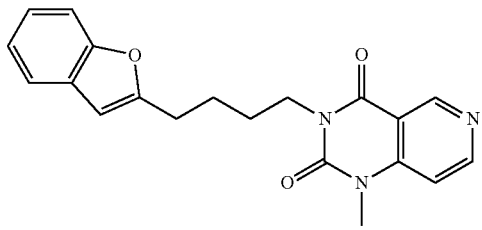

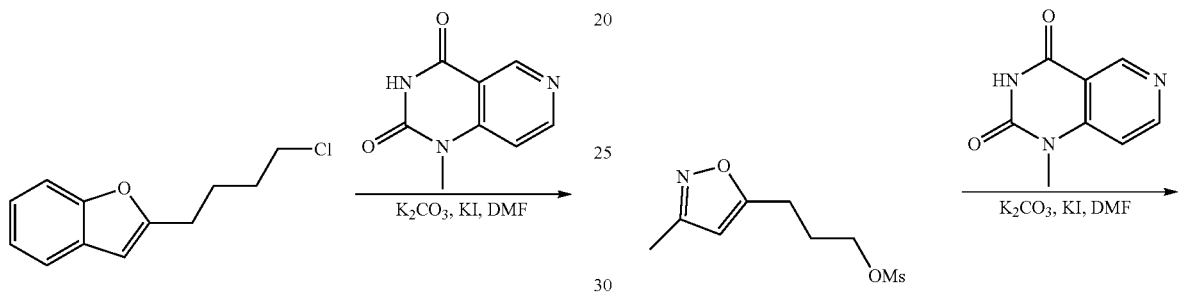

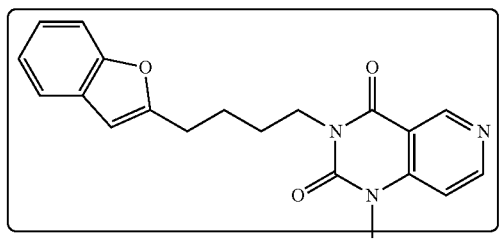

Step 1

3-(4-(Benzofuran-2-yl)butyl)-1-methylpyrido[4,3-d]pyrimidine-2,4-dione 2-(4-Chlorobutyl)benzofuran (45.9 mg, 0.220 mmol), 1-methylpyrido[4,3-d]pyrimidine-2,4-dione (30.0 mg, 0.169 mmol) and potassium carbonate (70.2 mg, 0.508 mmol) were dissolved in N,N-dimethylformamide (3 mL), potassium iodide (2.8 mg, 0.017 mmol) was added and the reaction was stirred at 120° C. for 3 hours. The reaction solution was directly filtered and the filtrate was concentrated under reduced pressure. The crude product was purified by preparative HPLC to give 3-(4-(benzofuran-2-yl)butyl)-1-methylpyrido[4,3-d]pyrimidine-2,4-dione (25.0 mg) with a yield of 42%. $^1$H NMR: (400 MHz, Methanol-$d_4$) δ 9.11 (s, 1H), 8.66 (d, J=6.0 Hz, 1H), 7.46-7.44 (m, 1H), 7.37 (d, J=6.0 Hz, 1H), 7.33 (d, J=7.2 Hz, 1H), 7.17-7.13 (m, 2H), 6.46 (s, 1H), 4.10 (t, J=7.0 Hz, 2H), 3.55 (s, 3H), 2.85 (t, J=6.8 Hz, 2H), 1.83-1.79 (m, 4H). MS-ESI calcd. [M+H]$^+$ 350, found 350.

Example 99

1-Methyl-3-(3-(3-methylisoxazol-5-yl)propyl)pyrido[4,3-d]pyrimidine-2,4-dione

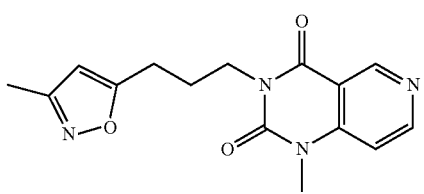

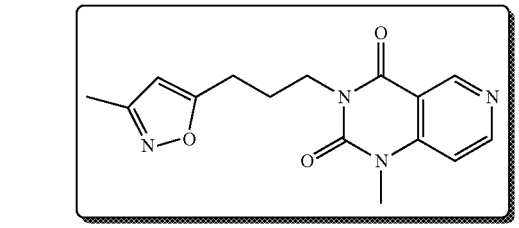

Step 1

1-Methyl-3-(3-(3-methylisoxazol-5-yl)propyl)pyrido[4,3-d]pyrimidine-2,4-dione 3-(3-Methylisoxazol-5-yl)propyl methanesulfonate (51.3 mg, 0.220 mmol), 1-methylpyrido[4,3-d]pyrimidine-2,4-dione (30 mg, 0.169 mmol) and potassium carbonate (70.2 mg, 0.508 mmol) were dissolved in N,N-dimethylformamide (3 mL), potassium iodide (2.8 mg, 0.017 mmol) was added and the reaction was stirred at 120° C. for 3 hours. The reaction solution was directly filtered and the filtrate was concentrated under reduced pressure. The crude product was purified by preparative HPLC to give 1-methyl-3-(3-(3-methylisoxazol-5-yl)propyl)pyrido[4,3-d]pyrimidine-2,4-dione (38.0 mg) with a yield of 69%. $^1$H NMR: (400 MHz, Methanol-$d_4$) δ 9.09 (s, 1H), 8.68 (d, J=6.0 Hz, 1H), 7.40 (d, J=6.0 Hz, 1H), 6.07 (s, 1H), 4.14 (t, J=7.0 Hz, 2H), 3.58 (s, 3H), 2.83 (t, J=7.2 Hz, 2H), 2.16 (s, 3H), 2.14-2.07 (m, 2H). MS-ESI calcd. [M+H]$^+$ 301, found 301.

Example 100

1-Methyl-3-[3-(3-methylisoxazol-5-yl)propyl]pyrido[3,2-d]pyrimidine-2,4-dione

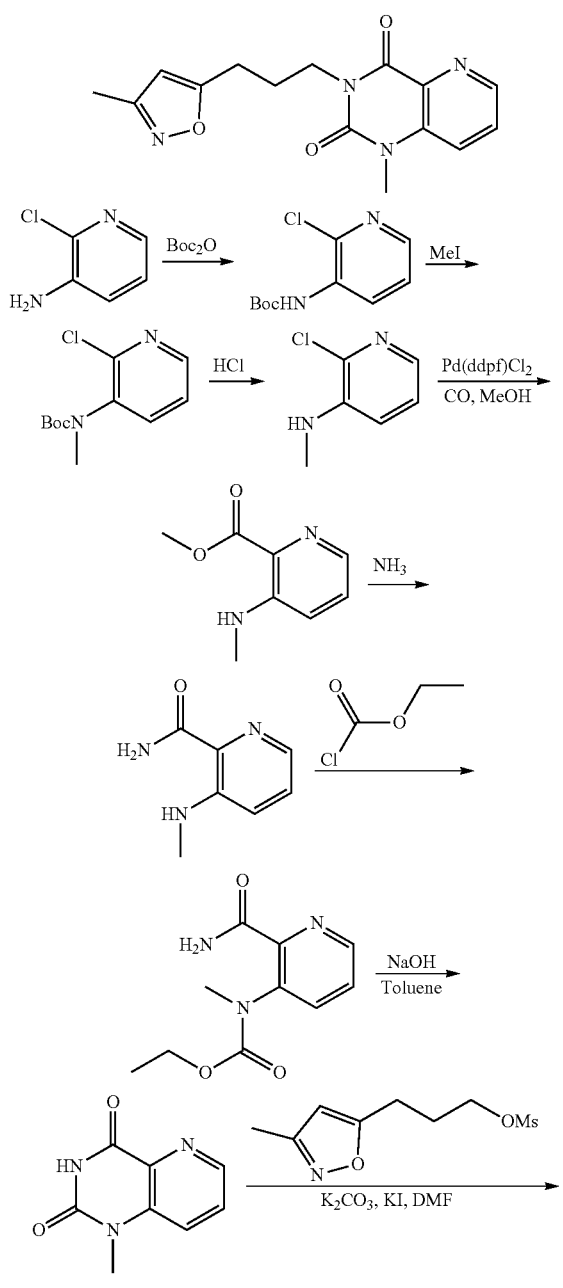

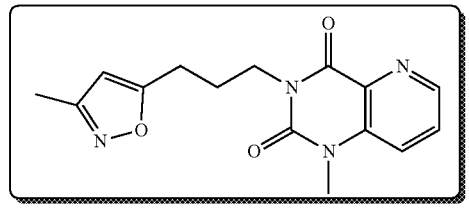

Step 1

N-(2-Chloro-3-pyridyl) tert-butyl carbamate

2-Chloropyridin-3-amine (30.0 g, 233 mmol) was dissolved in dichloromethane (250 mL) and triethylamine (47.2 g, 467 mmol) was added. Di-tert-butyl dicarbonate (102 g, 467 mmol) was added dropwise at 0° C. The reaction was stirred at 25° C. for 18 hours. Water (100 mL) was added to quench the reaction. The reaction was extracted with ethyl acetate (100 mL×3). The organic phases were combined, dried over anhydrous sodium sulfate, filtered and concentrated under reduced pressure. The residue was purified by silica gel column chromatography (15:1 petroleum ether/ethyl acetate, $R_f$=0.6) to give N-(2-chloro-3-pyridyl) tert-butyl carbamate (11.0 g, as a white solid) with a yield of 21%. $^1$H NMR: (400 MHz, DMSO-$d_6$) δ 8.89 (s, 1H), 8.17-8.16 (m, 1H), 8.03-8.01 (m, 1H), 7.43-7.39 (m, 1H), 1.47 (s, 9H).

Step 2

(2-Chloropyridin-3-yl)(methyl) tert-butyl carbamate

N-(2-Chloro-3-pyridyl) tert-butyl carbamate (11.0 g, 48.1 mmol) was dissolved in anhydrous tetrahydrofuran (150 mL). Sodium nitrogen (1.39 g, 57.7 mmol) was slowly added at 0° C. under nitrogen atmosphere and the reaction was stirred at 0° C. for half an hour. Methyl iodide (10.2 g, 72.2 mmol) was slowly added and stirred at room temperature for 12 hours. Water (50 mL) was added to quench the reaction. The reaction was extracted with ethyl acetate (80 mL×3) and the organic phases were combined and washed with brine (150 mL), dried over anhydrous sodium sulfate, filtered and the filtrate was concentrated under reduced pressure to give (2-chloropyridin-3-yl) (methyl) tert-butyl carbamate (11.0 g, as a colorless oil) with a yield of 94%. $^1$H NMR: (400 Hz, DMSO-$d_6$) δ 8.33 (d, J=6.0 Hz, 1H), 7.92-7.90 (m, 1H), 7.48 (d, J=6.0 Hz, 1H), 3.06 (s, 3H), 1.45-1.14 (m, 9H). MS-ESI calcd. [M+H]$^+$ 243, found 243.

Step 3

2-Chloro-N-methylpyridin-3-amine (2-Chloropyridin-3-yl)(methyl) tert-butyl carbamate (11.0 g, 45.3 mmol) was dissolved in ethyl acetate (50 mL). 4 M hydrochloric acid/ethyl acetate (150 mL) was added dropwise at 0° C. and then stirred at 25° C. for 15 hours. The reaction solution was concentrated under reduced pressure, and purified by silica gel column chromatography (10:1 petroleum ether/ethyl acetate, $R_f$=0.3) to give 2-chloro-N-methylpyridin-3-amine (5.50 g, as a colorless oil) with a yield of 85%. $^1$H NMR: (400 Hz, DMSO-$d_6$) δ 7.56 (d, J=6.0 Hz, 1H), 7.20-7.17 (m, 1H), 6.95 (d, J=6.0 Hz, 1H), 5.74 (br, 1H), 2.73 (s, 3H). MS-ESI calcd. [M+H]$^+$ 143, found 143.

Step 4

Methyl 3-(methylamino)picolinate

2-Chloro-N-methylpyridin-3-amine (5.50 g, 38.6 mmol) was dissolved in methanol (100 mL) and 1,1'-bis(diphenylphosphine)ferrocene palladium chloride (2.82 g, 3.86 mmol) was added to the reaction solution at 25° C. The reaction solution was reacted under carbon monoxide atmosphere (50 psi) at 50° C. for 56 hours. The reaction solution was cooled to 25° C. and concentrated under reduced pressure. The residue was purified by silica gel column chromatography (5:1 petroleum ether/ethyl acetate, $R_f$=0.5) to give methyl 3-(methylamino)picolinate (6.00 g, as a colorless oil) with a yield of 94%. $^1$H NMR: (400 MHz, Methanol-$d_4$) δ 7.84 (d, J=6.0 Hz, 1H), 7.45-7.42 (m, 1H), 7.29 (d, J=6.0 Hz, 1H), 3.93 (s, 3H), 2.94 (s, 3H). MS-ESI calcd. [M+H]$^+$ 167, found 167.

Step 5

3-(Methylamino)pyridine-2-carboxamide

Methyl 3-(methylamino)pyridine-2-carboxylate (6.00 g, 36.1 mmol) was dissolved in methanol (100 mL) and aqueous ammonia (1.27 g, 36.1 mmol) was added. The reaction was stirred at 40° C. for 18 hours. The reaction was added with water (200 mL) and extracted with ethyl acetate (100 mL×2). The organic phases were combined, dried over anhydrous sodium sulfate, filtered and concentrated under reduced pressure to give 3-(methylamino)pyridine-2-carboxamide (3.50 g, as a yellow solid) with a yield of 64%. $^1$H NMR: (400 MHz, DMSO-$d_6$) δ 8.25 (d, J=4.8 Hz, 1H), 8.02-7.98 (br, 1H), 7.76 (d, J=4.8 Hz, 1H), 7.37-7.32 (m, 2H), 7.11 (d, J=8.0 Hz, 1H), 2.79 (d, J=4.8 Hz, 3H).

Step 6

N-[(2-Formylamino-3-pyridyl)-N-methyl]-ethyl carbamate 3-(Methylamino)pyridine-2-carboxamide (1.70 g, 10.9 mmol) was dissolved in ethyl chloroformate (35.3 g, 326 mmol). The reaction was stirred at 90° C. for 1 hour. The reaction was quenched with saturated aqueous sodium bicarbonate solution (20 mL) and extracted with ethyl acetate (20 mL×2). The organic phase was concentrated under reduced pressure and the residue was purified by silica gel column chromatography (1:1 petroleum ether/ethyl acetate, $R_f$=0.2) to give N-[(2-formylamino-3-pyridyl)-N-methyl]-ethyl carbamate (2.00 g, as a white solid) with a yield of 83%. $^1$H NMR: (400 MHz, DMSO-$d_6$) δ 8.48 (d, J=4.8 Hz, 1H), 7.92-7.88 (br, 1H), 7.82 (d, J=8.0 Hz, 1H), 7.60-7.56 (m, 1H), 7.52-7.48 (br, 1H), 3.09 (q, J=7.2 Hz, 2H), 3.12 (s, 3H), 1.00 (t, J=7.2 Hz, 3H).

Step 7

1-Methylpyrido[3,2-d]pyrimidine-2,4-dione

N-[(2-Formylamino-3-pyridyl)-N-methyl]-ethyl carbamate (2.00 g, 8.96 mmol) and sodium hydroxide (717 mg, 17.9 mmol) were dissolved in toluene (25 mL). The reaction was stirred at 110° C. for 0.5 h. The reaction solution was diluted with water (15 mL) and adjusted to pH=7 with 1 N aqueous hydrochloric acid, then filtered and the filter cake was diluted with methanol (15 mL) and concentrated under reduced pressure to give 1-methylpyrido[3,2-d]pyrimidine-2,4-dione (1.09 g, as a white solid) with a yield of 69%. $^1$H NMR: (400 MHz, DMSO-$d_6$) δ 12.72 (s, 1H), 8.50 (d, J=8.8 Hz, 1H), 7.89 (d, J=8.8 Hz, 1H), 7.74-7.71 (m, 1H), 3.41 (s, 3H).

Step 8

1-Methyl-3-[3-(3-methylisoxazol-5-yl)propyl]pyrido[3,2-d]pyrimidine-2,4-dione

1-Methylpyrido[3,2-d]pyrimidine-2,4-dione (30.0 mg, 169 mmol), 3-(3-methylisoxazol-5-yl)propyl methanesulfonate (48.3 mg, 220 mmol) and potassium carbonate (70.2 mg, 508 mmol) were dissolved in N,N-dimethylformamide (4 mL), potassium iodide (2.8 mg, 16.9 ummol) was added and the reaction was stirred at 120° C. for 3 hours. The reaction solution was directly filtered and the filtrate was concentrated under reduced pressure. The crude product was purified by preparative HPLC to give 1-methyl-3-[3-(3-methylisoxazol-5-yl)propyl]pyrido[3,2-d]pyrimidine-2,4-dione (10.0 mg) with a yield of 20%. $^1$H NMR: (400 MHz, Methanol-$d_4$) δ 8.58-8.53 (m, 1H), 7.99-7.97 (m, 1H), 7.83-7.77 (m, 1H), 6.09 (s, 1H), 4.22 (t, J=7.2 Hz, 2H), 3.62 (s, 3H), 2.86 (t, J=7.2 Hz, 2H), 2.18-2.11 (m, 5H). MS-ESI calcd. [M+H]$^+$ 301, found 301.

Example 101

3-(2-(2,4-Dimethyl-5-yl)ethyl)-1-methylpyrido[3,2-d]pyrimidine-2,4-dione

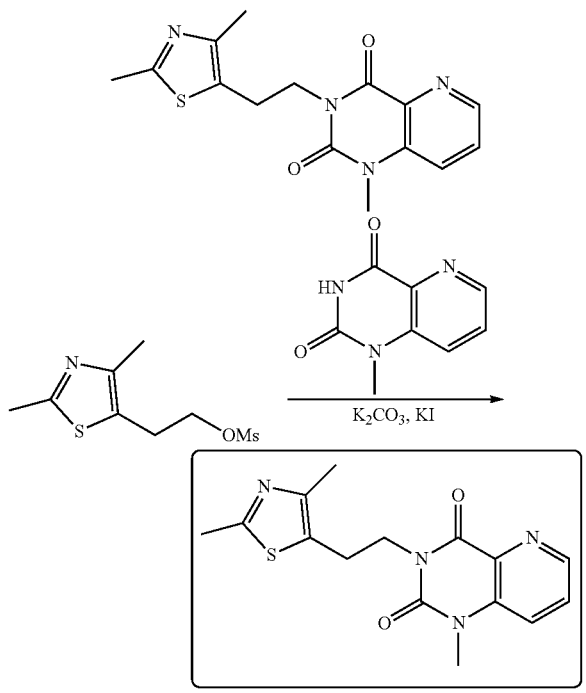

Step 1

3-(2-(2,4-Dimethyl-5-yl)ethyl)-1-methylpyrido[3,2-d]pyrimidine-2,4-dione 2-(2,4-Dimethylthiazol-5-yl)ethyl methanesulfonate (40.0 mg, 0.169 mmol), 1-methylpyrido[3,2-d]pyrimidine-2,4-dione (25.0 mg, 0.141 mmol), potassium iodide (2.3 mg, 0.014 mmol) and potassium carbonate (39.0 mg, 0.282 mmol) were dissolved in N,N-dimethylformamide (3 mL). The reaction was allowed to heat to 120° C. and stirred for 3 hours, cooled to room temperature, filtered, and the filtrate was concentrated under reduced pressure. The residue was purified by preparative HPLC to give 3-(2-(2,4-dimethyl-5-yl)ethyl)-1-methylpyrido[3,2-d]pyrimidine-2,4-dione (10.0 mg) with a yield of 22%. $^1$H NMR: (400 MHz, Methanol-$d_4$) δ 8.56-8.50 (m, 1H), 7.99 (d, J=8.4 Hz, 1H), 7.82-7.80 (m, 1H), 4.26 (t, J=7.6 Hz, 2H), 3.63 (s, 3H), 3.11 (t, J=7.6 Hz, 2H), 2.60 (s, 3H), 2.32 (s, 3H). MS-ESI calcd. [M+H]$^+$ 317, found 317.

Example 102

3-(3-(1H-indol-3-yl)propyl)-1-methylpyrido[3,2-d]pyrimidine-2,4-dione

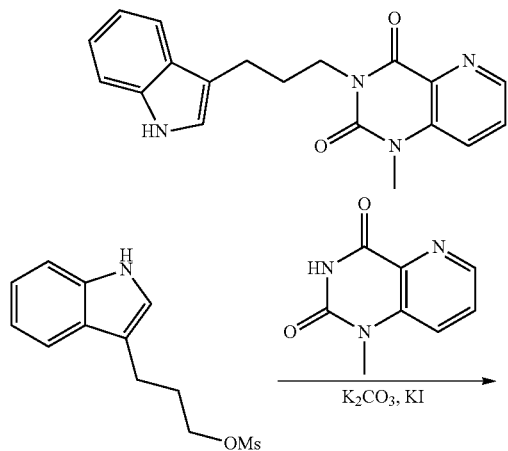

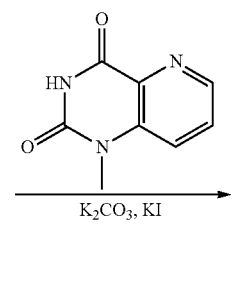

Step 1

3-(3-(1H-indol-3-yl)propyl)-1-methylpyrido[3,2-d]pyrimidine-2,4-dione 3-(1H-indol-3-yl)propyl methanesulfonate (40.5 mg, 0.169 mmol), 1-methylpyrido[3,2-d]pyrimidine-2,4-dione (25.0 mg, 0.141 mmol), potassium iodide (2.3 mg, 0.014 mmol) and potassium carbonate (39.0 mg, 0.282 mmol) were dissolved in N,N-dimethylformamide (3 mL). The reaction was allowed to heat to 120° C. and stirred for 3 hours, cooled to room temperature, filtered, and the filtrate was concentrated under reduced pressure. The residue was purified by preparative HPLC to give 3-(3-(1H-indol-3-yl)propyl)-1-methylpyrido[3,2-d]pyrimidine-2,4-dione (20.0 mg) with a yield of 42%. $^1$H NMR: (400 MHz, CDCl$_3$) δ 8.64 (d, J=4.0 Hz, 1H), 7.88 (br, 1H), 7.62-7.52 (m, 3H), 7.28-7.26 (m, 1H), 7.10-7.08 (m, 3H), 4.32-4.28 (m, 2H), 3.52 (s, 3H), 2.92-2.88 (m, 2H), 2.24-2.20 (m, 2H). MS-ESI calcd. [M+H]$^+$ 335, found 335.

Example 103

3-(4-(Benzofuran-3-yl)butyl)-1-methylpyrido[3,2-d]pyrimidine-2,4-dione

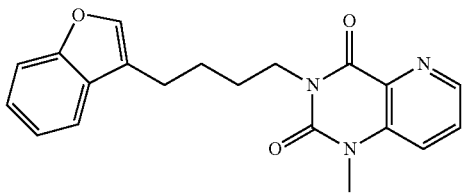

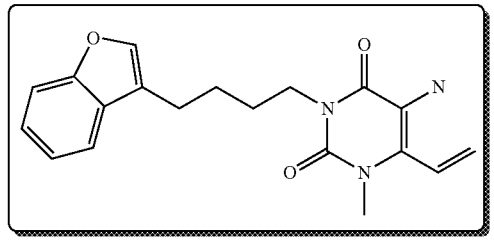

Step 1

3-(4-(Benzofuran-3-yl)butyl)-1-methylpyrido[3,2-d]pyrimidine-2,4-dione 2-(2,4-Dimethylthiazol-5-yl)ethyl methanesulfonate (35.3 mg, 0.186 mmol), 1-methylpyrido[3,2-d]pyrimidine-2,4-dione (25.0 mg, 0.141 mmol), potassium iodide (2.3 mg, 0.014 mmol) and potassium carbonate (58.5 mg, 0.423 mmol) were dissolved in N,N-dimethylformamide (5 mL). The reaction was allowed to heat to 120° C. and stirred for 3 hours, cooled to room temperature, filtered, and the filtrate was concentrated under reduced pressure. The residue was purified by preparative HPLC to give 3-(4-(benzofuran-3-yl)butyl)-1-methylpyrido[3,2-d]pyrimidine-2,4-dione (20.0 mg) with a yield of 40%. $^1$H NMR: (400 MHz, Methanol-d$_4$) δ 8.53-8.52 (m, 1H), 7.91 (d, J=8.4 Hz, 1H), 7.78-7.74 (m, 1H), 7.44-7.43 (m, 1H), 7.32 (d, J=8.0 Hz, 1H), 7.16-7.13 (m, 2H), 6.46 (s, 1H), 4.15 (t, J=6.8 Hz, 2H), 3.57 (s, 3H), 2.85 (t, J=6.4 Hz, 2H), 1.84-1.82 (m, 4H). MS-ESI calcd. [M+H]$^+$ 350, found 350.

Example 104

1-Methyl-3-[4-(3-methylisoxazol-5-yl)butyl]pyrido[3,2-d]pyrimidine-2,4-dione

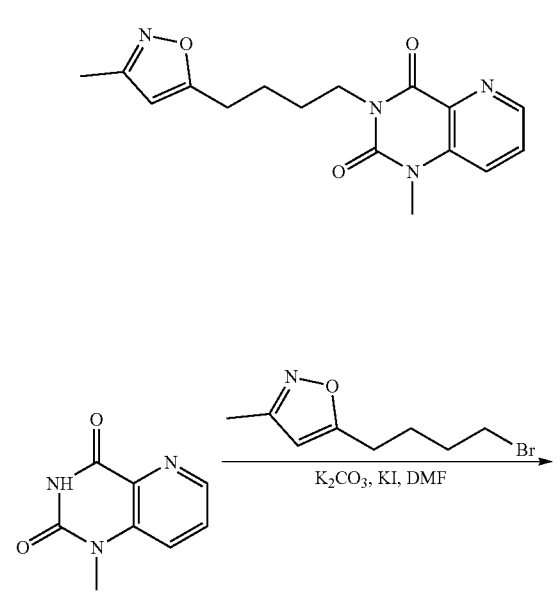

Step 1

1-Methyl-3-[4-(3-methylisoxazol-5-yl)butyl]pyrido[3,2-d]pyrimidine-2,4-dione 1-Methylpyrido[3,2-d]pyrimidine-2,4-dione (30.0 mg, 169 mmol), 5-(4-bromobutyl)-3-methyl-isoxazole (40.6 mg, 186 mmol) and potassium carbonate (58.5 mg, 423 mmol) were dissolved in N,N-dimethylformamide (4 mL), potassium iodide (2.8 mg, 0.017 mmol) was added and the reaction was stirred to reflux at 120° C. for 3 hours. The reaction solution was directly filtered and the filtrate was concentrated under reduced pressure. The crude product was purified by preparative HPLC to give 1-methyl-3-[4-(3-methylisoxazol-5-yl)butyl]pyrido[3,2-d]pyrimidine-2,4-dione (7.2 mg) with a yield of 13%. $^1$H NMR: (400 MHz, Methanol-$d_4$) δ 8.56 (d, J=4.0 Hz, 1H), 7.98 (d, J=8.8 Hz, 1H), 7.79 (dd, J=8.8, 4.0 Hz, 1H), 6.07 (s, 1H), 4.16 (t, J=6.4 Hz, 2H), 3.61 (s, 3H), 2.83 (t, J=6.4 Hz, 2H), 2.24 (s, 3H), 1.83-1.76 (m, 4H). MS-ESI calcd. [M+H]$^+$ 315, found 315.

Example 105

3-(2-(2,4-Dimethyl-5-yl)ethyl)-1-methylpterpine-2,4-dione

Step 1

6-Amino-1-methylpyrimidine-2,4-dione

Sodium (7.80 g, 340 mmol) was added in batches to ethanol (180 mL) while stirring at 25° C., heated to 80° C. to reflux for 0.5 hours. Methylurea (12.6 g, 170 mmol) was then added in batches and reflux was continued for 0.5 h. Ethyl cyanoacetate (19.0 g, 170 mmol) was added dropwise to the reaction solution, resulting in a large amount of precipitate. Reflux was continued for 3 hours, ethanol was recovered under reduced pressure. The residue was diluted with water (50 mL) and adjusted to pH=7 with dilute hydrochloric acid (1 N). The product was filtered to give 6-amino-1-methylpyrimidine-2,4-dione (7.60 g, as a white solid) with a yield of 32%. ¹H NMR: (400 MHz, DMSO-$d_6$) δ 10.39 (br, 1H), 6.79 (br, 2H), 4.54 (s, 1H), 3.14 (s, 3H). MS-ESI calcd. [M+H]⁺ 142, found 142.

Step 2

5,6-Diamino-1-methylpyrimidine-2,4-dione

6-Amino-1-methylpyrimidine-2,4-dione (10.0 g, 70.1 mmol) was dissolved in water (100 mL). Hydrochloric acid (7 mL, 84.0 mmol, 12 N) was added dropwise at 0° C. while stirring. Then sodium nitrite (5.80 g, 84.2 mmol) was dissolved in water (50 mL) and added dropwise to the reaction solution to give a purple precipitate. The reaction was stirred at 25° C. for 2 hours, filtered and washed with cold water to give a purple solid. The solid was dissolved in water (100 mL) and sodium hydrosulphite (18.7 g, 118 mmol) was added in batches while stirring, heated to 60° C. and stirred for 0.5 h, cooled to 25° C. and stirred for 16 h, filtered, washed with cold water (50 mL), ethanol (50 mL), acetone (50 mL) respectively, and dried to give 5,6-diamino-1-methylpyrimidine-2,4-dione (8.60 g, as a pale yellow solid) with a yield of 93%. ¹H NMR (400 MHz, DMSO-$d_6$) δ 10.49 (br, 1H), 6.15 (br, 2H), 3.25 (s, 3H), 2.95 (br, 2H). MS-ESI calcd. [M+H]⁺ 157, found 157.

Step 3

1-Methylpteridine-2,4-dione 5,6-Diamino-1-methylpyrimidine-2,4-dione (4.00 g, 25.6 mmol) was dissolved in water (150 mL). Glyoxal (5.58 g, 38.4 mmol, 40% aqueous solution) was added in one portion at 25° C. The reaction solution was heated to 60° C. for 16 hours. The resulting solid was washed with water (50 mL) to give the product 1-methylpteridine-2,4-dione (3.60 g, as a yellow solid) with a yield of 79%.

Step 4

3-(2-(2,4-Dimethyl-5-yl)ethyl)-1-methylpteridine-2,4-dione 2-(2,4-Dimethylthiazol-5-yl)ethyl methanesulfonate (172 mg, 0.729 mmol), 1-methylpteridine-2,4-dione (100 mg, 0.561 mmol) and potassium carbonate (233 mg, 1.68 mmol) were dissolved in N,N-dimethylformamide (5 mL), potassium iodide (9.3 mg, 0.056 mmol) was added and the reaction was stirred at 120° C. for 3 hours. The reaction solution was cooled to room temperature and filtered. The filtrate was concentrated under reduced pressure and the crude product was purified by preparative HPLC to give 3-(2-(2,4-dimethyl-5-yl)ethyl)-1-methylpteridine-2,4-dione (9.0 mg) with a yield of 5%. ¹H NMR: (400 MHz, CDCl₃) δ 8.66 (d, J=2.0 Hz, 1H), 8.61 (d, J=2.0 Hz, 1H), 4.30 (t, J=8.0 Hz, 2H), 3.72 (s, 3H), 3.11 (t, J=8.0 Hz, 2H), 2.62 (s, 3H), 2.36 (s, 3H). MS-ESI calcd. [M+H]⁺ 318, found 318.

Example 106

3-(3-(1H-indol-3-yl)propyl)-1-methylpteridine-2,4-dione

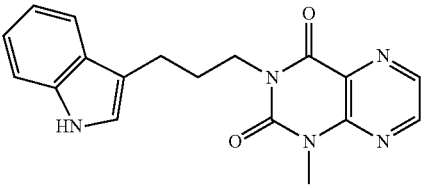

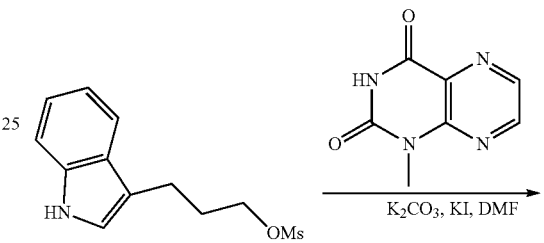

Step 1

3-(3-(1H-indol-3-yl)propyl)-1-methylpteridine-2,4-dione 3-(1H-indol-3-yl)propyl methanesulfonate (185 mg, 0.729 mmol), 1-methylpteridine-2,4-dione (100 mg, 0.561 mmol) and potassium carbonate (233 mg, 1.68 mmol) were dissolved in N,N-dimethylformamide (5 mL), potassium iodide (9.3 mg, 0.0561 mmol) was added. The reaction was allowed to heat to 120° C. and stirred for 3 hours, cooled to room temperature, filtered, and the filtrate was concentrated under reduced pressure. The crude product was purified by preparative HPLC to give 3-(3-(1H-indol-3-yl)propyl)-1-methylpteridine-2,4-dione (10.0 mg) with a yield of 5%. ¹H NMR: (400 MHz, CDCl₃) δ 8.60 (d, J=2.0 Hz, 1H), 8.56 (d, J=2.0 Hz, 1H), 7.90-7.85 (br, 1H), 7.61-7.59 (m, 1H), 7.26 (s, 1H), 7.15-7.06 (m, 3H), 4.29 (t, J=7.2 Hz, 2H), 3.63 (s, 3H), 2.91 (t, J=7.2 Hz, 2H), 2.27-2.20 (m, 2H). MS-ESI calcd. [M+Na]⁺358, found 358.

Example 107

3-(4-(Benzofuran-2-yl)butyl)-1-methylpteridine-2,4-dione

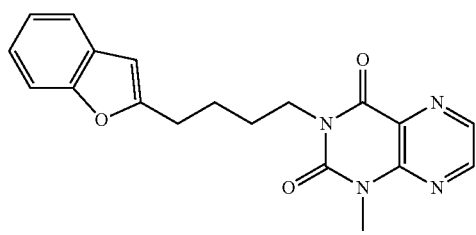

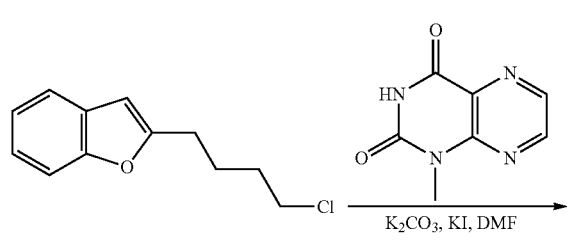

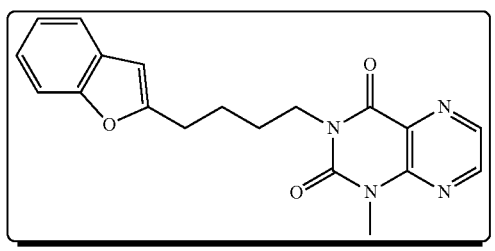

Step 1

3-(4-(Benzofuran-2-yl)butyl)-1-methylpteridine-2,4-dione

1-Methylpterpine-2,4-dione (60.0 mg, 0.342 mmol) was dissolved in N,N-dimethylformamide (4 mL). 2-(4-Chlorobutyl)benzofuran (84.0 mg, 0.401 mmol), potassium iodide (67.0 mg, 0.401 mmol) and potassium carbonate (93.0 mg, 0.670 mmol) were added at 25° C. and the reaction was heated to 120° C., stirred for 16 hours. The reaction solution was cooled to room temperature and filtered. The filtrate was concentrated under reduced pressure and the residue was purified by preparative HPLC to give 3-(4-(benzofuran-2-yl)butyl)-1-methylpteridine-2,4-dione (11.0 mg) with a yield of 9%. $^1$H NMR: (400 MHz, CDCl$_3$) δ 8.64 (d, J=2.0 Hz, 1H), 8.59 (d, J=2.0 Hz, 1H), 7.49-7.44 (m, 1H), 7.38 (d, J=7.6 Hz, 1H), 7.21-7.14 (m, 2H), 6.41 (s, 1H), 4.20 (t, J=6.8 Hz, 2H), 3.70 (s, 3H), 2.85 (t, J=6.4 Hz, 2H), 1.88-1.83 (m, 4H). MS-ESI calcd. [M+H]$^+$ 351, found 351.

Example 108

1-Methyl-3-(3-(3-methylisoxazol-5-yl)propyl)pteridine-2,4-dione

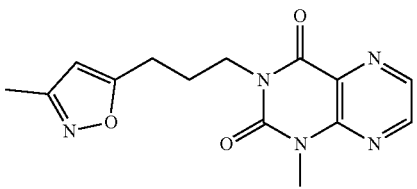

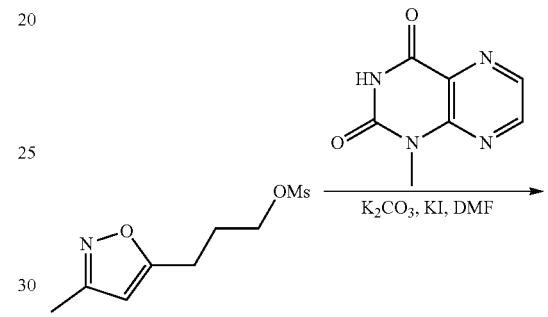

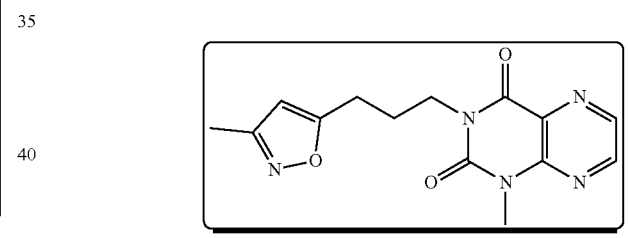

Step 1

1-Methyl-3-(3-(3-methylisoxazol-5-yl)propyl)pteridine-2,4-dione 3-(3-Methylisoxazol-5-yl)propyl methanesulfonate (160 mg, 0.729 mmol), 1-methylpteridine-2,4-dione (100 mg, 0.561 mmol) and potassium carbonate (233 mg, 1.68 mmol) were dissolved in N,N-dimethylformamide (5 mL), potassium iodide (9.3 mg, 0.056 mmol) was added and the reaction was stirred at 120° C. for 15 hours. The reaction solution was cooled to room temperature and filtered. The filtrate was concentrated under reduced pressure and the crude product was purified by preparative HPLC to give 1-methyl-3-(3-(3-methylisoxazol-5-yl)propyl)pteridine-2,4-dione (6.0 mg) with a yield of 3.6%.

$^1$H NMR: (400 MHz, Methanol-d$_4$) δ 8.76 (d, J=2.0 Hz, 1H), 8.56 (d, J=2.0 Hz, 1H), 6.10 (s, 1H), 4.21 (t, J=7.2 Hz, 2H), 3.70 (s, 3H), 2.87 (t, J=7.2 Hz, 2H), 2.18 (s, 3H), 2.17-2.12 (m, 2H). MS-ESI calcd. [M+H]$^+$ 302, found 302.

Example 109

1-Methyl-3-(4-(3-methylisoxazol-5-yl)butyl)pteridine-2,4-dione

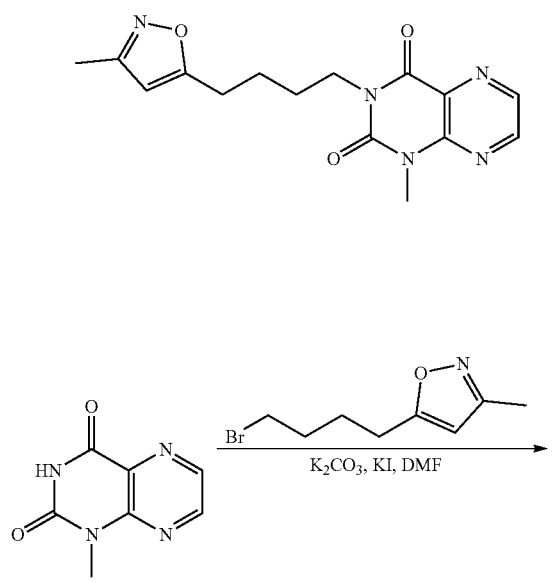

Step 1

1-Methyl-3-(4-(3-methylisoxazol-5-yl)butyl)pteridine-2,4-dione

1-Methylpteridine-2,4-dione (300 mg, 1.68 mmol) was dissolved in N,N-dimethylformamide (8 mL). 5-(4-Bromobutyl)-3-methylisoxazole (366 mg, 1.68 mmol), potassium carbonate (465 mg, 3.37 mmol) and potassium iodide (335 mg, 2.02 mmol) were added at 25° C. The reaction solution was heated to 120° C. and stirred for 17 hours. The reaction solution was cooled to room temperature and filtered. The filtrate was concentrated under reduced pressure and the residue was purified by HPLC to give 1-methyl-3-(4-(3-methylisoxazol-5-yl)butyl)pteridine-2,4-dione (13.0 mg) with a yield of 3%. $^1$H NMR: (400 MHz, CDCl$_3$) δ 8.64 (d, J=4.0 Hz, 1H), 8.58 (d, J=4.0 Hz, 1H), 5.83 (s, 1H), 4.15 (t, J=4.0 Hz, 2H), 3.70 (s, 3H), 2.76 (t, J=4.0 Hz, 2H), 2.23 (s, 3H), 1.82-1.74 (m, 4H). MS-ESI calcd. [M+H]$^+$ 316, found 316.

Example 110

3-((3-Isopropylisoxazol-5-yl)methyl)-1-methylpyrimido[4,5-d]pyrimidine-2,4-dione

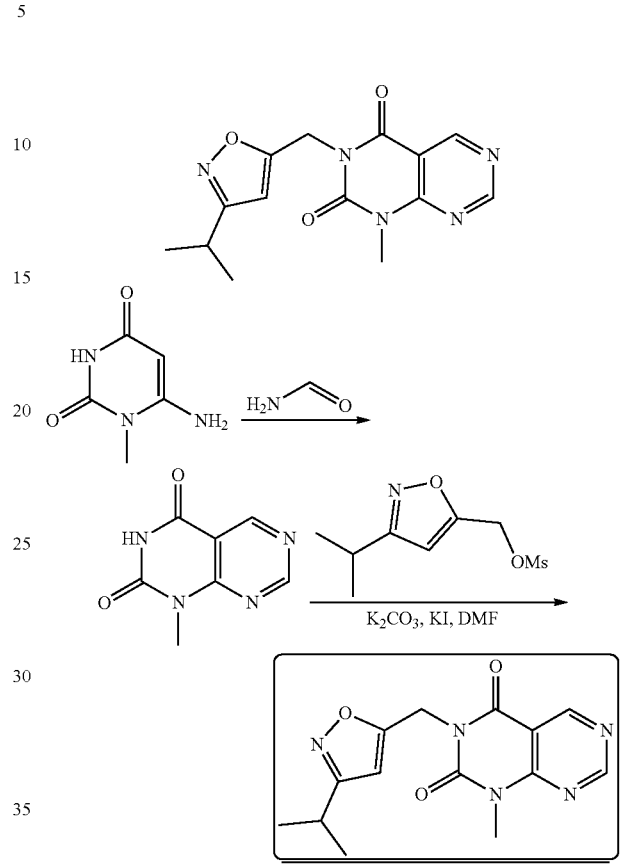

Step 1

1-Methylpyrimido[4,5-d]pyrimidine-2,4-dione

6-Amino-1-methylpyrimidine-2,4-dione (3.50 g, 24.8 mmol) was added to formamide (5.00 g, 111 mmol). The reaction was heated to 180° C. and stirred for 3 hours, and then cooled to room temperature and filtered. Water (10 mL) was added to the filtrate, stirred and filtered again to give 1-methylpyrimido[4,5-d]pyrimidine-2,4-dione (1.60 g, as a pale yellow solid) with a yield of 36%. $^1$H NMR: (400 MHz, DMSO-d$_6$) δ 9.16 (s, 1H), 9.08 (s, 1H), 3.43 (s, 3H).

Step 2

3-((3-Isopropylisoxazol-5-yl)methyl)-1-methylpyrimido[4,5-d]pyrimidine-2,4-dione 1-Methylpyrimido[4,5-d]pyrimidine-2,4-dione (20.0 mg, 0.112 mmol) was dissolved in N,N-dimethylformamide (2 mL). (3-Isopropylisoxazol-5-yl)methyl methanesulfonate (27.0 mg, 0.123 mmol), potassium iodide (4.0 mg, 0.0225 mmol) and potassium carbonate (31.0 mg, 0.225 mmol) were added at 25° C. The reaction was heated to 120° C. and stirred for 16 hours. The reaction solution was cooled to room temperature and filtered. The filtrate was concentrated under reduced pressure. The residue was purified by preparative HPLC to give 3-((3-isopropylisoxazol-5-yl)

methyl)-1-methylpyrimido[4,5-d]pyrimidine-2,4-dione (5.0 mg) with a yield of 15%. ¹H NMR: (400 MHz, CDCl₃) δ 9.33 (s, 1H), 9.17 (s, 1H), 6.18 (s, 1H), 5.35 (s, 2H), 3.71 (s, 3H), 3.07-3.00 (m, 1H), 1.26 (d, J=6.8 Hz, 6H). MS-ESI calcd. [M+H]⁺ 302, found 302.

Example 111

3-(2-(2,4-Dimethyl-5-yl)ethyl)-1-methylpyrimido[4,5-d]pyrimidine-2,4-dione

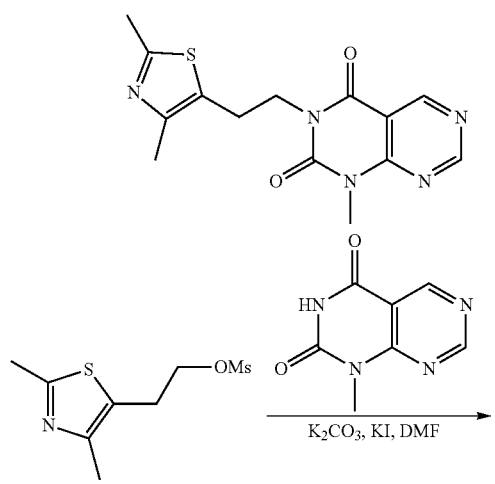

Step 1

3-(2-(2,4-Dimethyl-5-yl)ethyl)-1-methylpyrimido[4,5-d]pyrimidine-2,4-dione

1-Methylpyrimido[4,5-d]pyrimidine-2,4-dione (50.0 mg, 0.281 mmol) was dissolved in N,N-dimethylformamide (4 mL). 2-(2,4-Dimethylthiazol-5-yl)ethyl methanesulfonate (73.0 mg, 0.308 mmol), potassium iodide (9.0 mg, 0.056 mmol) and potassium carbonate (78.0 mg, 0.561 mmol) were added at 25° C. The reaction was heated to 120° C. and stirred for 16 hours. The reaction solution was cooled to room temperature and filtered. The filtrate was concentrated under reduced pressure. The residue was purified by preparative HPLC to give 3-(2-(2,4-dimethyl-5-yl)ethyl)-1-methylpyrimido[4,5-d]pyrimidine-2,4-dione (43.0 mg) with a yield of 48%. ¹H NMR: (400 MHz, CDCl₃) δ 9.30 (s, 1H), 9.16 (s, 1H), 4.25-4.21 (m, 2H), 3.70 (s, 3H), 3.10-3.06 (m, 2H), 2.62 (s, 3H), 2.36 (s, 3H). MS-ESI calcd. [M+H]⁺ 318, found 318.

Example 112

3-(3-(1H-indol-3-yl)propyl)-1-methylpyrimido[4,5-d]pyrimidine-2,4-dione

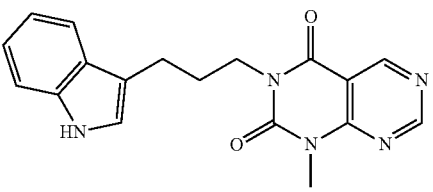 [SMILES: Cn1c(=O)n(CCCc2c[nH]c3ccccc23)c(=O)c2cncnc21]

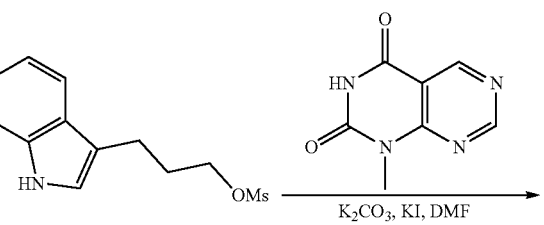

Step 1

3-(3-(1H-indol-3-yl)propyl)-1-methylpyrimido[4,5-d]pyrimidine-2,4-dione

1-Methylpyrimido[4,5-d]pyrimidine-2,4-dione (50.0 mg, 0.281 mmol) was dissolved in N,N-dimethylformamide (4 mL). 3-(1H-indol-3-yl)propyl methanesulfonate (78.0 mg, 0.308 mmol), potassium iodide (9.0 mg, 0.056 mmol) and potassium carbonate (76.0 mg, 0.561 mmol) were added at 25° C. The reaction solution was heated to 120° C. and stirred for 16 hours. The reaction solution was cooled to room temperature and filtered. The filtrate was concentrated under reduced pressure. The residue was purified by preparative HPLC to give 3-(3-(1H-indol-3-yl)propyl)-1-methylpyrimido[4,5-d]pyrimidine-2,4-dione (12.0 mg) with a yield of 13%. ¹H NMR: (400 MHz, CDCl₃) δ 9.22 (s, 1H), 9.09 (s, 1H), 7.95-7.90 (br, 1H), 7.59 (d, J=7.6 Hz, 1H), 7.28-7.26 (m, 1H), 7.16-7.07 (m, 3H), 4.21 (t, J=7.2 Hz, 2H), 3.60 (s, 3H), 2.89 (t, J=7.2 Hz, 2H), 2.21-2.17 (m, 2H). MS-ESI calcd. [M+H]⁺ 336, found 336.

Example 113

3-(4-(Benzofuran-2-yl)butyl)-1-methylpyrimido[4,5-d]pyrimidine-2,4-dione

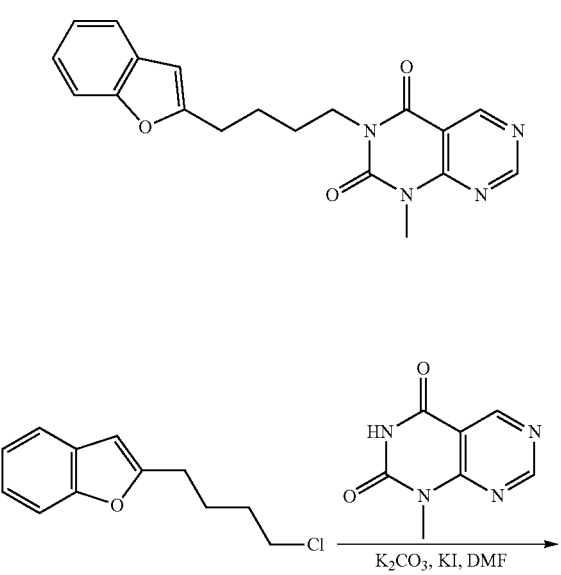

Step 1

3-(4-(Benzofuran-2-yl)butyl)-1-methylpyrimido[4,5-d]pyrimidine-2,4-dione

1-Methylpyrimido[4,5-d]pyrimidine-2,4-dione (50.0 mg, 0.281 mmol) was dissolved in N,N-dimethylformamide (4 mL). 2-(4-Chlorobutyl)benzofuran (64.0 mg, 0.308 mmol), potassium iodide (56.0 mg, 0.337 mmol) and potassium carbonate (78.0 mg, 0.561 mmol) were added at 25° C. and the reaction was heated to 120° C., stirred for 16 hours. The reaction solution was cooled to room temperature and filtered. The filtrate was concentrated under reduced pressure and the residue was purified by preparative HPLC to give 3-(4-(benzofuran-2-yl)butyl)-1-methylpyrimido[4,5-d]pyrimidine-2,4-dione (53.0 mg) with a yield of 54%. $^1$H NMR: (400 MHz, CDCl$_3$) δ 9.27 (s, 1H), 9.13 (s, 1H), 7.48-7.44 (m, 1H), 7.37 (d, J=7.6 Hz, 1H), 7.20-7.13 (m, 2H), 6.39 (s, 1H), 4.12 (m, 2H), 3.66 (s, 3H), 2.88-2.78 (m, 2H), 1.86-1.79 (m, 4H). MS-ESI calcd. [M+H]$^+$ 351, found 351.

Example 114

1-Methyl-3-(3-(3-methylisoxazol-5-yl)propyl)pyrimido[4,5-d]pyrimidine-2,4-dione

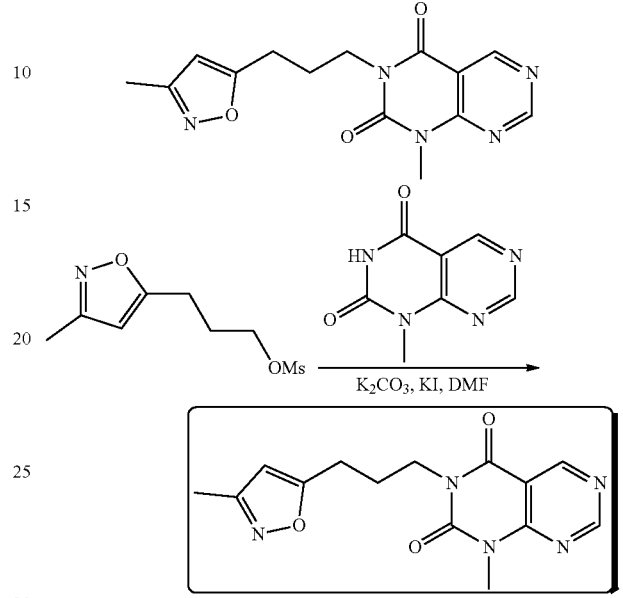

Step 1

1-Methyl-3-(3-(3-methylisoxazol-5-yl)propyl)pyrimido[4,5-d]pyrimidine-2,4-dione 3-(3-Methylisoxazol-5-yl)propyl methanesulfonate (80.0 mg, 0.364 mmol), 1-methylpyrimido[4,5-d]pyrimidine-2,4-dione (50 mg, 0.280 mmol) and potassium carbonate (116 mg, 0.842 mmol) were dissolved in N,N-dimethylformamide (5 mL), potassium iodide (4.7 mg, 0.028 mmol) was added. The reaction was stirred at 120° C. for 3 hours. The reaction solution was cooled to room temperature and filtered. The filtrate was concentrated under reduced pressure and the crude product was purified by preparative HPLC to give 1-methyl-3-(3-(3-methylisoxazol-5-yl)propyl)pyrimido[4,5-d]pyrimidine-2,4-dione (55.0 mg) with a yield of 65%. $^1$H NMR: (400 MHz, CDCl$_3$) δ9.30 (s, 1H), 9.16 (s, 1H), 5.93 (s, 1H), 4.17 (t, J=7.2 Hz, 2H), 3.69 (s, 3H), 2.83 (t, J=7.2 Hz, 2H), 2.23 (s, 3H), 2.14-2.08 (m, 2H). MS-ESI calcd. [M+Na]$^+$324, found 324.

Example 115

1-Methyl-3-(4-(3-methylisoxazol-5-yl)butyl)pyrimido[4,5-d]pyrimidine-2,4-dione

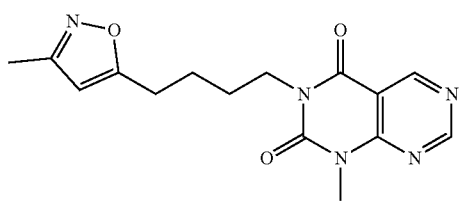

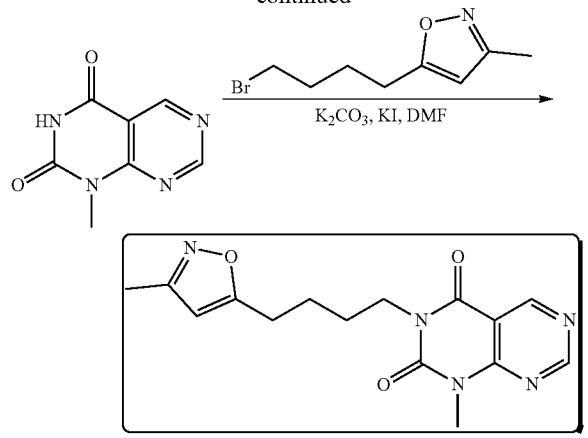

Step 1

1-Methyl-3-(4-(3-methylisoxazol-5-yl)butyl)pyrimido[4,5-d]pyrimidine-2,4-dione

1-Methylpyrimido[4,5-d]pyrimidine-2,4-dione (300 mg, 1.68 mmol) was dissolved in N,N-dimethylformamide (8 mL). 5-(4-Bromobutyl)-3-methylisoxazole (403 mg, 1.85 mmol), potassium carbonate (465 mg, 3.37 mmol) and potassium iodide (335 mg, 2.02 mmol) were added at 25° C. The reaction solution was heated to 120° C. and stirred for 16 hours. The reaction solution was cooled to room temperature and filtered. The filtrate was concentrated under reduced pressure and the residue was purified by HPLC to give 1-methyl-3-(4-(3-methylisoxazol-5-yl)butyl)pyrimido[4,5-d]pyrimidine-2,4-dione (11.0 mg) with a yield of 2%.
$^1$H NMR: (400 MHz, CDCl$_3$) δ 9.28 (s, 1H), 9.14 (s, 1H), 5.83 (s, 1H), 4.09 (t, J=7.2 Hz, 2H), 3.68 (s, 3H), 2.77 (t, J=7.2 Hz, 2H), 2.25 (s, 3H), 1.78-1.75 (m, 4H). MS-ESI calcd. [M+H]$^+$316, found 316.

Experimental Example 1: In Vitro Evaluation of PDE2 Phosphodiesterase Inhibitory Activity Experimental objectives: To detect the concentration of AMP/GMP produced in the reaction system by measuring the fluorescence intensity of the fluorescent dye AlexaFluor 633 substituted on AMP/GMP antibody and to calculate the PDE2 phosphodiesterase inhibitory IC$_{50}$ value of the test compound.

Experimental Materials:
Test buffer solution: 10 mM Tris-HCl, pH 7.5, 5 mM MgCl$_2$, 0.01% Brij 35, 1 mM DTT, and 1% DMSO.
Enzyme: Full length human PDE2A protease expressed and recombined in insect Sf9 cells with baculovirus using N-terminal GST tag
Substrate: 1 μM cGMP
Detection Method:
Transcreener® AMP$^2$/GMP$^2$ antibody, AMP2/GMP2 AlexaFluor 633 fluorescent dye
Experimental Operations:
The enzyme solution was prepared with freshly prepared buffer solution and then added to the reaction wells. The DMSO solution of the test compound was added by Echo550 non-contact nanoscale sonicate pipetting system and preincubated for 10 minutes at room temperature. The reaction was initiated by addition of substrate (1 μM cGMP) and allowed to react for one hour at room temperature. The detection system (Transcreener® AMP$^2$/GMP$^2$ antibody, AMP2/GMP2 AlexaFluor 633 fluorescent dye) was then added and reacted for 90 minutes at room temperature before fluorescence polarization was detected using Ex/Em 620/688.

The intensity of fluorescence polarization was converted to nM concentration by the AMP/GMP standard curve and then relative inhibition of enzyme activity relative to DMSO blank was calculated. IC$_{50}$ values and curves were calculated using the Prism software package (GraphPad Software, San Diego Calif., USA)

Experimental Results:

TABLE 1

The Testing Results of PDE2 Phosphodiesterase Inhibitory Activity

| Test products (the compounds prepared in the examples) | PDE2 phosphodiesterase inhibitory activity |
|---|---|
| Example 1 | — |
| Example 2 Product 1 | + |
| Example 2 Product 2 | + |
| Example 7 | — |
| Example 8 | — |
| Example 11 Product 1 | — |
| Example 11 Product 2 | + |
| Example 12 | + |
| Example 13 | — |
| Example 14 Isomer 1 | + |
| Example 14 Isomer 2 | — |
| Example 15 | ++ |
| Example 16 | — |
| Example 17 Isomer 1 | — |
| Example 17 Isomer 2 | — |
| Example 19 | + |
| Example 20 | + |
| Example 22 | + |
| Example 23 | — |
| Example 25 | + |
| Example 27 | + |
| Example 28 | ++ |
| Example 29 | + |
| Example 30 | — |
| Example 31 | ++ |
| Example 34 | + |
| Example 35 | + |
| Example 36 Isomer 1 | + |
| Example 36 Isomer 2 | + |
| Example 36 Isomer 3 | — |
| Example 37 | + |
| Example 38 Isomer 1 | + |
| Example 38 Isomer 2 | — |
| Example 39 | + |
| Example 40 Isomer 1 | + |
| Example 40 Isomer 2 | + |
| Example 41 | ++ |
| Example 42 | ++ |
| Example 43 | + |
| Example 44 | + |
| Example 45 | ++ |
| Example 47 | — |
| Example 48 | + |
| Example 49 Isomer 1 | + |
| Example 50 | ++ |
| Example 51 | + |
| Example 52 | ++ |
| Example 53 | + |
| Example 54 | + |
| Example 55 | ++ |
| Example 56 | ++ |
| Example 57 | ++ |
| Example 58 | ++ |
| Example 59 | ++ |
| Example 60 | ++ |
| Example 61 | + |

TABLE 1-continued

The Testing Results of PDE2 Phosphodiesterase Inhibitory Activity

| Test products (the compounds prepared in the examples) | PDE2 phosphodiesterase inhibitory activity |
|---|---|
| Example 66 | + |
| Example 67 | + |
| Example 69 | + |
| Example 75 | + |
| Example 81 | + |
| Example 82 | ++ |
| Example 83 | + |
| Example89 | + |
| Example 109 | — |

Note:
10 μM ≤ + < 50 μM;
1 μM ≤ ++ < 10 μM;
+++ < 1 μM;

Conclusion: the compounds of the present invention have significant or even unexpected PDE2A protease inhibitory activity.

Experimental Example 2: In Vitro Evaluation of the Effect of the Compound on LPS-Induced Expression of TNF-α in Rat Blood Experimental Objectives: To detect in vitro the effect of the test compound on LPS-induced expression of TNF-α in rat blood and evaluate the inhibitory effect of the compound on LPS-induced expression of TNF-α in rat blood.

Experimental Materials:
Sprague Dawley rats (male, 210-260 g, 8-10 weeks old, Shanghai Slack)
Rat TNF-alpha Quantikine ELISA Kit (R & D, #SRTA00)
Experimental Operations:
A solution of the test compound with a concentration of 1 mM was prepared and 40 μL (final compound concentration was 100 μM) was added to a 48-well cell culture plate. Rats were anesthetized with isoflurane and blood was collected from the heart (heparin anticoagulation). The blood was added to the 48-well cell plate to which the test compound has been added, with 320 μL per well. The 48-well plate was placed in a cell incubator, incubated for 30 minutes and then removed, added with 40 μL LPS solution (100 μg/mL), mixed and placed in the incubator to continue the incubation. 5 hours later, the 48-well plate was removed and the blood sample was transferred to a 1.5 mL centrifuge tube and centrifuged in a centrifuge (4,500 rpm, 4° C., 5 minutes). The plasma was separated from the supernatant, frozen quickly after packing and stored in −80° C. refrigerator. The next day the R&D ELISA kit was used to measure TNF-α levels in plasma samples according to the instructions of the kit.

Experimental Results:

TABLE 2

The Test Results of TNFα Inhibitory Activity

| Test products (the compounds prepared in the examples) | TNF-α inhibitory ratio |
|---|---|
| Example 3 | — |
| Example 15 | + |
| Example 19 | — |
| Example 25 | — |
| Example 27 | — |
| Example 31 | — |
| Example 59 | ++ |
| Example 82 | + |
| Example 89 | ++ |

Note:
80% ≥ + > 60%;
++ > 80%;
— N/A

Conclusion: the compounds of the present invention have significant or even unexpected TNFα inhibitory activity.

What is claimed is:
1. A compound of the formula (I), a tautomer thereof or a pharmaceutically acceptable salt thereof:

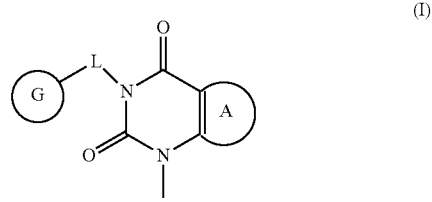

(I)

wherein,
ring A is imidazolyl, which is optionally substituted by 1 or 2 $R_1$ on the nitrogen atom of the imidazolyl;
G is selected from

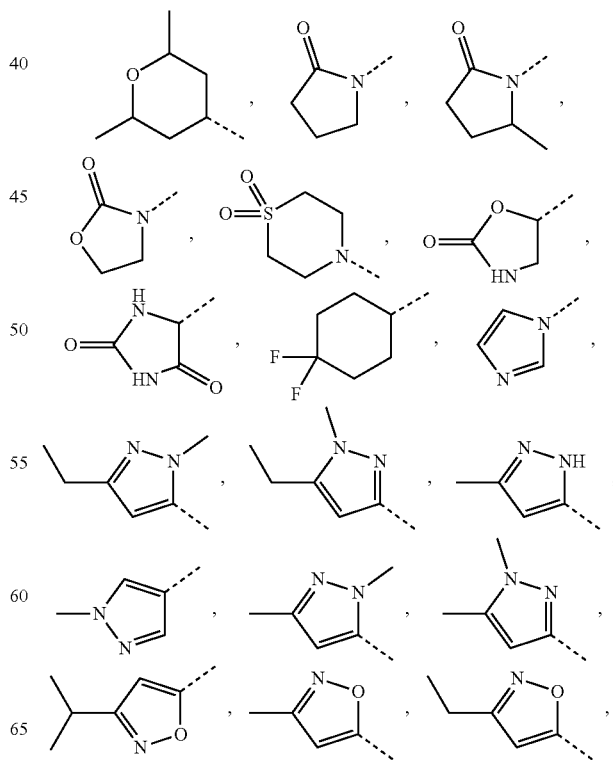

-continued

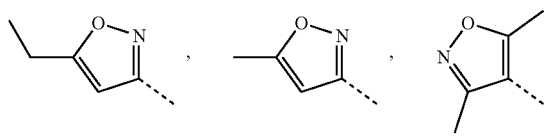

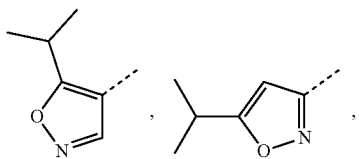

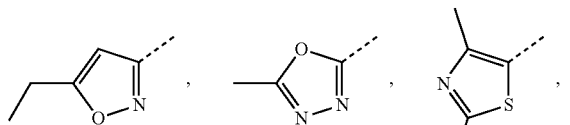

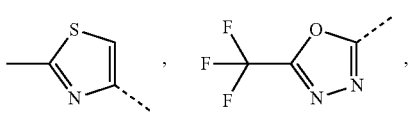

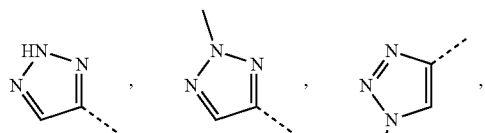

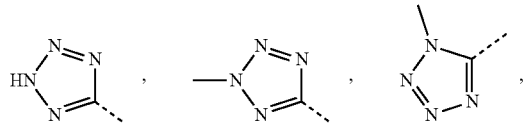

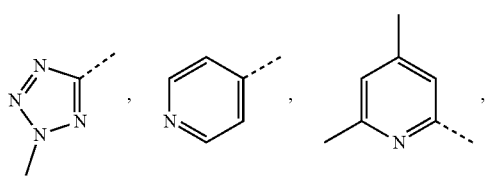

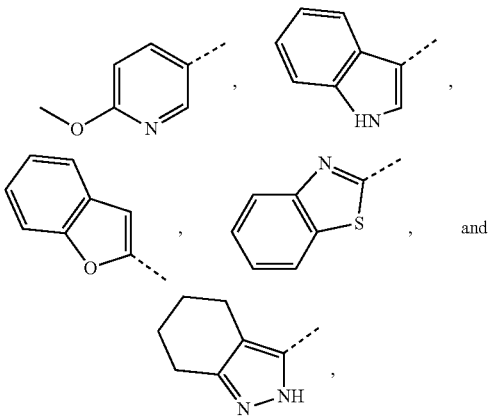

each of which is optionally substituted by 1 to 3 R;

the "hetero-" refers to a heteroatom or a heteroatomic group, each of which is independently selected from N(R), O, S, C(=O), S(=O), S(=O)$_2$, and —C(=O)N(R)—, the number of the heteroatom on each of the defined groups is independently selected from 1, 2 and 3;

L is

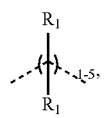

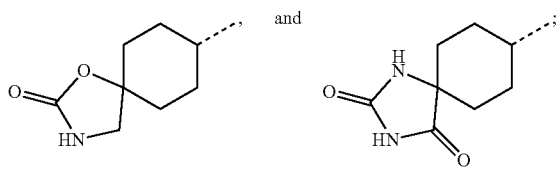

each of $R_1$ is independently selected from H, a halogen, OH, NH$_2$, and the group consisting of a $C_{1-6}$ alkyl or heteroalkyl, a 3- to 6-membered cycloalkyl or heterocycloalkyl, a $C_{1-6}$ alkyl or heteroalkyl substituted by a 3- to 6-membered cycloalkyl or heterocycloalkyl, and a $C_{1-6}$ alkyl or heteroalkyl substituted by a 5- to 6-membered aryl or heteroaryl, each of which is optionally substituted by 1 to 3 $R_2$;

$R_2$ is selected from a halogen, OH, NH$_2$, Me, CF$_3$, OMe and OCF$_3$;

when L is

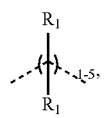

$R_1$ is optionally connected to G to form a spiro ring which is selected from

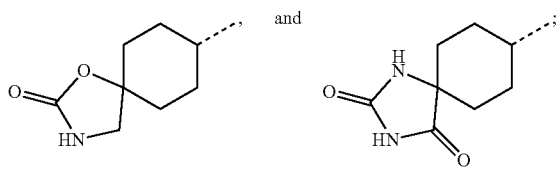

R is selected from H, a halogen, N(R')(R'), or a $C_{1-3}$ alkyl or heteroalkyl, optionally substituted by 1 to 3 R';

R' is selected from H, a halogen, NH$_2$, Me, CF$_3$, OMe and OCF$_3$.

2. The compound, the tautomer thereof or the pharmaceutically acceptable salt thereof according to claim 1, wherein $R_1$ is independently selected from H, a halogen, OH, NH$_2$, and the group consisting of a $C_{1-4}$ alkyl or heteroalkyl, a 3- to 5-membered cycloalkyl or heterocycloalkyl, a $C_{1-3}$ alkyl or heteroalkyl substituted by a 3- to 6-membered cycloalkyl or heterocycloalkyl, or a $C_{1-3}$ alkyl or heteroalkyl substituted by a 5- to 6-membered aryl and heteroaryl, each of which is optionally substituted by 1 to 3 $R_2$.

3. The compound, the tautomer thereof or the pharmaceutically acceptable salt thereof according to claim 1, wherein L is selected from

4. The compound, the tautomer thereof or the pharmaceutically acceptable salt thereof according to claim 1, wherein the moiety

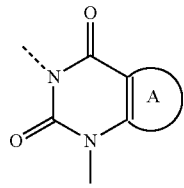

is selected from

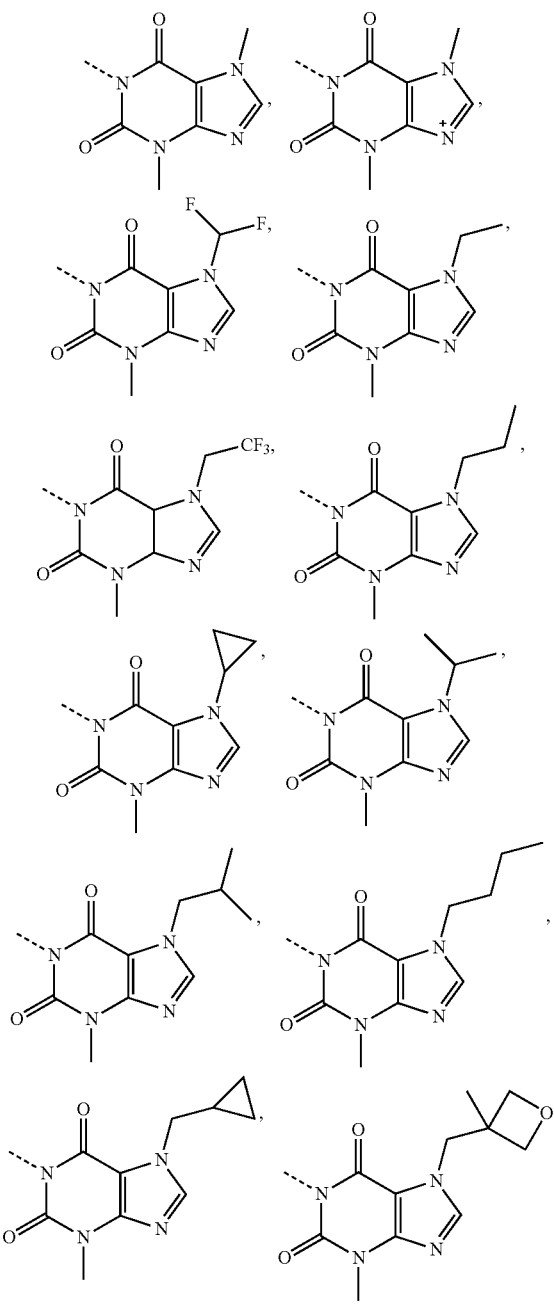

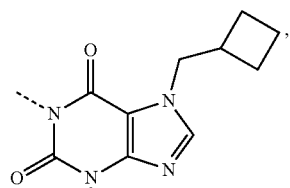

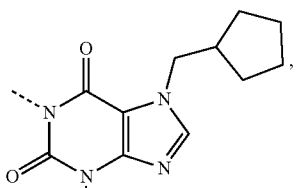

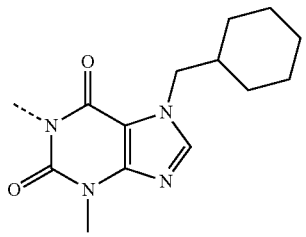

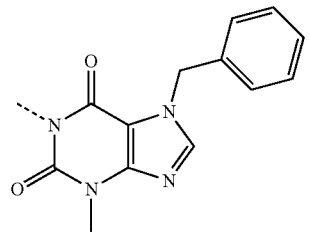 and

5. The compound, the tautomer thereof or the pharmaceutically acceptable salt thereof according to claim 1, wherein R is selected from H, Me,

6. The compound, tautomer thereof or pharmaceutically acceptable salt thereof according to claim 1, which is selected from:

| Compound | Structure |
| --- | --- |
| 3 | 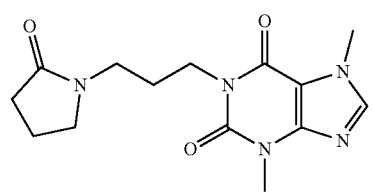 [SMILES: Cn1cnc2c1c(=O)n(CCCN1CCCC1=O)c(=O)n2C] |

-continued

| Compound | Structure |
|---|---|
| 4 | 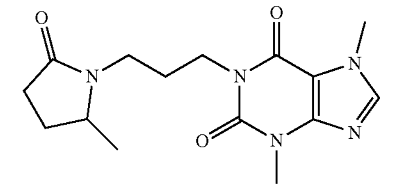 [SMILES: CC1CCC(=O)N1CCCn1c(=O)c2c(ncn2C)n(C)c1=O] |
| 5 | 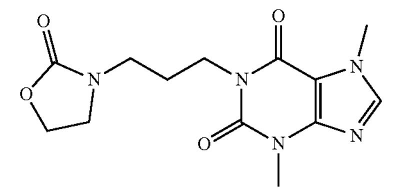 [SMILES: Cn1cnc2c1c(=O)n(CCCN1CCOC1=O)c(=O)n2C] |
| 6 | 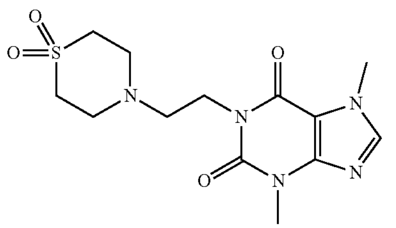 [SMILES: Cn1cnc2c1c(=O)n(CCN1CCS(=O)(=O)CC1)c(=O)n2C] |
| 7 | 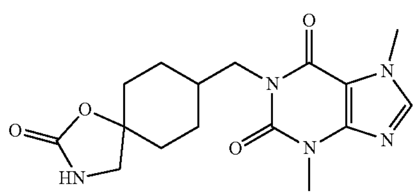 [SMILES: Cn1cnc2c1c(=O)n(CC1CCC3(CC1)CNC(=O)O3)c(=O)n2C] |
| 8 | 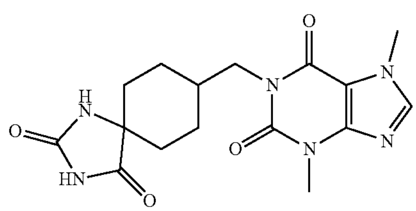 [SMILES: Cn1cnc2c1c(=O)n(CC1CCC3(CC1)NC(=O)NC3=O)c(=O)n2C] |
| 9 | 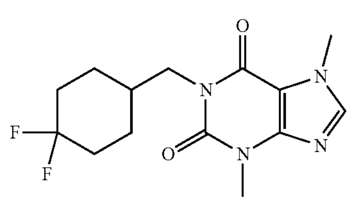 [SMILES: Cn1cnc2c1c(=O)n(CC1CCC(F)(F)CC1)c(=O)n2C] |
| 10 | 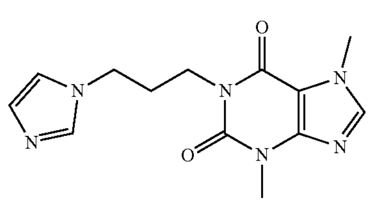 [SMILES: Cn1cnc2c1c(=O)n(CCCn1ccnc1)c(=O)n2C] |

-continued

| Compound | Structure |
|---|---|
| 11 | 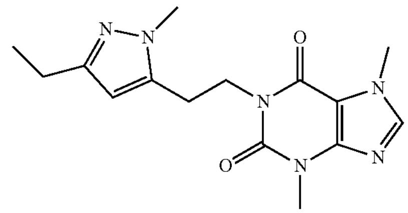 [SMILES: CCc1cc(CCn2c(=O)c3c(ncn3C)n(C)c2=O)n(C)n1] |
| 12 | 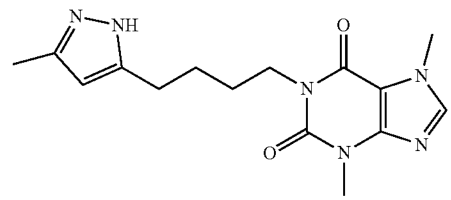 [SMILES: Cc1cc(CCCCn2c(=O)c3c(ncn3C)n(C)c2=O)[nH]n1] |
| 13 | 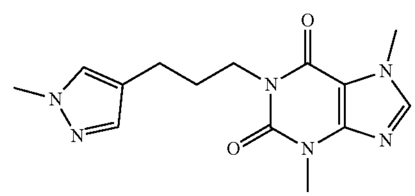 [SMILES: Cn1cc(CCCn2c(=O)c3c(ncn3C)n(C)c2=O)cn1] |
| 14 | 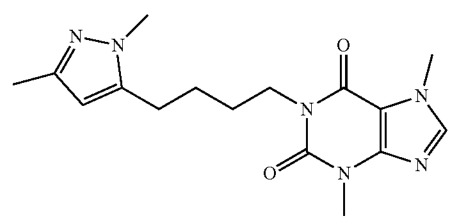 [SMILES: Cc1cc(CCCCn2c(=O)c3c(ncn3C)n(C)c2=O)n(C)n1] |
| 15 | 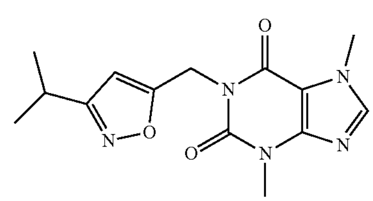 [SMILES: CC(C)c1cc(Cn2c(=O)c3c(ncn3C)n(C)c2=O)on1] |

| Compound | Structure |
|---|---|
| 16 | 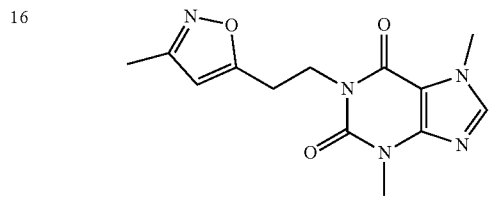 |
| 17 | 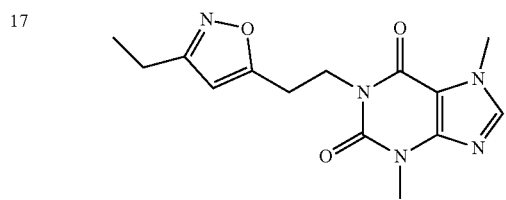 |
| | 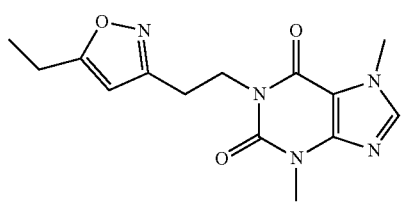 [SMILES: CCc1cc(CCn2c(=O)c3c(ncn3C)n(C)c2=O)no1] |
| 18 | 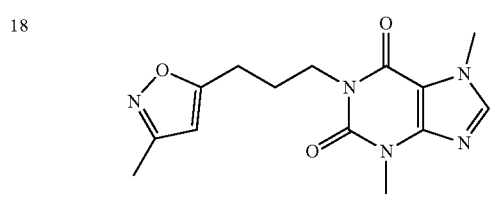 |
| 19 | 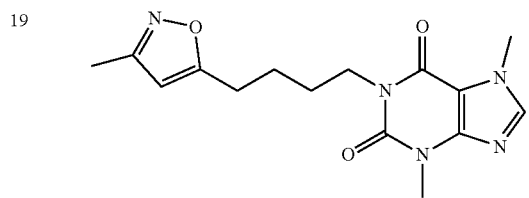 |
| 20 | 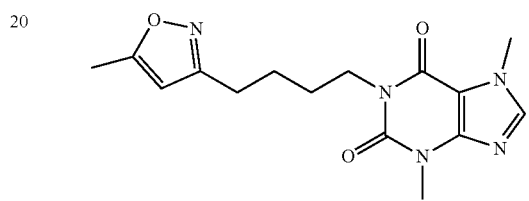 |
| 21 | 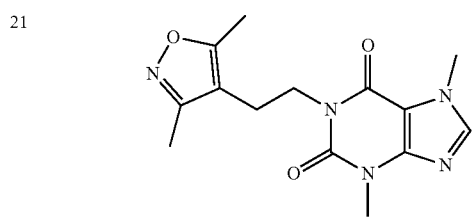 |
| Compound | Structure |
|---|---|
| 22 | 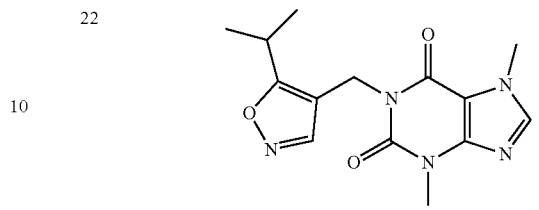 |
| 23 | 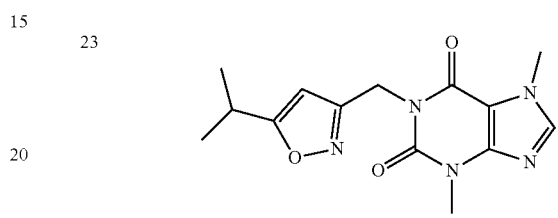 |
| 24 | 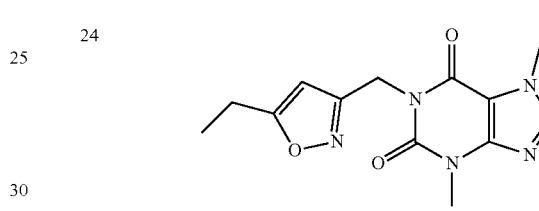 |
| 25 | 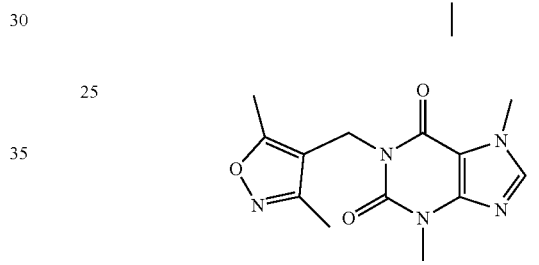 |
| 26 | 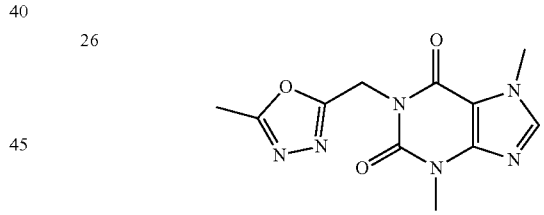 |
| 27 | 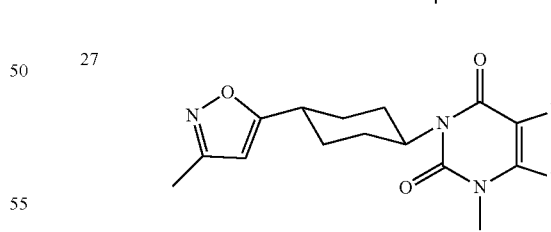 |
| 28 | 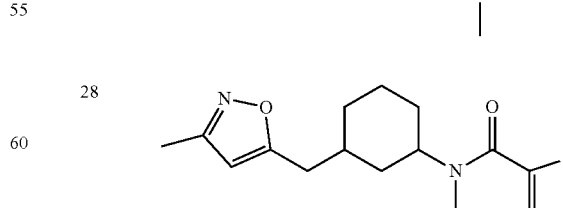 |

TABLE 225-continued
| Compound | Structure |
|---|---|
| 29 | 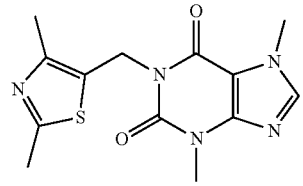 [SMILES: Cc1nc(C)c(Cn2c(=O)c3c(ncn3C)n(C)c2=O)s1] |
| 30 | 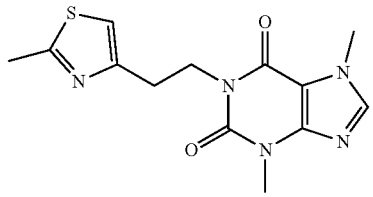 [SMILES: Cc1nc(CCn2c(=O)c3c(ncn3C)n(C)c2=O)cs1] |
| 31 | 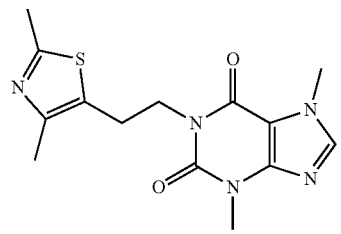 [SMILES: Cc1nc(C)c(CCn2c(=O)c3c(ncn3C)n(C)c2=O)s1] |
| 32 | 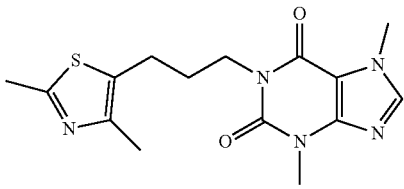 [SMILES: Cc1nc(C)c(CCCn2c(=O)c3c(ncn3C)n(C)c2=O)s1] |
| 33 | 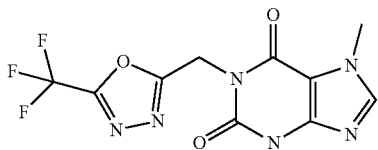 |
| 34 | 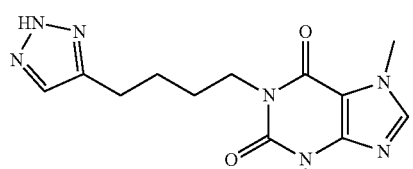 |
| 35 | 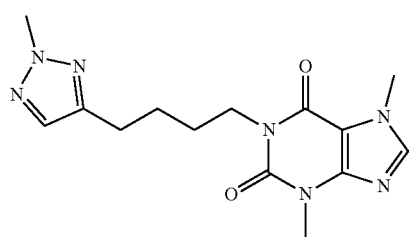 [SMILES: Cn1ncc(CCCCn2c(=O)c3c(ncn3C)n(C)c2=O)n1] |
TABLE 226-continued
| Compound | Structure |
|---|---|
| 36 | 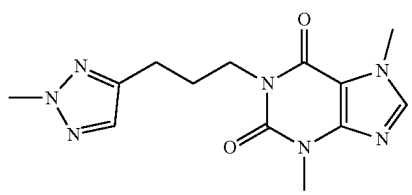 [SMILES: Cn1ncc(CCCn2c(=O)c3c(ncn3C)n(C)c2=O)n1] |
| | 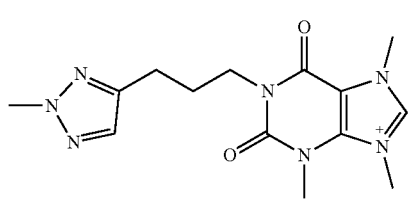 |
| | 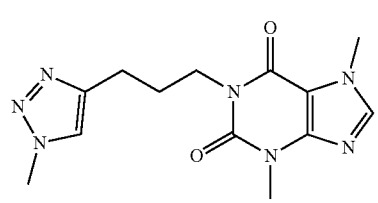 [SMILES: Cn1cc(CCCn2c(=O)c3c(ncn3C)n(C)c2=O)nn1] |
| 37 | 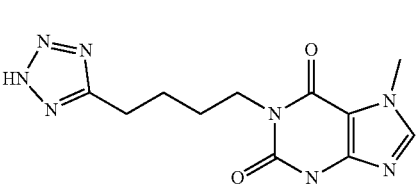 |
| 38 | 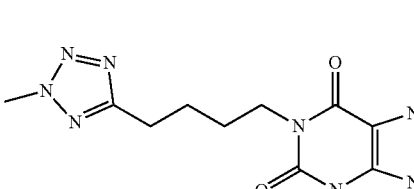 |
| | 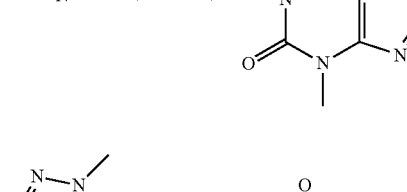 |
| 39 | 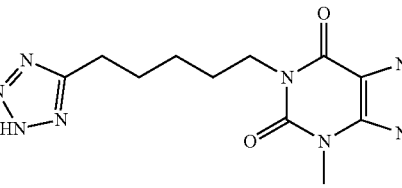 |

| Compound | Structure |
|---|---|
| 40 | 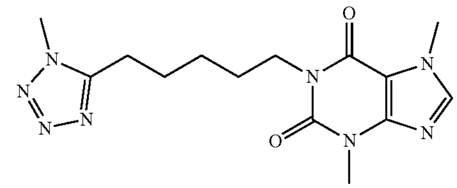 [SMILES: Cn1nnnc1CCCCCn1c(=O)c2c(ncn2C)n(C)c1=O] |
| 41 | 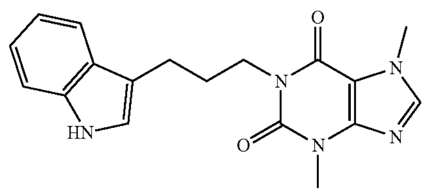 [SMILES: Cn1cnc2c1c(=O)n(CCCc1c[nH]c3ccccc13)c(=O)n2C] |
| 42 | 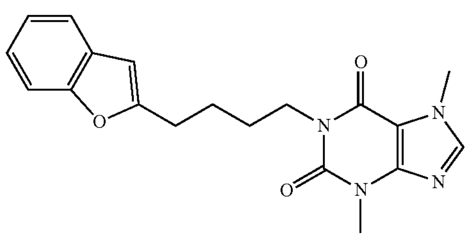 [SMILES: Cn1cnc2c1c(=O)n(CCCCc1cc3ccccc3o1)c(=O)n2C] |
| 43 | 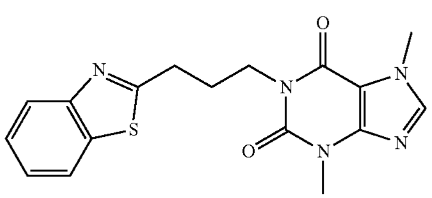 [SMILES: Cn1cnc2c1c(=O)n(CCCc1nc3ccccc3s1)c(=O)n2C] |
| 44 | 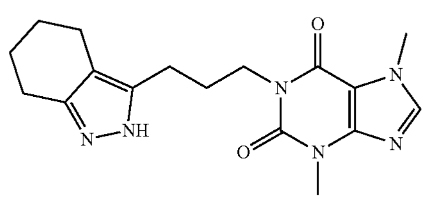 [SMILES: Cn1cnc2c1c(=O)n(CCCc1[nH]nc3c1CCCC3)c(=O)n2C] |
| 45 | 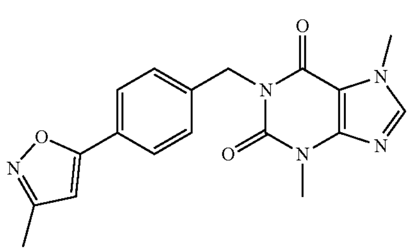 [SMILES: Cc1cc(-c2ccc(Cn3c(=O)c4c(ncn4C)n(C)c3=O)cc2)on1] |

| Compound | Structure |
|---|---|
| 46 | 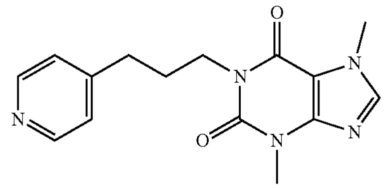 [SMILES: Cn1cnc2c1c(=O)n(CCCc1ccncc1)c(=O)n2C] |
| 47 | 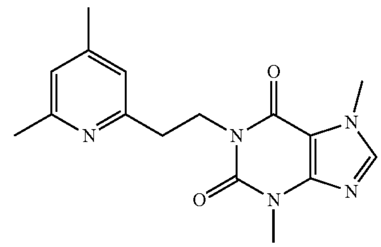 [SMILES: Cc1cc(C)nc(CCn2c(=O)c3c(ncn3C)n(C)c2=O)c1] |
| 48 | 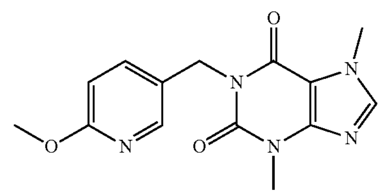 [SMILES: COc1ccc(Cn2c(=O)c3c(ncn3C)n(C)c2=O)cn1] |
| 49 | 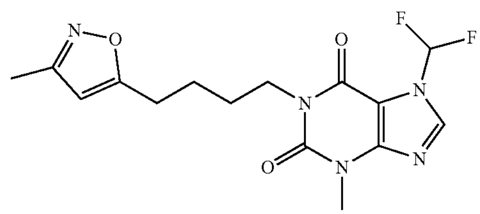 [SMILES: Cc1cc(CCCCn2c(=O)c3c(ncn3C(F)F)n(C)c2=O)on1] |
| 50 | 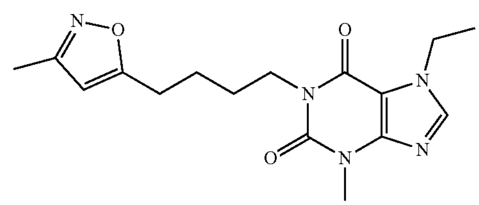 [SMILES: CCn1cnc2c1c(=O)n(CCCCc1cc(C)no1)c(=O)n2C] |
| 51 | 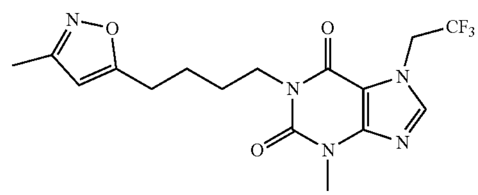 [SMILES: Cc1cc(CCCCn2c(=O)c3c(ncn3CC(F)(F)F)n(C)c2=O)on1] |

| Compound | Structure |
|---|---|
| 52 |  |
| 53 | |
| 54 | |
| 55 | |
| 56 | |
| 57 | |
| 58 | |
| Compound | Structure |
|---|---|
| 59 | 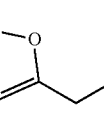 |
| 60 | |
| 61 | |
| 62 | |
| 63 | |
| 64 | |
| 65 | |
7. The compound, the tautomer thereof or the pharmaceutically acceptable salt thereof according to claim 2, wherein each of $R_1$ is independently selected from selected from H, a halogen, OH, $NH_2$, and the group consisting of Me,

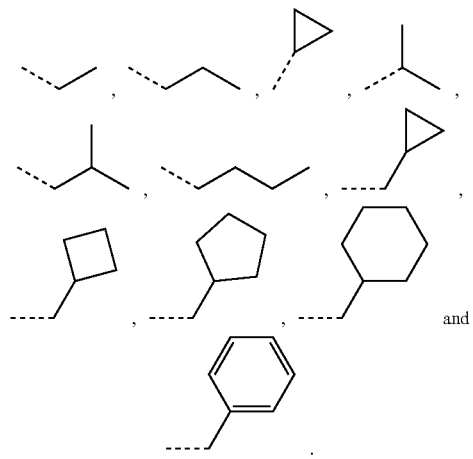

each of which is optionally substituted by 1 to 3 $R_2$.

8. The compound, the tautomer thereof or the pharmaceutically acceptable salt thereof according to claim 2, wherein each of $R_1$ is independently selected from selected from H, a halogen, OH, $NH_2$, Me,

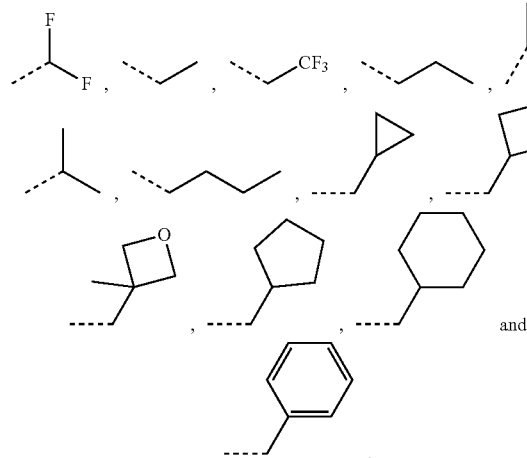

9. The compound, the tautomer thereof or the pharmaceutically acceptable salt thereof according to claim 1, wherein the ring A is selected from the group consisting of

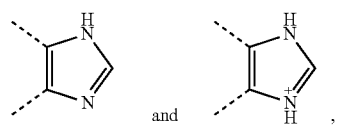

each of which is optionally substituted by 1 or 2 $R_1$.

10. The compound, the tautomer thereof or the pharmaceutically acceptable salt thereof according to claim 1, wherein the ring A is selected from

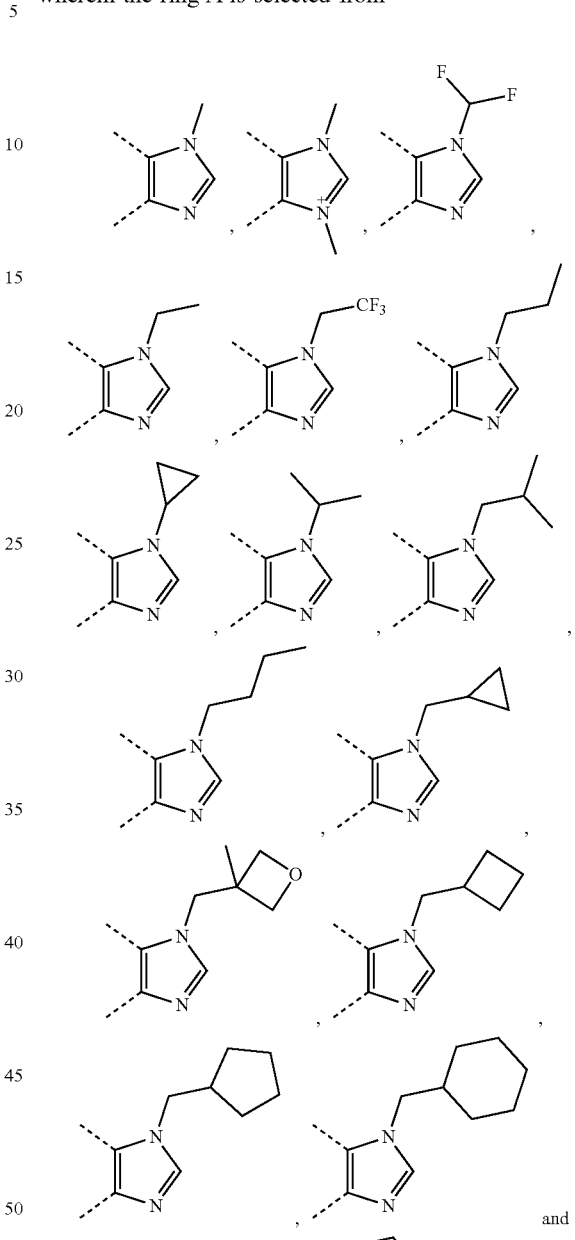

* * * * *